US006573262B2

(12) United States Patent
Wallace et al.

(10) Patent No.: US 6,573,262 B2
(45) Date of Patent: Jun. 3, 2003

(54) COMPOSITION AND ANTIVIRAL ACTIVITY OF SUBSTITUTED INDOLEOXOACETIC PIPERAZINE DERIVATIVES

(75) Inventors: Owen B. Wallace, Zionsville, IN (US); Tao Wang, Middletown, CT (US); Kap-Sun Yeung, Middletown, CT (US); Bradley C. Pearce, East Hampton, CT (US); Nicholas A. Meanwell, East Hampton, CT (US); Zhilei Qiu, Middletown, CT (US); Haiquan Fang, Wallingford, CT (US); Qiufen May Xue, Glastonbury, CT (US); Zhiwei Yin, Meriden, CT (US)

(73) Assignee: Bristol-Myers Sqibb Company, Princeton, NJ (US)

( * ) Notice: Subject to any disclaimer, the term of this patent is extended or adjusted under 35 U.S.C. 154(b) by 0 days.

(21) Appl. No.: 10/027,612

(22) Filed: Dec. 19, 2001

(65) Prior Publication Data
US 2003/0069245 A1 Apr. 10, 2003

Related U.S. Application Data

(63) Continuation-in-part of application No. 09/888,686, filed on Jun. 25, 2001, now abandoned.
(60) Provisional application No. 60/265,978, filed on Feb. 2, 2001, and provisional application No. 60/217,444, filed on Jul. 10, 2000.

(51) Int. Cl.$^7$ .................. A61K 31/496; A61K 31/5377; C07D 403/06; C07D 403/14; C07D 413/14
(52) U.S. Cl. ................. 514/235.2; 514/252.19; 514/253.05; 514/253.09; 514/253.1; 514/254.03; 514/254.05; 514/254.09; 514/241; 514/242; 514/252.02; 514/252.11; 514/253.04; 514/253.06; 544/121; 544/295; 544/363; 544/364; 544/366; 544/367; 544/369; 544/370; 544/373; 544/180; 544/182; 544/179; 544/238; 544/357; 544/362; 544/371
(58) Field of Search ................. 544/121, 295, 544/364, 373, 366, 367, 369, 370, 363; 514/235.2, 252.19, 253.05, 253.09, 253.1, 254.03–254.05, 254.09

(56) References Cited

U.S. PATENT DOCUMENTS

| 5,124,327 A | 6/1992 | Greenlee et al. |
| 5,413,999 A | 5/1995 | Vacca et al. |
| 5,424,329 A | 6/1995 | Boschelli et al. |

FOREIGN PATENT DOCUMENTS

| EP | 0484071 A2 | 5/1992 |
| EP | 0530907 A1 | 3/1993 |
| GB | 1126245 | 11/1966 |
| WO | WO 93/01181 | 1/1993 |
| WO | WO 99/55696 | 11/1999 |
| WO | WO 00/71535 | 11/2000 |
| WO | WO 00/76521 A1 | 12/2000 |

OTHER PUBLICATIONS

Drug Evaluations by American medical Association (6th Ed.), pp. 1615–1627 (1986).*

M. Font, et al, "Indoles and Pyridazino[4,5–b]Indoles as Nonnucleoside Analog Inhibitors of HIV–1 Reverse Transcriptase," Eur. J. Med. Chem., 30, pp. 963–971, 1995.

D. L. Romero, et al, J. Med. Chem., 36, pp. 1505–1508, 1993.

S. D. Young, et al, "2–Heterocyclic Indole–3–Sulfones as Inhibitors of HIV–1 Reverse Transcriptase," Bioorganic & Medicinal Chemistry Letters, 5(5), pp. 491–496, 1995.

M. J. Genin, et al, "Synthesis and Bioactivity of Novel Bis(Heteroaryl)Piperazine (BHAP) Reverse Transcriptase Inhibitors: Structure–Activity Relationships and Increased Metabolic Stability of Novel Substituted Pyridine Analogs," J. Med. Chem., 39, pp. 5267–5275, 1996.

R. Silvestri, et al, Antiviral Chemistry & Chemotherapy, 9, pp. 139–148, 1998.

A. Fredenhagen et al, "Semicochliodinol A and B: Inhibitors of HIV–1 Protease and EGF–R Protein Tyrosine Kinase Related to Asterriquinones Produced by the Fungus *Chrysosporium Merdarium*," Journal of Antibiotics, 50(5), pp. 395–401, 1997.

K. Brewster, et al, Chim. Ther., 2, pp. 169–172, 1973.

J. L. Archibald, et al, J. Med. Chem., 17(7), pp. 745–747, 1974.

T. J. Dueweke, et al, J. Biol. Chem., 267(1), pp. 27–30, 1992.

T. J. Dueweke, et al, Antimicrob. Agent. Chemother., 37(5), pp. 1127–1131, 1993.

* cited by examiner

Primary Examiner—Emily Bernhardt
(74) Attorney, Agent, or Firm—Samuel J. DuBoff

(57) ABSTRACT

The invention comprises substituted indoleoxoacetic piperazine derivatives of general Formula I,

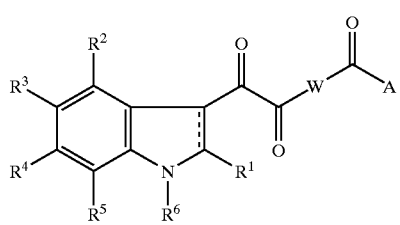

compositions thereof and their use as antiviral agents, and particularly for treating HIV infection.

33 Claims, No Drawings

COMPOSITION AND ANTIVIRAL ACTIVITY OF SUBSTITUTED INDOLEOXOACETIC PIPERAZINE DERIVATIVES

REFERENCE TO RELATED APPLICATIONS

This application is a Continuation-in-Part of U.S. Ser. No. 09/888,686 filed Jun. 25, 2001 now abandoned which claims the benefit of U.S. Provisional Application Serial Nos. 60/265,978 filed Feb. 2, 2001 and 60/217,444 filed Jul. 10, 2000.

BACKGROUND OF THE INVENTION

1. Field of the Invention

This invention provides compounds having drug and bio-affecting properties, their pharmaceutical compositions and method of use. In particular, the invention is concerned with indoleoxoacetyl piperazine derivatives. These compounds possess unique antiviral activity. More particularly, the present invention relates to the treatment of HIV and AIDS.

2. Background Art

HIV-1 (human immunodeficiency virus-1) infection remains a major medical problem, with an estimated 33.4 million people infected worldwide. Currently available HIV drugs include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz) as well as five peptidomimetic protease inhibitors (saquinavir, indinavir, ritonavir, nelfinavir and amprenavir). Each of these drugs can only transiently restrain viral replication if used alone. However, when used in combination, these drugs have a profound effect on disease progression. In fact, significant reductions in death rates among AIDS patients have been recently documented. Despite these results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when suboptimal drug concentrations are present (Larder and Kemp, Gulick, Morris-Jones, et al, Kuritzkes, Vacca and Condra, Schinazi, et al and Flexner, Ref. 6–12). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections. At least 30 different classes of NNRTIs have been published in the literature (DeClercq, Ref. 13). Dipyridodiazepinone (nevirapine), benzoxazinone (efavirenz) and bis(heteroaryl) piperazine derivatives (delavirdine) are already approved for clinical use. In addition, several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1, Williams et al, Ref. 2, Romero et al, Ref. 3, Font et al, Ref. 14, Romero et al, Ref. 15, Young et al, Ref. 16, Genin et al, Ref. 17, and Silvestri et al, Ref. 18). Other indole derivatives exhibiting antiviral activity useful for treating HIV are disclosed in PCT WO 00/76521, Ref. 102). Also, indole derivatives are disclosed in PCT WO 00/71535, Ref. 103). Indole 2-carboxamides have also been described as inhibitors of cell adhesion and HIV infection (Boschelli et al. in U.S. Pat. No. 5,424,329, Ref. 4). Finally, 3-substituted indole natural products (Semicochliodinol A and B, didemethylasterriquinone and isocochliodinol) were disclosed as inhibitors of HIV-1 protease (Fredenhagen et al, Ref. 19). However, nothing in these references can be construed to disclose or suggest the novel compounds of this invention and their use to inhibit viral infections, including HIV infection.

Structurally related compounds have been disclosed previously (Brewster et al, Ref. 20, Archibald et al, Ref. 21, American Home Products in GB 1126245, Ref. 5). However, the structures differ from those claimed herein in that they are symmetrical bis(3-indolylglyoxamides) rather than unsymmetrical aroyl indoleoxoacetyl piperazine derivatives, and there is no mention of use for treating viral infections. Interestingly, the indole moiety present in the compounds disclosed here is the common feature of many non-nucleoside HIV-1 reverse transcriptase inhibitors including Delavirdine from Upjohn (Dueweke et al. 1992, 1993, Ref. 22 and 23).

A recent PCT application, WO 99/55696, described substituted indoles as phosphodiester 4 inhibitors.

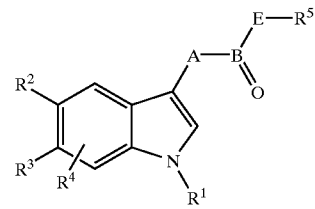

REFERENCES CITED

Patent Documents

1. Greenlee, W. J.; Srinivasan, P. C., Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D., Indoles as inhibitors of HIV reverse transcriptase. European Patent 530907.
3. Romero, D. L.; Thomas, R. C., Preparation of substituted indoles as anti-AIDS pharmaceuticals. PCT WO 93/01181.
4. Boschelli, D. H.; Connor, D. T.; Unangst, P. C., Indole-2-carboxamides as inhibitors of cell adhesion. U.S. Pat. No. 5,424,329.
5. Therapeutic bis(indolyl) compounds. British Patent 1126245 (American Home Products Corp.).

Other Publications

6. Larder B. A & Kemp S. D., Multiple mutations in the HIV-1 reverse transcriptase confer high-level resistance to zidovudine (AZT), *Science* 1989, 246,1155–1158.
7. Gulick R. M., Current antiretroviral therapy: an overview., *Quality of Life Research* 1997, 6, 471–474.
8. Kuritzkes D. R., HIV resistance to current therapies, *Antiviral Therapy* 1997, 2(Supplement 3), 61–67.
9. Morris-Jones S, Moyle G & Easterbrook P. J., Antiretroviral therapies in HIV-1 infection, *Expert Opinion on Investigational Drugs* 1997, 6(8), 1049–1061.

10. Schinazi R. F, Larder B. A & Mellors J. W., Mutations in retroviral genes associated with drug resistance, *International Antiviral News*, 1997, 5, 129–142.
11. Vacca J. P & Condra J. H., Clinically effective HIV-1 protease inhibitors, *Drug Discovery Today* 1997, 2, 261–272.
12. Flexner D., HIV-protease inhibitors, *Drug Therapy* 1998, 338, 1281–1292.
13. De Clercq E., The role of non-nucleoside reverse transcriptase inhibitors (NNRTIs) in the therapy of HIV-1 infection, *Antiviral Research* 1998, 38,153–179.
14. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F., Indoles and pyrazino[4,5-b]indoles as nonnucleoside analog inhibitors of HIV-1 reverse transcriptase, *Eur. J. Med. Chem.* 1995, 30, 963–971.
15. Romero, D. L.; Morge, R. A.; Genin, M. J.; Biles, C.; Busso, M,; Resnick, L.; Althaus, I. W.; Reusser, F.; Thomas, R. C and Tarpley, W. G., Bis(heteroaryl) piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate, *J. Med. Chem.* 1993, 36, 1505–1508.
16. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase, *Bioorg. Med. Chem. Lett.* 1995, 5, 491–496.
17. Genin, M. J.; Poel, T. J.; Yagi, Y.; Biles, C.; Althaus, I.; Keiser, B. J.; Kopta, L. A.; Friis, J. M.; Reusser, F.; adams, W. J.; Olmsted, R. A.; Voorman, R. L.; Thomas, R. C. and Romero, D. L., Synthesis and bioactivity of novel bis (heteroaryl)piperazine (BHAP) reverse transcriptase inhibitors: structure-activity relationships and increased metabolic stability of novel substituted pyridine analogs, *J. Med. Chem.* 1996, 39, 5267–5275.
18. Silvestri, R.; Artico, M.; Bruno, B.; Massa, S.; Novellino, E.; Greco, G.; Marongiu, M. E.; Pani, A.; De Montis, A and La Colla, P., Synthesis and biological evaluation of 5H-indolo[3,2-b][1,5]benzothiazepine derivatives, designed as conformationally constrained analogues of the human immunodeficiency virus type 1 reverse transciptase inhibitor L-737, 126. *Antiviral Chem. Chemother.*, 1998, 9, 139–148.
19. Fredenhagen, A.; Petersen, F.; Tintelnot-Blomley, M.; Rosel, J.; Mett, H and Hug, P. J., Semicochliodinol A and B: inhibitors of HIV-1 protease and EGF-R protein Tyrosine Kinase related to Asterriquinones produced by the fungus *Chrysosporium nerdarium*, *Antibiotics* 1997, 50, 395–401.
20. Brewster, K.; Green, D. M.; Pinder, R. M.; Thompson, P. B. J., Antihypertensive 1,4-bis(2-indol-3-ylethyl) piperazines, *Chim. Ther.* 1973, 8,169–72.
21. Archibald, John L.; Freed, Meier E., 1,4-Bis(2-indol-3-ylethyl)piperazines, *J. Med. Chem.* 1974, 17, 745–747.
22. Dueweke T. J. et al, The binding of a novel bisheteroaryliperazine mediates inhibition of human immunodeficiency virus type 1 reverse transcriptase, *J. Biol. Chem.* 1992, 267, 27–30.
23. Dueweke T. J. et al, U-90152, a potent inhibitor of human immunodeficiency virus replication, *Antimicrob. Agent. Chemother.* 1993, 37, 1127–1131.
24. Gribble, G. W., Recent developments in indole ring synthesis-methodology and applications, *Contemp. Org. Synth.* 1994, 1, 145–72.
25. Lingens, F.; Lange, J., Synthesis of 3-indol-3-yl)glycerol and of 3-(N-methylindol-3-yl)glycerol., *Justus Liebigs Ann. Chem.* 1970, 738, 46–53.
26. Desai, M.; Watthey, J. W. H.; Zuckerman, M., A convenient preparation of 1-aroylpiperazines, Org. Prep. Proced. Int. 1976, 8, 85–86.
27. Potts, B. J., Mini Reverse transcriptase (RT) assay, In Aldovini A., B. D. Walker (ed), Techniques in HIV Research, Stockton Press, NY, p.103–106, 1990.
28. Weislow, O. S., R. Kiser, D. L. Fine, J. Bader, R. H. Shoemaker, and Boyd, M. R., New soluble-formazan assay for HIV-1 cytopathic effects: application to high-flux screening of synthetic and natural products for AIDS-antiviral activity, *Journal of National Cancer Institute* 1989, 81, 577–586.
29. Johnson, V. A. and R. E. Byrington, Infectivity assay, p. 71–76 in A. Aldovini and B. D. Walker (ed), Techniques in HIV Research, Stockton Press, New York, 1990.
30. (a) Harada, S., Koyanagi, Y., and N. Yamamoto, Infection of HTLV-III/LAV in HTLV-I carrying cells MT-2 and MT-4 and application in a plaque assay, *Science* 1985, 229, 563–566. (b) Chen, B. K., Saksela, K., Andino, R., and D. Baltimore; Distinct modes of human immunodeficiency type 1 proviral latency revealed by superinfection of nonproductively infected cell lines with recombinant luciferase-encoding viruses. *J. Virol.* 1994, 68, 654–660.
31. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419–6422. (c) Jenneskens, L. W.; Mahy, J.; den Berg, E. M. M. de B.-v.; Van der Hoef, I.; Lugtenburg, J. *Recl. Trav. Chim. Pays-Bas* 1995, 114, 97.
32. Wang, T.; Zhang, Z.; Meanwell, N. A. Benzoylation of Dianions: Preparation of mono-Benzoylated Symmetric Secondary Diamines. *J. Org. Chem.*, 1999, 64, 7661–7662.
33. (a) Adamczyk, M.; Fino, J. R. Synthesis of procainamide metabolites. N-acetyl desethylprocainamide and desethylprocainamide. Org. Prep. Proced. Int. 1996, 28, 470–474. (b) Wang, T.; Zhang, Z.; Meanwell, N. A. Regioselective mono-Benzoylation of Unsymmetrical Piperazines. *J. Org. Chem.* 2000, 65, 4740.
34. Masuzawa, K.; Kitagawa, M.; Uchida, H. *Bull Chem. Soc. Jpn.* 1967, 40, 244–245.
35. Furber, M.; Cooper, M. E.; Donald, D. K. *Tetrahedron Lett.* 1993, 34, 1351–1354.
36. Bartoli et al. a) *Tetrahedron Lett.* 1989, 30, 2129. b) *J. Chem. Soc. Perkin Trans.* 1 1991, 2757. c) *J. Chem. Soc. Perkin Trans. II* 1991, 657.
37. Pindur, U.; Adam, R. *J. Heterocyclic Chem.* 1988, 25, 1.
38. Fukuda, T. et al. *Tetrahedron* 1999, 55, 9151.
39. Iwao, M. et al. *Heterocycles* 1992, 34(5), 1031.
40. Richard A. Sundberg, *The Chemistry of Indoles*; Academic Press: London 1970.
41. Hulton et al. *Synth. Comm.* 1979, 9, 789.
42. Anderson, B. A. et al. *J. Org. Chem.* 1997, 62, 8634.
43. Crozet, M. P. et al. *Heterocycles* 1993, 36(1), 45–54.
44. Pattanayak, B. K. et al. *Indian J. Chem.* 1978, 16, 1030.
45. Feist, F. *Chemische Berichte* 1902, 35,1545.
46. Benary, E. *Chemische Berichte* 1911, 44, 493.

47. Moubarak, I. et al. *Synthesis* 1980, 52–54.
48. Iyer, R. N. et al. *Ind J. Chem.* 1973, 11, 1260.
49. Roomi et. al. *Can J. Chem.* 1970, 48, 1689.
50. Scholkopf et al. *Angew. Int. Ed. Engl.* 1971, 10(5), 333.
51. Nitz, T.J. et al. *J. Org. Chem.* 1994, 59, 5828–5832.
52. Chimichi, S. *Synth. Comm.* 1992, 22, 2909.
53. Shawali, A. S. et al. *J. Heterocyclic Chem.* 1976, 13, 989.
54. Bowden, K. et al. *J. Chem. Soc.* 1946, 953.
55. Home, D. A. *Heterocycles* 1994, 39, 139.
56. Sorrel, T. N. *J. Org. Chem.* 1994, 59, 1589.
57. Short Course in Heterocyclic Chemistry by Professors Will Pearson and Albert Padwa (Can be purchased from these professors).
58. Protective groups in organic synthesis $3^{rd}$ ed. Theodora W. Greene and Peter G. M. Wuts. New York: Wiley, 1999.
59. Bodanszky, M.; Bodanszky, A. *"The Practice of Peptide Synthesis"* $2^{nd}$ Ed., Springer-Verlag: Berlin Heidelberg, Germany, 1994.
60. Albericio, F. et al. *J. Org. Chem.* 1998, 63, 9678.
61. Knorr, R. et al. *Tetrahedron Lett.* 1989, 30, 1927.
62. (a) Jaszay Z. M. et al. *Synth. Commun.*, 1998 28, 2761 and references cited therein; (b) Bernasconi, S. et al. *Synthesis*, 1980, 385.
63. a) Jaszay Z. M. et al. *Synthesis*, 1989, 745 and references cited therein; (b) Nicolaou, K. C. et al. *Angew. Chem. Int. Ed.* 1999, 38, 1669.
64. Ooi, T. et al. *Synlett*. 1999, 729.
65. Ford, R. E. et al. *J. Med. Chem.* 1986, 29, 538.
66. (a) Yeung, K.-S. et al. Bristol-Myers Squibb Unpublished Results. (b) Wang, W. et al. *Tetrahedron Lett.* 1999, 40, 2501.
67. Brook, M. A. et al. *Synthesis*, 1983, 201.
68. Yamazaki, N. et al. *Tetrahedron Lett.* 1972, 5047.
69. Barry A. Bunin "The Combinatorial Index" 1998 Academic Press, San Diego/London pages 78–82.
70. Albert M. van Leusen et. Al. *J. Org. Chem.* 1981, 46, 2069.
71. Norio Miyaura and Akiro Suzuki *Chem Rev.* 1995, 95, 2457.
72. Farina, Vittorio; Roth, Gregory P. Recent advances in the Stille reaction; *Adv. Met.-Org. Chem.* 1996, 5, 1–53.
73. Farina, Vittorio; Krishnamurthy, Venkat; Scott, William J. The Stille reaction; Org. React. (N. Y.) (1997), 50, 1–652.
74. Stille, J. K. *Angew. Chem. Int. Ed. Engl.* 1986, 25, 508–524.
75. a) Kende, A. S. et al. *Org. Photochem. Synth.* 1972, 1, 92. B) Hankes, L. V.; *Biochem. Prep.* 1966, 11, 63. C) *Synth. Meth.* 22, 837.
76. Kamitori, Y. et. al. *Heterocycles*, 1994, 37(1), 153.
77. Katritzky, Alan R. Lagowski, Jeanne M. The principles of heterocyclic ChemistryNew York: Academic Press, 1968.
78. Paquette, Leo A. Principles of modern heterocyclic chemistry New York: Benjamin.
79. Katritzky, Alan R.; Rees, Charles W.; Comprehensive heterocyclic chemistry: the structure, reactions, synthesis, and uses of heterocyclic compounds $1^{st}$ ed.Oxford (Oxfordshire); New York: Pergamon Press, 1984. 8 v.
80. Katritzky, Alan RHandbook of heterocyclic 1st edOxford (Oxfordshire); New York: Pergamon Press, 1985.
81. Davies, David I Aromatic Heterocyclic Oxford; New York: Oxford University Press, 1991.
82. Ellis, G. P. Synthesis of fused Chichester [Sussex]; New York: Wiley, c1987–c1992. Chemistry of heterocyclic compounds; v. 47.
83. Joule, J. A Mills, K. Smith, G. F. Heterocyclic Chemistry, $3^{rd}$ ed London. New York Chapman & Hall, 1995.
84. Katritzky, Alan R., Rees, Charles W., Scriven, Eric F. V. Comprehensive heterocyclic chemistry II: a review of the literature 1982–1995.
85. The structure, reactions, synthesis, and uses of heterocyclic compounds $1^{st}$ ed. Oxford; New York: Pergamon, 1996. 11 v. in 12: ill.; 28 cm.
86. Eicher, Theophil, Hauptmann, Siegfried. The chemistry of heterocycles: structure, reactions, syntheses, and applications Stuttgart; New York: G. Thieme, 1995.
87. Grimmett, M. R. Imidazole and benzimidazole Synthesis London; San Diego: Academic Press, 1997.
88. Advances in heterocyclic chemistry. Published in New York by Academic Press, starting in 1963-present.
89. Gilchrist, T. L. (Thomas Lonsdale) Heterocyclic chemistry $3^{rd}$ ed. Harlow, Essex: Longman, 1997. 414 p.: ill.; 24 cm.
90. Gilmore et. al. *Synlett* 1992, 79–80.
91. Richard C. Larock Comprehensive Organic Transormations $2^{nd}$ Ed. 1999, John Wiley and Sons New York.
92. M. D. Mullican et. al. *J.Med. Chem.* 1991, 34, 2186–2194.
93. R. D. Clark et al. *Heterocycles*, 1984, 22, 195.
94. D. Hughes Organic Preparations and Procedures 1993, 609.
95. A. Guy et. al *Synthesis* 1980, 222.
96. Gassman, P. G.; Van Bergen, T. J.; Gilbert, D. P.; Cue, B. W. *J. Am. Chem. Soc.* 1974, 96(17), 5495–5508.
97. Muratake et al. *Heterocycles* 1990, 31, 683.
98. T. Fukuyama et. al. *J. Am. Chem. Soc.* 1994, 116, 3127.
99. Gribble, G. Recent Developments in indole ring synthesis-methodology and applications, *J. Chem Soc. Perkin Trans* 1, 2000, 1045–1075.
100. a) Littke, Adam F.; Dai, Chaoyang; Fu, Gregory C. *J. Am. Chem. Soc.* 2000, 122(17), 4020–4028. b) Varma, Rajender S.; Naicker, Kannan P. *Tetrahedron Lett.* 1999, 40(3), 439–442. c) Wallow, Thomas I.; Novak, Bruce M. *J. Org. Chem.* 1994, 59(17), 5034–7. d) Buchwald, Stephen; Old, David W.; Wolfe, John P.; Palucki, Michael; Kamikawa, Ken; Chieffi, Andrew; Sadighi, Joseph P.; Singer, Robert A.; Ahman, Jens. PCT Int. Appl. WO 0002887, 2000. e) Wolfe, John P.; Buchwald, Stephen L. *Angew. Chem., Int. Ed.* 1999, 38(23), 3415. f) Wolfe, John P.; Singer, Robert A.; Yang, Bryant H.; Buchwald, Stephen L. *J. Am. Chem. Soc.* 1999, 121(41), 9550–9561. g) Wolfe, John P.; Buchwald, Stephen L. *Angew. Chem., Int. Ed.* 1999, 38(16), 2413–2416.
101. a) Das, B. P.; Boykin, D. W. *J. Med. Chem.* 1977, 20, 531; b) Czarny, A.; Wilson, W. D.; Boykin, D. W. *J. Heterocyclic Chem.* 1996, 33, 1393; c) Francesconi, I.; Wilson, W. D.; Tanious, F. A.; Hall, J. E.;
Bender, B. C.; Tidwell, R. R.; McCurdy, D.; Boykin, D. W. *J. Med. Chem.* 1999, 42, 2260.
102. Blair, W. S. et. al. PCT WO 00/76521 published Dec. 21, 2000.
103. Mavuhkel, B. J. et al, PCT WO 00/71535 published Nov. 30, 2000.
104. (a) Okauchi, T. et al. *Org. Lett.* 2000, 2, 1485. (b) Ottoni, O. et al. *Org. Lett.* 2001, 3, 1005.
105. (a) Lo, Y. S. et al. *J. Heterocyclic Chem.* 1980, 17, 1663. (b) Walsh, D. A. et al. *J. Med. Chem.* 1984, 27, 1379. (c) Murakami, Y. et al. *Heterocycles*, 1984, 22, 241. (d) Black, D. St. C. et al. *Aust. J. Chem.* 1996, 49, 311.
106. Kondo, Y. et al. *Heterocycles*, 1996, 43, 2741.
107. Moyer, M. P. et al. *J. Org. Chem.* 1986, 51, 5106.
108. Kim, P. T. et al. *J. Heterocyclic Chem.* 1981, 18, 1373.
109. (a) Eloy, F. et al. *Helv. Chim. Acta* 1966, 49, 1430. (b) Diana, G. D. et al. *J. Med. Chem.* 1994, 37, 2421. (c)

Tilley, J. W. et al. *Helv. Chim. Acta* 1980, 63, 832. (d) Yurugi, S. et al. *Chem. Pharm. Bull.* 1973, 21, 1641.

SUMMARY OF THE INVENTION

The present invention comprises compounds of Formula I, their pharmaceutical formulations, and their use in patients suffering from or susceptible to a virus such as HIV. The compounds of Formula I which include nontoxic pharmaceutically acceptable salts and/or hydrates thereof have the formula and meaning as described below.

A first embodiment of a first aspect of the present invention are compounds of Formula I, including pharmaceutically acceptable salts thereof,

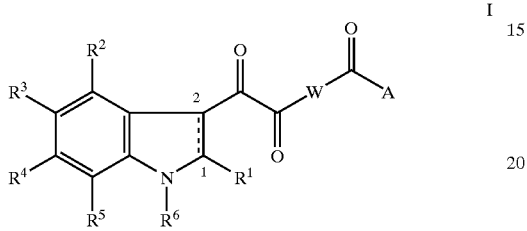

I wherein:

A is selected from the group consisting of $C_{1-6}$alkoxy, aryl and heteroaryl; in which said aryl is phenyl or napthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different amino, nitro, cyano, $C_{1-6}$alkoxy, —C(O)NH$_2$, halogen or trifluoromethyl;

—W— is

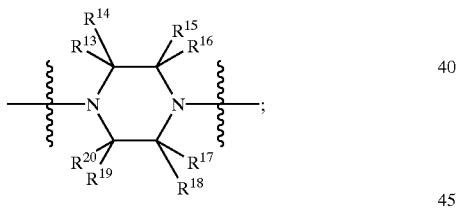

— may represent a carbon-carbon bond; (i.e. when — represents a carbon-carbon bond the carbons denoted 1 and 2 are attached to each other by a carbon-carbon double; when — does not represent a carbon-carbon bond then the carbons denoted 1 and 2 are attached to each other by a carbon-carbon single bond);

$R^1$ is hydrogen;

$R^2$, $R^3$, $R^4$, and $R^5$ are each independently selected from the group (a)–(r) consisting of:
(a) hydrogen,
(b) halogen,
(c) cyano,
(d) nitro,
(e) amino,
(f) $C_{1-4}$alkylamino,
(g) di($C_{1-4}$alkyl)amino,
(h) hydroxy,
(i) $C_{1-6}$alkyl optionally substituted with one to three same or different halogen, hydroxy, $C_{1-6}$alkoxy, amino, $C_{1-4}$alkylamino, di($C_{1-4}$alkyl)amino, cyano or nitro,
(j) $C_{3-7}$cycloalkyl optionally substituted with one to three same or different halogen, hydroxy, $C_{1-6}$alkoxy, amino, $C_{1-4}$alkylamino, di($C_{1-4}$alkyl) amino, cyano or nitro,
(k) $C_{1-6}$alkoxy,
(l) —C(O)OR$^7$,
(m) —C(O)R$^8$,
(n) —C(O)NR$^9$R$^{10}$,
(o) —C(=NR$^{12}$)(R$^{11}$),
(p) aryl, said aryl is phenyl or napthyl, and said aryl is optionally substituted with one to two of the same or different amino, $C_{1-4}$alkylamino, di($C_{1-4}$alkyl) amino, cyano, C-amido, N-amido, $C_{1-6}$, alkoxy, $C_{1-6}$thioalkoxy or halogen,
(q) heteroaryl, said heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl, and said heteroaryl is optionally substituted with one to two same or different groups selected from (aa)–(pp) consisting of: (aa) halogen, (bb) $C_{1-6}$alkyl, said $C_{1-6}$alkyl optionally substituted with one to three same or different halogen, hydroxy, cyano, amino, $C_{1-4}$alkylamino or di($C_{1-4}$alkyl)amino, (cc) $C_{3-6}$alkenyl, (dd) $C_{1-6}$alkoxy, (ee) phenyl optionally substituted with one or two same or different halogen, (ff) heteroaryl, said heteroaryl selected from the group consisting of pyridinyl, pyrimidinyl, furanyl, thienyl, oxazolyl, isoxazolyl, pyrazolyl, triazolyl and tetrazolyl, and said heteroaryl optionally substituted with one or two same or different $C_{1-4}$alkyl, $C_{1-4}$alkoxy, halogen, amino, $C_{1-4}$alkylamino and di($C_{1-4}$alkyl)amino, (gg) heteroaryl$C_{1-6}$alkyl-, in which the heteroaryl of said heteroaryl $C_{1-6}$alkyl- is selected from the group consisting of pyridinyl, furanyl, thienyl and pyrazolyl, the heteroaryl of said heteroaryl$C_{1-6}$alkyl- is optionally substituted with one or two same or different $C_{1-4}$alkyl, halogen or amino, and in which a carbon of the $C_{1-6}$alkyl of said heteroaryl$C_{1-6}$alkyl- is optionally replaced by one sulfur or sulfonyl, (hh) amino, (ii) $C_{1-4}$alkylamino, in which the $C_{1-4}$alkyl of said $C_{1-4}$alkylamino is optionally substituted with amino, $C_{1-4}$alkylamino, di($C_{1-4}$alkyl)amino, morpholinyl, piperazinyl or piperidinyl, (jj) di($C_{1-4}$alkyl)amino, (kk) $C_{3-7}$cycloalkylamino, (ll) —(CH$_2$)$_q{}^a$C(O)R$^{23}$, (mm) —CH$_2$OC(O)C$_{1-6}$alkyl, (nn) —NH—(CH$_2$)$_q{}^b$C(O)R$^{24}$, (oo) —CO$_2$CH$_2$C(O) R$^{25}$, (pp) phenylmethyl, in which the phenyl of said phenylmethyl is optionally substituted with a —(CH$_2$)$_q{}^c$C(O)R$^{26}$; and
(r) heteroalicyclic, said heteroalicyclic selected from the group consisting of piperazinyl, piperidinyl, morpholinyl, 5-oxo-4,5-dihydro-[1,2,4]oxadiazol-3-yl, 4,5-dihydro-thiazol-2-yl, 5-oxo-4,5-dihydro-[1,3,4]oxadiazol-2-yl and 4,5-dihydro-1H-imidazol-2-yl, and said heteroalicyclic is optionally substituted with one or two same or different $C_{1-6}$alkyl, $C_{1-4}$alkoxy, hydroxy, cyano or amino;

$R^6$ and $R^7$ are each independently selected from hydrogen or $C_{1-6}$alkyl;

$R^8$ is selected from the group consisting of $C_{1-6}$alkyl, phenyl and heteroaryl in which said heteroaryl is selected from the group consisting of oxazolyl, isoxazolyl, imidazolyl, pyrazolyl, thiazolyl, isothiazolyl, oxadiazolyl, thiadiazolyl, pyridinyl, and pyrimidinyl and said heteroaryl is optionally substituted with one to two of the same or different $C_{1-6}$alkyl, amino, $CO_2H$ or $CO_2C_{1-6}$alkyl;

$R^9$ and $R^{10}$ are each independently selected from the group (a)–(l) consisting of:
(a) hydrogen,
(b) $C_{1-6}$alkyl, said $C_{1-6}$alkyl is optionally substituted with in one to two of the same or different amino, di($C_{1-6}$alkyl)amino or $C_{1-6}$alkoxy,
(c) $C_{1-6}$alkoxy,
(d) heteroaryl, in which said heteroaryl is selected from the group consisting of pyridinyl, isoxazolyl, benzoimidazolyl, tetrazolyl, pyrazolyl, thiazolyl, oxadiazolyl, thiadiazolyl, benzothiazolyl, pyrimidinyl and isoquinolinyl and said heteroaryl is optionally substituted with one to two of the same or different $C_{1-6}$alkyl or $C_{1-6}$alkoxy,
(e) heteroaryl-$C_{1-6}$alkyl-, in which said heteroaryl is selected from the group consisting of indolyl, imidazolyl, benzoimidazolyl, pyridinyl, pyrimidinyl, thiazolyl, triazolyl, tetrazolyl, furanyl and thienyl,
(f) heteroalicyclic, in which said heteroalicyclic is morpholinyl, piperazinyl or dihydrothiazolyl, and said heteroalicyclic is optionally substituted with a $C_{1-6}$alkoxycarbonyl,
(g) morpholin-4-ylethyl,
(h) phenylsulfonyl,
(i) $C_{1-4}$alkylsulfonyl,
(j) amino,
(k) ($C_{1-6}$alkoxy)—C(O)NH—, and
(l) ($C_{1-6}$alkyl)—NHC(O)NH; or $R^9$ and $R^{10}$ taken together with the nitrogen to which they are attached are 4-benzylpiperazin-1-yl or 4-benzoylpiperazin-1-yl;

$R^{11}$ is selected from the group consisting of hydrogen, $C_{1-6}$alkoxy and $NR^{21}R^{22}$;

$R^{12}$ is selected from the group consisting of hydrogen, hydroxy, $NHCO_2$ $C_{1-6}$alkyl and $C_{1-6}$alkoxy, said $C_{1-6}$alkoxy optionally substituted with one $CO_2H$ or $CO_2C_{1-6}$alkyl;

$R^{13}$, $R^{14}$, $R^{15}$, $R^{16}$, $R^{17}$, $R^{18}$, $R^{19}$ and $R^{20}$ are each independently selected from hydrogen or $C_{1-6}$alkyl;

$R^{21}$ and $R^{22}$ are each independently selected from the group consisting of hydrogen, amino, $C_{1-6}$alkyl, $C_{3-7}$cycloalkyl and $NHCO_2C_{1-6}$alkyl;

$R^{23}$, $R^{24}$, $R^{25}$ and $R^{26}$ are each independently selected from the group consisting of hydroxy, $C_{1-4}$alkyl, $C_{1-4}$alkoxy optionally substituted with morpholin-4-yl or di($C_{1-4}$alkyl)amino, amino, pyrolidin-1-yl, ($C_{1-4}$alkyl)amino and di($C_{1-4}$alkyl)amino;

$q^a$, $q^b$ and $q^c$ are each independently 0 or 1; and provided that at least one of $R^2$, $R^3$, $R^4$, and $R^5$ is selected from the group consisting of —C(O)$R^8$, —C(O)NR$^9$R$^{10}$, —C(=NR$^{12}$)(R$^{11}$), aryl, heteroaryl, and heteroalicyclic when - - represents a carbon-carbon bond.

A second embodiment of the first aspect of the present invention is a compound of the first embodiment of the first aspect, including pharmaceutically acceptable salts thereof wherein: A is selected from the group consisting of $C_{1-6}$alkoxy, phenyl and heteroaryl in which said heteroaryl is selected from pyridinyl, furanyl and thienyl, and said phenyl or said heteroaryl is optionally substituted with one to two of the same or different amino, nitro, cyano, $C_{1-6}$alkoxy, —C(O)NH$_2$, halogen or trifluoromethyl; - - represents a carbon-carbon bond; $R^6$ is hydrogen; $R^{13}$, $R^{14}$, $R^{16}$, $R^{17}$ and $R^{18}$ are each hydrogen; and $R^{15}$, $R^{19}$ and $R^{20}$ are each independently hydrogen or $C_{1-6}$alkyl.

A third embodiment of the first aspect of the present invention is a compound of the second embodiment of the first aspect or a pharmaceutically acceptable salt thereof, wherein: $R^2$ is selected from the group consisting of hydrogen, halogen and $C_{1-6}$alkoxy; $R_3$ and $R_4$ are hydrogen; and $R^5$ is selected from the group consisting of: —C(O)$R^8$, —C(O)NR$^9$R$^{10}$, —C(=NR$^{12}$)(R$^{11}$), aryl, heteroaryl and heteroalicyclic.

A fourth embodiment of the first aspect of the present invention is a compound of the third embodiment of the first aspect or a pharmaceutically acceptable salt thereof, wherein: $R^2$ is halogen or $C_{1-6}$alkoxy; $R^5$ is phenyl, said phenyl optionally substituted with a $C_{1-4}$alkoxy, $C_{1-4}$thioalkoxy or halogen; $R^{15}$ and $R^{19}$ are each hydrogen; $R^{20}$ is hydrogen or methyl; and A is phenyl.

A fifth embodiment of the first aspect of the present invention is a compound of the fourth embodiment of the first aspect wherein: $R^2$ is fluoro or methoxy; $R^5$ is phenyl, said phenyl optionally substituted with a methoxy, thiomethoxy, or fluoro; and $R^{20}$ is hydrogen.

A sixth embodiment of the first aspect of the present invention is a compound of the third embodiment of the first aspect or a pharmaceutically acceptable salt thereof, wherein: $R^2$ is halogen or $C_{1-6}$alkoxy; $R^5$ is selected from the group consisting of —C(O)NR$^9$R$^{10}$, —C(=NR$^{12}$)(R$^{11}$) and heteroaryl in which said heteroaryl is tetrazolyl or oxadiazolyl and said heteroaryl is optionally substituted with one to two $C_{1-6}$alkyl, dihalomethyl, trihalomethyl or halogen; $R^{15}$ and $R^{19}$ are each hydrogen; $R^{20}$ is hydrogen or $C_{1-6}$ alkyl; and A is heteroaryl, said heteroaryl selected from the group consisting of pyridinyl, furanyl and thienyl and said heteroaryl optionally substituted with a halogen.

A seventh embodiment of the first aspect of the present invention is a compound of the sixth embodiment of the first aspect wherein: $R^2$ is fluoro; $R^5$ is selected from the group consisting of 2H-tetrazolyl, 2-dihalomethyl-2H-tetrazolyl, [1,2,4]-oxadiazolyl, 5-amino-[1,2,4]-oxadiazolyl, 5-trihalomethyl-[1,2,4]-oxadiazolyl, —C(O)NH$_2$ and —C(=NOH)NH$_2$; $R^{20}$ is hydrogen or methyl; and A is pyridinyl.

A eighth embodiment of the first aspect of the present invention is a compound of the sixth embodiment of the first aspect wherein: $R^2$ is fluoro; $R^5$ is 2H-tetrazolyl or 2-methyl-2H-tetrazolyl; $R^{20}$ is hydrogen; and A is furanyl or thienyl, in which said furanyl is optionally substituted with a chloro or bromo.

A ninth embodiment of the first aspect of the present invention is a compound of the third embodiment of the first aspect wherein: $R^2$ is selected from the group consisting of hydrogen, fluoro or methoxy; $R^5$ is —C(O)NR$^9$R$^{10}$; $R^{15}$ and $R^{19}$ are each hydrogen; $R^{20}$ is hydrogen or methyl; and A is phenyl.

A tenth embodiment of the first aspect of the present invention is a compound of the ninth embodiment of the first aspect wherein: $R^2$ is hydrogen; and $R^9$ and $R^{10}$ are each independently selected from the group consisting of hydrogen, $C_{1-6}$ alkyl optionally substituted with a di($C_{1-4}$alkyl)amino, methylsulfonyl, phenylsulfonyl, and tetrazolyl, or $R^9$ and $R^{10}$ taken together with the nitrogen to which they are attached are 4-benzylpiperazin-1-yl.

An eleventh embodiment of the first aspect of the present invention is a compound of the ninth embodiment of the first aspect wherein $R^2$ is methoxy; $R^{20}$ is hydrogen; and $R^9$ and $R^{10}$ are each independently hydrogen or methyl.

A twelth embodiment of the first aspect of the present invention is a compound of the ninth embodiment of the first aspect wherein: $R^2$ is fluoro; $R^{20}$ is methyl; and $R^9$ and $R^{10}$ are each independently selected from the group consisting of hydrogen, $C_{1-6}$alkyl and morpholin-4-ylethyl.

A thirteenth embodiment of the first aspect of the present invention is a compound of the ninth embodiment of the first aspect wherein: $R^2$ is fluoro; and $R^{20}$ is hydrogen.

A fourteenth embodiment of the first aspect of the present invention is a compound of the third embodiment of the first aspect wherein: $R^2$ is hydrogen, methoxy or fluoro; $R^5$ is —C(O)$R^8$; $R^{15}$ and $R^{19}$ are each hydrogen; $R^{20}$ is hydrogen or methyl; and A is phenyl.

A fifteenth embodiment of the first aspect of the present invention is a compound of the fourteenth embodiment of the first aspect wherein: $R^2$ is methoxy or fluoro; and $R^8$ is $C_{1-6}$alkyl.

A sixteenth embodiment of the first aspect of the present invention is a compound of the fifteenth embodiment of the first aspect wherein: $R^2$ is methoxy; $R^8$ is methyl; and $R^{20}$ is hydrogen.

A seventeenth embodiment of the first aspect of the present invention is a compound of the third embodiment of the first aspect wherein: $R^2$ is selected from the group consisting of hydrogen, methoxy and halogen; $R^5$ is heteroaryl; $R^{15}$ and $R^{19}$ are each hydrogen; $R^{20}$ is hydrogen or methyl; and A is phenyl, said phenyl optionally substituted with one to two of the same or different cyano, fluoro, trifluoromethyl, amino, nitro, and C(O)$NH_2$.

An eighteenth embodiment of the first aspect of the present invention is a compound of the seventeenth embodiment of the first aspect wherein: $R^5$ is heteroaryl, said heteroaryl selected from the group consisting of pyridinyl, pyrimidinyl, furanyl, thienyl, benzothienyl, thiazolyl, oxazolyl, benzooxazolyl, imidazolyl, benzoimidazolyl, oxadiazolyl, pyrazolyl, triazolyl, tetrazolyl, 1H-imidazo[4,5-b]pyridin-2-yl, and 1H-imidazo[4,5-c]pyridin-2-yl.

A nineteenth embodiment of the first aspect of the present invention is a compound of the third embodiment of the first aspect wherein: $R^2$ is selected from the group consisting of hydrogen, methoxy and fluoro; $R^5$ is heteroalicyclic, said heteroalicyclic selected from the group consisting of 5-oxo-4,5-dihydro-[1,2,4]oxadiazol-3-yl, 4,5-dihydro-thiazol-2-yl, 5-oxo-4,5-dihydro-[1,3,4]oxadiazol-2-yl and 4,5-dihydro-1H-imidazol-2-yl; $R^{15}$ and $R^{19}$ are each hydrogen; $R^{20}$ is hydrogen or methyl; and A is phenyl.

A twentieth embodiment of the first aspect of the present invention is a compound of the third embodiment of the first aspect wherein: $R^2$ is selected from the group consisting of hydrogen, methoxy and fluoro; $R^5$ is —C(=N$R^{12}$)($R^{11}$); A is phenyl or $C_{1-6}$alkoxy; $R^{11}$ is selected from the group consisting of hydrogen, hydroxy, $NHCO_2C(CH_3)_3$ and $OCH_2CO_2H$; and $R^{12}$ is selected from the group consisting of hydrogen, ethoxy and $NR^{21}R^{22}$; $R^{15}$ and $R^{19}$ are each hydrogen; $R^{20}$ is hydrogen or methyl; and $R^{21}$ and $R^{22}$ are each independently selected from the group consisting of hydrogen, amino, $C_{1-6}$alkyl, cyclopropyl and $NHCO_2C(CH_3)_3$.

A twentyfirst embodiment of the first aspect of the present invention is a compound selected from the group consisting of:

1-(4-Benzoyl-piperazin-1-yl)-2-(4-fluoro-7-oxazol-5-yl-1H-indol-3-yl)-ethane-1,2-dione;
1-(4-Benzoyl-2-(R)-methyl-piperazin-1-yl)-2-[4-fluoro-7-(2H-tetrazol-5-yl)-1H-indol-3-yl]-ethane-1,2-dione;
3-[2-(4-Benzoyl-piperazin-1-yl)-2-oxo-acetyl]-4-fluoro-1H-indole-7-carboxylic acid amide;
3-[2-(4-Benzoyl-piperazin-1-yl)-2-oxo-acetyl]-4-fluoro-1H-indole-7-carboxylic acid thiazol-2-ylamide;
3-[2-(4-Benzoyl-piperazin-1-yl)-2-oxo-acetyl]-1H-indole-7-carboxylic acid (1H-tetrazol-5-yl)-amide;
3-[2-(4-Benzoyl-2-(R)-methyl-piperazin-1-yl)-2-oxo-acetyl]-1H-indole-7-carboxylic acid methylamide;
3-[2-(4-Benzoyl-2-(R)-methyl-piperazin-1-yl)-2-oxo-acetyl]-1H-indole-7-carboxylic acid dimethylamide;
1-(4-Benzoyl-piperazin-1-yl)-2-[4-fluoro-7-(5-methyl-2H-[1,2,4]triazol-3-yl)-1H-indol-3-yl]-ethane-1,2-dione;
1-(4-Benzoyl-piperazin-1-yl)-2-(4-fluoro-7-[1,2,4]oxadiazol-3-yl-1H-indol-3-yl)-ethane-1,2-dione;
1-(4-Benzoyl-piperazin-1-yl)-2-(4-fluoro-7-(5-methyl-[1,2,4]oxadiazol-3-yl)-1H-indol-3-yl)-ethane-1,2-dione;
1-(4-Benzoyl-piperazin-1-yl)-2-[7-(5-cyclopropylamino-[1,2,4]oxadiazol-3-yl)-4-fluoro-1H-indol-3-yl]-ethane-1,2-dione;
1-(4-Benzoyl-piperazin-1-yl)-2-[7-(5-amino-[1,2,4]oxadiazol-3-yl)-4-fluoro-1H-indol-3-yl]-ethane-1,2-dione;
1-(4-Benzoyl-piperazin-1-yl)-2-[4-fluoro-7-(3H-imidazol-4-yl)-1H-indol-3-yl]-ethane-1,2-dione
1-(4-Benzoyl-piperazin-1-yl)-2-(4-fluoro-7-[1,3,4]oxadiazol-2-yl-1H-indol-3-yl)-ethane-1,2-dione;
1-[7-(5-Amino-[1,3,4]oxadiazol-2-yl)-4-fluoro-1H-indol-3-yl]-2-(4-benzoyl-piperazin-1-yl)-ethane-1,2-dione;
1-(4-Benzoyl-piperazin-1-yl)-2-[4-fluoro-7-(1H-[1,2,4]triazol-3-yl)-1H-indol-3-yl]-ethane-1,2-dione;
1-(4-Benzoyl-piperazin-1-yl)-2-[4-methoxy-7-(1H-[1,2,4]triazol-3-yl)-1H-indol-3-yl]-ethane-1,2-dione;
1-(4-Benzoyl-piperazin-1-yl)-2-(4-fluoro-7-pyrazol-1-yl-1H-indol-3-yl)-ethane-1,2-dione;
1-(4-Benzoyl-piperazin-1-yl)-2-(4-fluoro-7-imidazol-1-yl-1H-indol-3-yl)-ethane-1,2-dione;
1-(7-Acetyl-4-methoxy-1H-indol-3-yl)-2-(4-benzoyl-piperazin-1-yl)-ethane-1,2-dione;
3-[2-(4-Benzoyl-piperazin-1-yl)-2-oxo-acetyl]-4-methoxy-1H-indole-7-carboxylic acid amide;
1-(4-Fluoro-7-[1,2,4]oxadiazol-3-yl-1H-indol-3-yl)-2-[4-(3-nitro-benzoyl)-piperazin-1-yl]-ethane-1,2-dione;
1-[4-(3-Amino-benzoyl)-piperazin-1-yl]-2-(4-fluoro-7-[1,2,4]oxadiazol-3-yl-1H-indol-3-yl)-ethane-1,2-dione;
1-(4-Benzoyl-2-(R)-methyl-piperazin-1-yl)-2-[7-(5-cyclobutylamino-[1,2,4]oxadiazol-3-yl)-4-fluoro-1H-indol-3-yl]-ethane-1,2-dione;
1-(4-Benzoyl-2-(R)-methyl-piperazin-1-yl)-2-(4-fluoro-7-[1,2,4]oxadiazol-3-yl-1H-indol-3-yl)-ethane-1,2-dione;
3-[2-(4-Benzoyl-2-(R)-methyl-piperazin-1-yl)-2-oxo-acetyl]-4-fluoro-1H-indole-7-carboxylic acid amide;
1-[7-(5-Amino-[1,2,4]oxadiazol-3-yl)-4-fluoro-1H-indol-3-yl]-2-[4-(pyridine-2-carbonyl)-piperazin-1-yl]-ethane-1,2-dione; and
1-(4-Fluoro-7-[1,2,4]oxadiazol-3-yl-1H-indol-3-yl)-2-[4-(pyridine-2-carbonyl)-piperazin-1-yl]-ethane-1,2-dione.

A first embodiment of a second aspect of the present invention is a pharmaceutical formulation which comprises an antiviral effective amount of a compound of Formula I, including pharmaceutically acceptable salts thereof, and a pharmaceutically acceptable carrier, adjuvant or diluent.

A second embodiment of the second aspect of the present invention is a pharmaceutical formulation of a compound of Formula I, useful for treating a viral infection, such as HIV, which additionally comprises an antiviral effective amount of an AIDS treatment agent selected from the group consisting of: (a) an AIDS antiviral agent; (b) an anti-infective agent; (c) an immunomodulator; and (d) HIV entry inhibitors.

A first embodiment of a third aspect of the present invention is a method for treating mammals infected with or susceptible to a virus, comprising administering to said mammal an antiviral effective amount of a compound of Formula I as described previously for the first through twentyfirst embodiments of the first aspect, or a nontoxic pharmaceutically acceptable salt, solvate or hydrate thereof together with a conventional adjuvant, carrier or diluent.

A second embodiment of the third aspect of the present invention is a method for treating mammals infected with a virus, wherein said virus is HIV, comprising administering to said mammal an antiviral effective amount of a compound of Formula I.

A third embodiment of the third aspect of the present invention is a method for treating mammals infected with a virus, such as HIV, comprising administering to said mammal an antiviral effective amount of a compound of Formula I in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

The description of the invention herein should be construed in congruity with the laws and principals of chemical bonding.

DEFINITIONS

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthyl and anthracenyl. The aryl group may be substituted or unsubstituted as specified. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are independently selected from the group consisting of hydrogen, alkyl, cycloalkyl, alkenyl, alkynyl, aryl, carbonyl, C-carboxy, sulfonyl, trihalomethanesulfonyl, trihalomethanecarbonyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are furyl, thienyl, benzothienyl, thiazolyl, imidazolyl, oxazolyl, oxadiazolyl, thiadiazolyl, benzthiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1–20", is stated herein, it means that the group, in this case the alkyl group may contain 1 carbon atom, 2 carbon atoms, 3 carbon atoms, etc. up to and including 20 carbon atoms). For example, the term "C$_{1-6}$alkyl" as used herein and in the claims (unless specified otherwise) mean straight or branched chain alkyl groups such as methyl, ethyl, propyl, isopropyl, butyl, isobutyl, t-butyl, amyl, hexyl and the like. More preferably, it is a medium size alkyl having 1 to 10 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanecarbonyl" group refers to an $Z_3$CC(=O)— group with X as defined above.

A "trihalomethanesulfonyl" group refers to an $Z_3$CS(=O)$_2$— groups with Z as defined above.

A "trihalomethanesulfonamido" group refers to a $Z_3$CS(=O)$_2$$NR^x$— group with Z and $R^x$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2$$NR^xR^y$, with $R^x$ and $R^y$ as defined herein.

A "N-Sulfonamido" group refers to a R"S(=O)$_2$$NR_x$— group with $R_x$ as defined herein.

A "O-carbamyl" group refers to a —OC(=O)$NR^xR^y$ as defined herein.

A "N-carbamyl" group refers to a $R^x$OC(=O)$NR^y$ group, with $R^x$ and $R^y$ as defined herein.

A "O-thiocarbamyl" group refers to a —OC(=S)$NR^xR^y$ group with $R^{x\ and\ Ry}$ as defined herein.

A "N-thiocarbamyl" group refers to a $R^x$OC(=S)$NR^y$— group with $R^x$ and $R^y$ as defined herein.

An "amino" group refers to an —$NH_2$ group.

A "C-amido" group refers to a —C(=O)$NR^xR^y$ group with $R^x$ and $R^y$ as defined herein.

A "C-thioamido" group refers to a —C(=S)$NR^xR^y$ group, with $R^x$ and $R^y$ as defined herein.

A "N-amido" group refers to a $R^x$C(=O)$NR^y$— group, with $R^x$ and $R^y$ as defined herein.

An "ureido" group refers to a —$NR^x$C(=O)$NR^yR^{y2}$ group with $R^x$ and $R^y$ as defined herein and $R^{y2}$ defined the same as $R^x$ and $R^y$.

A "guanidino" group refers to a —$R^x$NC(=N)$NR^yR^y$ group, with $R^x$, $R^y$ and $R^{y2}$ as defined herein.

A "guanyl" group refers to a $R^xR^y$NC(=N)— group, with $R^x$ and $R^y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with $R^x$ as defined herein.

A "hydrazino" group refers to a —$NR^xNR^yR^{y2}$ group with $R^x$, $R^y$ and $R^{y2}$ as defined herein.

The term "spiro" as used herein refers to ring systems in which there is one carbon atom common to two rings. Examples of "spiro" ring systems include, but are not limited to, spiropentane and spirohexane, shown below.

 

The term "fused" as used herein refers to ring systems in which two adjacent atoms are common to two rings. Examples of "fused" ring systems include, but are not limited to, decalin and indole, shown below.

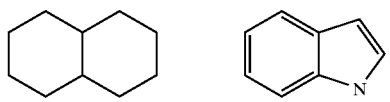

The term "bridged" as used herein refers to ring systems in which two non adjacent atoms are common to two or more rings. Examples of "bridged" ring systems include, but are not limited to, quinuclidine and norbornane, shown below.

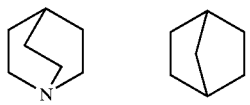

Any two adjacent R groups may combine to form an additional aryl, cycloalkyl, heteroary or heterolicyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |

-continued

| Drug Name | Manufacturer | Indication |
|---|---|---|
| DMP-450 | AVID (Camden, NJ) | HIV infection, AIDS, ARC (protease inhibitor) |
| Efavirenz (DMP 266) (-)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |

-continued

| Drug Name | Manufacturer | Indication |
|---|---|---|
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal Meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT Therapy |
| Recombinant Human Growth Hormone | Serono | AIDS-related wasting, cachexia |
| Megestrol Acetate | Bristol-Myers Squibb | Treatment of Anorexia assoc. W/AIDS |
| Testosterone | Alza, Smith Kline | AIDS-related wasting |
| Total Enteral Nutrition | Norwich Eaton Pharmaceuticals | Diarrhea and malabsorption Related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355–1362; CELL, Vol. 99, pp. 243–246, Oct. 29, 1999; and DRUG DISCOVERY TODAY, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the invention and the examples. Some of the abbreviations used are as follows:

| | | |
|---|---|---|
| h | = | hour(s) |
| rt | = | room temperature |
| mol | = | mole(s) |
| mmol | = | millimole(s) |
| g | = | gram(s) |
| mg | = | milligram(s) |
| mL or ml | = | milliliter(s) |
| $\mu$l | = | microliter(s) |
| TFA | = | Trifluoroacetic Acid |
| DCE | = | 1,2-Dichloroethane |
| $CH_2Cl_2$ | = | Dichloromethane |
| THF | = | Tetrahydofuran |
| DEPBT | = | 3-(Diethoxyphosphoryloxy)-1,2,3-benzotriazin-4(3H)-one |
| P-EDC | = | Polymer supported 1-(3-dimethylaminopropyl)-3-ethylcarbodiimide |
| EDC | = | 1-(3-dimethylaminopropyl)-3-ethylcarbodiimide |
| DMF | = | N,N-dimethylformamide |
| DMAP | = | 4-dimethylaminopyridine |
| HOBT | = | 1-hydroxybenzotriazole |
| TOSMIC | = | tosylmethylisocyanide |
| Cbz | = | carbobenzyloxy |
| TPAP | = | tetrapropylammonium perruthenate |
| NMO | = | 4-methylmorpholine N-oxide |
| TMEDA | = | N,N,N',N'-tetramethyl ethylenediamine |

-continued

| NMM | = | 4-methylmorpholine |
| MeOH | = | methanol |
| EtOH | = | ethanol |
| EtOAc | = | ethyl acetate |

Chemistry

The synthesis procedures and anti-HIV-1 activities of indoleoxoacetic piperazine analogs are summarized below. Procedures for making intermediates and compounds of Formula I are shown in Schemes 1–41.

It should be noted that in many cases reactions are depicted for only one position of an intermediate, such as the $R^5$ position, for example. It is to be understood that such reactions could be used at other positions, such as $R^2$–$R^4$, of the various intermediates. Reaction conditions and methods given in the specific examples are broadly applicable to compounds with other substitution and other tranformations in this application. Schemes 1 and 2 describe general reaction schemes for taking appropriately substituted indoles and converting them to compounds of Formula I. While these schemes are very general, other permutations such as carrying a precursor or precursors to substituents $R^2$ through $R^5$ through the reaction scheme and then converting it to a compound of Formula I in the last step are also contemplated methods of this invention. Nonlimiting examples of such strategies follow in subsequent schemes.

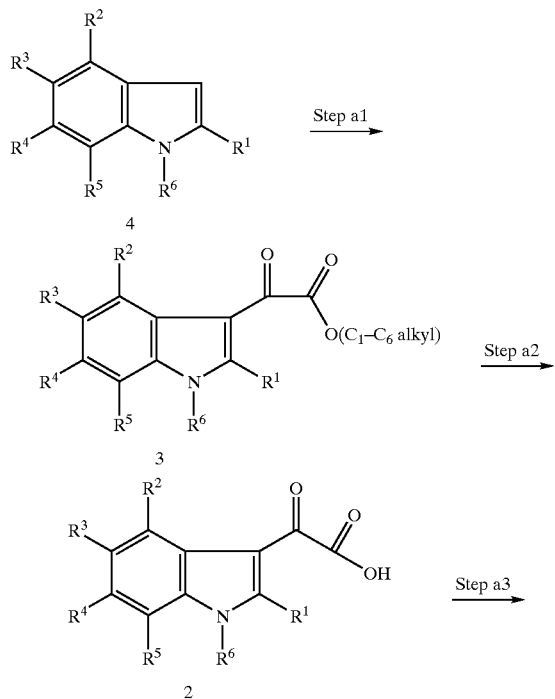

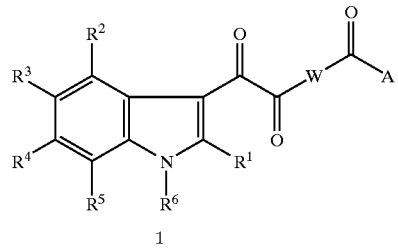

Starting indole intermediates of formula 4 (Scheme 1) are known or are readily prepared according to literature procedures, such as those described in Gribble, G. (Refs. 24 and 99), Bartoli et al (Ref. 36), reference 37, or the book by Richard A. Sundberg in reference 40. Other methods for the preparation of indole intermediates include: the Leimgruber-Batcho Indole synthesis (reference 93); the Fisher Indole synthesis (references 94 and 95); the 2,3-rearrangement protocol developed by Gassman (reference 96); the annelation of pyrroles (reference 97); tin mediated cyclizations (reference 98); and the Larock palladium mediated cyclization of 2-alkynyl anilines. Many other methods of indole synthesis are known and a chemist with typical skill in the art can readily locate conditions for preparation of indoles which can be utilized to prepare compounds of Formula I.

Intermediates of Formula 3 are prepared by attachment of an oxalyl ester moiety at the 3-position of the Formula 4 intermediate as described in Step al of Scheme 1. This transformation can be carried out by sequentially treating the Formula 4 intermediate with an alkyl Grignard reagent, followed by a zinc halide and then an oxalic acid mono ester in an aprotic solvent. Typical Grignard reagents used include methyl magnesium bromide and ethyl magnesium bromide. The zinc halide is selected from zinc bromide or zinc chloride. Oxalic acid esters such as methyl oxalate or ethyl oxalate are used and aprotic solvents such as $CH_2Cl_2$, $Et_2O$, benzene, toluene, DCE, or the like may be used alone or in combination for this sequence. A preferred sequence is to treat intermediate 4 with 1) methylmagnesium bromide, 2) zinc bromide, 3) methyl oxalate, to provide intermediate 3.

An alternative method for carrying out step 1a is acylation of the Formula 4 intermediate with ethyl oxalyl chloride in the presence of aluminum chloride in an inert solvent such as dichloromethane to provide the Formula 3 intermediate. Other alkyl mono esters of oxalic acid could also suffice for either method shown above. As listed in reference 104, Lewis acids other than aluminum chloride and solvents other than dichloromethane might also be used for the transformation in step a1.

The hydrolysis of the ester intermediate of Formula 3 to form the 3-indole oxoacetic acid of Formula 2 is shown in step a2 of Scheme 1. The usual conditions employ methanolic or ethanolic sodium hydroxide followed by acidification with aqueous hydrochloric acid of varying molarity but 1M HCl is preferred. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as $CH_2Cl_2$ or THF in the presence of Triton B. Temperatures of $-70°$ C. to the boiling point of the solvent may be employed but $-10°$ C. is preferred. Other conditions for ester hydrolysis are listed in reference 58 and both this reference and many of the conditions for ester hydrolysis are well known to chemists of average skill in the art. As shown in Scheme 2, step a4, oxalyl chloride can be used to install the oxoacetyl chloride group at the indole 3 position of intermediate 4 to provide the intermediate of Formula 5. Typically, inert solvents such as $CH_2Cl_2$ or DCE are used as solvents but THF and diethyl ether will also work. Step a4 might also be performed in the presence of a catalyst. The catalyst most preferred is aluminum chloride. Tin tetrachloride or titanium IV chloride might also be utilized in some applications. The chloride intermediate of Formula 5 can be coupled to an amine H—W—C(O)A in an inert solvent (e.g. $CH_2Cl_2$) in the presence of a tertiary amine (e.g. N,N-diisopropylethylamine) or pyridine to gives compounds of Formula I (Step a5). The chloride could also be directly reacted with a low molecular weight alcohol such as MeOH to provide the an ester (intermediate of Formula 3, as shown in Scheme 1). The entire reaction sequence shown in Scheme 2, including reaction with oxalyl chloride and coupling to an alcohol or H—W—(O)A could be carried out in a solvent such as pyridine in the case of some indole intermediates of Formula 4. The amide coupling with amine H—W—C(O)A is shown in Scheme 1, step a3. The group W as referred to herein is

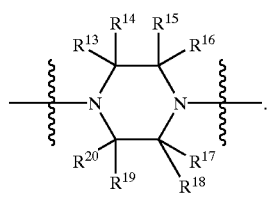

One preferred method for carrying out this reaction is the use of the peptide coupling reagent 3-(diethoxyphosphoryloxy)-1,2,3-benzotriazin-4(3H)-one (DEPBT) and an amine H—W—C(O)A in DMF solvent containing a tertiary amine such as N,N-diisopropylethylamine.

Commonly used amide bond coupling conditions, e.g. EDC with HOBT or DMAP, are also employed in some examples. Typical stoichiometries are given in the specific examples but these ratios may be modified.

The amide bond construction reactions depicted in step a3 or step a5 of Schemes 1 and 2 respectively could be carried out using the specialized conditions described herein or alternatively by applying the conditions or coupling reagents for amide bond construction described for steps a16–a18 of this application. Some specific nonlimiting examples are given in this application.

Additional procedures for synthesizing, modifying and attaching groups: $(C=O)_m$—WC(O)—A are contained in PCT WO 00/76521.

Scheme 2

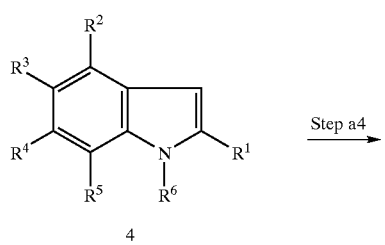

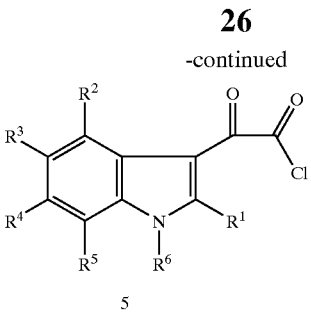

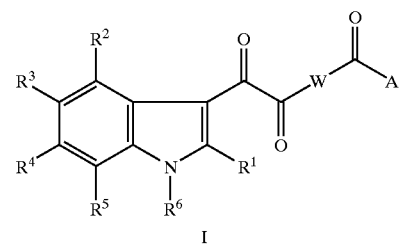

Scheme 3

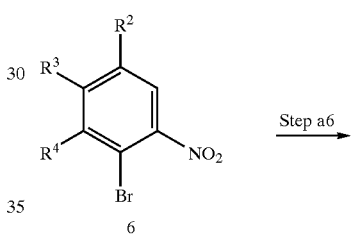

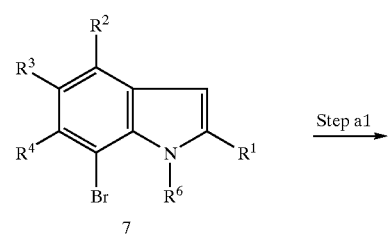

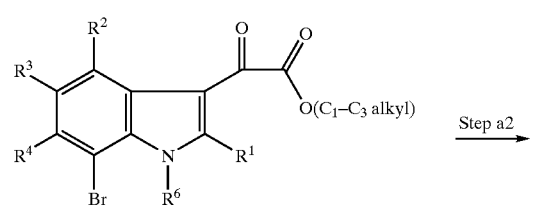

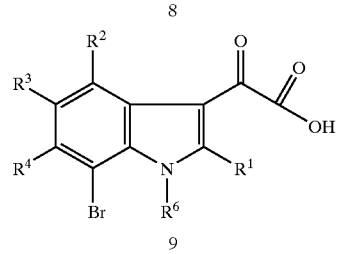

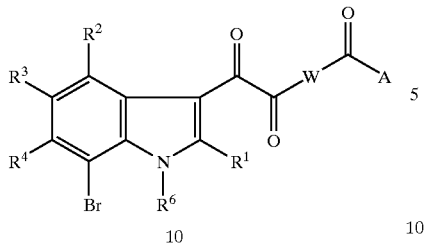

10

Scheme 3 provides a general example of how a bromide, such as intermediate 6, may be carried through the sequences shown in Schemes 1 and 2, to provide a key bromo intermediate, 10. Intermediate 7 was prepared from 6 (Step a6) using the indole synthesis of Bartoli et. al. contained in reference 36c. Intermediate 7 may be prepared by other methods and from other starting materials but the indole synthesis of Bartoli et. al. has proven to be a useful method. Introduction of the oxalate moiety to provide intermediate 8 (Scheme 3, Step a1) is carried out as described above with ethyl oxalyl chloride in the presence of aluminum chloride as a preferred method. The use of oxalyl chloride as depicted in scheme 2, step a4, followed by esterification, could also be employed for this transformation but the preferred method is depicted. Ester hydrolysis as in step a2 followed by amide coupling as in step a3 provides an example of a key bromo intermediate. In this case a carbodiimide-mediated amide coupling using EDC is the preferred method for carrying out step a3. Schemes 4 and 5 provide more specific examples of Scheme 3 and are provided for illustrative purposes.

Scheme 4

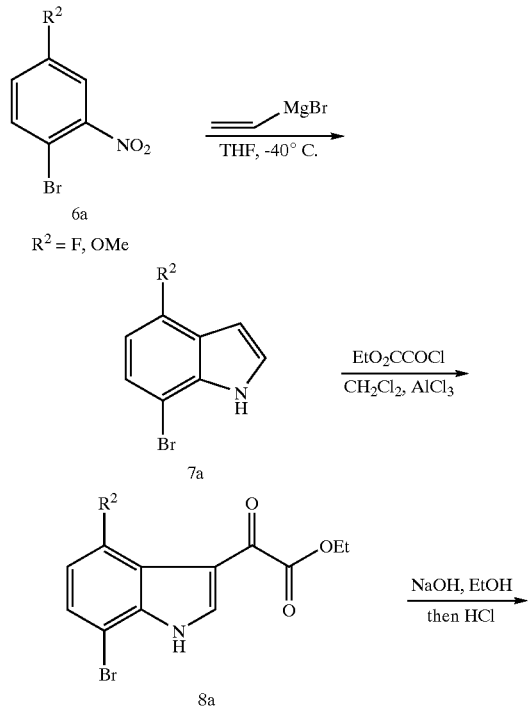

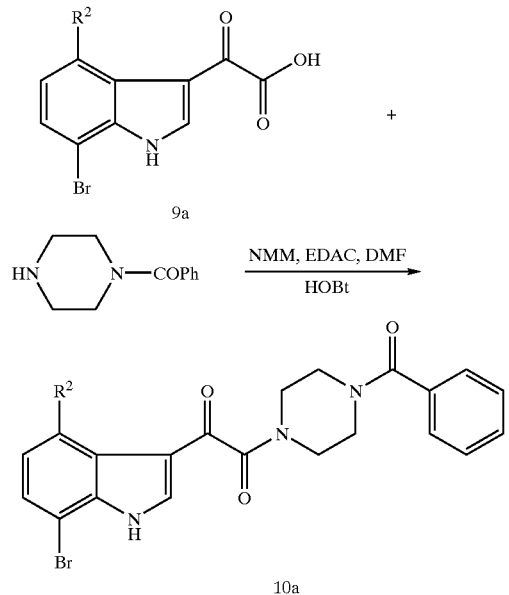

Scheme 4 shows the preparation of an indole intermediate 7a, acylation of 7a with ethyl oxalyl chloride to provide intermediate 8a, followed by ester hydrolysis to provide intermediate 9a, and amide formation to provide intermediate 10a.

Alternatively, the acylation of an indole intermediate, such as 7a', could be carried out directly with oxalyl chloride followed by base mediated piperazine coupling to provide an intermediate of Formula 10a' as shown in Scheme 5.

Scheme 5

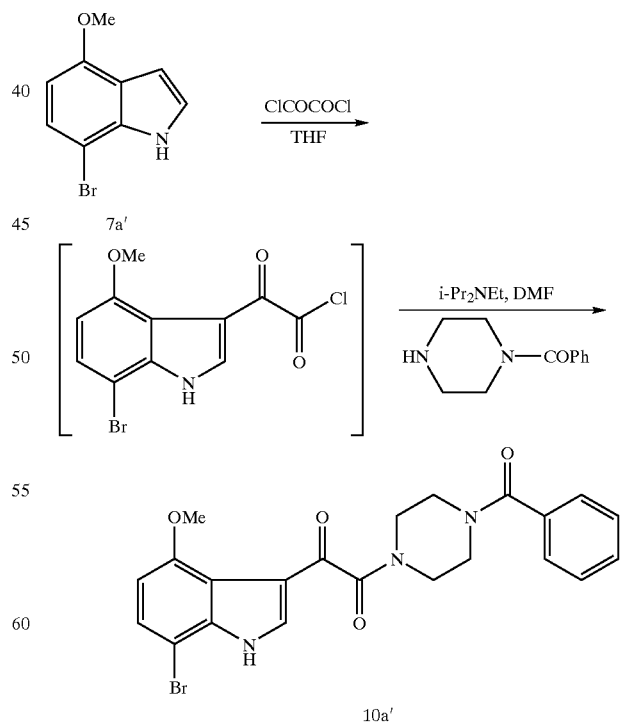

Scheme 6 depicts the preparation of a key aldehyde intermediate, 14, using a procedure adapted from reference 90 which are the methods of Gilmore et.al. The aldehyde substituent is shown only at the $R^5$ position for the sake of clarity, and should not be considered as a limitation of the methodology as the aldehyde functionality could be introduced at any of positions $R^1$–$R^5$. In Scheme 6, step a7, a bromide intermediate, 7, is converted into an aldehyde intermediate, 11, by metal-halogen exchange and subsequent reaction with dimethylformamide in an appropriate aprotic solvent. Typical bases used include, but are not limited to, alkyl lithium bases such as n-butyl lithium, sec butyl lithium or tert butyl lithium or a metal such as lithium metal. A preferred aprotic solvent is THF. Typically the transmetallation with n butyl lithium is initiated at −78° C. The reaction may be allowed to warm to allow the transmetalation to go to completion depending on the reactivity of the bromide intermediate, 7. The reaction is then recooled to −78° C. and allowed to react with N,N-dimethylformamide. (allowing the reaction to warm may be required to enable complete reaction) to provide intermediate 11. Intermediate 11 was then further elaborated to intermediates 12, 13 and 14 as shown in Scheme 6 (steps a1, a2, a3) according to the method described in Scheme 1. The amide coupling step utilized 3-(diethoxyphosphoryloxy)-1, 2,3-benzotriazin-4(3H)-one (DEPBT) as the preferred method.

Other methods for introduction of an aldehyde group to form intermediates of formula 11 include transition metal catalyzed carbonylation reactions of suitable bromo, trifluoromethane sulfonates(yl), or stannanes(yl) indoles. Alternative the aldehydes can be introduced by reacting indolyl anions or indolyl Grignard reagents with formaldehyde and then oxidizing with $MnO_2$ or TPAP/NMO or other suitable oxidants to provide intermediate 11.

References 38 and 39 provide methods for preparing indoles with substituents at the 7-position (i.e. position to which $R^5$ is attached). These references provide methods for functionalizing the C-7 position of indoles by either 1) protecting the indole nitrogen with 2,2-diethyl propanoyl group and then deprotonating the 7-position with sec/BuLi in TMEDA to give an anion. This anion may be quenched with DMF, formaldehyde, or carbon dioxide to give the aldehyde, benzyl alcohol, or carboxylic acid respectively. Similar tranformations can be achieved by converting indoles to indoline, lithiation at C-7 and then reoxidation to the indole. The oxidation level of any of these products may be adjusted by methods well known in the art as the interconversion of alcohol, aldehyde, and acid groups has been well studied. It is also well understood that a protected alcohol, aldehyde, or acid group could be present in the starting indole and carried through the synthetic steps to a compound of Formula I in a protected form until they can be converted into the desired substituent at the $R^1$ through $R^5$ position. For example, a hydroxymethyl group can be protected as a benzyl ether or silyl ether or other alcohol protecting group; an aldehyde may be carried as an acetal, and an acid may be protected as an ester or ortho ester until deprotection is desired and carried out by literature methods.

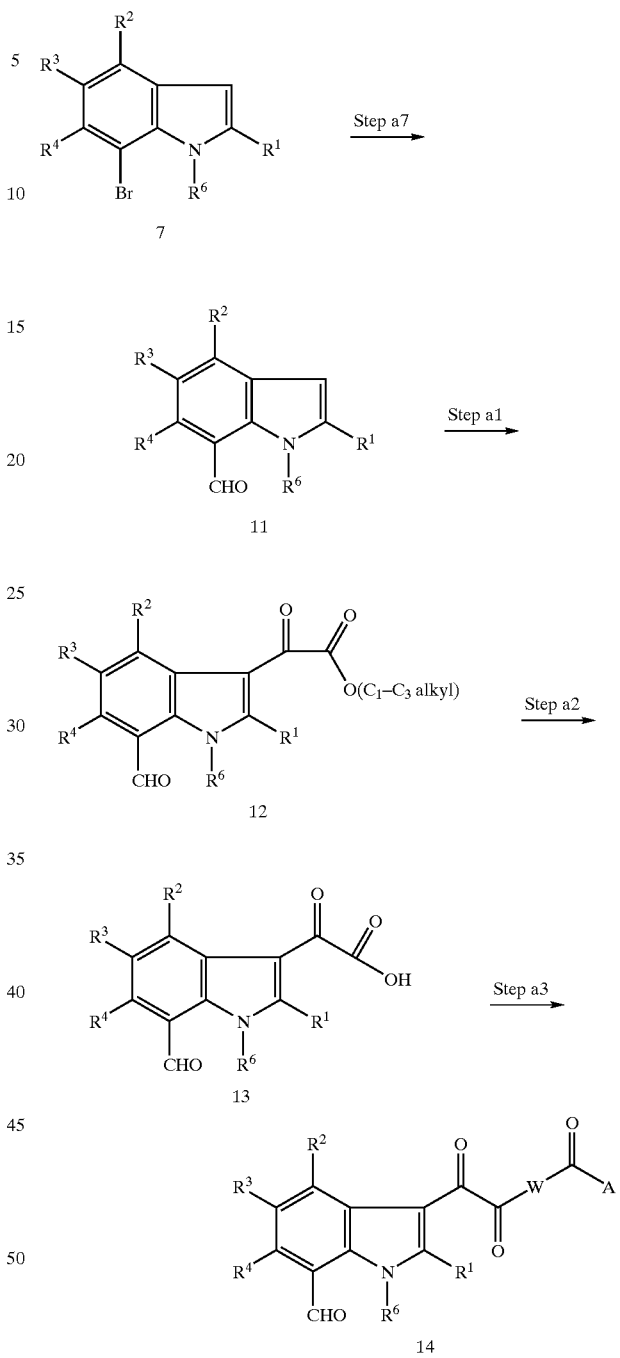

Scheme 6

Scheme 7 provides a more specific example of the method of Gilmore for preparation of an important aldehyde intermediate, 14a. Bromo indole intermediate, 7a, is treated with n-butyl lithium followed by N,N-dimethylformamide in THF at−78° C. to provide the aldehyde intermediate, 11a. Intermediate 11a is then acylated with ethyl oxalyl chloride to provide intermediate 12a which is hydrolyzed to give intermediate 13a. Intermediate 13a is subjected to amide formation as shown to provide intermediate 14a.

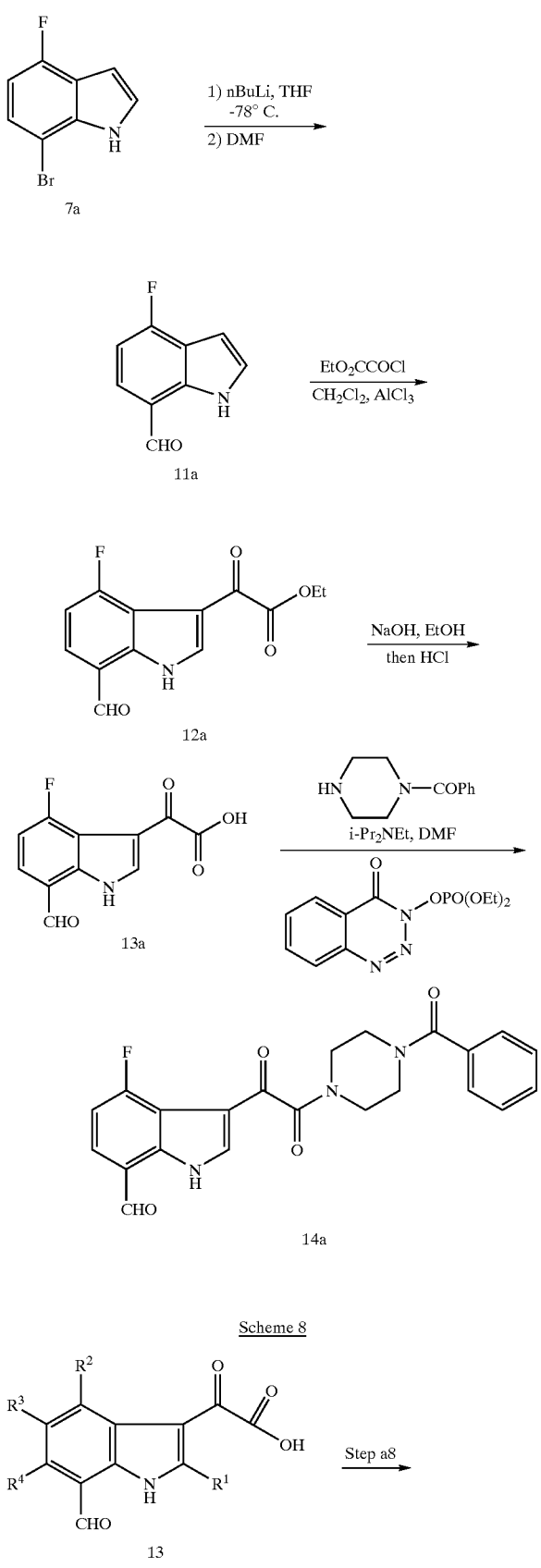

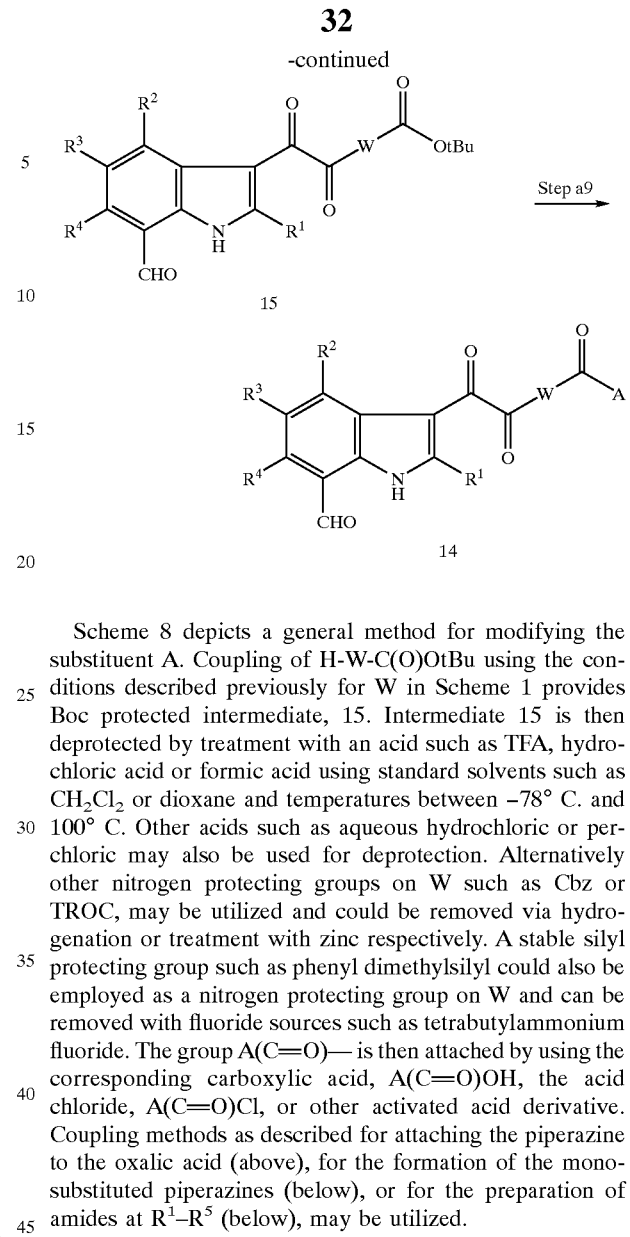

Scheme 8 depicts a general method for modifying the substituent A. Coupling of H-W-C(O)OtBu using the conditions described previously for W in Scheme 1 provides Boc protected intermediate, 15. Intermediate 15 is then deprotected by treatment with an acid such as TFA, hydrochloric acid or formic acid using standard solvents such as $CH_2Cl_2$ or dioxane and temperatures between −78° C. and 100° C. Other acids such as aqueous hydrochloric or perchloric may also be used for deprotection. Alternatively other nitrogen protecting groups on W such as Cbz or TROC, may be utilized and could be removed via hydrogenation or treatment with zinc respectively. A stable silyl protecting group such as phenyl dimethylsilyl could also be employed as a nitrogen protecting group on W and can be removed with fluoride sources such as tetrabutylammonium fluoride. The group A(C=O)— is then attached by using the corresponding carboxylic acid, A(C=O)OH, the acid chloride, A(C=O)Cl, or other activated acid derivative. Coupling methods as described for attaching the piperazine to the oxalic acid (above), for the formation of the monosubstituted piperazines (below), or for the preparation of amides at $R^1$–$R^5$ (below), may be utilized.

Scheme 9 provides a method for the preparation of indole intermediates bearing a carboxylic acid group, such as intermediate 20. As shown in the Scheme 9, step a10, one method for forming the nitrile intermediate, 16, is by cyanide displacement of the bromide at the C-7 position (the $R^5$ position) of the requisite indole intermediate, 7. The cyanide reagent used can be sodium cyanide, or more preferably copper or zinc cyanide. The reactions may be carried out in numerous solvents which are well known in the art. For example DMF is used in the case of copper cyanide. The conversion of the cyano intermediate, 16, to the carboxylic acid intermediate, 17, is depicted in step a11. Many methods for the conversion of nitriles to acids are well known in the art and may be employed. Suitable conditions for the conversion of intermediate 16 to intermediate 17 employ potassium hydroxide, water, and an aqueous alcohol such as ethanol. Typically the reaction must be heated at refluxing temperatures for one to 100 h. The acid intermediate, 17, may then be esterified to give intermediate 18. Intermediate 16 can also be converted directly to intermediate 18 by treating a solution of intermediate 16 in an alcohol (typically methanol) saturated with hydrogen chloride. Typically, refluxing temperature is required for the transformation. Intermediate 18 may then be converted to intermediate 19 according to the procedure described in Scheme 2. Intermediate 19 may then be hydrolyzed to provide intermediate 20.

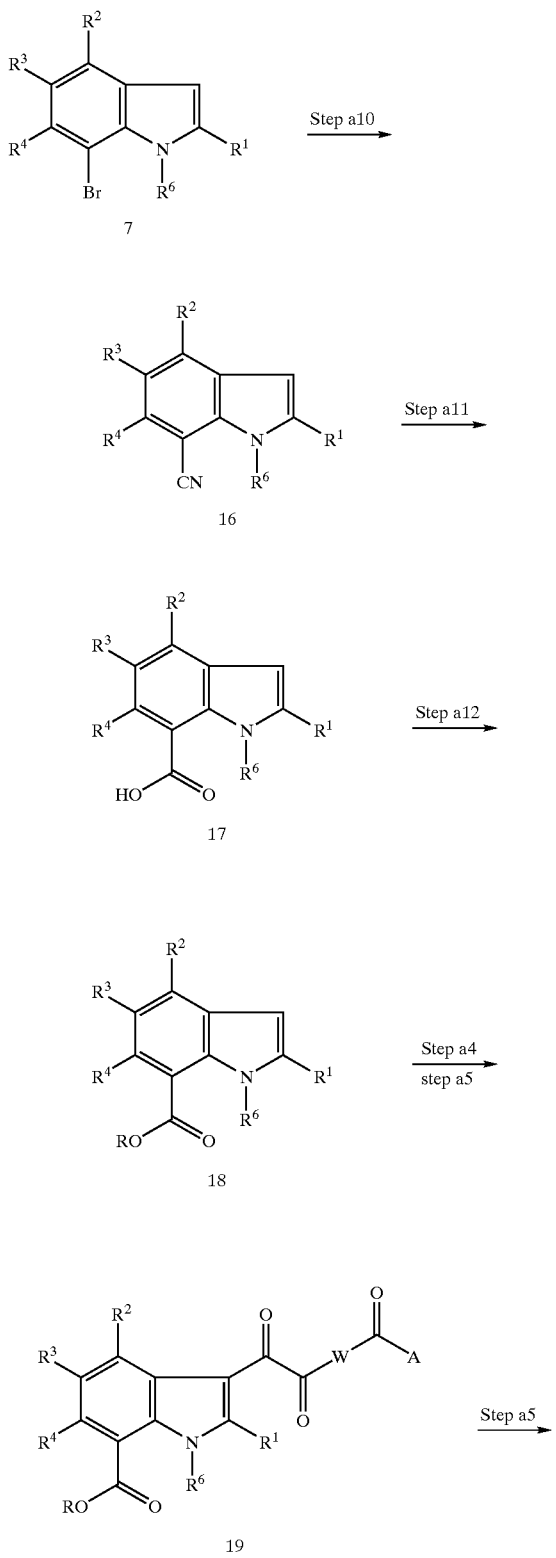

As shown in Scheme 10, step a13, another preparation of the indoleoxoacetylpiperazine 7-carboxylic acids, 20, is carried out by oxidation of the corresponding 7-carboxaldehyde, 14. The preparation of the aldehyde intermediate, 14, has been described previously in this application. Numerous oxidants are suitable for the conversion of aldehyde to acid and many of these are described in standard organic chemistry texts such as: Larock, Richard C., Comprehensive organic transformations: a guide to functional group preparations 2nd ed. New York: Wiley-VCH, 1999. One preferred method is the use of silver nitrate or silver oxide in a solvent such as aqueous or anhydrous MeOH at a temperature of ~25° C. or as high as reflux. The reaction is typically carried out for one to 48 h and is typically monitored by TLC or LC/MS until complete conversion of product to starting material has occurred. Alternatively, $KMnO_4$ or $CrO_3/H_2SO_4$ could be utilized (see ref. 91).

Scheme 11 gives a specific example of the oxidation of an aldehyde intermediate, 14a, to provide the carboxylic acid intermediate, 20a.

Scheme 11

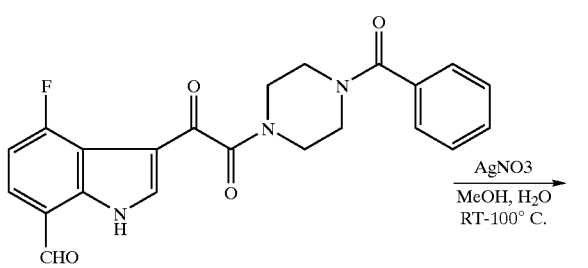

14a

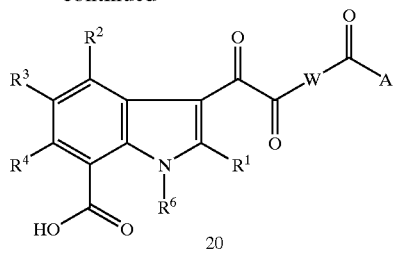

20

Alternatively, intermediate 20 can be prepared by the nitrile method of synthesis carried out in an alternative order as shown in Scheme 12. The nitrile hydrolysis step can be delayed and the nitrile carried through the synthesis to provide a nitrile 22, which could be hydrolyzed to provide the free acid, 20, as above. As described for the conversion of intermediate 16 to intermediate 18, nitrile 22 could also be converted to an ester of acid 20 under similar conditions.

Scheme 12

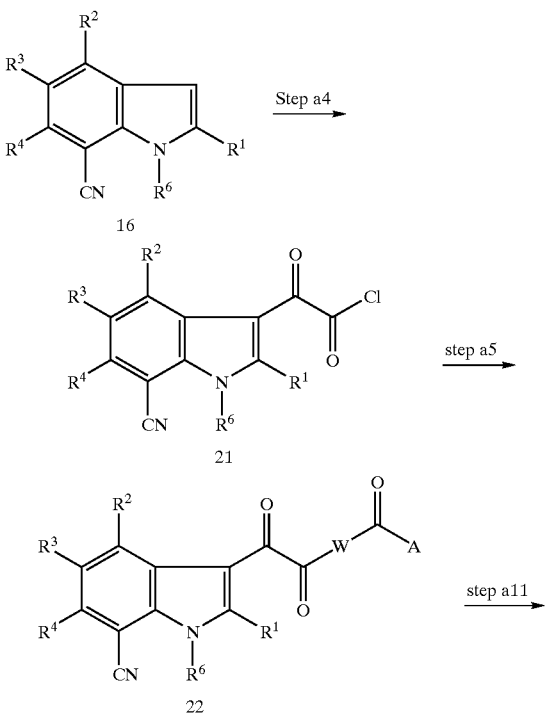

It is well known in the art that heterocycles may be prepared from an aldehyde, carboxylic acid, carboxylic acid ester, carboxylic acid amide, carboxylic acid halide, or cyano moiety or attached to another carbon substituted by a bromide or other leaving group such as a triflate, mesylate, chloride, iodide, or phosponate. The methods for preparing such intermediates from intermediates typified by the carboxylic acid intermediate, 20, bromo intermediate, 10, or aldehyde intermediate, 14 described above are known by a typical chemist practitioner. The methods or types of heterocycles which may be constructed are described in the chemical literature. Some representative references for finding such heterocycles and their construction are included in reference 77 through 89 but should in no way be construed as limiting. However, examination of these references shows that many versatile methods are available for synthesizing diversely substituted heterocycles and it is apparent to one skilled in the art that these can be applied to prepare compounds of Formula I. Chemists well versed in the art can now easily, quickly, and routinely find numerous reactions for preparing heterocycles, amides, oximes or other substituents from the above mentioned starting materials by searching for reactions or preparations using a conventional electronic database such as Scifinder (American Chemical Society), Crossfire (Beilstein), Theilheimer, or Reaccs (MDS). The reaction conditions identified by such a search can then be employed using the substrates described in this application to produce all of the compounds envisioned and covered by this invention. In the case of amides, commercially available amines can be used in the synthesis. Alternatively, the above mentioned search programs can be used to locate literature preparations of known amines or procedures to synthesize new amines. These procedures are then carried out by one with typical skill in the art to provide the compounds of Formula I for use as antiviral agents.

As shown below in Scheme 13, step a13, suitable substituted indoles, such as the bromoindole intermediate, 10, may undergo metal mediated couplings with aryl groups, heterocycles, or vinyl stannanes to provide compounds within Formula I wherein $R^5$ is aryl, heteroaryl, or heteroalicyclic for example. The bromoindole intermediates, 10 (or indole triflates or iodides) may undergo Stille-type coupling with heteroarylstannanes as shown in Scheme 13, step a14. Conditions for this reaction are well known in the art and references 72–74 as well as reference 91 provide numerous conditions in addition to the specific examples provided in Scheme 14 and in the specific embodiments. It can be well recognized that an indole stannane could also couple to a heterocyclic or aryl halide or triflate to construct compounds of Formula I. Suzuki coupling (reference 71) between the bromo intermediate, 10, and a suitable boronate could also be employed and some specific examples are contained in this application. Other Suzuki conditions, partners, and leaving groups have utility. Suzuki couplings between chloro intermediates are also feasible. If standard conditions fail new specialized catalysts and conditions can be employed. Procedures describing catalysts which are useful for coupling boronates with aryl and heteroaryl chlorides are known in the art (reference 100 a–g). The boronate could also be formed on the indole and then subjected to Suzuki coupling conditions.

Scheme 13

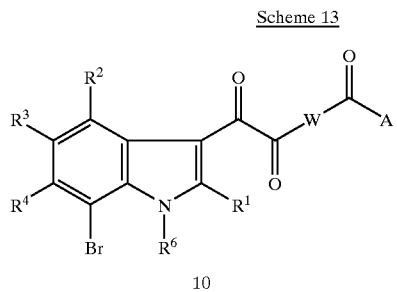

Scheme 14

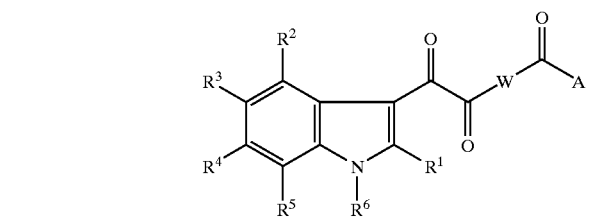

As shown in Scheme 15, step a15, aldehyde intermediates, 14, may be used to generate numerous compounds within Formula I. The aldehyde group may be a precursor for any of the substituents $R^1$ through $R^5$ but the transformation for $R^5$ is depicted below for simplicity.

Scheme 15

The aldehyde intermediate 14, may be reacted to become incorporated into a ring as described in the claims or be converted into an acyclic group. The aldehyde, 14, may be reacted with a Tosmic based reagent to generate oxazoles (references 42 and 43 for example). The aldehyde, 14, may be reacted with a Tosmic reagent and than an amine to give imidazoles as in reference 55 or the aldehyde intermediate, 14, may be reacted with hydroxylamine to give an oxime which is a compound of Formula I as described below. Examples of imidazole synthesis are contained within the experimental section. Oxidation of the oxime with NBS, t-butyl hypochlorite, or the other known reagents would provide the N-oxide which react with alkynes or 3 alkoxy vinyl esters to give isoxazoles of varying substitution. Reaction of the aldehyde intermediate 14, with the known reagent, 23 (reference 70) shown below under basic conditions would provide 4-aminotrityl oxazoles.

Removal of the trityl group under standard acidic conditions (TFA, anisole for example) would provide 4-amino oxazoles which could be substituted by acylation, reductive alkylation or alkylation reactions or heterocycle forming reactions. The trityl could be replaced with an alternate protecting group such as a monomethoxy trityl, Cbz, benzyl, or appropriate silyl group if desired. Reference 76 demonstrates the preparation of oxazoles containing a triflouoromethyl moiety and the conditions described therein demonstrates the synthesis of oxazoles with fluorinated methyl groups appended to them.

The aldehyde could also be reacted with a metal or Grignard (alkyl, aryl, or heteroaryl) to generate secondary alcohols. These would be efficacious or could be oxidized to the ketone with TPAP or $MnO_2$ or PCC for example to provide ketones of Formula I which could be utilized for treatment or reacted with metal reagents to give tertiary alcohols or alternatively converted to oximes by reaction with hydroxylamine hydrochlorides in ethanolic solvents. Alternatively, the aldehyde could be converted to benzyl amines via reductive amination. An example of oxazole formation via a Tosmic reagent is shown below in Scheme 16.

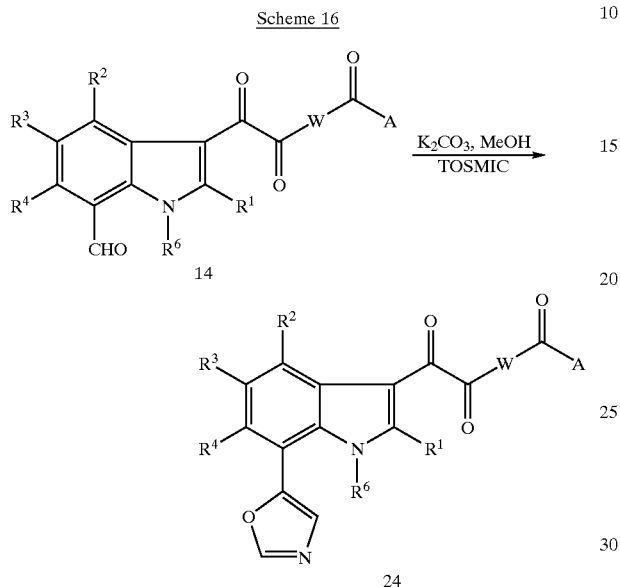

As can be seen from Scheme 17 in step a16, a cyano intermediate, such as 22, may be directly converted to compounds within Formula I via heterocycle formation or reaction with organometallic reagents.

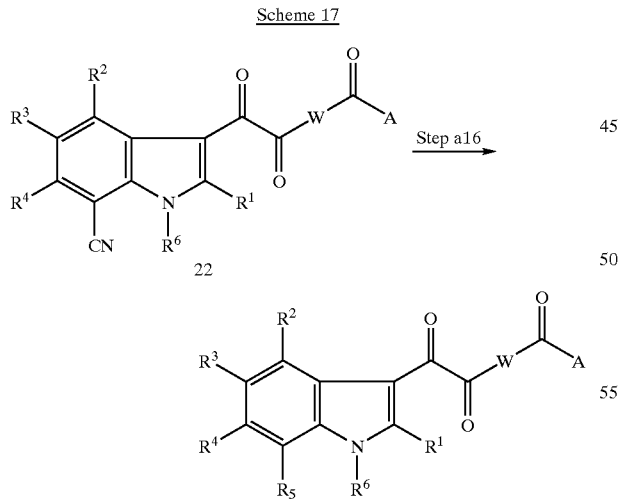

Scheme 18 shows acylation of a cyanoindole intermediate of formula 16 with oxalyl chloride to give acid chloride, 21, which was coupled with the appropriate benzoylpiperazine or pyridinylcarbonylpiperazine derivative in the presence of base to provide 25.

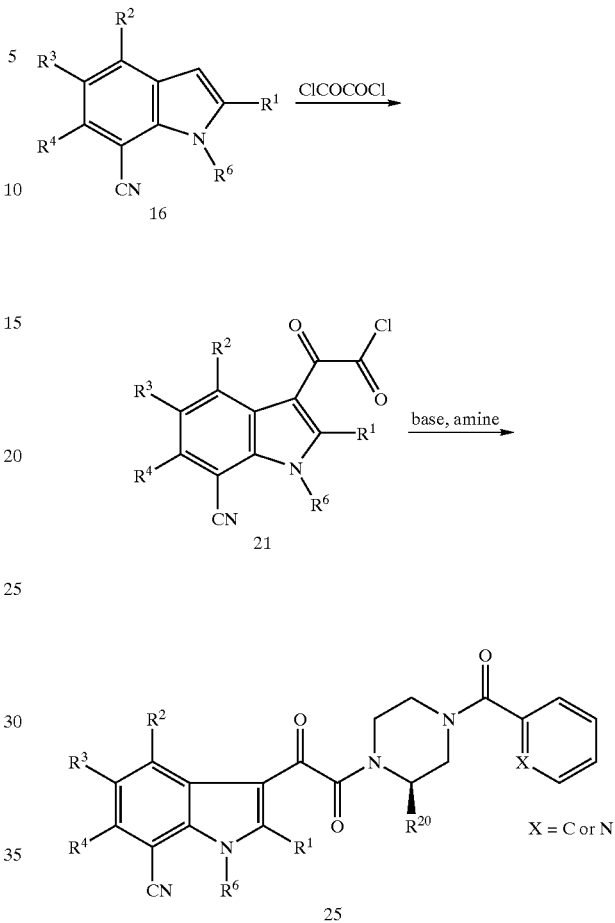

The nitrile intermediate, 25, was converted to the tetrazole of formula 26, which was alkylated with trimethylsilyldiazomethane to give the compound of formula 27 (Scheme 19).

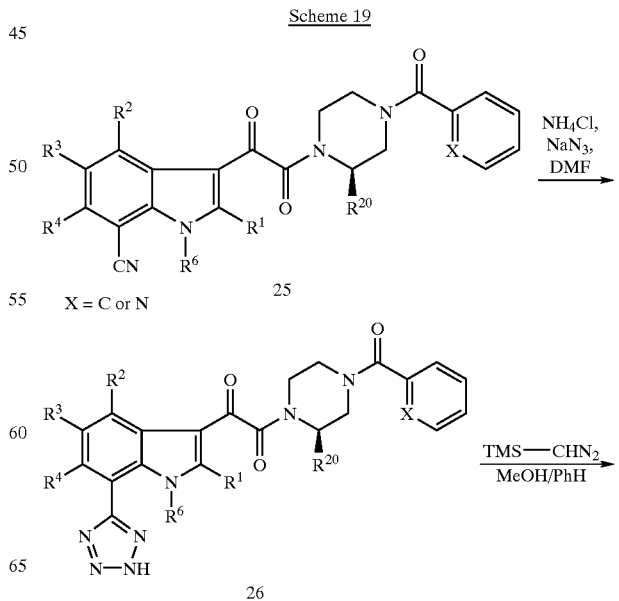

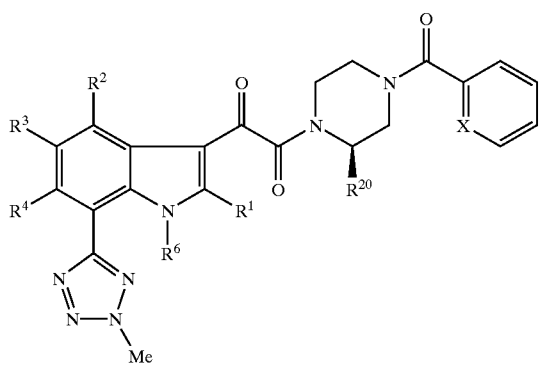

27

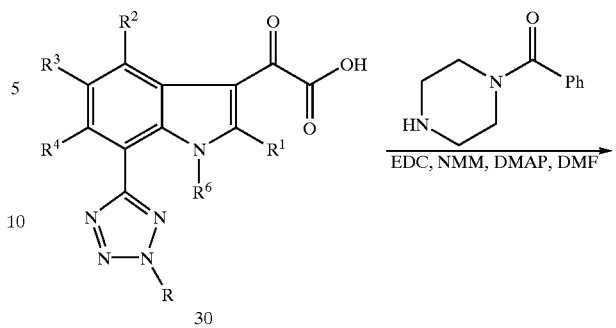

30

Tetrazole alkylation with alkyl halides (R—X, Scheme 20) required alkylation prior to indole acylation as shown in Scheme 20 but indole acylation prior to alkylation is useful in certain other circumstances. Intermediate 16 was converted to tetrazole, 28, which was alkylated to provide 29. Intermediate 29 was then acylated and hydrolyzed to provide 30 which was subjected to amide formation to provide 31. The group appended to the tetrazole may be quite diverse in both size and structure and this substitution has been found to modulate the properties of compounds of Formula I.

Scheme 20

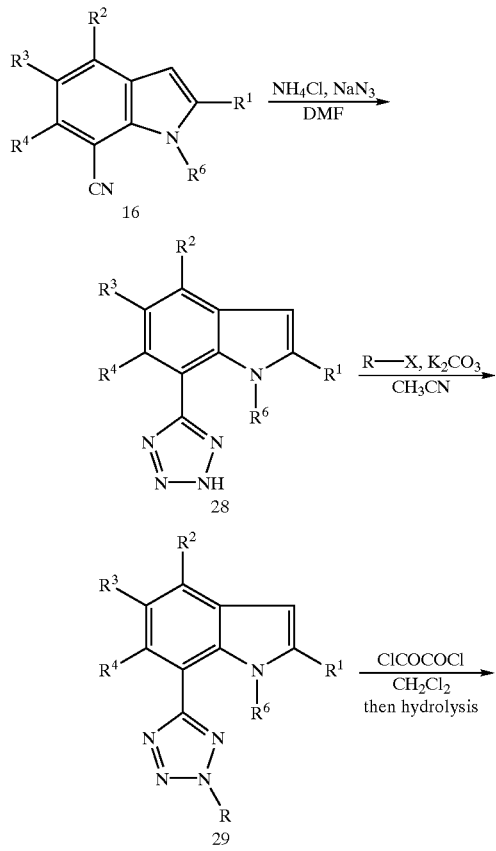

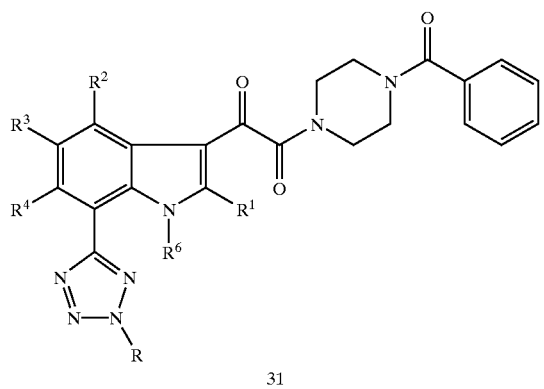

31

Scheme 21, eq.1, shows the oxadiazolone, 34a, was prepared by the addition of hydroxylamine to the nitrile, 32, followed by ring closure of intermediate 33 with phosgene. Alkylation of oxadiazolone, 34a, with trimethylsilyldiazomethane gave the compound of formula 35a.

Scheme 21

(eq. 1)

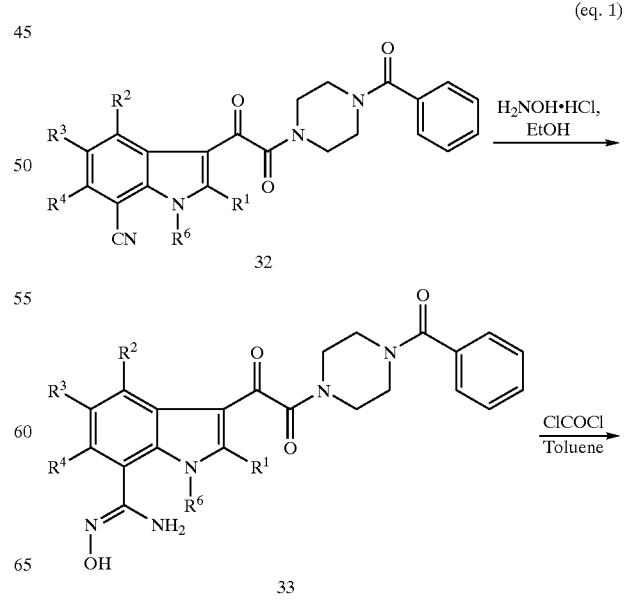

-continued

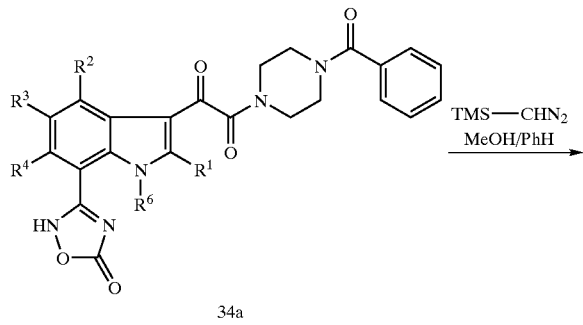

34a

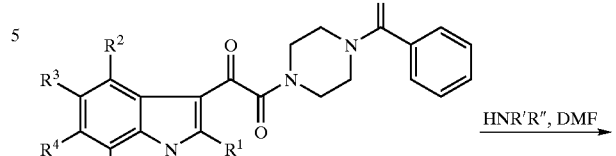

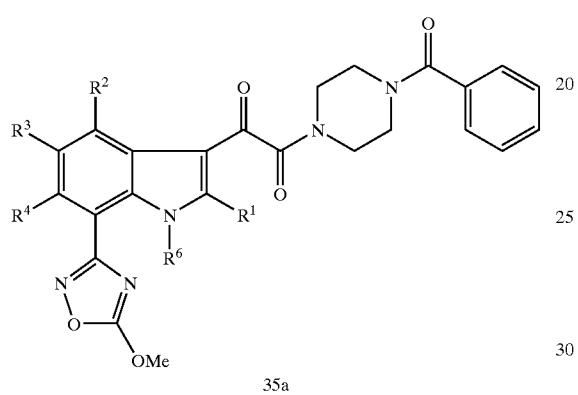

35a (eq. 2)

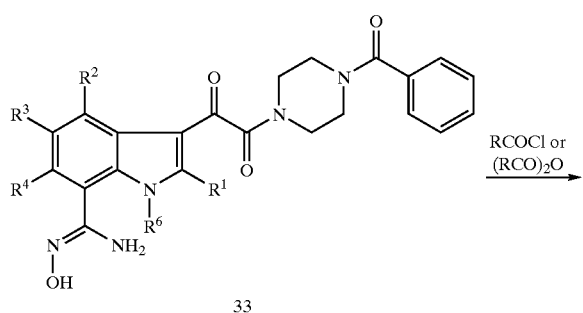

33

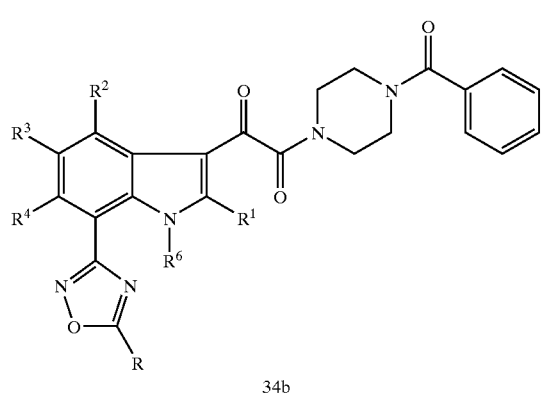

34b

-continued (eq. 3)

34b R = CCl₃

35b

Cyclization of intermediate 33 with orthoformate (e.g. trimethylorthoformate or triethylorthoformate) will give oxadiazole. An example of such chemistry is provided in Example 79 of the experimental section. Cyclization of intermediate 33 to 5-subastituted oxadiazoles of Formula 34b can be performed using acid chlorides or anhydrides (eq. 2). These cyclization reactions require the use of elevated temperature, and with or without an added base (tertiary alkylamine e.g. N,N-disopropylethylamine, or pyridine). When R=CCl₃ in Formula 34b, the trichloromethyl oxadiazole intermediate can undergo nucleophilic substitution (Reference 109) in a polar solvent (e.g. DMF). Primary and secondary amine nucleophiles (R' and R" can represent hydrogen, $C_{1-6}$alkyl, $C_{3-7}$cycloalkyl etc.) are prefered in these reactions to provide aminooxadiazole of Formula 35b (eq.3).

The 7-cyanoindole, 32, can also be efficiently converted to the imidate ester under conventional Pinner conditions using 1,4-dioxane as the solvent. The imidate ester can be reacted with nitrogen, oxygen and sulfur nucleophiles to provide C7-substituted indoles, for example: imidazolines, benzimidazoles, azabenzimidazoles, oxazolines, oxadiazoles, thiazolines, triazoles, pyrimidines and amidines etc. (reference 101). An example of such chemistry used to prepare triazoles is shown in Example 78, Example 111 and Example 127 to 131 of the experimental section.

Scheme 22 shows addition of either hydroxylamine or hydroxylamine acetic acid to aldehyde intermediate 36 gave oximes of Formula 37.

Scheme 22

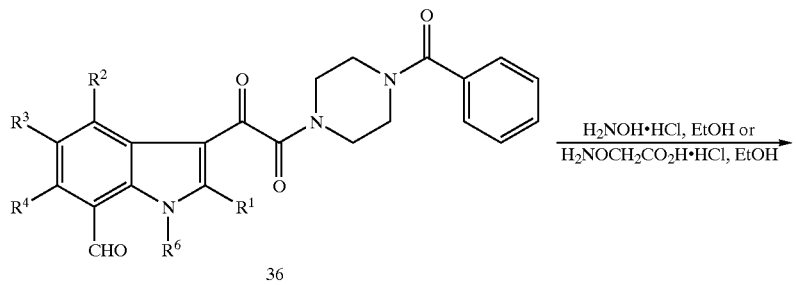

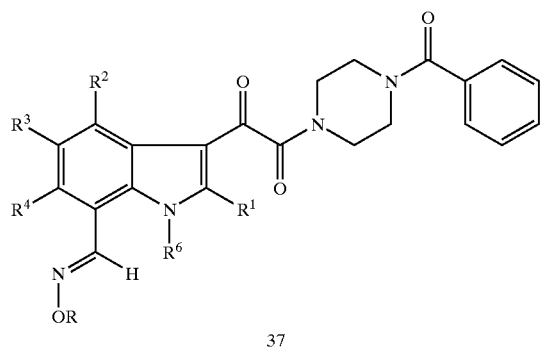

An acid may be a precursor for substituents $R^1$ through $R^5$ when it occupies the corresponding position such as $R^5$ as shown in Scheme 23.

Scheme 23

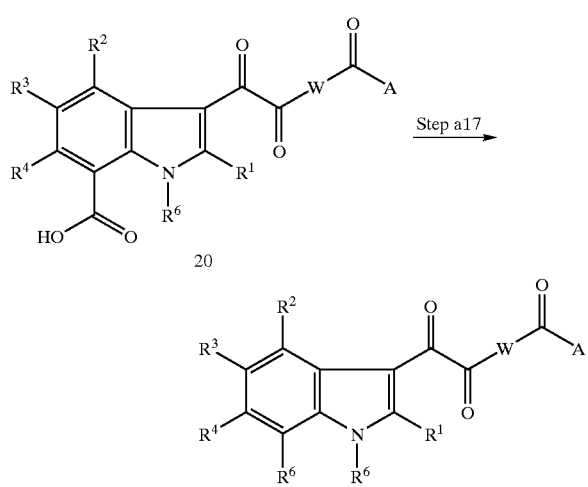

An acid intermediate, such as 20, may be used as a versatile precursor to generate numerous substituted compounds. The acid could be converted to hydrazonyl bromide and then a pyrazole via reference 53. Methodology for pyrazole synthesis is contained in the experimental section. One method for general heterocycle synthesis would be to convert the acid to an alpha bromo ketone (ref 75) by conversion to the acid chloride using standard methods, reaction with diazomethane, and finally reaction with HBr. The alpha bromo ketone could be used to prepare many different compounds of Formula I as it can be converted to many heterocycles or other compounds of Formula I. Alpha amino ketones can be prepared by displacement of the bromide with amines. Alternatively, the alpha bromo ketone could be used to prepare heterocycles not available directly from the aldeheyde or acid. For example, using the conditions of Hulton in reference 41 to react with the alpha bromo ketone would provide oxazoles. Reaction of the alpha bromoketone with urea via the methods of reference 44 would provide 2-amino oxazoles. The alpha bromoketone could also be used to generate furans using beta keto esters(ref 45–47) or other methods, pyrroles (from beta dicarbonyls as in ref 48 or by Hantsch methods (ref 49) thiazoles, isoxazoles and imidazoles (ref 56) example using literature procedures. Coupling of the aforementioned acid chloride with N-methyl-O-methyl hydroxyl amine would provide a "Weinreb Amide" which could be used to react with alkyl lithiums or Grignard reagents to generate ketones. Reaction of the Weinreb amide with a dianion of a hydroxyl amine would generate isoxazoles (ref 51). Reaction with an acetylenic lithium or other carbanion would generate alkynyl indole ketones. Reaction of this alkynyl intermediate with diazomethane or other diazo compounds would give pyrazoles (ref 54). Reaction with azide or hydroxyl amine would give heterocycles after elimination of water. Nitrile oxides would react with the alkynyl ketone to give isoxazoles (ref 52). Reaction of the initial acid to provide an acid chloride using for example oxalyl chloride or thionyl chloride or triphenyl phosphine/carbon tetrachloride provides a useful intermediate as noted above. Reaction of the acid chloride with an alpha ester substituted isocyanide and base would give 2-substituted oxazoles (ref 50). These could be converted to amines, alcohols, or halides using standard reductions or Hoffman/Curtius type rearrangements.

Scheme 24

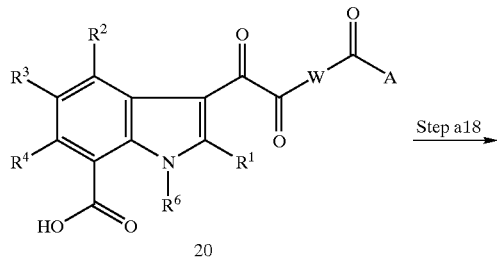

20

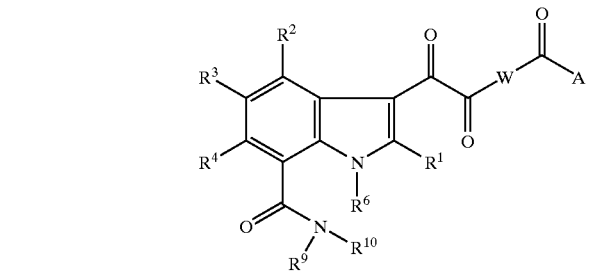

38

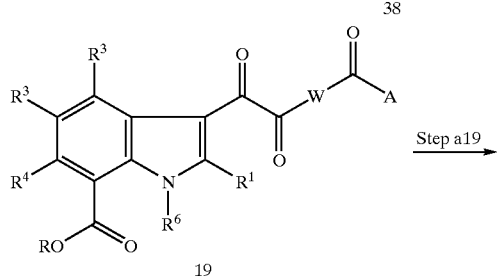

19

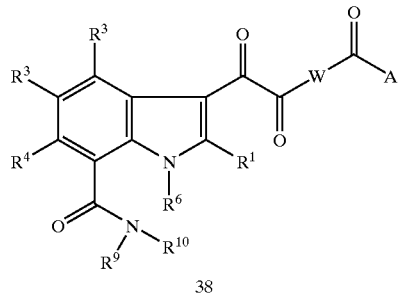

38

Steps a17, a18, and a19 encompasses reactions and conditions for 10, 20 and 30 amide bond formation as shown in Scheme 23 and 24 which provide compounds such as those of Formula 38.

The reaction conditions for the formation of amide bond encompass any reagents that generate a reactive intermediate for activation of the carboxylic acid to amide formation, for example (but not limited to), acyl halide, from carbodiimide, acyl iminium salt, symmetrical anhydrides, mixed anhydrides (including phosphonic/phosphinic mixed anhydrides), active esters (including silyl ester, methyl ester and thioester), acyl carbonate, acyl azide, acyl sulfonate and acyloxy N-phosphonium salt. The reaction of the indole carboxylic acids with amines to form amides may be mediated by standard amide bond forming conditions described in the art. Some examples for amide bond formation are listed in references 59–69 and 91, and 92 but this list is not limiting. Some carboxylic acid to amine coupling reagents which are applicable are EDC, Diisopropylcarbodiimide or other carbodiimides, PyBop (benzotriazolyloxytris (dimethylamino) phosphonium hexafluorophosphate), 2-(1H-benzotriazole-1-yl)-1,1,3,3-tetramethyl uronium hexafluorophosphate (HBTU). Some references for amide bond formation are provided in references 59–69. A particularly useful method for indole 7-carboxylic acid to amide reactions is the use of carbonyl imidazole as the coupling reagent as described in reference 92. The temperature of this reaction may be lower than in the cited reference, from 80° C. (or possibly lower) to 150° C. or higher. A more specific application is depicted in Scheme 25.

Scheme 25

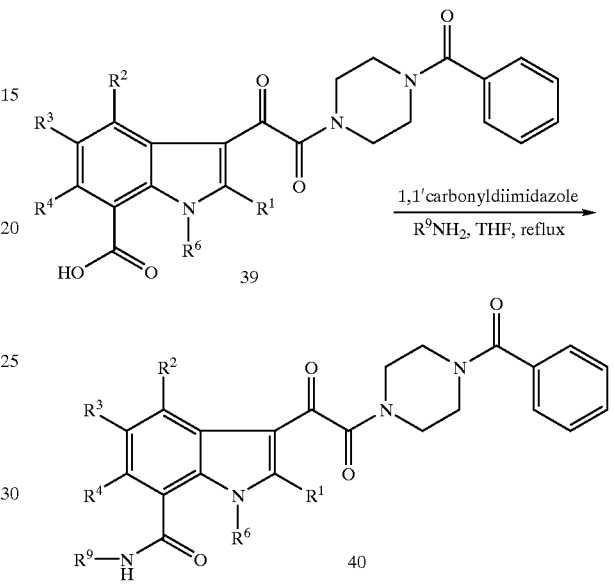

The following four general methods provide a more detailed description for the preparation of indolecarboamides and these methods were employed for the synthesis of compounds of Formula I.

Method 1:
To a mixture of an acid intermediate, such as 20, (1 equiv., 0.48 mmol), an appropriate amine (4 equiv.) and DMAP (58 mg, 0.47 mmol) dissolved $CH_2Cl_2$ (1 mL) was added EDC (90 mg, 0.47 mmol). The resulting mixture was shaken at rt for 12 h, and then evaporated in vacuo. The residue was dissolved in MeOH, and subjected to preparative reverse phase HPLC purification.

Method 2:
To a mixture of an appropriate amine (4 equiv.) and HOBT (16 mg, 0.12 mmol) in THF (0.5 mL) was added an acid intermediate, such as 20, (25 mg, 0.06 mmol) and NMM (50 μl, 0.45 mmol), followed by EDC (23 mg, 0.12 mmol). The reaction mixture was shaken at rt for 12 h. The volatiles were evaporated in vacuo; and the residue dissolved in MeOH and subjected to preparative reverse phase HPLC purification.

Method 3:
To a mixture of an acid intermediate, such as 20, (0.047 mmol), amine (4 equiv.) and DEPBT (prepared according to Li, H.; Jiang, X. Ye, Y.; Fan, C.; Todd, R.; Goodman, M. *Organic Letters* 1999, 1, 91; 21 mg, 0.071 mmol) in DMF (0.5 mL) was added TEA (0.03 mL, 0.22 mmol). The resulting mixture was shaken at rt for 12 h; and then diluted with MeOH (2 mL) and purified by preparative reverse phase HPLC.

Method 4:
A mixture of an acid intermediate, such as 20, (0.047 mmol) and 8.5 mg (0.052 mmol) of 1,1-carbonyldiimidazole in anhydrous THF (2 mL) was heated to reflux under nitrogen. After 2.5 h, 0.052 mmol of amine was added and heating continued. After an additional period of 3~20 h at reflux, the reaction mixture was cooled and concentrated in vacuo. The residue was purified by chromatography on silica gel to provide compounds of Formula I or precursors of such compounds.

In addition, the carboxylic acid may be converted to an acid chloride using reagents such as thionyl chloride (neat or in an inert solvent) or oxalyl chloride in a solvent such as benzene, toluene, THF, or $CH_2Cl_2$. The amides may alternatively, be formed by reaction of the acid chloride with an excess of ammonia, primary, or secondary amine in an inert solvent such as benzene, toluene, THF, or $CH_2Cl_2$ or with stoichiometric amounts of amines in the presence of a tertiary amine such as triethylamine or a base such as pyridine or 2,6-lutidine. Alternatively, the acid chloride may be reacted with an amine under basic conditions (Usually sodium or potassium hydroxide) in solvent mixtures containing water and possibly a miscible co solvent such as dioxane or THF. Scheme 25B depicts a typical preparation of an acid chloride and derivatization to an amide of Formula I. Additionally, the carboxylic acid may be converted to an ester preferably a methyl or ethyl ester and then reacted with an amine. The ester may be formed by reaction with diazomethane or alternatively trimethylsilyl diazomethane using standard conditions which are well known in the art. References and procedures for using these or other ester forming reactions can be found in reference 58 or 91.

Scheme 25A

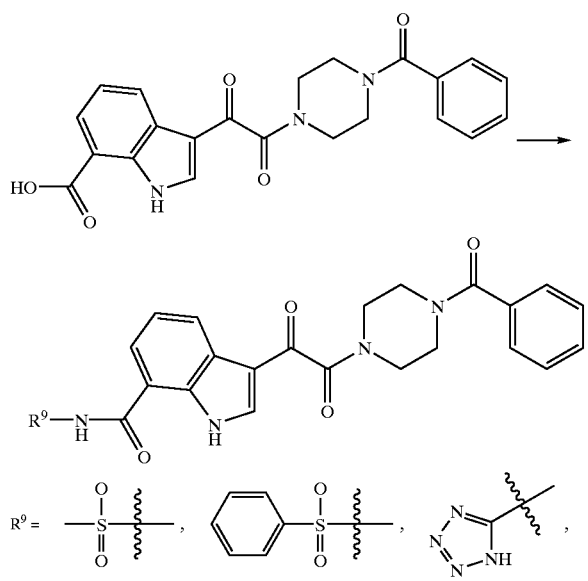

Scheme 25A depicts amide formation from either sulfonamide derivatives or amines. The transformation was carried out as follows: To a suspension of the acid shown above (Reference 102, 30 mg, 0.074 mmol) and sulfonamide (such as methylsulfonamide or phenylsulfonamide) or amine (such as 3-aminotetrazole) (0.296 mmol) in $CH_2Cl_2$ (1 mL), was added DMAP (36 mg, 0.295 mmol) and EDC (56 mg, 0.293 mmol). The resulting mixture was stirred at rt for 16 h, and then evaporated in vacuo. The residue was dissolved in MeOH, and subjected to preparative reverse phase HPLC purification.

Scheme 25B

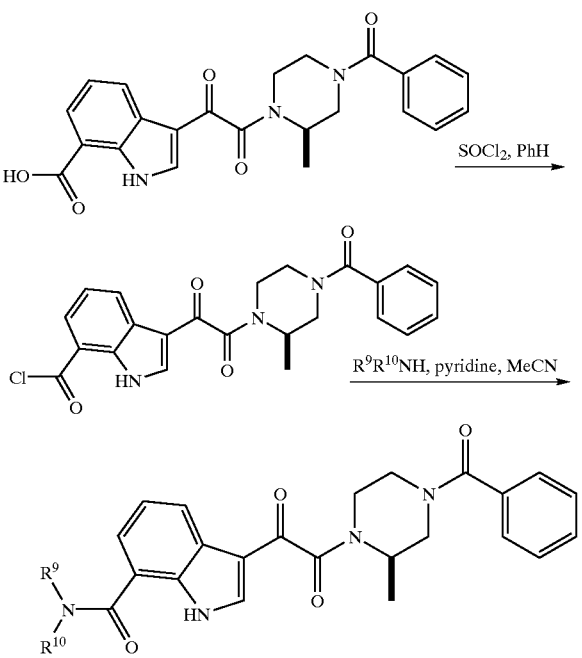

The general procedure for making compounds of Formula I as depicted in Scheme 25B is as follows:

The crude acid chloride was obtained by refluxing a mixture of the acid (Reference 102) shown and excess $SOCl_2$ (1.0 mL per 0.03 mmol of acid) in benzene (15 mL) for 3 h, followed by evaporation of the volatile. A mixture of the acid chloride (30.0 mg, 0.07 mmol) and excess amine (0.14 to 0.22 mmol, 1.0 mL of a 2 M solution of methylamine in MeOH for example) in $CH_3CN$ (7.0 mL) was stirred at rt for 10 min. After adding excess pyridine (1.0 mL, 12 mmol), the mixture was stirred overnight and then evaporated in vacuo to give a residue. The residue was dissolved in MeOH and subjected to purification by preparative reverse phase HPLC.

The above reaction can also be run without solvent. For example, a mixture of the acid chloride (ca. 0.03 mmol) in neat ethylamine (0.5 mL, 7.6 mmol) was stirred at rt for 2 h. The excess amine was then removed by evaporation in vacuo to give a residue, which was dissolved in MeOH and subjected to purification by preparative reverse phase HPLC.

Scheme 25C below provides an example of how a simple methyl amide can be prepared.

Scheme 25C

-continued

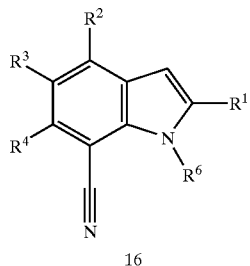

16

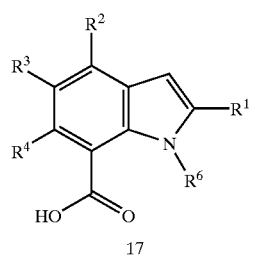

17

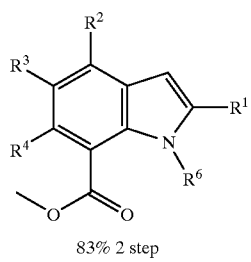

83% 2 step

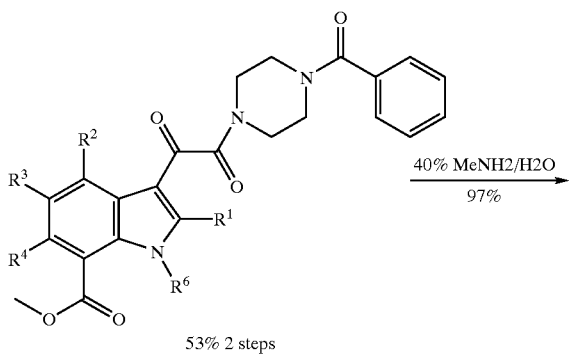

53% 2 steps

-continued

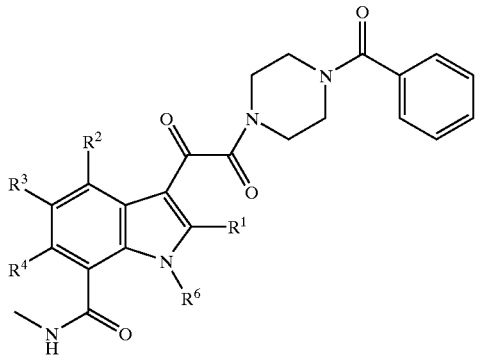

Scheme 25D shows a method of using the acid of Formula 39 to prepare of oxadiazoles of Formula 41 (isomers of Formula 34b). The acid 39 is coupled to hydroxyamidine (R represents a suitable heteroaryl substituent) using EDC as activating agent in an inert solvent (e.g. $CH_2Cl_2$). The intermediate amidino ester is then cyclized in the presence of pyridine at elevated temperature to give oxadiazoles of Formula 41.

Scheme 25D

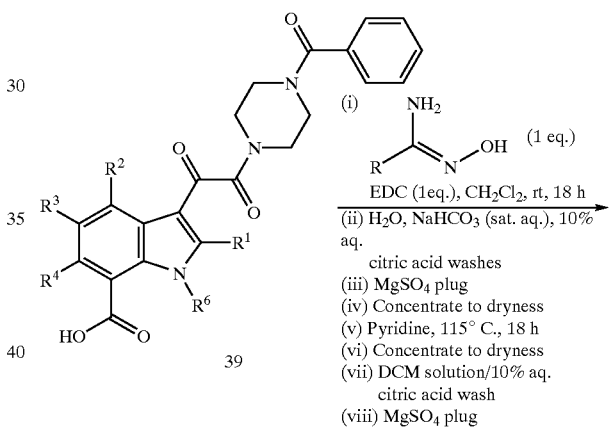

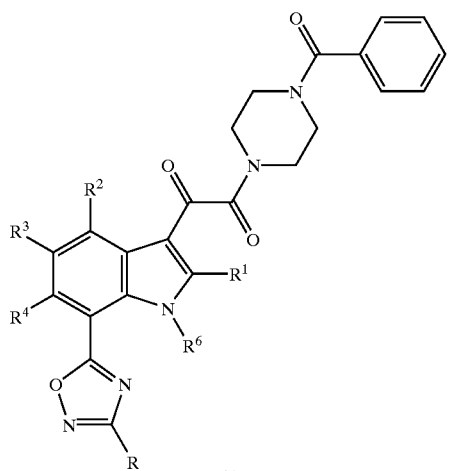

41

In addition to the use of "Weinreb Amide" of Formula 38 to generate ketones as described above, aldehydes of Formula 14 could also be used for this purpose. As shown in Scheme 26a, aldehydes of Formula 14 could react with organometallic reagents (e.g. Grignard reagents such as $R^8MgBr$, or organolithium reagents such as $R^8Li$) in Step a20 to form an alcohol of Formula 42, which could then be oxidized in Step a21 to give the ketones of Formula 43. Numerous reaction conditions for organometallic addition to aldehydes and oxidation of secondary alcohols to ketones are well known to the art and are also provided in reference 91.

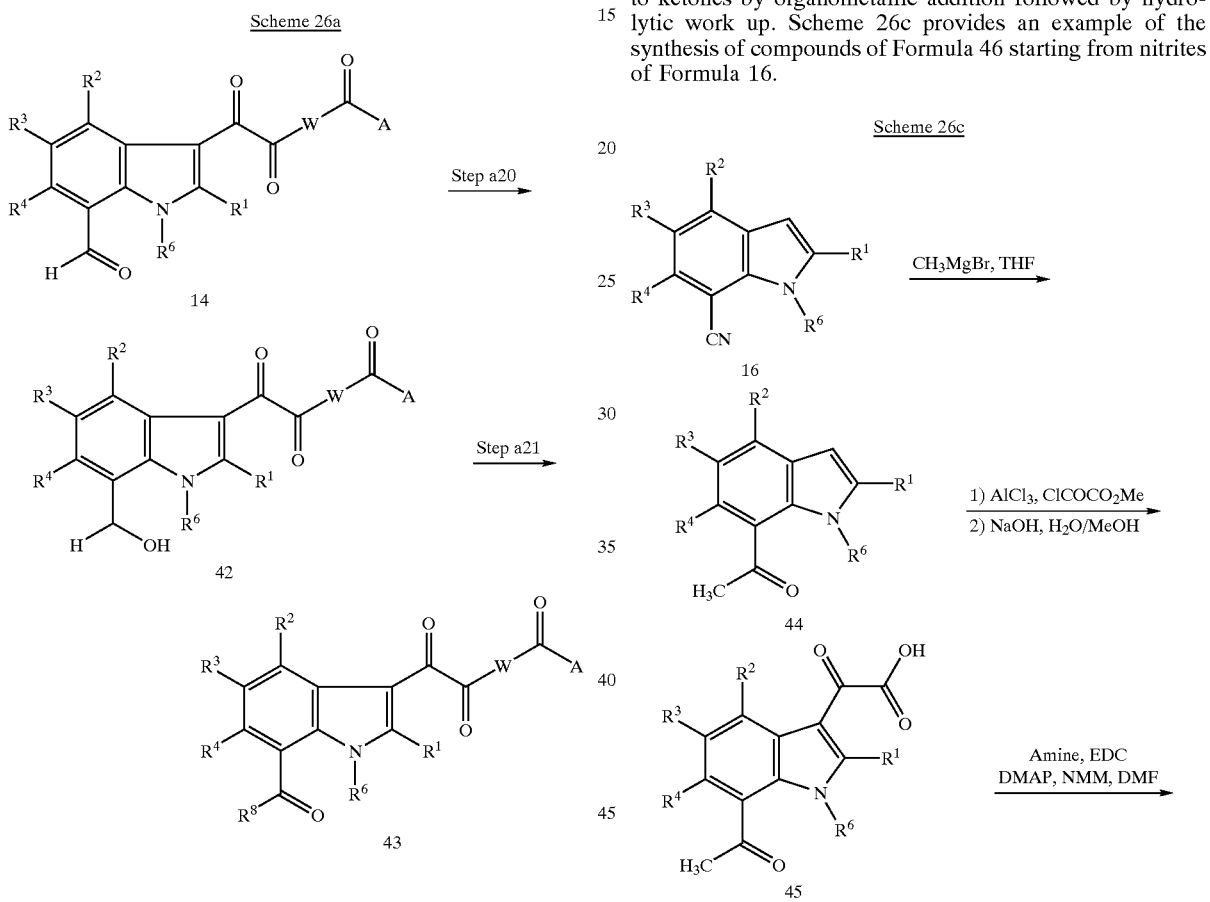

Another method for the preparation of ketones of Formula 43 is shown in Scheme 26b. Nitriles of Formula 22 could react with organometallic reagents (e.g. Grignard reagents, lithium reagents) to give ketones after hydrolytic work up.

Alternatively, nitrites of Formula 16 can be converted first to ketones by organometallic addition followed by hydrolytic work up. Scheme 26c provides an example of the synthesis of compounds of Formula 46 starting from nitrites of Formula 16.

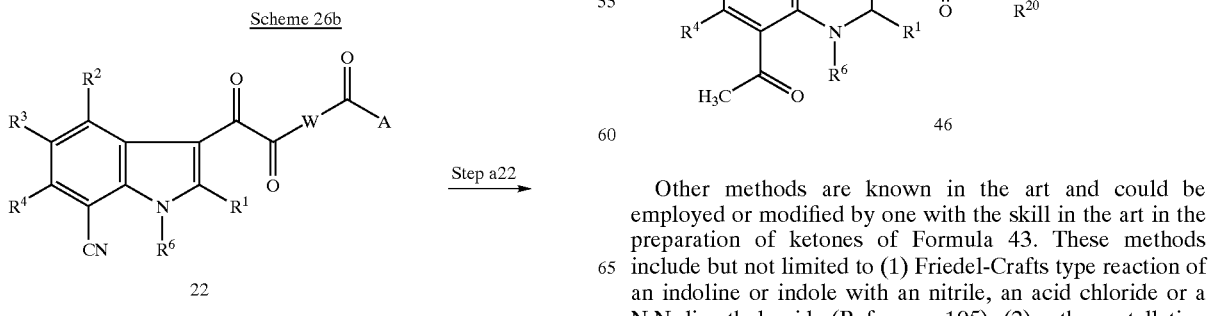

Other methods are known in the art and could be employed or modified by one with the skill in the art in the preparation of ketones of Formula 43. These methods include but not limited to (1) Friedel-Crafts type reaction of an indoline or indole with an nitrile, an acid chloride or a N,N-dimethylamide (Reference 105); (2) ortho-metallation of N-Boc protected aniline followed by quenching with a suitable electrophile, e.g. Weinreb amide (Reference 106); (3) reaction of indoyl organometallic reagents with a suitable electrophile, e.g. Weinreb amide (Reference 107); (4) the use of a substituted phenone as indole precusor (Reference 108).

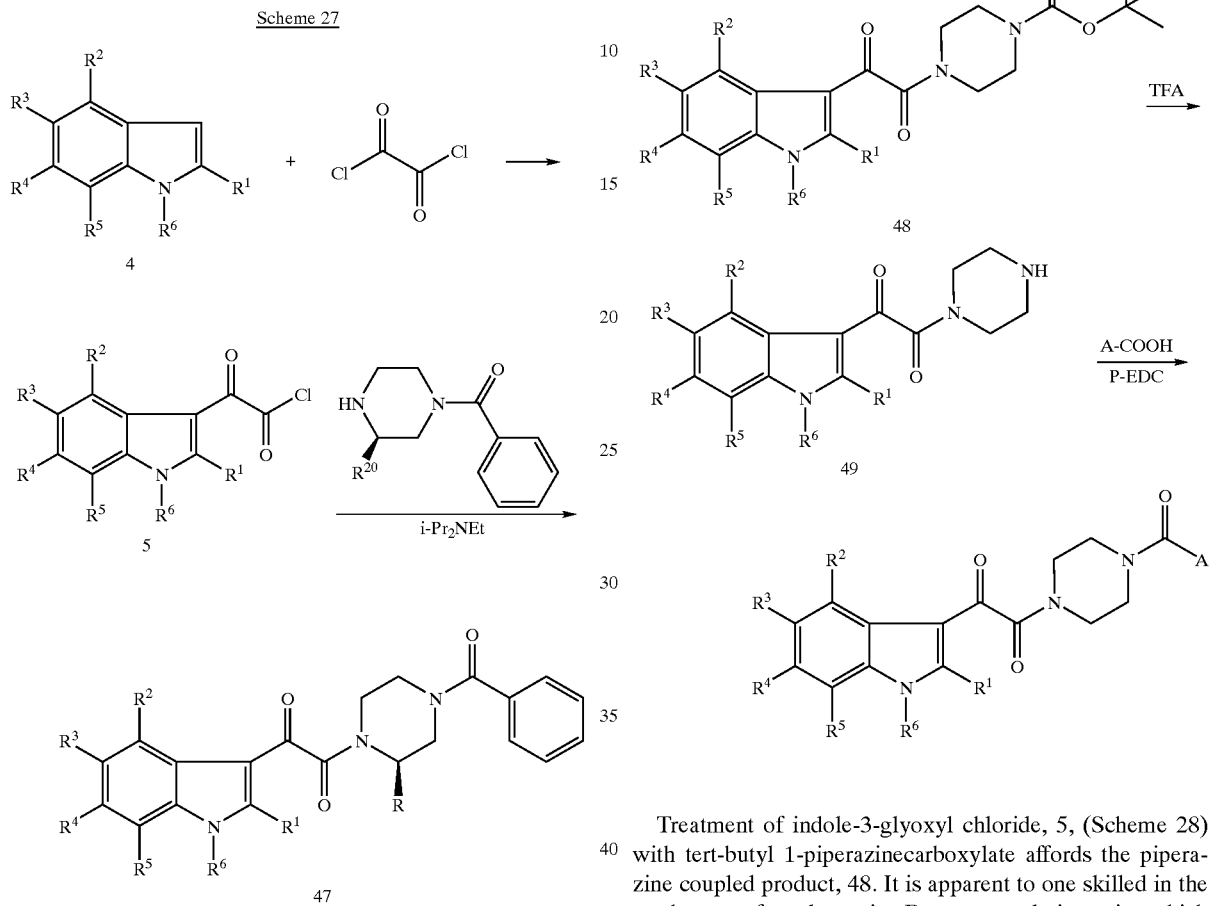

The remaining schemes provide additional background, examples, and conditions for carrying out this invention. Specific methods for preparing W and modifying A are presented. As shown in Scheme 27, the indoles 4 are treated with oxalyl chloride in either THF or ether to afford the desired glyoxyl chlorides 5 according to literature procedures (Lingens, F. et al, Ref. 25). The intermediate glyoxyl chlorides 5 are then coupled with benzoyl piperazine (Desai, M. et al, Ref. 26) under basic conditions to afford 47.

Treatment of indole-3-glyoxyl chloride, 5, (Scheme 28) with tert-butyl 1-piperazinecarboxylate affords the piperazine coupled product, 48. It is apparent to one skilled in the art that use of an alternative Boc protected piperazine which are synthesized as shown below would provide compounds of formula I with alternative groups of formula W. As discussed earlier, other amine protecting groups which do not require acidic deprotection conditions could be utilized if desired. Deprotection of the Boc group of is effected with 20% TFA/CH$_2$Cl$_2$ to yield the free piperazine, 49. This product is then coupled with carboxylic acid in the presence of polymer supported 1-(3-Dimethylaminopropyl)-3-ethylcarbodiimide (P-EDC) to afford products of Formula I. This sequence provides a general method for synthesizing compounds of varied group A in formula 1.

Scheme 28

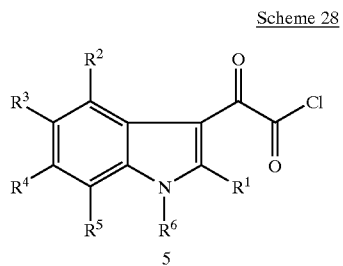

Scheme 29

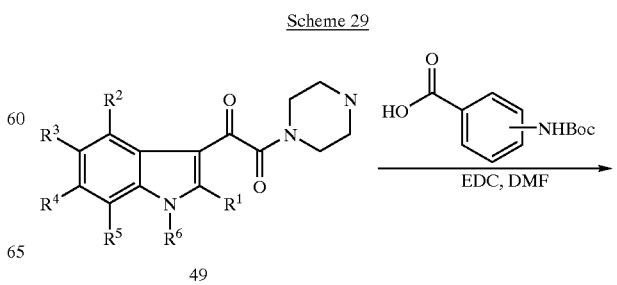

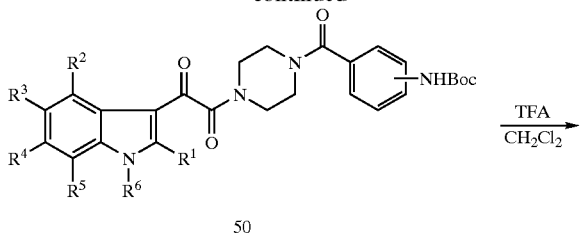

50

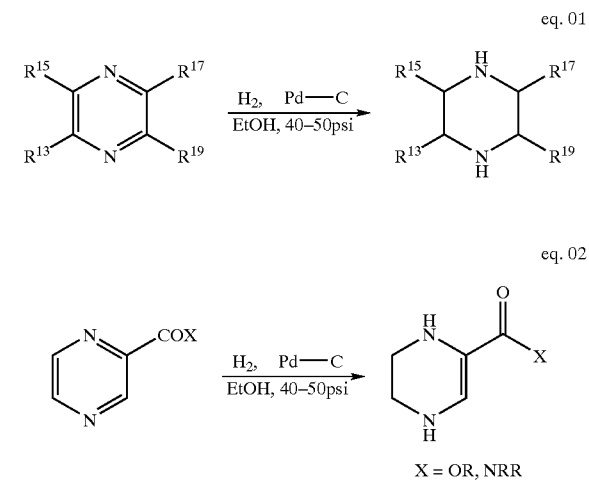

51

An example for preparing compounds of Formula I which possess substituents in A (or other parts of the molecule) which might interfere with the standard reactions is shown in scheme 29. piperazine 49 (Scheme 29) was treated with Boc-protected aminobenzoic acid in the presence of EDC to afford 50. A portion of the resulting product was separated and subjected to TFA in order to remove the Boc group, thus yielding amino derivatives 51.

Scheme 30

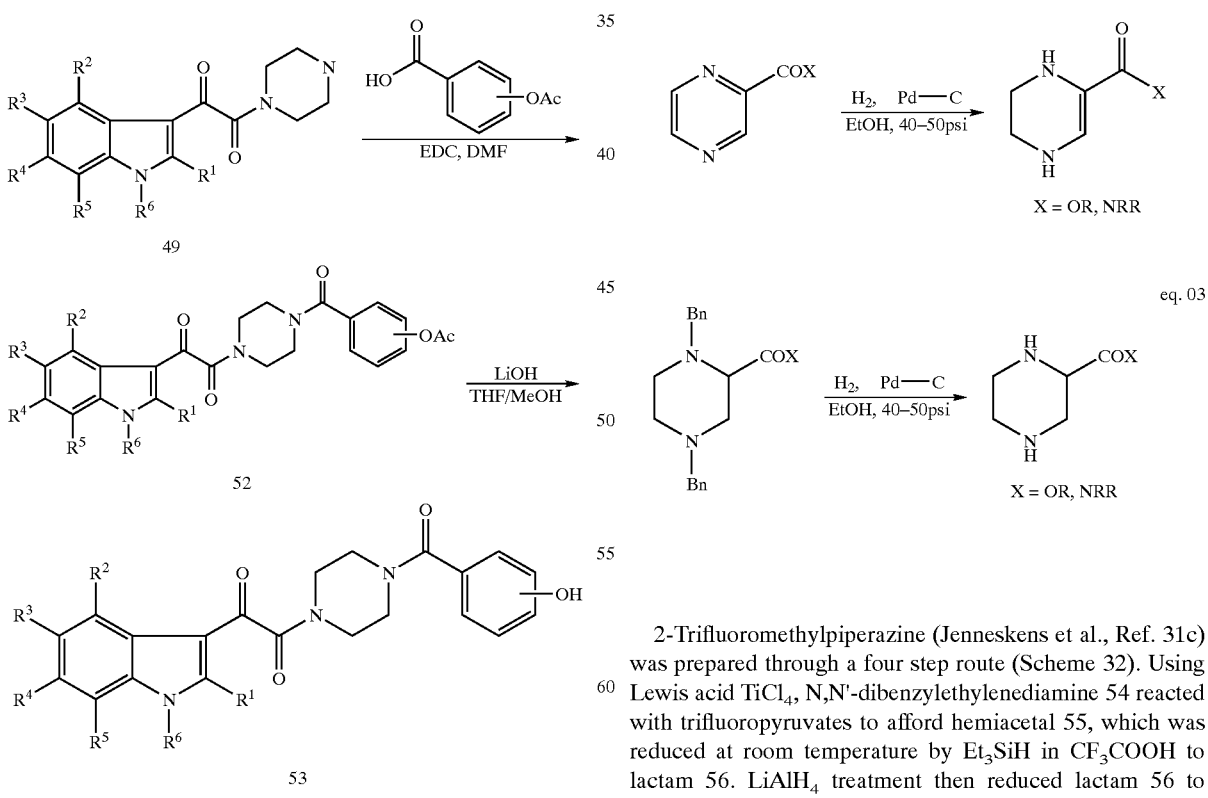

Similarly, substituents which possess a reactive alcohol can be incorporated as below. Piperazine 49 (Scheme 30) was treated with acetoxybenzoic acid in the presence of EDC to afford 52. A portion of the resulting product was separated and subjected to LiOH hydrolysis in order to remove the acetate group, thus yielding hydroxy derivatives 53.

Examples containing substituted piperazines are prepared using the general procedures outlined in Schemes 31–38. Substituted piperazines are either commercially available from Aldrich, Co. or prepared according to literature procedures (Behun et al, Ref. 31(a), Scheme 31, eq. 01). Hydrogenation of alkyl substituted pyrazines under 40 to 50 psi pressure in ethanol afforded substituted piperazines. When the substituent was an ester or amide, the pyrazine systems could be partially reduced to the tetrahydropyrazine (Rossen et al, Ref. 31(b), Scheme 31, eq. 02). The carbonyl substituted piperazines could be obtained under the same conditions described above by using commercially available dibenzyl piperazines (Scheme 31, eq. 03).

Scheme 31

2-Trifluoromethylpiperazine (Jenneskens et al., Ref. 31c) was prepared through a four step route (Scheme 32). Using Lewis acid $TiCl_4$, N,N'-dibenzylethylenediamine 54 reacted with trifluoropyruvates to afford hemiacetal 55, which was reduced at room temperature by $Et_3SiH$ in $CF_3COOH$ to lactam 56. $LiAlH_4$ treatment then reduced lactam 56 to 1,4-dibenzyl-2-trifluoromethylpiperazine 57. Finally, hydrogenation of compound 57 in HOAc gave the desired product 2-trifluoromethylpiperazine 58.

Scheme 32

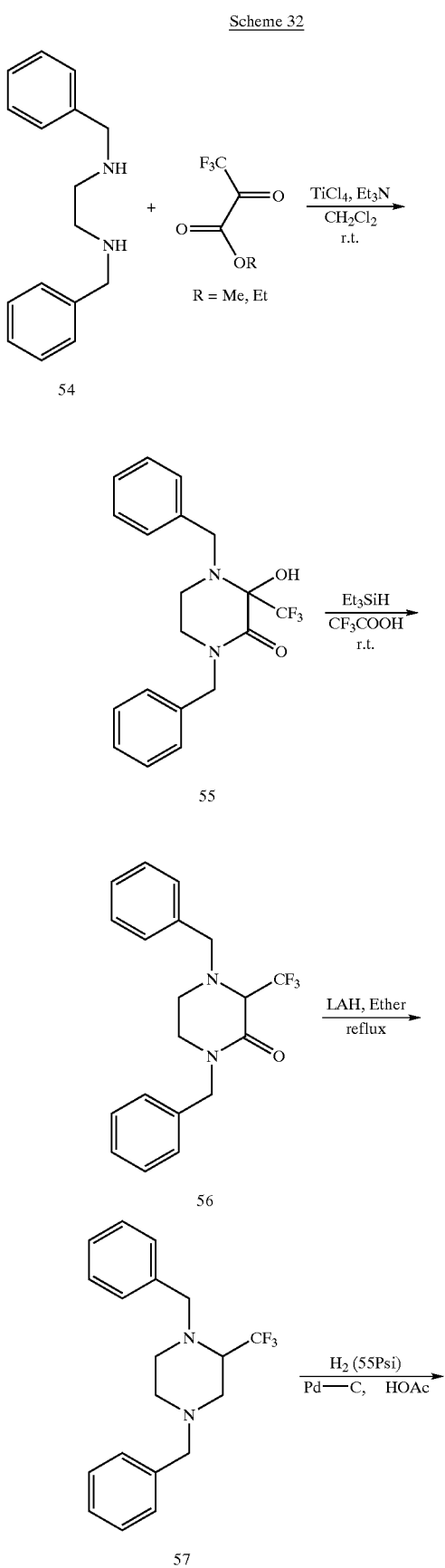

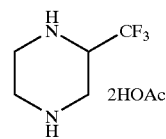

Mono-benzoylation of symmetric substituted piperazines could be achieved by using one of the following procedures (Scheme 33). (a) Treatment of a solution of piperazine in acetic acid with acetyl chloride afforded the desired mon-benzoylated piperazine (Desai et al. Ref. 26, Scheme 33, eq. 04). (b) Symmetric piperazines were treated with 2 equivalents of n-butyllithium, followed by the addition of benzoyl chloride at room temperature (Wang et al, Ref. 32, Scheme 33, eq. 05).

Scheme 33 eq. 04

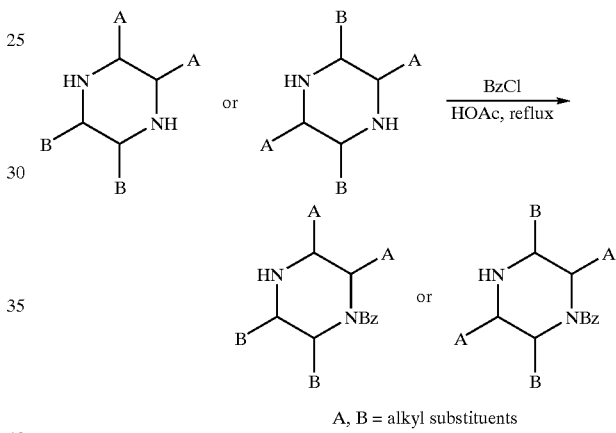

A, B = alkyl substituents eq. 05

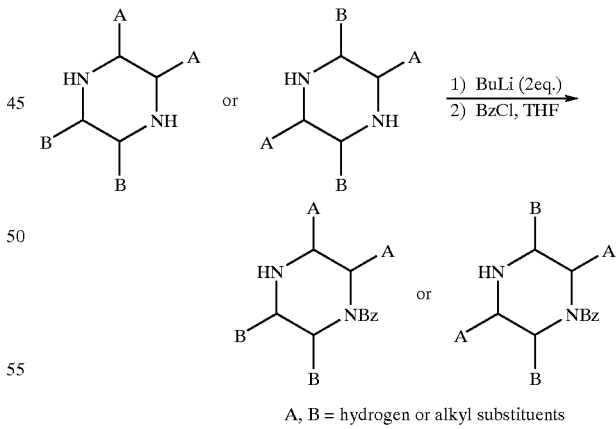

A, B = hydrogen or alkyl substituents

Mono-benzoylation of unsymmetric substituted piperazines (A and B in Scheme 33 represent, for example $R^{14}$, $R^{16}$, $R^{18}$ and $R^{20}$ once incorporated into a compound of Formula I) could be achieved by using one of the following procedures (Scheme 33), in which all the methods were exemplified by mono-alkyl substituted piperazines. (a) Unsymmetric piperazines were treated with 2 equivalents of n-butyllithium, followed by the addition of benzoyl chloride at room temperature to afford a mixture of two regioisomers, which could be separated by chromatography (Wang et al, Ref.32 and 33(b), Scheme 34 eq. 06); (b) Benzoic acid was converted to its pentafluorophenyl ester, and then further reaction with 2-alkylpiperazine to provide the mono-benzoylpiperazines with the benzoyl group at the less hindered nitrogen (Adamczyk et al, Ref. 33(a), Scheme 34, eq. 07); (c) A mixture of piperazine and methyl benzoate was treated with dialkylaluminum chloride in methylene chloride for 24 days to yield the mono-benzoylpiperazine with the benzoyl group at the less hindered nitrogen (Scheme 34 eq. 08); (d) Unsymmetric piperazines were treated with 2 equivalents of n-butyllithium, followed by subsequent addition of triethylsilyl chloride and benzoyl chloride in THF at room temperature to afford mono-benzoylpiperazines with the benzoyl group at the more hindered nitrogen (Wang et al, Ref. 33(b), Scheme 34, eq. 09). When the substituent at position 2 was a ester or amide, the mono-benzoylation with benzoyl chloride occurred at the less hindered nitrogen of the piperazine with triethylamine as base in THF (Scheme 34, eq. 10).

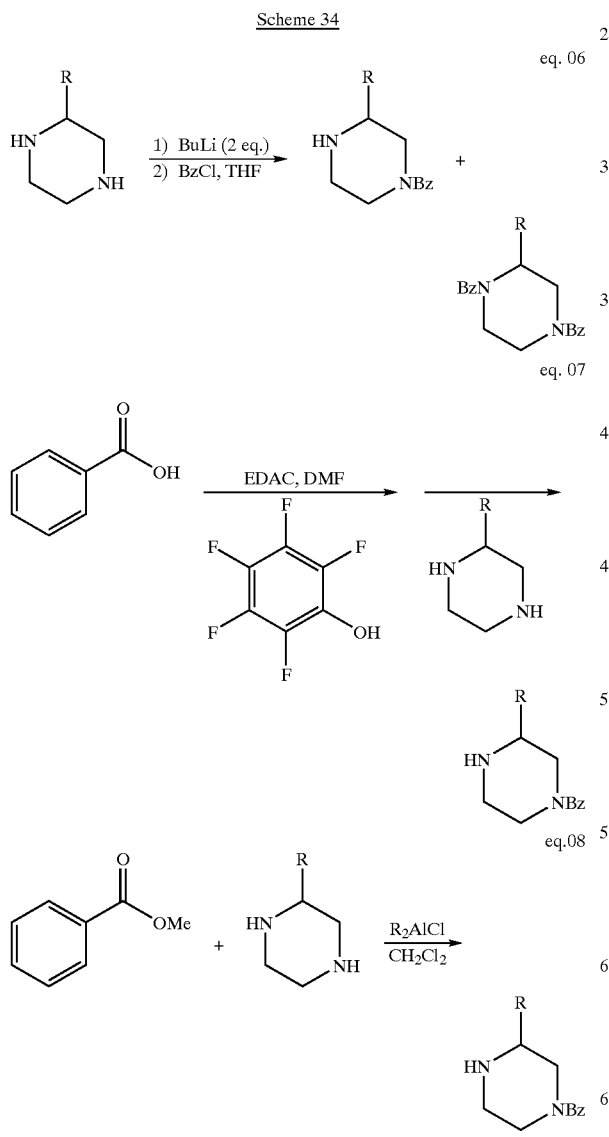

Scheme 34

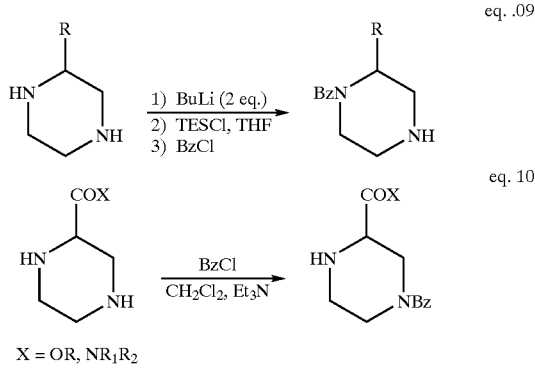

$X = OR, NR_1R_2$

In the case of tetrahydropyrazines (Scheme 35, eq. 11), mono-benzoylation occurred at the more hindered nitrogen under the same conditions as those in equation 10 of Scheme 34, in the well precedented manner. (Rossen et al, Ref. 31(b)).

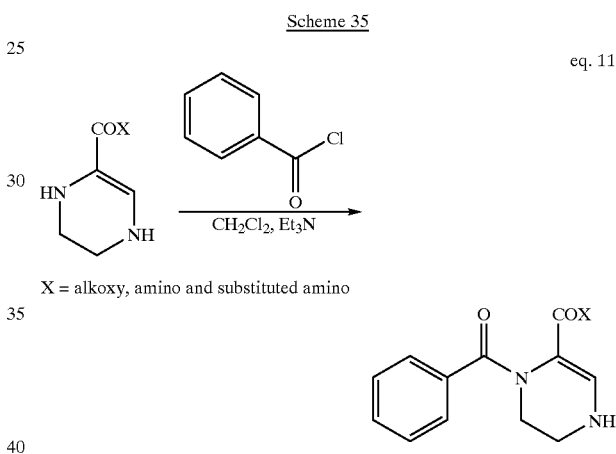

Scheme 35

X = alkoxy, amino and substituted amino

Furthermore, the ester group can be selectively reduced by $NaBH_4$ in the presence of the benzamide (Masuzawa et al, Ref. 34), which is shown in Scheme 36.

Scheme 36

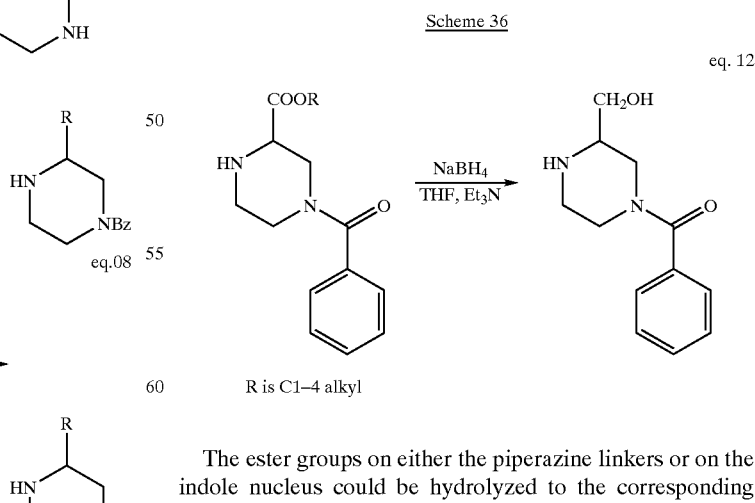

R is C1–4 alkyl

The ester groups on either the piperazine linkers or on the indole nucleus could be hydrolyzed to the corresponding acid under basic conditions such as $K_2CO_3$ (Scheme 37, eq. 13) or NaOMe (Scheme 37, eq. 14) as bases in MeOH and water.

Scheme 37 eq. 13

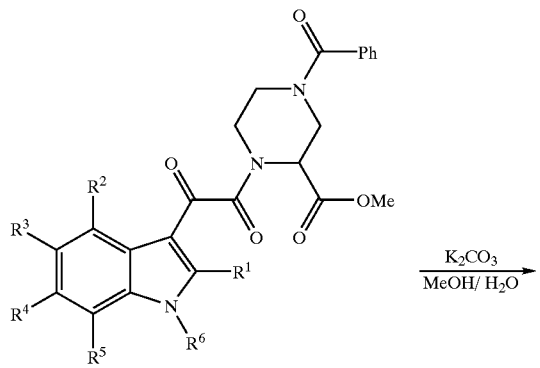

Scheme 38

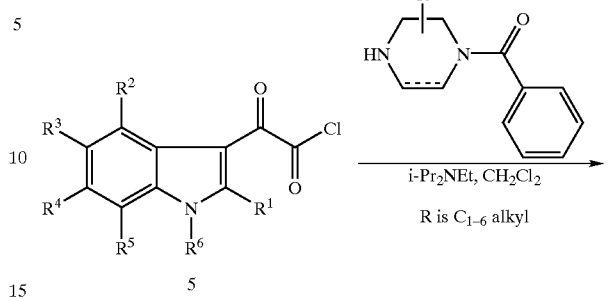

Reaction of glyoxyl chloride 5 with substituted benzoyl piperazines or tetrahydropyrazines in $CH_2Cl_2$ using i-$Pr_2NEt$ as base afforded the coupled products 59.

In the case of coupling reactions using 3-hydroxylmethylbenzoylpiperazine, the hydroxyl group was temporarily protected as its TMS ether with BSTFA (N,O-bistrimethylsilyl)fluoroacetamide) (Furber et al, Ref. 35). The unprotected nitrogen atom was then reacted with glyoxyl chlorides 5 to form the desired diamides. During workup, the TMS masking group was removed to give free hydroxylmethylpiperazine diamides 60 (Scheme 39).

eq. 14

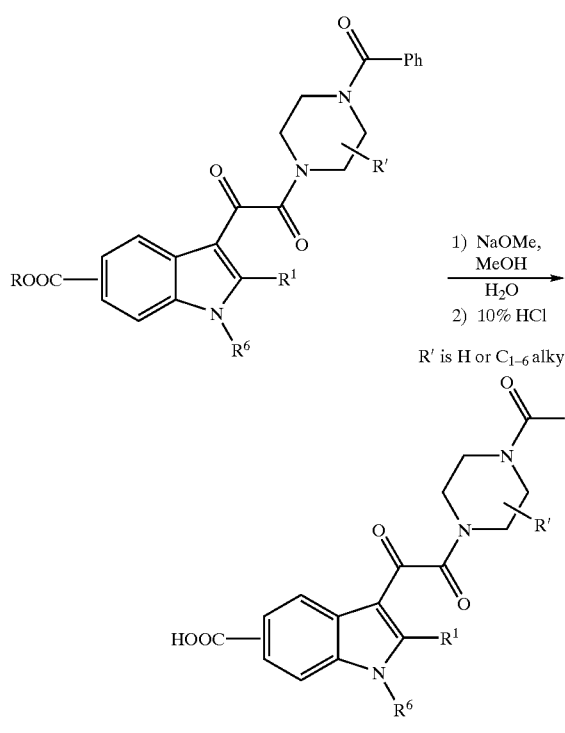

Scheme 39

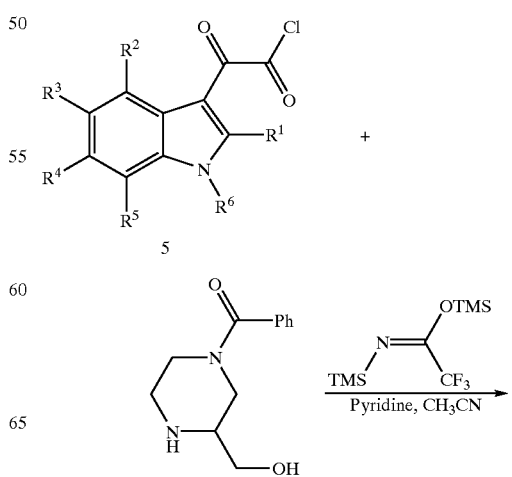

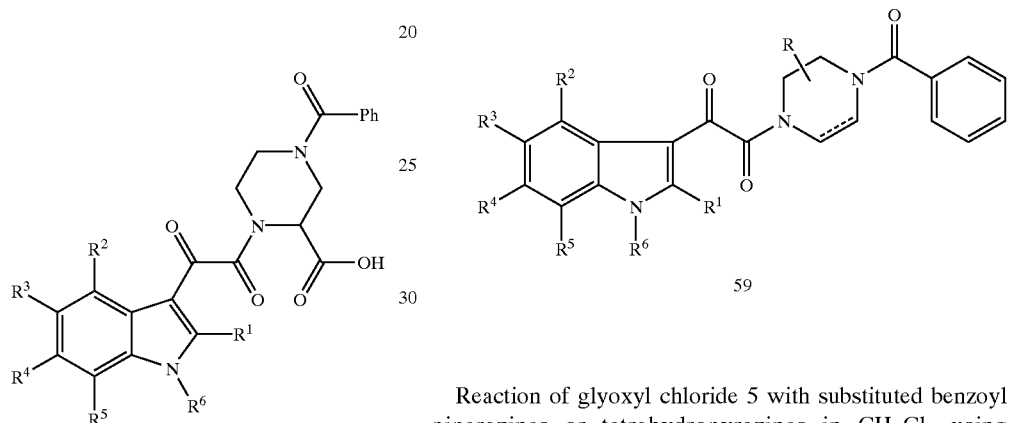

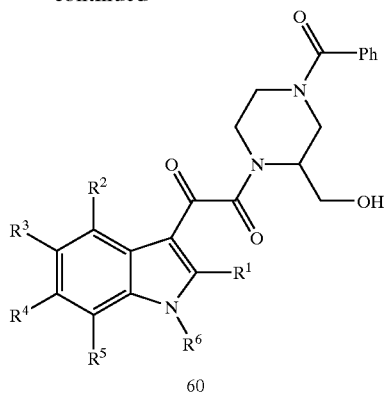

60

Piperazine intermediates were prepared using standard chemistry as shown in Schemes 40 and 41.

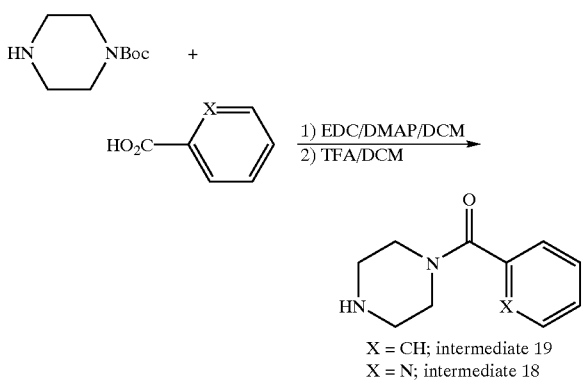

X = CH; intermediate 19
X = N; intermediate 18

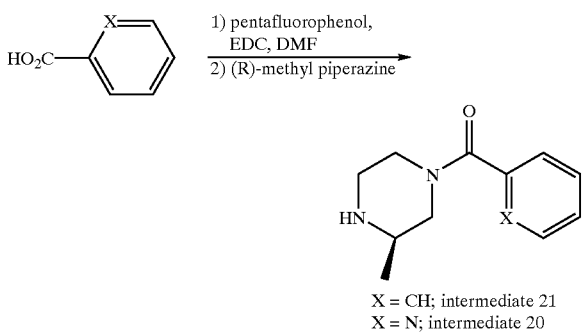

X = CH; intermediate 21
X = N; intermediate 20

Throughout the chemistry discussion, chemical transformations which are well known in the art have been discussed. The average practioner in the art knows these transformations well and a comprehensive list of useful conditions for nearly all the transformations is available to organic chemists and this list is contained in reference 91 authored by Larock and is incorporated in its entirety for the synthesis of compounds of Formula I.

DESCRIPTION OF SPECIFIC EMBODIMENTS

Experimental Section

Unless otherwise stated, solvents and reagents were used directly as obtained from commercial sources, and reactions were performed under an nitrogen atmosphere. Flash chromatography was conducted on Silica gel 60 (0.040–0.063 particle size; EM Science supply). $^1$H NMR spectra were recorded on Buker DRX-500 at 500 MHz (or Buker DPX-300/Varian Gemini 300 at 300 MHz as stated). The chemical shifts were reported in ppm on the δ scale relative to δTMS=0. The following internal references were used for the residual protons in the following solvents: $CDCl_3$ ($\delta_H$ 7.26), $CD_3OD$ ($\delta_H$ 3.30) and DMSO-$d_6$ ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray mode (ES+). The analytical reverse phase HPLC method is as follow unless otherwise noted: Column YMC ODS-A C18 S7 (3.0×50 mm), Start %B=0, Final %B=100, Gradient Time=2 min, Flow rate 5 ml/min. Wavelength=220 nm, Solvent A=10% MeOH—90% $H_2O$—0.1% TFA, Solvent B=90% MeOH—10% $H_2O$—0.1% TFA; and $R_t$ in min. Preparative reverse phase HPLC was performed on a Shimadzu LC-8A automated preparative HPLC system with detector (SPD-10AV UV-VIS) wavelength and solvent systems (A and B) the same as above.

For examples 195 through 214, the following methodology was used to obtain the LC retention times and mass spectral data. The methods were run on a MUX HPLC-MS instrument (MS8) comprising: Waters 600E HPLC pump and controller, Gilson Multiprobe liquid handler, Gilso889 injector module, Waters 2487 UV detectors (×8) fitted with micro-flow cells, and a Micromass LCT mass spectrometer with MUX 8 way interface. The HPLC pump delivers rhe mobile phase at 8 ml/min to an 8 way splitter where the flow is distributed to eight flow lines. The flow down each line is proportional to the back pressure of that line and is nominally 1 mL/min. Post splitter, the flow runs to eight Rheodyne injectors mounted in one unit and then into eight identical HPLC columns and eight UV detectors. The HPLC eleunt from each detector is split and approximately 30–80 uL/min per line enters the MUX interface housing attached to the LCT mass spectromphotometer. The HPLC pump, liquid handler, injector module, and mass spectrometer are controlled using the MicroMass Mass Lynx software under Windows NT. The eight UV detectors are operated manually from their fronmt panels but do receive auto zero signals from the injector module. Analogue signals from the UV detectors are fed both into the Mass Lynx software, via connectors on the mass spectrometer, and also into the Millenium Chromatography Data System via standard SAT/IN and LACE interfaces. Samples are prepared at concentrations of 0.5 mg/mL in acetonitrile water. The following HPLC conditions are used: Mobile Phase: Aqueous, Water+0.1+TFA; Organic, Acetonitrile+0.1% TFA. Column: Hypersil BDS C18, 50 mm×2.1 mmid., 5 µ packing. Gradient:

| Time (min) | % Organic | Curve |
|---|---|---|
| 0.00 | 12 | 1 |
| 0.80 | 60 | 6 |
| 1.80 | 95 | 6 |

-continued

| Time (min) | % Organic | Curve |
|---|---|---|
| 2.10 | 12 | 6 |
| 2.40 | 12 | 6 |

Run time: 2.4 min.
Flow rate: 8.0 mL/min, split eight ways to each column.
Injection volume: 30 μL into a 5 μL loop, filled loop method.

I. PREPARATION OF INTERMEDIATES

Intermediate 1 (example of Scheme 3)

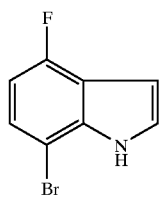

A solution of 2-bromo-5-fluoronitrobenzene (4.4 g, 20 mmol) in dry THF (200 mL) under $N_2$ was cooled to −65° C. (acetone/$CO_2$). A solution of vinylmagnesium bromide (60 mL, 1 M, 60 mmol) in THF was added to the nitrobenzene solution as rapidly as possible maintaining the reaction temperature below −40° C. After addition of the Grignard reagent, the cooling bath was switched to a −40° C. bath ($CH_3CN/CO_2$), and the mixture was stirred at −40° C. for 30 min. The reaction mixture was quenched with sat. $NH_4Cl$ solution (500 mL) and extracted with ether (2×200 mL), then dried (brine, $Na_2SO_4$) and concentrated in vacuo. The resulting material was purified by $SiO_2$ flash column chromatography (5:95) EtOAc/Hexanes to give 4-fluoro-7-bromoindole, as a light brown oil (2.03 g, 9.5 mmol, 54%). $^1$H NMR ($CDCl_3$) δ 6.72 (m, 2H), 7.24 (m, 2H), 8.4 (br s, 1H). MS m/e 215 $(MH^+)$.

Intermediate 2

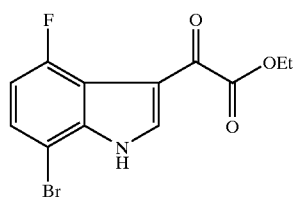

To a solution of ethyl chlorooxoacetate (1.397 g, 10.25 mmol) and 4-Fluoro-7-bromoindole (1.1 g, 5.14 mmol) in $CH_2Cl_2$ (10 mL) at 0° C. was added aluminum chloride (1.367 g, 10.25 mmol). The mixture was stirred for 1 h at 0° C. then quenched with 1 N HCl. The mixture was extracted with $CH_2Cl_2$ and the organic layers concentrated in vacuo. The crude material was purified by $SiO_2$ flash column chromatography (gradient 10–30%) EtOAc/Hexanes to give the ester, intermediate 2, as a yellow solid (846 mg, 2.69 mmol, 52%). $^1$H NMR ($CDCl_3$) δ 1.43 (t, J=6.9 Hz, 3H), 4.42 (q, J=6.9 Hz, 1H), 6.92 (m, 1H), 7.40 (m, 1H), 8.42 (d, J=3 Hz, 1H), 9.04 (br s, 1H).

Intermediate 3

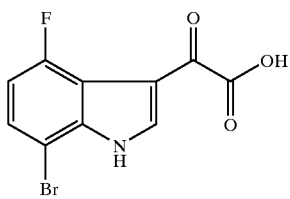

The ester, intermediate 2, was directly hydrolyzed in MeOH (10 mL) with 1 N NaOH (5.4 mL, 5.4 mmol) at reflux temperature for 15 min. The sodium salt was treated with 1 N HCl (5.4 mL, 5.4 mmol) and the solvents were removed in vacuo to give the free acid, intermediate 3, as a white solid.

Intermediate 4

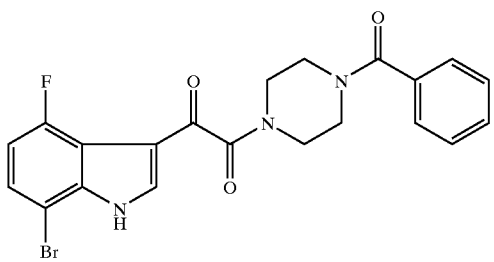

A mixture of the acid, intermediate 3; (2.69 mmol)], N-benzoyl piperazine (563 mg, 2.96 mmol), EDC.HCl (622 mg, 3.24 mmol), N-methylmorpholine (330 mg, 3.24 mmol), and hydroxybenzotriazole (405 mg, 2.96 mmol) in DMF (5 mL) was stirred at ambient temperature for 2 h then warmed to 90° C. for 30 min. The mixture was poured into water and extracted into EtOAc. The EtOAc layers were dried (brine, $MgSO_4$) and concentrated in vacuo. The resulting material was purified by $SiO_2$ flash column chromatography (gradient 40–100%) EtOAc/Hexanes to give intermediate 4 as a white solid (250 mg, 0.55 mmol, 20%). $^1$H NMR ($CDCl_3$) δ 3.5 (m, 4H), 3.75 (m, 4H), 6.85 (m, 1H), 7.35 (m, 1H), 7.39 (m, 5H), 8.06 (d, J=3.3 Hz, 1H). MS m/e 458, 460 $(MH^+)$.

Intermediate 5

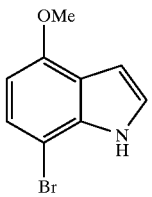

4-Methoxy-7-bromoindole, was prepared in the same manner as 4-fluoro-7-bromoindole, (intermediate 1) in 38% yield. $^1$H NMR ($CDCl_3$) δ 3.95 (s, 3H), 6.44 (d, J=4.8 Hz, 1H), 6.73 (s, 1H), 7.17 (s, 1H), 6.24 (d, J=4.8 Hz, 1H), 8.4 (br s, 1H). MS m/e 223.9, 225.9 $(M-H^-)$. Anal. Calcd for $C_9H_8BrNO$: C, 47.82; H, 3.57; N, 6.20; Found: C, 47.91; H, 3.56; N, 6.11.

Intermediate 6

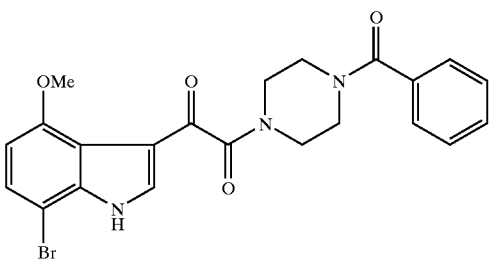

4-methoxy-7-bromoindole, intermediate 5, (1.06 g, 4.71 mmol) was dissolved in THF (10 mL) and oxalyl chloride (3 g, 23.6 mmol) was added. The mixture was stirred at ambient temperature for 5 h then at 50° C. for 30 min. The volatile solvents were removed in vacuo leaving a green solid, which was used directly in the next step. The acid chloride was dissolved in THF (20 mL) and N-benzoyl piperazine (1070 mg, 5.65 mmol) was added followed by diisopropylethylamine (1220 mg, 9.42 mmol). The mixture was stirred at ambient temperature for 18 h then heated to reflux temperature for 30 min. The mixture was poured into water and extracted into EtOAc. The EtOAc layers were dried (brine, MgSO$_4$) and concentrated in vacuo. The resulting material was purified by SiO$_2$ flash column chromatography (gradient 50–80%) EtOAc/Hexanes to give intermediate 6 as a slightly yellow solid (520 mg, 1.1 mmol, 23%). $^1$H NMR (CDCl$_3$) δ 3.5 (m, 4H), 3.75 (m, 4H), 3.92 (s, 1H), 6.60 (d, J=5 Hz, 1H), 7.33 (d, J=5 Hz, 1H), 7.43 (m, 5H), 8.03 (s, 1H), 9.07 (br s, 1H). MS m/e 470, 472 (MH$^+$). HPLC R$_t$=1.347.

Intermediate 7

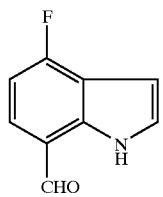

To a THF solution (15 mL) of 4-fluoro-7-bromoindole, intermediate 1 (1 g, 4.67 mmol) at −78° C. was added n-butyllithium (5.6 mL, 2.5 M, 14 mmol) dropwise over 15 min. The mixture was warmed to 5° C. and stirred for 30 min before cooling back down to−78° C. DMF (1.8 mL, 23.2 mmol) was added and the mixture was warmed to ambient temperature for 15 min. The solution was poured into water and extracted into EtOAc. The EtOAc layers were dried (brine, MgSO$_4$) and concentrated in vacuo. The resulting material was purified by SiO$_2$ flash column chromatography (1:4) EtOAc/Hexanes to give intermediate 7 as a slightly yellow solid (403 mg, 2.48 mmol, 53%). $^1$H NMR (CDCl$_3$) δ 6.71 (d, J=2 Hz, 1H), 6.92 (t, J=4.9 Hz, 1H), 7.33 (t, J=1.7 Hz, 1H), 7.63 (dd, J=2.9, 4.9 Hz, 1H), 10.05(s, 1H), 10.25 (brs, 1H).

Intermediate 8

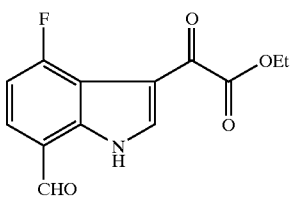

Intermediate 7 (2.27 g, 13.92 mmol) and ethyl chlorooxoacetate (3.2 mL, 27.85 mmol) were dissolved in CH$_2$Cl$_2$ (25mL). The solution was cooled to 0° C. and aluminum chloride was added portionwise (3.71 g, 27.85 mmol) followed by an additional 15 mL of CH$_2$Cl$_2$. The mixture was stirred at 0° C. for 30 min then warmed to ambient temperature for 1 h, and recooled to 0° C. before quenching with 1 N HCl. The solution was poured into water and extracted into EtOAc. The EtOAc layers were dried (brine, MgSO$_4$) and concentrated in vacuo. The resulting material was crystallized from EtOAc/Hexanes to give intermediate 8 as a slightly yellow solid (2.72 g, 10.34 mmol, 74%).

Intermediate 9

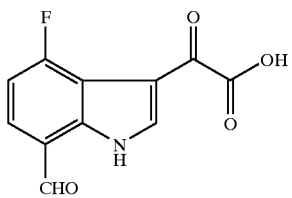

Aqueous NaOH (2.07 mL, 10 N, 20.7 mmol) was added to an EtOH solution (10 mL) of the ester, intermediate 8, (2.72 g, 10.34 mmol) and the mixture was stirred at ambient temperature for 2 h. Aqueous 6 N HCl was added until the pH was approximately 2. The EtOH was removed in vacuo and the solid remaining was filtered and washed with cold water followed by dry ether to give the acid, intermediate 9 (2.27 g, 9.66 mmol, 93%).

Intermediate 10

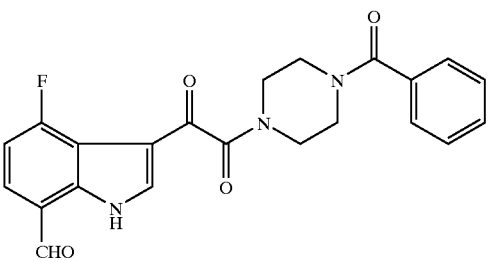

Prepared from intermediate 9 as described in Reference 102.

Intermediate 11

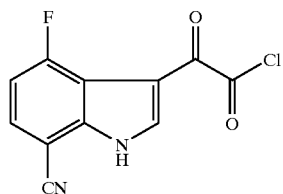

To a solution of 4-fluoro-7-cyanoindole (Reference 102, 350 mg, 2.18 mmol) in CH$_2$Cl$_2$ (14 ml) was added oxalyl chloride (7.0 ml, 80.2 mmol). The mixture was heated to reflux for 3 days, and then concentrated in vacuo to afford intermediate 11 as a yellow solid. $^1$H NMR (300 MHz, CD$_3$OD) δ 8.51 (s, 1H), 7.74 (app dd, J=8.5, 4.2, 1H), 7.12 (app dd, J=10.1, 8.5,1H).

Intermediate 12

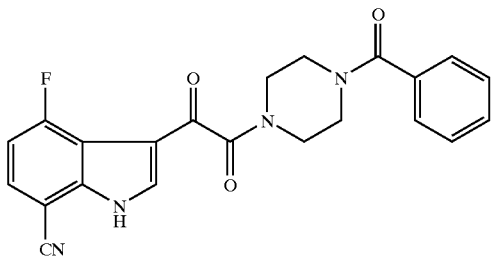

To a solution of indole, intermediate 11, in THF (15 mL), was added intermediate 19 (596 mg, 2.63 mmol) and N,N-diisopropylethylamine (3.8 mL, 21.8 mmol). The resulting mixture was stirred at rt for 16 h. After quenching with MeOH (15 mL), the reaction mixture was concentrated in vacuo to give a brownish oil, which was subjected to flash chromatography using a gradient elution (50% to 90% EtOAc/Hexane) to give intermediate 12 as a white solid (550 mg, 62% two steps). $^1$H NMR (CDCl$_3$) δ 10.39 (s, 1H), 8.18 (d, J=3.3, 1H), 7.64 (app dd, J=8.2, 4.4, 1H), 7.45 (b s, 5H), 7.08 (app t, J=9.3, 1H), 4.00–3.45 (b m, 8H); LC/MS (ES+) m/z (M+H)$^+$=405, HPLC R$_t$=1.243.

Intermediate 13

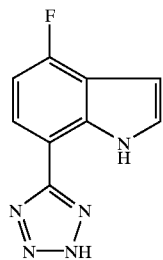

To a solution of 4-fluoro7-cyanoindole (300 mg, 1.87 mmol) in DMF (6 ml) were added ammonium chloride (386 mg, 6.18 mmol) and sodium azide (365 mg, 5.62 mmol). After stirring at 100° C. for 17 h, the reaction mixture was cooled to rt and quenched carefully with excess hydrochloric acid (10 mL, 1 N aq.). The mixture was then diluted with water (~50 mL) to induce precipitation. The light brown precipitates were filtered, washed with 3 times of excess water and dried under high vacuum to provide the tetrazole, intermediate 13 (338.5 mg, 89%). $^1$H NMR (CD$_3$OD) δ 7.73 (dd, J=8.2, 4.6, 1H), 7.45 (d, J=3.3, 1H), 6.92 (dd, J=10.0, 8.2, 1H), 6.66 (d, J=3.3, 1H). LC/MS (ES+) m/z (M+H)$^+$= 204, HPLC R$_t$=1.223.

Intermediate 14

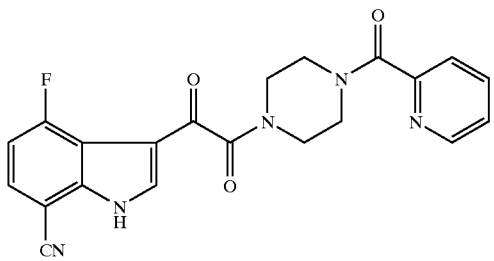

Prepared in the same manner as intermediate 12. $^1$H NMR (mixture of conformers, CD$_3$OD) δ 8.64 and 8.55 (app d, J=4.4, 1H), 8.28 (app d, J=4.4, 1H), 7.96 (m, 1H), 7.74 (m, 1H), 7.65 (m1H), 7.48 (m, 1H), 7.11 (m, 1H) 3.94–3.55 (b m, 8H); LC/MS (ES+) m/z (M+H)$^+$=406, HPLC R$_t$=1.047.

Intermediate 15

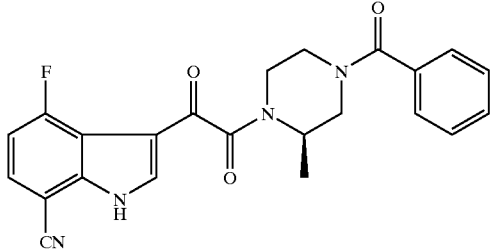

Prepared in the same manner as intermediate 12. $^1$H NMR (mixture of conformers, CD$_3$OD) δ 8.29 and 8.23 (app s, 1H), 7.72 (app b s, 1H), 7.46 (app b s, 5H), 7.11 (app b s, 1H), 5.00–3.00 (b m, 7H), 1.40–1.22 (b m, 3H); LC/MS (ES+) m/z (M+H)$^+$=419, HPLC R$_t$=1.263.

Intermediate 16

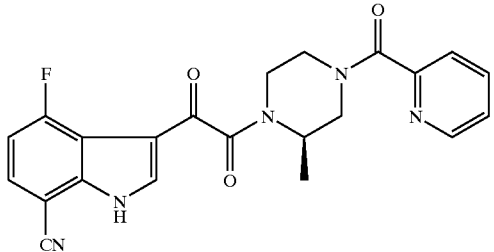

Prepared in the same manner as intermediate 12. $^1$H NMR (CD$_3$OD) δ 8.64–8.52 (m, 1H), 8.31–8.24 (m, 1H), 8.00–7.91 (m, 1H), 7.74 (m, 1H), 7.66 (m, 1H), 7.55–7.45 (m, 1H), 7.12 (m, 1H), 4.95–3.10 (b m, 7H), 1.42–1.23 (m, 3H); LC/MS (ES+) m/z (M+H)$^+$=420, HPLC R$_t$=1.127.

Intermediate 17

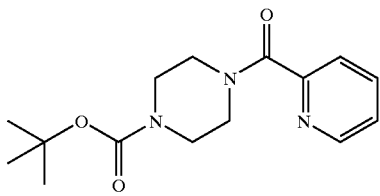

To a solution of tert-butyl 1-piperazinecarboxylate (10.0 g. 53.7 mmol) and picolinic acid (6.01 g, 48.8 mmol) in $CH_2Cl_2$ (300 mL), was added DMAP (6.564 g, 53.7 mmol) and EDC (10.261 g, 53.7 mmol). The reaction mixture was stirred at rt for 16 h, and then washed with hydrochloric acid (5×250 mL, 1 N aq.) and water (350 mL). The organic layer was dried ($MgSO_4$) and evaporated in vacuo to give the N-Boc piperazine, intermediate 17, as white solid (9.9 g, 70%). $^1$H NMR (300 MHz, $CD_3OD$) δ 8.56 (app d, J=5.5, 1H), 7.91 (app t, J=6.8, 1H), 7.57 (d, J=6.8, 1H), 7.45 (m, 1H), 3.70 (m, 2H), 3.50 (m, 2H), 3.43 (m, 4H), 1.41 (b s, 9H); LC/MS (ES+) m/z $(M+H)^+=291$, $(2M+H)^+=581$, HPLC $R_f=1.173$.

Intermediate 18

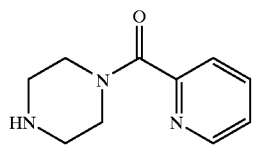

To the N-Boc piperazine derivative, intermediate 17, (9.9 g, 34 mmol) was charged a solution of HCl in Dioxane (40 mL, 4 M), and the mixture was stirred at rt for 5 h. Removal of the excess reagent in vacuo afforded the hydrochloride salt, intermediate 18, as a white solid (100% conversion). $^1$H NMR (300 MHz, $CD_3OD$) δ 8.94 (m, 1H), 8.63 (m, 1H), 8.22 (app d, J=7.9, 1H), 8.11 (m, 1H); LC/MS (ES+) m/z $(M+H)^+=192$, $(2M+H)^+=383$, HPLC $R_f=0.113$.

Intermediate 19

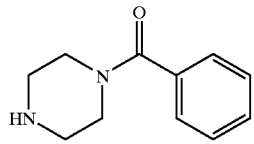

Prepared in the same manner as intermediate 18. To a solution of tert-butyl 1-piperazinecarboxylate (15.0 g. 80.5 mmol) and benzoic acid (8.94 g, 73.2 mmol) in $CH_2Cl_2$ (500 mL), was added DMAP (9.84 g, 80.5 mmol) and EDC (15.39 g, 80.5 mmol). The reaction mixture was stirred at rt for 17 h, and then washed with excess hydrochloric acid (5×250 mL, 1 N aq.) and water (350 mL). The organic layer was dried ($MgSO_4$) and evaporated in vacuo to give N-Benzoyl-N'-Boc piperazine as an off white solid (21 g, 99%). $^1$H NMR (300 MHz, $CD_3OD$) δ 7.46 (m, 5H), 3.80–3.30 (b m, 8H), 1.47 (s, 9H); LC/MS (ES+) m/z $(M+H)^+=291$, $(2M+H)^+=581$, HPLC $R_f=1.430$.

To the N-Benzoyl-N'-Boc piperazine was charged a solution of HCl in Dioxane (80 mL, 4 M), and the mixture stirred at room temperature for 5 h. The reaction mixture was then concentrated in vacuo to afford the hydrochloride salt, intermediate 19, as a white solid (100% conversion). $^1$H NMR (300 MHz, $CD_3OD$) δ 7.5 (m, 5H), 4.0–3.7 (b, 4H), 3.7–3.6 (b m, 4H); LC/MS (ES+) m/z $(M+H)^+=191$, $(2M+H)^+=381$, HPLC $R_f=0.210$.

Intermediate 20

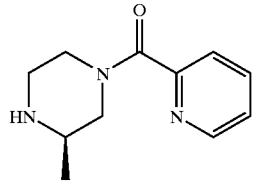

To a solution of picolinic acid (4.06 g, 32.9 mmol) and pentafluorophenol (6.06 g, 32.9 mmol) in DMF (50 mL) was added EDC (6.30 g, 32.9 mmol). The reaction mixture was stirred for 4 h at rt until LC/MS analysis showed the complete formation of the intermediate ester. (R)-methyl piperazine (3.0 g, 30 mmol) was then added and the resulting mixture stirred at rt for 16 h. Removal of the solvent in vacuo afforded a yellow oil, which was subjected to flash chromatography using a gradient elution (50% EtOAc/Hexane, to 5% to 15% MeOH/EtOAc, to 1/3/17 $NH_3$(sat. aq.)/MeOH/EtOAc) to give intermediate 20 as a yellow oil (1.67 g, 27%). $^1$H NMR (300 MHz, $CD_3OD$) δ 8.60 (app d, J=4.7, 1H), 7.98 (m, 1H), 7.60 (m, 1H), 7.5(m, 1H), 4.53 (app d, J=12.6, 1H), 3.62 (m, 1H), 3.10–2.59 (b m, 5H), 1.19 and 1.00 (app d, J=6.4, 5.4, 3H); LC/MS (ES+) m/z $(M+H)^+=206$, $(2M+H)^+=411$, HPLC $R_f=0.153$.

Intermediate 21

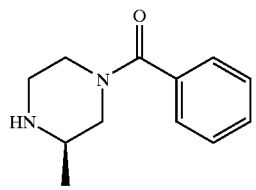

Prepared in the same manner as intermediate 20. $^1$H NMR (300 MHz, $CD_3OD$) δ 7.47 (m, 5H), 4.50 (app d, J=10.6, 1H), 3.59 (b s, 1H), 3.14–2.57(b m, 5H), 1.15–0.97 (b m, 3H); LC/MS (ES+) m/z $(M+H)^+=205$, $(2M+H)^+=409$, HPLC $R_f=0.310$.

Intermediate 22

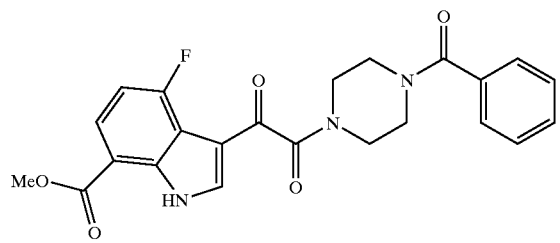

To a solution of methyl (4-fluoro)indole-7-carboxylate (1 eq) in dry THF was added dropwise oxalyl chloride (1.2eq ) at 0° C. After 5 min., the reaction was warmed to rt and was stirred at rt until completion. The mixture was then concentrated under reduced pressure to provide crude glyoxyl chloride. To a solution of crude 3-glyoxyl chloride of methyl (4-fluoro)indole-7-carboxylate (5.39 mmol) in THF (50 mL) was added intermediate 19 (1.23 g, 5.42 mmol) and diisopropylethylamine (5.6 ml, 32.2 mmol). The reaction mixture was stirred at rt for 14 h, then MeOH (5 mL) was added and the mixture was concentrated in vacuo. The yellow residue was purified by flash chromatography (50% to 100% EtOAc/Hexane) to afford intermediate 22, as a pale yellow solid (1.25 g, 53% based on methyl (4-fluoro)indole-7-carboxylate). $^1$H NMR (CD$_3$OD) δ 8.17 (s, 1H), 8.00 (dd, J=8.0, 4.5, 1H), 7.44 (b, s, 5H), 7.05 (app t, J=9.0, 1H), 3.99 (s, 3H), 3.84–3.51 (b m, 8H); LC/MS (ES+) m/z (M+H)$^+$= 438, HPLC R$_t$=1.283.

Intermediate 23

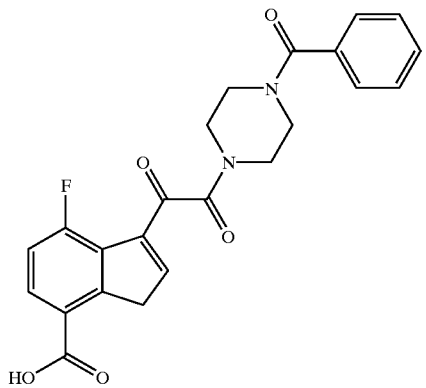

To a solution of intermediate 22, (1.0 g, 2.3 mmol) in MeOH (5 mL) was added NaOH (1N, 5 mL, 1 N, aq.). The reaction mixture was stirred at rt for 6 h. After which time, 10 pipet drops of NaOH (10 N, aq.) was added, and the mixture was stirred for an additional 4 h until HPLC analysis showed the completion of the reaction. The reaction mixture was then acidified to pH 1 using HCl (5.5 N aq.). The precipitates were collected by filtration, washed with water and dried under high vacuum to give intermediate 23 as a white solid (837 mg, 86%). $^1$H NMR (DMSO-d$_6$) δ 13.45 (b, 1H), 12.34 (s, 1H), 8.08 (app d, J=3.0, 1H), 7.93 (dd, J=8.0, 4.0, 1H) 7.44 (b, s, 5H), 7.14 (app t, J=9.2, 1H), 3.79–3.34 (b m, 8H); LC/MS (ES+) m/z (M+H)$^+$=424, HPLC R$_t$=1.297.

Alternatively, the acid, intermediate 23 can be prepared by oxidation of the carboxaldehyde, intermediate 10, as follows.

AgNO$_3$ (166 mg, 0.98 mmol) was dissolved in water (1 mL). NaOH (79 mg, 1.96 mmol) in MeOH/H$_2$O (1:1) was added to this solution, and a brown precipitate was formed. The aldehyde, intermediate 10, (200 mg, 0.49 mmol)] was added to the above reaction mixture in one portion, and the reaction was heated at 90–100° C. for about 2–3 h. The reaction mixture was then cooled to rt and filtered through celite. The filter cake was washed with hot water (3x) and the cooled filtrate was extracted with EtOAc. The aqueous extract was acidified with 2N HCl to about pH 2. The resulting light grey solid was collected by filtration to yield the acid, intermediate 23, (109 mg).

Intermediate 24

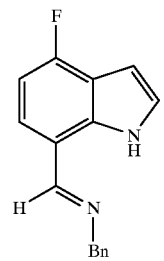

A mixture of 4-fluoro-7-formylindole, intermediate 7 (100 mg, 0.613 mmol) and benzylamine (0.1 ml, 0.915 mmol) in EtOH (1.5 ml) was stirred at room temperature for 20 hours. After which time, the volatile was evaporated in vacuo to give the imine product as a light brown oil. $^1$H NMR: (CDCl$_3$) δ 10.87 (b s, 1H), 8.58 (s, 1H), 7.39–7.35 (overlapping m, 4H), 7.31–7.25 (overlapping m, 3H), 6.83 (dd, J=8.0, 10.0, 1H), 6.65 (t, J=2.7, 1H), 4.88 (2, 2H); LC/MS: (ES+) m/z (M+H)$^+$=253, HPLC R$_t$=1.330.

Intermediate 25

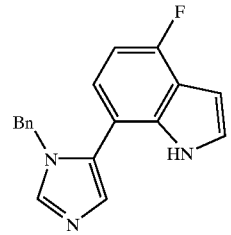

A mixture of the imine, intermediate 24 (48.3 mg, 0.191 mmol) in DMF (1.0 ml) was added TOSMIC (47.3 mg, 0.297 mmol) and powdered K$_2$CO$_3$ (54.7 mg, 0.396 mmol), and the reaction mixture was stirred at room temperature for 72 hours. The mixture was diluted with brine (50 ml) and the resulting white suspension extracted with EtOAc (50 ml). The organic extract was washed with sodium bicarbonate (25 ml, sat. aq.), followed by brine (50 ml), dried (MgSO$_4$) and evaporated in vacuo. The crude material was purified by preparative TLC (10% MeOH/CH$_2$Cl$_2$, 2x500 μm×20 cm×20 cm plates) to give the imidazole product as a light yellow oil (26.7 mg, 48% 2 steps). $^1$H NMR: (CD$_3$OD) δ 7.90 (s, 1H), 7.19 (d, J=3.2, 1H), 7.15–7.13 (overlapping m, 3H), 7.10 (s, 1H), 6.87 (dd, J=8.0, 10.2, 1H), 6.82–6.80 (overlapping m, 2H), 6.71 (dd, J=4.9, 8.0, 1H), 6.54 (d, J=3.2, 1H), 5.08 (s, 2H); LC/MS: (ES+) m/z (M+H)$^+$=292, HPLC R$_t$=1.413.

Intermediate 26

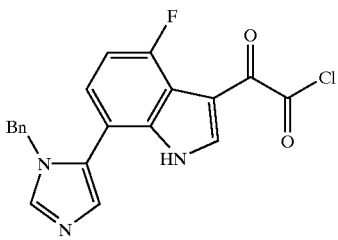

To the imidazole intermediate 25 (26.7 mg, 0.092 mmol) was added a solution of oxalyl chloride in dichloromethane (1.0 ml, 2.90 mmol, 2 M). The mixture was stirred at room temperature for 5 hours and the volatile evaporated under a stream of nitrogen to give a yellow solid product, which was further dried under high vacuum.

Intermediate 27

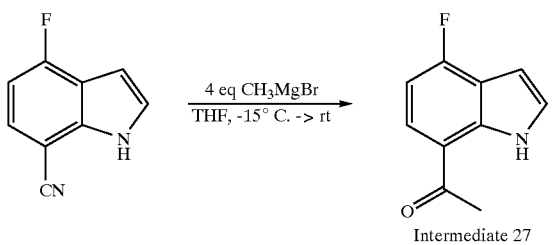

To an oven dried 250 ml flask was charged with CH$_3$MgBr (16.7 ml, 50 mmol, 3 M in Et$_2$O) at r.t. under N$_2$. It was then cooled down to −18° C. in a NaCl/ice bath, and 7-cyano-4-fluoroindole (2.0 g, 12.5 mmol) in dry THF (100 ml) was added dropwise using an addition funnel over 45 min. After 10 min, the reaction mixture was allowed to warm to r.t., and stirred for 2 hr. The reaction was slowly quenched with 5% sulfuric acid and the mixture stirred for 10 min. The reaction mixture was concentrated in vacuo and the residue poured into CHCl$_3$ (150 ml). After neutralization with aqueous NH$_3$ (50 ml), water (100 ml) was added, and the two layers were separated using a separation funnel. The aqueous layer was back extracted with CHCl$_3$ (2×100 ml), and the combined organic extracts washed with H$_2$O (100 ml), brine (100 ml), and dried (MgSO$_4$). After evaporation in vacuo, the resulted crude compound was purified by flash chromatography (20% EtOAc/Hexane) to give 7-acetyl-4-fluoroindole (1.3 g, 59%) as a light gray solid. $^1$H NMR: (CDCl$_3$) δ 10.55 (b s, 1H), 7.76 (dd, J=4.8, 8.3, 1H), 7.31 (app t, J=2.7, 1H), 6.83 (dd, J=8.4, 9.6, 1H), 6.67 (app t, J=2.9, 1H), 2.68 (s, 3H); HPLC R$_t$=1.343.

Intermediate 28

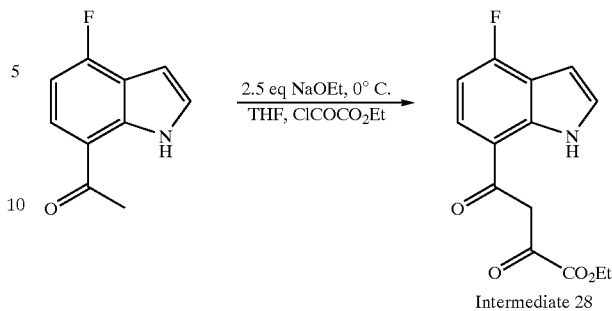

To the 7-acetyl-4-fluoroindole (500 mg, 2.82 mmol) in dry THF (10 ml) was added NaOEt (2.3 ml, 7.06 mmol, 21% w/w in EtOH) dropwise over 10 min at 0° C., and the resulting mixture stirred for 1 hr. Ethyl chlorooxoacetate (424 mg, 3.10 mmol) in dry THF (1 ml) was then added dropwise over 5 min. to the reaction mixture. After stirring for another 3 hr at 0° C., the reaction was quenched with 1 N hydrochloric acid to pH ~4, and added CH$_2$Cl$_2$ (50 ml). The organic layer was separated, washed with H$_2$O (30 ml) and brine (30 ml), dried (MgSO$_4$), and evaporated in vacuo. The residue was purified by flash chromatography (30 to 50% EtOAc/Hexane) to give the a,y-diketoester (464 mg, 59%) as yellow solids. $^1$H NMR (CDCl$_3$, indicated an enol form) δ 10.50 (b s, 1H), 7.84 (dd, J=4.8, 8.5, 1H), 7.34 (appt, J=2.7, 1H), 7.2 (s, 1H), 6.88 (dd, J=8.5, 9.5, 1H), 6.70 (dd, J=2.4, 3.2, 1H), 4.42 (q, J=7.2, 2H), 1.43 (t, J=7.2, 3H); HPLC R$_t$=1.393.

Intermediate 29

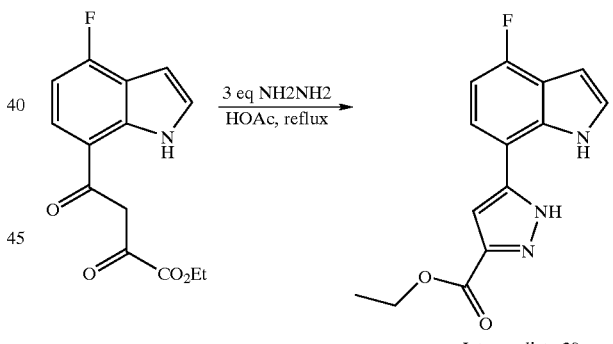

An oven dried 15 ml flask was charged with the α,γ-diketoester intermediate 28 (180 mg, 0.650 mmol) and HOAc (5 ml), followed by anhydrous hydrazine (61 μl, 1.95 mmol) at r.t. The mixture was then refluxed at 140° C. under N$_2$ for 3 hr. After cooling to r.t., the volatile was evaporated in vacuo. The residue was dissolved in CH$_2$Cl$_2$ (50 ml), and the resulting solution washed with H$_2$O (2×30 ml) and dried (MgSO$_4$). After evaporation in vacuo, the yellow solid residue was triturated with ether (2×0.5 ml) and dried under high vacuum to afford the ethyl pyrrazole-3-carboxylate (110 mg, 62%) as yellow solids. $^1$H NMR (CDCl$_3$) δ 10.33 (b s, 1H), 7.46 (dd, J=4.7, 8.1, 1H), 7.31 (app t, J=2.7, 1H), 6.84 (dd, J=8.1, 9.9, 1H), 6.68 (dd, J=2.4, 3.2, 1H), 4.45 (q, J=7.1, 2H), 1.44 (t, J=7.2, 3H); LC/MS: (ES+) m/z (M+H)$^+$= 274, HPLC R$_t$=1.717.

Intermediate 30

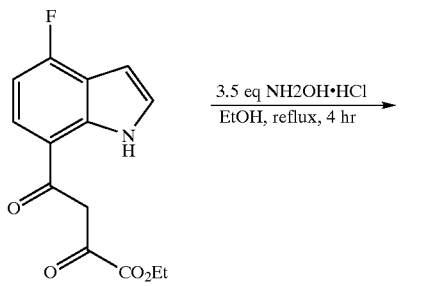

3.5 eq NH2OH·HCl
EtOH, reflux, 4 hr

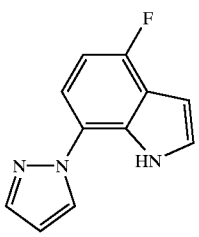

Intermediate 30

An oven dried 50 ml flask was charged with the α,γ-diketoester intermediate 28 (437 mg, 1.58 mmol) and absolute ethanol (20 ml) to give a suspension, which at rt was added hydroxyamine hydrochloride (387 mg, 5.52 mmol). The reaction mixture was refluxed at 85° C. for 4 h, then cooled to rt and evaporated in vacuo. The solution of the residue in CH$_2$Cl$_2$ (100 ml) was washed with H$_2$O (2×20 ml) and brine (20 ml), and dried (MgSO4). After evaporation in vacuo, the solids obtained were triturated with dry ether (2×1 ml) to give the ethyl isoxazole-3-carboxylate as a light yellow solid (384 mg, 89%). $^1$H NMR (CDCl3), δ 9.47 (b s, 1H), 7.51 (dd, J=4.8, 8.3, 1H), 7.36 (app t, J=2.8, 1H), 6.97 (s, 1H), 6.90 (dd, J=8.4, 9.5, 1H), 6.74 (dd, J=2.3, 3.1, 1H), 4.5 (q, J=7.1, 2H), 1.47 (t, J=7.1, 3H); LC/MS: (ES+) m/z (M+H)$^+$=275, HPLC (0.2% H$_3$PO$_4$ buffer, gradient time=4 min, flow rate=2 ml/min) R$_t$=4.60.

Intermediate 31

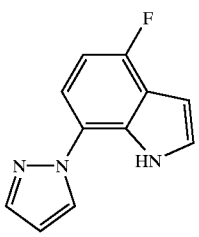

Intermediate 31 was prepared by heating a mixture of intermediate 1 (1.0 g, 4.67 mmol), pyrazole (636 mg, 9.34 mmol), Cs$_2$CO$_3$ (3.04 g, 9.33 mmol) and CuBr (134 mg, 0.934 mmol) in PhNO$_2$ (2.0 ml) in a reusable sealed tube at 140° C. for 20 h. The crude product was used without further purification. $^1$H NMR: (CDCl$_3$) δ 10.46 (b s, 1H), 8.06 (d, J=2.6, 1H), 7.78 (d, J=1.7, 1H), 7.30 (t, J=2.7, 1H), 7.18 (dd, J=8.4, 3.9, 1H), 6.80 (app t, 1H), 6.68 (t, J=2.7, 1H), 6.51 (t, J=2.0, 1H); LC/MS: (ES+) m/z (M+H)$^+$=202, HPLC R$_t$=1.437.

Intermediate 32

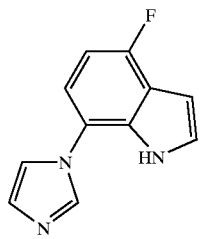

Intermediate 32 was prepared in the same manner as intermediate 31. The crude product was used without further purification. LC/MS: (ES+) m/z (M+H)$^+$=202, HPLC R$_t$=0.893.

Intermediate 33

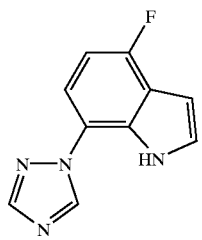

Intermediate 33 was prepared in the same manner as intermediate 31. The crude product was purified by preparative TLC (5% MeOH/CH$_2$Cl$_2$, 500 μm×20 cm×20 cm plates). The position of indole ring at the triazole N1 was supported by NOE studies. $^1$H NMR: (CD$_3$OD) δ 9.07 (s, 1H), 8.28 (s, 1H), 7.43 (dd, J=8.5, 4.0, 1H), 7.37 (d, J=3.2, 1H), 6.84 (dd, J=9.6, 8.5, 1H), 6.64 (d, J=3.2, 1 H); LC/MS: (ES+) m/z (M+H)$^+$=203, HPLC R$_t$=1.223.

Intermediate 34a, b, c

Intermediate 34a

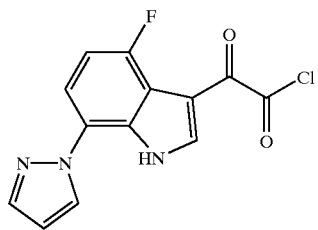

34b

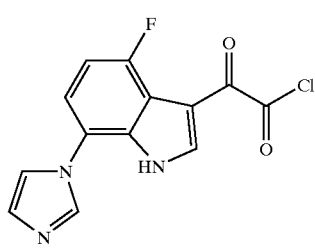

-continued

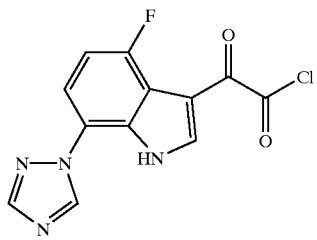

34c

Intermediate 34a, b, and c were prepared in the same manner as intermediate 26.

Intermediate 35

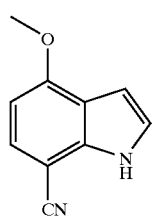

To an oven dried 500 ml round bottom flask at rt. was charged with 4-methoxy-7-bromo-indole intermediate 5 (12.8 g, 56.6 mmol) and dry DMF (120 ml), followed by CuCN (25.3 g, 283 mmol). The reaction mixture was refluxed at 165° C. for 16 hr. After cooling to rt., the mixture was slowly added ammonium hydroxide (100 ml), stirred for 10 min, concentrated in vacuo to ~50 ml and diluted with CHCl$_3$ (250 ml). The organic mixture was washed with H$_2$O (250 ml), and the aqueous layer back extracted with CHCl$_3$ (2×200 ml). The combined organic extracts were filtered through a filter paper to remove some solids, and washed again with H$_2$O (100 ml) and brine (100 ml), and then dried (MgSO$_4$). After evaporation in vacuo, the residue was purified by flash column chromatography (10% EtOAc/Hexane (250 ml), then 25% EtOAc/Hexanes (1250 ml)) to afford 4-methoxy-7-cyanoindole intermediate 35 (8.0 g, 82%) as yellow solids. $^1$H NMR: (CDCl$_3$) δ 8.73 (b s, 1H), 7.50 (d, J=8.3 Hz), 7.22 (app t, J=2.8 Hz, 1H), 6.73 (dd, J=2.3, 3.2 Hz, 1H), 6.58 (d, J=8.3 Hz, 1H), 4.01 (s, 3H); LC/MS: (ES+) m/z (M+H)$^+$=173, HPLC (YMC C18 S7 3×50 mm, Flow Rate 4 ml/min, Gradient Time 3 min) R$_t$=1.700.

Intermediate 36

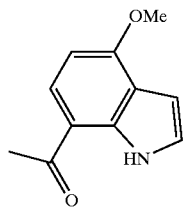

Intermediate 36 was prepared in the same manner as intermediate 27. The crude product was used without further purification. $^1$H NMR: (CDCl$_3$) δ 10.48 (b s, 1H), 7.77 (d, J=8.4, 1H), 7.22 (app t, 1H), 6.67 (dd, J=3.1, 2.4, 1H), 6.56 (d, J=8.4, 1H), 4.04 (s, 3H), 2.65 (s, 3H); LC/MS: (ES+) m/z (M+H)$^+$=190, HPLC R$_t$=1.277.

Intermediate 37

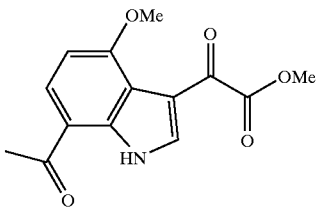

A mixture of intermediate 36 (153.3 mg, 0.81 mmol) and AlCl$_3$ (864.0 mg, 6.48 mmol) in CH$_2$Cl$_2$ (3.0 ml) was stirred at 0° C. for 2 h before adding methyl chlorooxoacetate (0.9 ml, 9.79 mmol). The mixture was stirred at 0° C. for 2 h, left standing in a freezer for 15 h and then stirred at 0° C. again for 5 h. After which time, the mixture was carefully added water (~10 ml) and extracted with EtOAc (30 ml). The organic extract was evaporated in vacuo and purified by flash chromatography (2% to 5% MeOH/CH$_2$Cl$_2$) to give intermediate 37. $^1$H NMR: (CD$_3$OD) δ 8.12 (s, 1H), 8.01 (d, J=8.5, 1H), 6.86 (d, J=8.5, 1H), 4.00 (s, 3H), 3.91 (s, 3H), 2.64 (s, 3H); LC/MS: (ES+) m/z (M+H)$^+$=276, HPLC R$_t$=1.140.

Intermediate 38

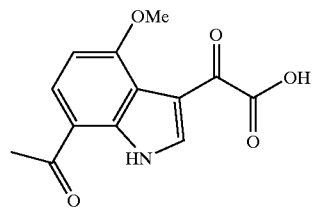

Intermediate 37 (30.0 mg, 0.109 mmol) was hydrolysed using NaOH (1 N, aq.) in MeOH. After reaction, the mixture was concentrated, and the residue obtained dissolved in water and acidified with HCl (1 N, aq.). The aqueous mixture was filtered and the filtrate evaporated to give intermediate 38, which was used without further purification. LC/MS: (ES+) m/z (M+H)$^+$=262, HPLC R$_t$=0.833.

Intermediate 39

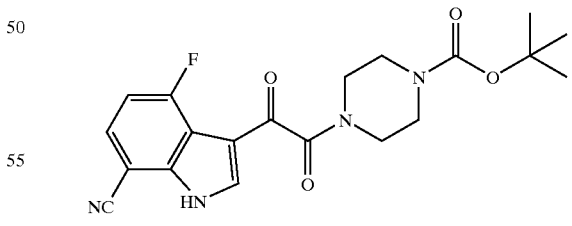

Intermediate 39 was prepared analogously to intermediate 12 by coupling intermediate 11 with 1-tert-butyl piperazinecarboxylate, and purified by preparative TLC (60% EtOAc/Hexane, 500 μm×20 cm×20 cm plates). $^1$H NMR: (CDCl$_3$) δ 9.68, (b s, 1H), 8.19 (d, J=3, 1H), 7.64 (dd, J=8.4, 4.2, 1H), 7.08 (dd, J=10.0, 8.4, 1H), 3.74 (app t, 2H), 3.57 (app t, 2H), 3.51 (b s, 4H), 1.48 (s, 9H); LC/MS: (ES+) m/z (M+H)$^+$=401, HPLC R$_t$=1.453.

Intermediate 40

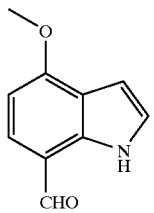

To an oven dried 250 ml round bottom flask was charged 7-bromo-4-methoxyindole intermediate 5 (5.0 g, 22.2 mmol) and dry THF (100 ml) at rt. The mixture was cooled to −78° C., and added "BuLi (26.7 ml, 66.7 mmol, 2.5 M in hexanes) dropwise via a syringe over 30 min. After 10 min., the mixture was warmed to 0° C. and stirred for 30 min. The mixture was then cooled to −78° C., and added anhydrous DMF (8.6 ml, 111 mmol) dropwise over 5 min. After 10 min., the mixture was warmed gradually to rt. and stirred for 2 hr. The reaction was then quenched by adding $H_2O$ (100 ml) and the mixture extracted with $Et_2O$ (3×100 ml). The combined organic extracts were washed with brine (100 ml) and dried ($MgSO_4$). After evaporation in vacuo, the residue was purified by flash column chromatography (EtOAc/hexane) to afford the aldehyde 40 (3.7 g, 95%) as a white solid. $^1$H NMR: (300 MHz, $CDCl_3$) δ 10.15 (b s, 1H), 9.96 (s, 1H), 7.62 (d, J=7.8 Hz, 1H), 7.21–7.26 (m, 1H), 6.67–6.72 (m, 1H), 6.66 (d, J=8.4 Hz, 1H), 4.06 (s, 3H); LC/MS: (ES+) m/z (M+H)$^+$=176, HPLC (YMC C18 S7 3×50 mm, Flow Rate 4 ml/min, Gradient Time 2 min) $R_t$=1.196.

Intermediate 41

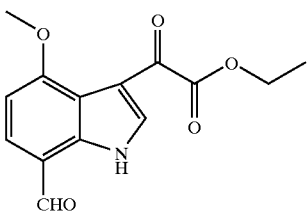

To an oven dried 100 ml round bottom flask was charged with the aldehyde 40 (1.78 g, 10.2 mmol) and anhydrous $CH_2Cl_2$ (60 ml) to give a solution, which was cooled to 0° C., and added $AlCl_3$ (2.72 g, 20.3 mmol) portionwise. The color of the reaction mixture turned purple immediately and was stirred at 0° C. for 3 hr. Ethyl chlorooxoacetate (2.77 g, 2.27 ml, 20.3 mmol) was then added dropwise to the mixture via a syringe. After stirring for 1 hr, the reaction mixture was warmed to rt., and stirred overnight. The reaction was then quenched with hydrochloric acid (30 ml, 1 N), $H_2O$ (100 ml), and the resulting mixture extracted with $CHCl_3$ (3×100 ml). The combined organic extracts were washed with $H_2O$ (100 ml), brine (100 ml) and dried ($MgSO_4$). After evaporation in vacuo, the residue was purified by flash column chromatography (30~50% EtOAc/hexane) to give the expected intermediate 41 (1.3 g, 46%). $^1$H NMR: ($CDCl_3$) δ 10.76 (b s, 1H), 9.97 (s, 1H), 8.18 (d, J=3 Hz, 1H), 7.71 (d, J=8.3 Hz, 1H), 6.79 (d, J=8.3 Hz, 1H), (4.40 (q, J=7.2 Hz, 2H), 4.03 (s, 3H), 1.40 (t, J=5 7.2 Hz, 3H); LC/MS: (ES+) m/z (M+H)$^+$=276, HPLC (YMC C18 S7 3×50 mm, Flow Rate 4 ml/min, Gradient Time 2 min) $R_t$=1.200.

Intermediate 42

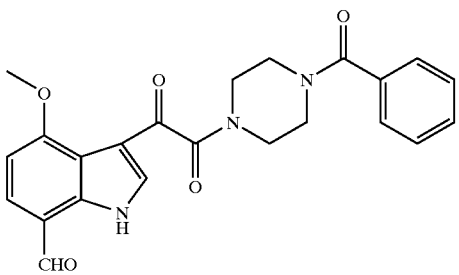

To the ethyl ester intermediate 41 (1.3 g, 4.73 mmol) in MeOH (50 ml) at rt. was added aqueous NaOH (2 ml, 10 mmol, 5 N), and the mixture stirred overnight. After removing part of the solvent in vacuo, the residue was acidified with concentrated hydrochloric acid to pH ~2 to form a white solid. The solid was filtered, washed with $H_2O$ (2 ml) and dried to give 1.4 g of the acid, which was used directly in the coupling reaction without further purification. To the acid in DMF (50 ml) was added benzoylpiperazine hydrochloride (1.18 g, 5.20 mmol), N,N-diisopropylethylamine (3.06 g, 4.1 ml, 23.7 mmol) and 3-(diethoxyphosphoryloxy)-1,2,3-benzotriazo-4(3H)-one (1.56 g, 5.20 mmol). The reaction mixture was stirred at rt. overnight. After removing part of the solvent in vacuo, the residue was dissolved in $CH_2Cl_2$ (200 ml), and washed with $NaHCO_3$ (100 ml, sat. aq.), $H_2O$ (100 ml), brine (100 ml), and dried ($MgSO_4$). After evaporation in vacuo, the crude compound was purified by flash column chromatography to give the desired intermediate 42 (1.64 g, 83% two steps). $^1$H NMR: ($CDCl_3$) δ0 10.8 (b s, 1H), 9.98 (s, 1H), 8.09 (s, 1H), 7.73 (d, J=8.0 Hz, 1H), 7.56–7.32 (b, 5H), 6.82 (d, J=8.1 Hz, 1H), 4.06 (s, 3H), 3.324.2 (m, 8H); LC/MS: (ES+) m/z (M+H)$^+$=30 420, HPLC (YMC C18 S7 3×50 mm, Flow Rate 4 ml/min, Gradient Time 2 min) $R_t$=1.213.

Intermediate 43

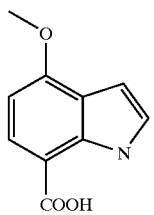

A mixture of 4-methoxy-7-cyanoindole (intermediate 35) in EtOH (20 ml) was added to a solution of KOH (2.45 g, 43.8 mmol) in $H_2O$ (2 ml) at rt., and the reaction mixture refluxed overnight. After cooling to rt., the solvent was partially removed in vacuo, and the residue acidified with 10% hydrochloric acid to pH ~2. The resulting white precipitates weres filtered and washed with $CH_2Cl_2$ (4×10 ml). The combined organic washings were washed with $H_2O$ (10 ml), dried ($MgSO_4$) and evaporated in vacuo to afford 2.1 g of the crude acid, which was used in the next step without further purification. LC/MS: (ES+) m/z (M+H)$^+$=192, HPLC (YMC C18 S7 3×50 mm, Flow Rate 4 ml/min, Gradient Time 2 min) $R_t$=1.217.

Intermediate 44

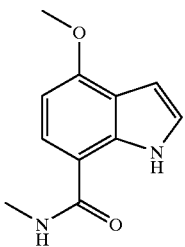

To a mixture of the acid intermediate 43 (179.3 mg, 0.94 mmol) in MeOH/PhH (6 ml, 50:50) at rt. was added TMSCHN₂ (4 ml, ~2 M in hexane) dropwise, and the mixture stirred for 1 hr. The solvent and excess reagent were removed in vacuo, and the residue dissolved in MeOH and then purified by reverse phase preparative HPLC to give the methyl ester (165.2 mg, 86%); $^1$H NMR: (the methyl ester CDCl₃) δ 9.85 (b s, 1H), 7.87 (d, J=8.4 Hz, 1H), 7.21 (t, J=2.7 Hz, 1H), 6.68 (t, J=2.8 Hz, 1H), 6.56 (d, J=8.4 Hz, 1H), 4.02 (s, 3H), 3.96 (s, 3H). The methyl ester was treated with CH₃NH₂ (4 ml, 40% in H₂O) and stirred at rt. overnight. After removing the excess reagent in vacuo, the residue was purified by reverse phase preparative HPLC to afford the methylamide (134.8 mg, 82%); LC/MS (the methylamide): (ES+) m/z (M+H)⁺=205, HPLC (YMC C18 S7 3×50 mm, Flow Rate 4 ml/min, Gradient Time 2 min) $R_f$=1.400.

Intermediate 45

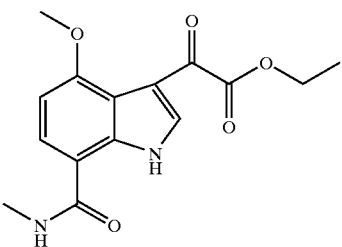

To a mixture of the methylamide intermediate 44 (80 mg, 0.392 mmol) in CH₂Cl₂ (10 ml) at 0° C. was added AlCl₃ (104.5 mg, 0.784 mmol). The reaction mixture stirred for 3 hr at 0° C., added ethyl chlorooxoacetate (88 μl, 0.788 mmol), and then stirred for a further 1 hr at 0° C. before warming to rt. and stirred overnight. The mixture was then acidified with 1 N hydrochloric acid to pH<7, followed by usual aqueous work-up (extracted with CHCl₃). The color of the combined organic extracts turned purple during removal of the solvent in vacuo. The purple residue obtained was purified by flash column chromatography (EtOAc/hexane) to give the expected intermediate 45 (17 mg, 14%) as a gray solid. $^1$H NMR: (CDCl₃) δ 11.20 (b s, 1H), 11.19 (b s, 1H), 8.18 (d, J=3.1 Hz, 1H), 7.40 (d, J=8.4 Hz, 1H), 6.65 (d, J=8.4 Hz, 1H), 4.40 (q, J=7.2 Hz, 2H), 3.98 (s, 3H), 3.05 (d, J=3.1 Hz, 3H), 1.39 (t, J=7.2 Hz, 3H); LC/MS: (ES+) m/z (M+H)⁺=305, HPLC (YMC C18 S7 3×50 mm, Flow Rate 5 ml/min, Gradient Time 2 min) $R_f$=1.180.

Intermediate 46

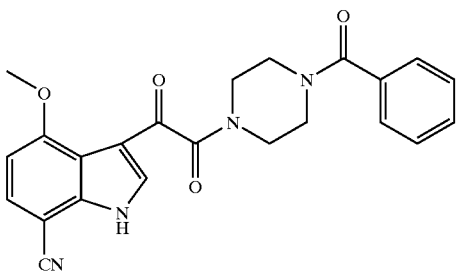

To an oven dried 100 ml round bottom flask was charged with 4-methoxy-7-cyanoindole intermediate 35 (0.902 g, 5.24 mmol) and 1,2-dichloroethane (30 ml) at rt. to give a solution. Oxalyl chloride (2.3 ml, 26.2 mmol) was added dropwise and the reaction mixture was refluxed at ~85° C. for 3 hr. After cooling to rt., the solvent and excess reagent were removed in vacuo. The residue was dissolved in THF (30 ml), and the mixture added benzoylpiperzine hydrochloride salt (1.43 g, 6.29 mmol) and then stirred for 10 min. The suspension was then cooled to 0° C., added dropwise N,N-diisopropylethylamine (3.39 g, 4.6 ml, 26.2 mmol) and stirred for 5 min. After stirring at rt. for 1 hr., the solvent was partially removed in vacuo, and the resulting mixture dissolved in MeOH and purified by reverse phase preparative HPLC to afford intermediate 46 as a light yellow solid (1.26 g, 58% two steps). $^1$H NMR: (CD₃OD) δ 8.17 (s, 1H), 7.66 (d, J=8.4 Hz, 1H), 7.47 (b s, 5H), 6.90 (d, J=8.4 Hz, 1H), 4.00 (s, 3H), 3.44–3.97 (m, 5H); LC/MS: (ES+) m/z (M+H)⁺=417, HPLC (YMC C18 S7 3×50 mm, Flow Rate 4 ml/min, Gradient Time 2 min) $R_f$=1.220.

Alternatively, intermediate 46 was prepared from 4-methoxy-7-cyanoindole intermediate 35 in 3 steps: (1) acylation: methyl chlorooxoacetate, AlCl₃, CH₂Cl₂ 0° C. to r.t.; (2) hydrolysis: 1N NaOH (aq.), MeOH, r.t.; and (3) coupling: benzoylpiperazine hydrochloride, EDC, DMAP, NMM, DMF, r.t.

Intermediate 47

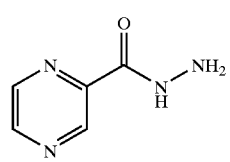

A solution of methyl pyrazinecarboxylate (600 mg, 4.34 mmol) in hydrazine (3 ml) was stirred overnight for 20 hours, then at 60° C. for 4 hours. Removal of excess hydrazine under high vacuum afforded pyrazine hydrazide intermediate 47 as a yellow solid (550 mg, 92%). $^1$H NMR: (CD₃OD) δ 9.19 (d, J=1.5, 1H), 8.76 (d, J=2.4, 1H), 8.65 (app t, 1H); LC/MS: (ES+) m/z (M+H)⁺=139, HPLC $R_f$=0.087.

Intermediate 48

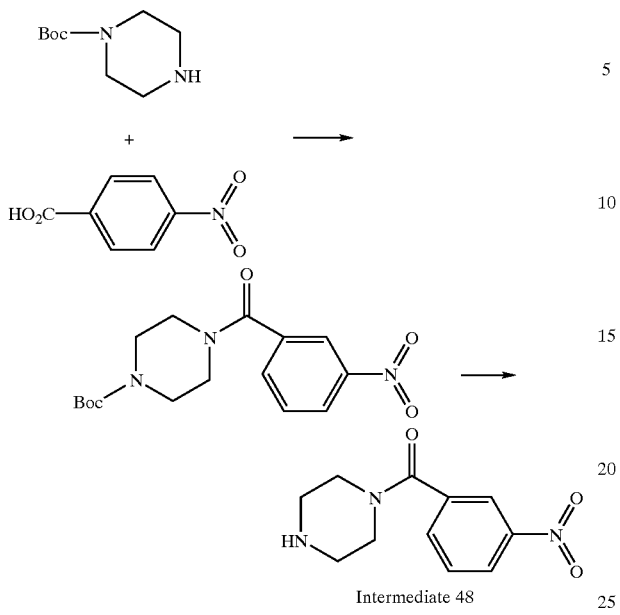

Intermediate 48

To a mixture of Boc-piperazine (3.678 g, 19.7 mmol) and 4-nitrobenzoic acid (3.0 g, 18 mmol) in $CH_2Cl_2$ (50 ml) was added DMAP (3.290 g, 26.9 mmol) and EDC (5.146 g, 26.9 mmol). The reaction mixture was stirred at room temperature for 16 hours, and then diluted with $CH_2Cl_2$ (50 ml). The organic mixture was washed with hydrochloric acid (2×100 ml, 1 N, aq.) and water (250 ml), dried ($MgSO_4$), filtered, and then evaporated in vacuo to afford the amide intermediate as a white solid (5.80 g, 96%). The amide intermediate was subsequently charged with a solution of hydrogen chloride in dioxane (20 ml, 4 M). The reaction mixture was stirred at room temperature for 4 hours. Removal of the excess reagent under high vacuum afforded Intermediate 48 as a white solid (4.67 g, 99%). $^1$H NMR ($CD_3OD$) δ 8.38 (m, 2H), 7.90 (m, 1H), 7.75 (m, 1H), 4.10–3.54 (b m, 8H); LC/MS (ES+) m/z (M+H)$^+$=236, HPLC $R_t$=0.193.

Intermediate 49

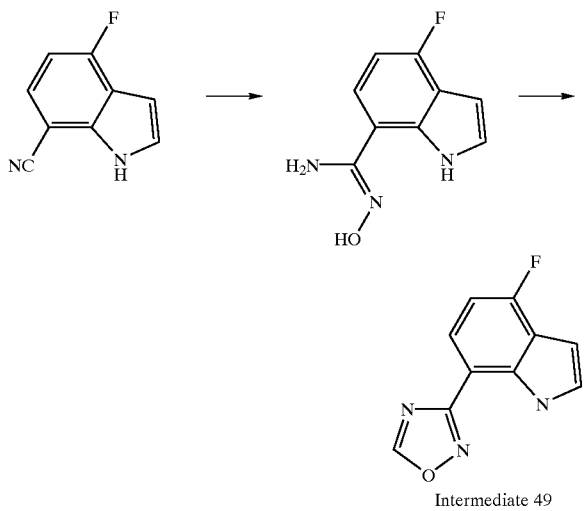

Intermediate 49

To a mixture of 4-fluoro-7-cyanoindole (reference 102, 1.0 g, 6.24 mmol) in EtOH (50 ml) was added hydroxylamine hydrochloride (651 mg, 9.37 mmol) and triethylamine (1.7 ml). The reaction mixture was refluxed for 16 hours. After removal of the volatile under high vacuum, the residue was added water (10 ml) and filtered to afford the crude hydroxyamindine intermediate. To this intermediate was added triethylorthoformate (10 ml) and the mixture heated at 110° C. for 16 hours. After removal of most of the excess reagent, the residue was purified by flash chromatography with ($CH_2Cl_2$) to give intermediate 49 as pale yellow solid (419 mg, 33%). $^1$H NMR ($CDCl_3$) δ 9.90 (s, 1H), 8.80 (s, 1H), 8.01 (app dd, J=8.3, 4.8, 1H), 7.34 (app t, J=2.8, 1H), 6.93 (app dd, J=9.8, 8.3, 1H), 6/74 (app dd, J=3.2, 2.3, 1H); LC/MS (ES+) m/z (M+H)$^+$=204, HPLC $R_t$=1.910.

Intermediate 50

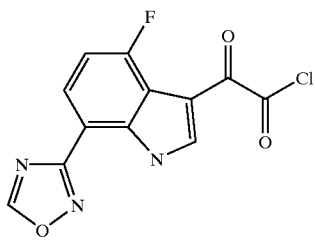

To a solution of intermediate 49 (200 mg, 0.984) in $CH_2Cl_2$ (10 ml) was added oxalyl chloride (1 ml), and the reaction mixture stirred under gentle reflux for 16 hours. Removal of solvent in vacuo and the excess reagent under high vacuum afforded intermediate 50 as a yellow solid, which was used without further purification.

II. PREPARATION OF FORMULA I COMPOUNDS

Example 1

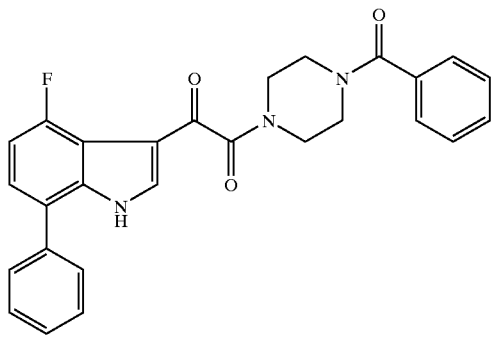

Example of the general procedure for bromide/aryl- or heteroaryl-stannane coupling as described in Schemes 1 and 3:

To the 7-bromoindole, intermediate 4, (100 mg, 0.218 mmol) in 3 mL of anhydrous 1,4-dioxane was added 1.2 eq. of tri-n-butylphenyltin (96 mg, 0.262 mmol), and tetrakis (triphenylphosphine)palladium(0) (10 mg, 0.009 mmol). The reaction mixture was heated at 120° C. for 48 h. The reaction mixture was dissolved in EtOAc (10 mL) then washed with water (2×10 mL), dried (brine, $MgSO_4$) and concentrated in vacuo. The resulting material was purified by $SiO_2$ flash column chromatography (EtOAc, $R_f$=0.2–0.6) using a gradient system (1:1 to 4:1 ) EtOAc/Hexanes to give a yellow solid. $^1$H NMR (CDCl$_3$) δ 3.5–3.8 (m, 8H), 7.05 (dd, 1H), 7.25 (t, 1H), 7.35–7.45 (s, 5H), 7.5–7.6 (m, 4H), 7.65 (dd, 1H), 8.02 (d, 1H), 9.45 (s, 1H). MS m/e 456.07 (MH$^+$).

Example 2

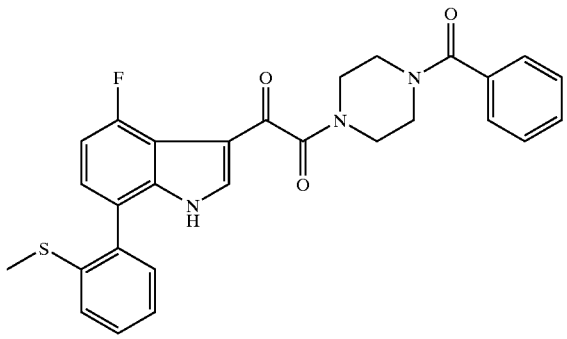

The 7-bromoindole, intermediate 4, (100 mg, 0.218 mmol), (2-methylthio)phenylboronic acid (44 mg, 0.262 mmol), tetrakis(triphenylphosphine) palladium(0) (10 mg, 0.009 mmol), and powdered potassium carbonate (60 mg, 0.436 mmol) were dissolved in DMF/water (3 mL, 2:1) and placed into a sealed glass reaction tube. The mixture was heated under nitrogen at 120° C. for 48 h. The reaction mixture was dissolved in 10 mL EtOAc then washed with 10 mL of water (×2), dried (brine, MgSO$_4$) and concentrated in vacuo. The resulting material was purified by SiO$_2$ flash column chromatography (EtOAc, R$_f$=0.2–0.6) using a gradient system (1:1 to 4:1) EtOAc/Hexanes to give a white solid. $^1$H NMR (CDCl$_3$) δ 2.35 (s, 3H), 3.5–3.8 (m, 8H), 7.05 (t, 1H), 7.19 (m, 1H), 7.27 (d, 2H), 7.32 (d, 1H), 7.35–7.45 (m, 6H), 8.05 (s, 1H), 8.78 (s, 1H). MS m/e 502.04 (MH$^+$).

Example 3

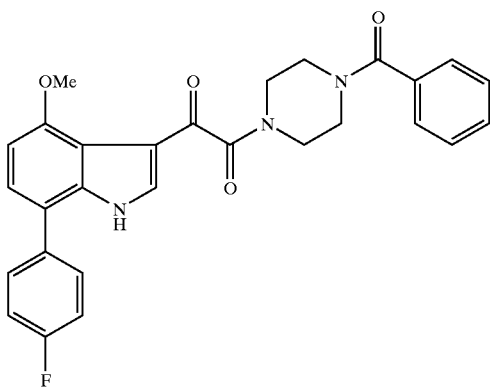

Prepared in the same manner as the compound of Example 2 using intermediate 6 and 4-Fluorophenyl boronic acid. $^1$H NMR (CDCl$_3$) δ 3.5–3.8 (m, 8H), 3.96 (s, 3H), 6.77 (d, 1H), 7.19 (t, 2H), 7.35–7.45 (s, 5H), 7.47 (m, 2H), 7.66 (m, 1H), 7.98 (s, 1H), 9.11 (s, 1H). MS m/e 486.11 (MH$^+$).

Example 4

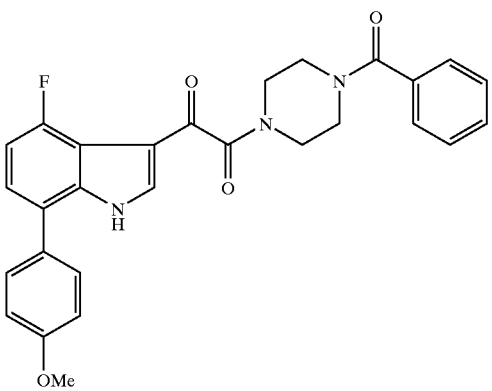

Prepared in the same manner as Example 2 from intermediate 4 and 4-methoxyphenyl boronic acid. $^1$H NMR (CDCl$_3$) δ 3.5–3.8 (m, 8H), 3.85 (s, 3H), 7.01 (d, 1H), 7.03 (d, 2H), 7.42 (d, 2H), 7.35–7.45 (s, 5 H), 8.00 (s, 1H). MS m/e 486.11 (MH$^+$).

Example 5

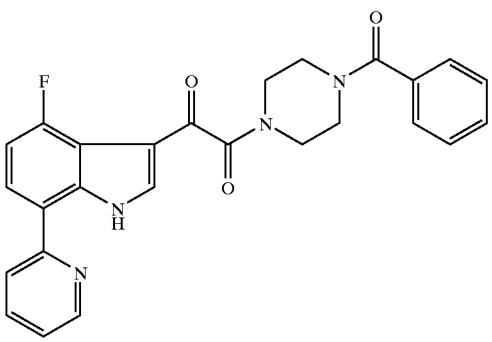

Prepared in the same manner as Example 1 from intermediate 4 and tri-n-butyl(2-pyridinyl)tin. $^1$H NMR (CDCl$_3$) δ 3.5–3.8 (m, 8H), 7.05 (t, 1H), 7.30 (t, 1H), 7.35–7.45 (s, 5H), 7.6–8.0 (m, 3H), 7.65 (dd, 1H), 8.17 (s, 1H), 8.64 (s, 1H). MS m/e 457.15 (MH$^+$).

Example 6

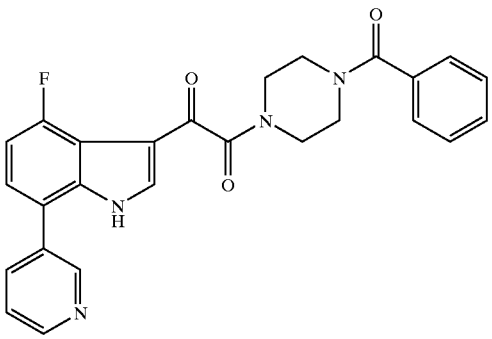

Prepared in the same manner as Example 1 from intermediate 4 and tri-n-butyl(3-pyridinyl)tin. $^1$H NMR (CDCl$_3$) δ 3.5–3.8 (m, 8H), 7.08 (t, 1H), 7.22 (m, 1H), 7.35–7.45 (s, 6H), 8.05 (t, 1H), 8.16 (s, 1H), 8.54 (d, 1H), 8.80 (s, 1H), 9.24 (s, 1H). MS m/e 457.21 (MH$^+$).

Example 7

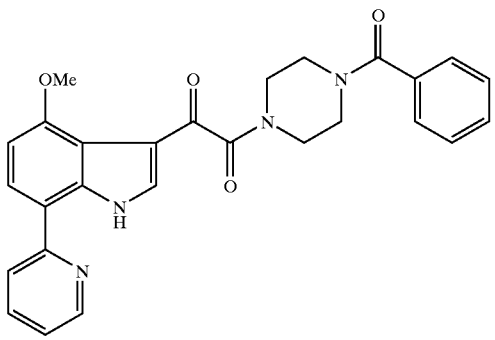

Prepared in the same manner as Example 1 using bromide intermediate 6 and tri-n-butyl(2-pyridinyl)tin. $^1$H NMR (CDCl$_3$) δ 3.5–3.8 (m, 8H), 4.00 (s, 3H), 6.78 (d, 1H), 7.21 (t, 1H), 7.42 (s, 5H), 7.78 (d, 1H), 7.82 (t, 1H), 7.95 (d, 1H), 8.11 (s, 1H), 8.56 (s, 1H). MS m/e 469.19 (MH$^+$).

Example 8

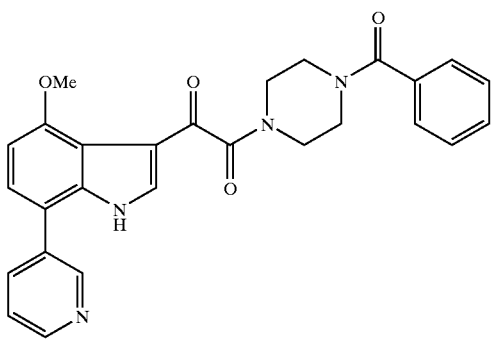

Prepared in the same manner as Example 1 using bromide intermediate 6 and tri-n-butyl(3-pyridinyl)tin. $^1$H NMR (CDCl$_3$) δ 3.5–3.8 (m, 8H), 4.06 (s, 3H), 6.79 (d, 1H), 7.22 (d, 1H), 7.35–7.45 (s, 6H), 7.99 (d, 1H), 8.05 (s, 1H), 8.51 (d, 1H), 8.73 (s, 1H), 9.18 (s, 1H). MS m/e 469.25 (MH$^+$).

Example 9

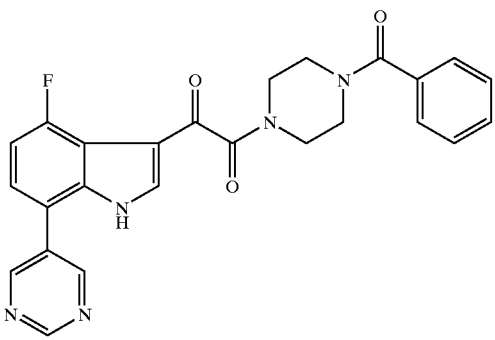

Prepared in the same manner as Example 1 using intermediate 4 and tri-n-butyl (5-pyrimidinyl)tin. $^1$H NMR (CDCl$_3$) δ 3.5–3.8 (m, 8H), 7.05 (t, 1H), 7.33 (dd, 1H), 7.35–7.45 (s, 5H), 8.15 (s, 1H), 9.39 (s, 1H), 9.54 (s, 2H), 9.59 (s, 1H). MS m/e 458.12 (MH$^+$).

Example 10

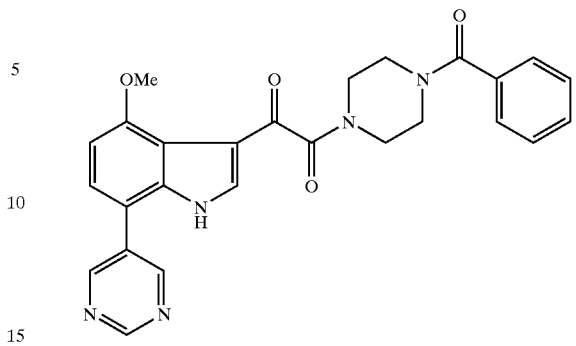

Prepared in the same manner as Example 1 using bromide intermediate 6 and tri-n-butyl (5-pyrimidinyl)tin. $^1$H NMR (CDCl$_3$) δ 3.5–3.8 (m, 8H), 7.05 (t, 1H), 7.33 (dd, 1H), 7.35–7.45 (s, 5H), 8.15 (s, 1H), 9.39 (s, 1H), 9.54 (s, 2H), 9.59 (s, 1H). MS m/e 458.12 (MH$^+$).

Example 11

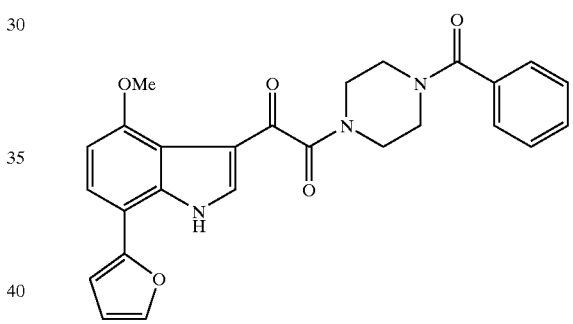

Prepared in the same manner as Example 2 using bromide intermediate 6 and 2-Furanyl boronic acid. MS m/e 458.06 (MH$^+$), HPLC R$_t$=1.427.

Example 12

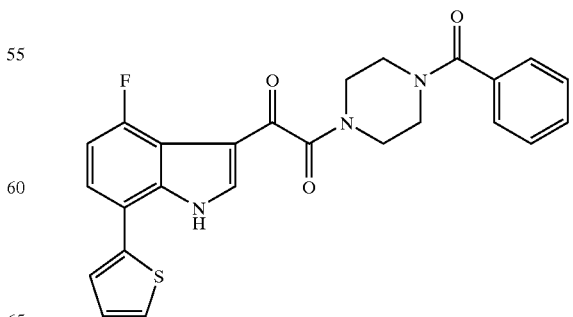

Prepared in the same manner as Example 1 using intermediate 4 and tri-n-butyl (2-thienyl)tin. $^1$H NMR (CDCl$_3$) δ 3.5–3. (m, 8H), 7.0 (t, 1H), 7.15 (t, 1H), 7.25–7.35 (m, 3H), 7.35–7.45 (s, 5H), 8.05 (d, 1H). MS m/e 462.16 (MH$^+$).

Example 13

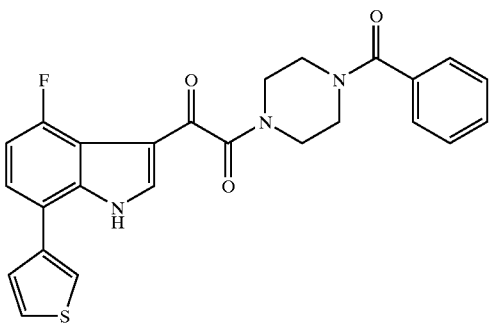

Prepared in the same manner as Example 2 from intermediate 4 and 3-Thienylboronic acid. $^1$H NMR (CDCl$_3$) δ 3.5–3.8 (m, 8H), 7.01 (t, 1H), 7.24–7.36 (m, 2H), 7.35–7.65 (m, 7H), 8.00 (s, 1H), 9.70 (s, 1H). MS m/e 462.04 (MH$^+$).

Example 14

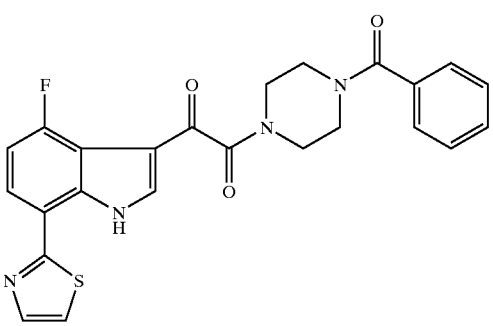

Prepared in the same manner as Example 2 from intermediate 4 and 2-Thiazolylboronic acid. $^1$H NMR (CDCl$_3$) δ 3.5–3.8 (m, 8H), 7.0 (t, 1H), 7.25 (m, 2H), 7.35–7.45 (s, 5H), 8.05 (s, 1H), 8.15 (s, 1H), 9.25 (s, 1H). MS m/e 463 (MH$^+$).

Example 15

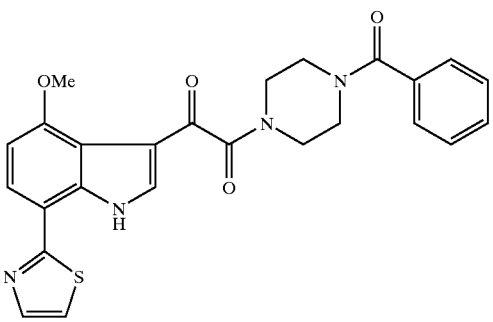

Prepared in the same manner as Example 2 using bromide intermediate 6 and 2-Thiazolyl boronic acid. $^1$H NMR (CDCl$_3$) δ 3.5–3.8 (m, 8H), 3.94 (s, 3H), 6.68 (d, 1H), 7.23 (d, 1H), 7.35–7.45 (s, 6H), 8.08 (s, 1H), 8.77 (s, 1H). MS m/e 475.15 (MH$^+$).

Example 16

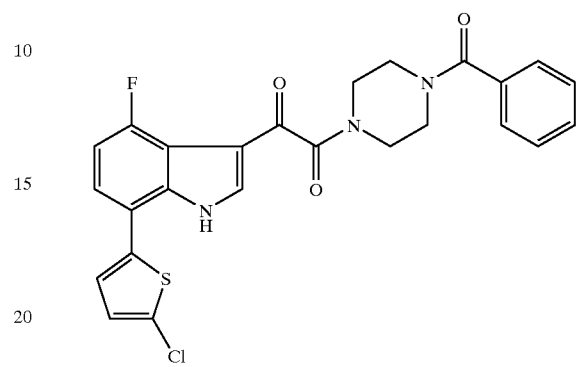

Prepared in the same manner as Example 2 from intermediate 4 and (5-Chlorothien-2-yl)boronic acid. $^1$H NMR (CDCl$_3$) δ 3.5–3.8 (m, 8H), 7.0 (t, 1H), 7.05 (m, 1H), 7.28 (t, 1H), 7.35–7.45 (s, 5H), 7.53–7.77 (m, 1H), 8.06 (d, 1H), 9.68 (s, 1H). MS m/e 496/497 (MH$^+$).

Example 17

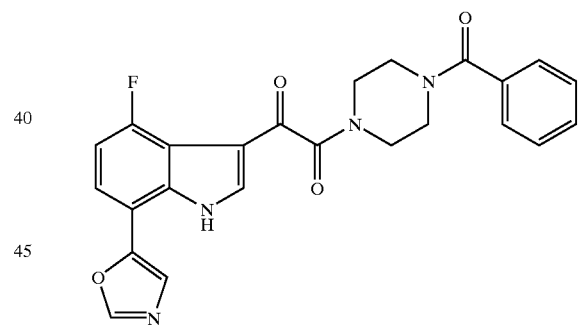

The indole carboxaldehyde, intermediate 10, (90 mg, 0.22 mmol), TOSMIC (43 mg, 0.22 mmol) and powdered K$_2$CO$_3$ (31 mg, 0.22 mmol) were dissolved in MeOH (2 mL) and the solution heated to reflux temperature for 3 h. The MeOH was concentrated in vacuo and the crude material was dissolved in EtOAc then washed with water (2×10 mL), dried (brine, MgSO$_4$) and concentrated in vacuo. The resulting material was purified by SiO$_2$ flash column chromatography (95:5) EtOAc/MeOH to give the product as a white solid (39 mg, 0.09 mmol, 40%). IR (KBr cm$^{-1}$) 3435 (br), 1635,1433, 1264, 1008, 710. $^1$H NMR (DMSO-d$_6$) δ 3.5 (m, 4H), 3.7 (m, 4H), 7.15 (t, J=5 Hz, 1H), 7.45 (m, 5H), 7.66 (m, 1H), 7.77 (s, 1H), 8.18 (s, 1H), 8.50 (s, 1H). MS m/e 447.15 (MH$^+$). Anal. Calcd for C$_{24}$H$_{19}$FN$_4$O$_4$.2.5H$_2$O: C, 58.65; H, 4.92; N, 11.40; Found: C, 58.85; H, 4.29; N, 11.29.

Example 18

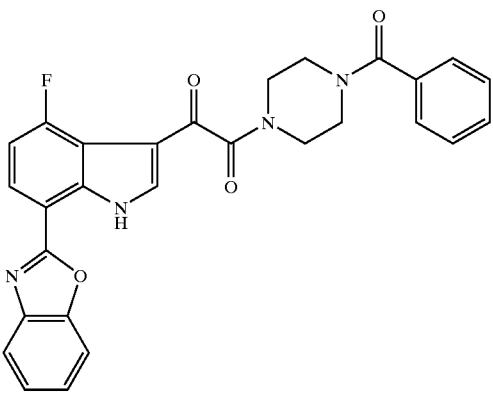

Prepared in the same manner as Example 1 from intermediate 4 and tri-n-butyl (2-benzoxazolyl)tin. $^1$H NMR (CDCl$_3$) δ 3.5–3.8 (m, 8H), 6.95 (t, 1H), 7.22 (m, 1H), 7.35–7.45 (m, 9H), 8.00 (s, 1H). MS m/e 497 (MH$^+$).

Example 19

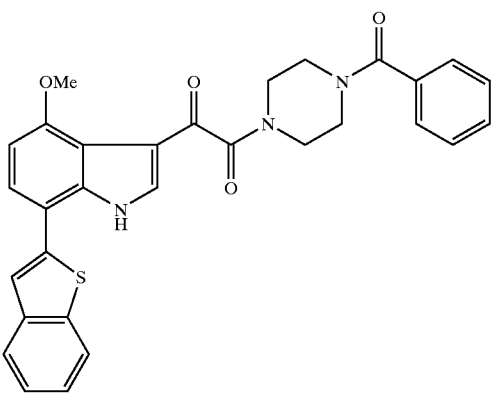

Prepared in the same manner as Example 1 using bromide intermediate 6 and tri-n-butyl (2-thianapthenyl)tin. $^1$H NMR (CDCl$_3$) δ 3.5–3.8 (m, 8H), 4.00 (s, 3H), 6.78 (d, 1H), 7.43 (m, 1H), 7.35–7.55 (m, 7H), 7.66 (m, 1H), 7.81 (d, 1H), 7.87 (d, 1H), 8.05 (s, 1H), 9.42 (s, 1H). MS m/e 524.01 (MH$^+$).

Example 20

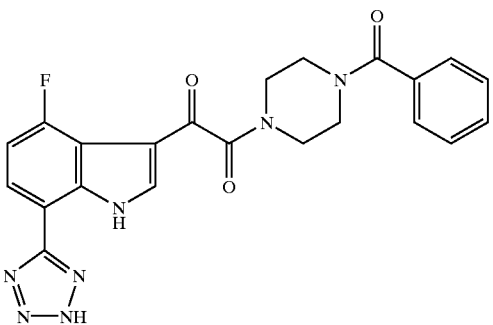

A mixture of intermediate 12 (95 mg, 0.23 mmol), NaN$_3$ (47 mg, 0.72 mmol), and NH$_4$Cl (38 mg, 0.71 mmol) in DMF (2 mL) was stirred at 85° C. for 12 h. The reaction mixture was then quenched with HCl (10 drops, 1 N aq.), diluted with MeOH (2 mL), and subjected to purification by preparative reverse phase HPLC to afford the tetrazole product as a white solid (61 mg, 59%). Separation method: Start %B=30, Final %B=100, Gradient time=10 min, Flow Rate=30 mL/min, Column: YMC C18 S5 30×100 mm, Fraction Collection: 6.16–6.68 min. $^1$H NMR (DMSO) δ 12.52 (s, 1H), 8.18 (s, 1H), 7.98 (app dd, J=8.0, 4.0, 1H), 7.44 (b s, 5H), 7.31 (app t, J=9.3, 1H), 4.35–3.20 (b, m, 8H). LC/MS (ES+) m/z (M+H)$^+$=448, HPLC R$_t$=1.223.

Example 21

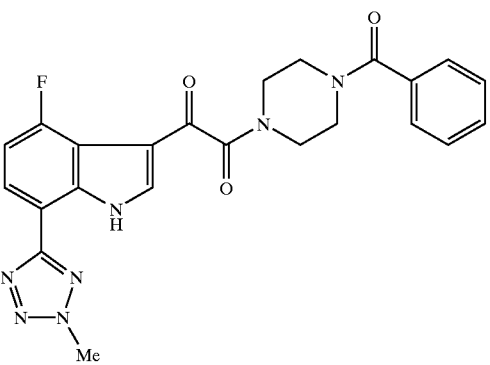

To a suspension of the compound of Example 20 (15 mg, 0.034 mmol) in a mixture of MeOH (0.2 mL)/benzene (0.4 mL) was added (trimethylsilyl)diazomethane (0.04 ml, 0.08 mmol, 2 M in hexane). The resulting mixture was stirred at rt for 90 min., then quenched with excess acetic acid and evaporated in vacuo. Purification was performed by preparative reverse phase HPLC using the method: Start %B=0, Final %B=85, Gradient time=12 min, Flow Rate=30 ml/min, Column: YMC C18 S5 20×50 mm, Fraction Collection: 9.05–9.42 min. The position of the methyl group at tetrazole N$^2$ was supported by H—N HMBC. $^1$H NMR (CDCl$_3$) δ 10.88 (s, 1H), 8.08 (s, 1H), 7.94 (app dd, J=8.3, 4.4, 1H), 7.30 (b s, 5H), 6.98 (app t, J=9.4, 1H), 4.35 (s, 3H), 3.80–3.35 (b, m, 8H); LC/MS (ES+) m/z (M+H)$^+$=462, HPLC R$_t$=1.340.

Example 22

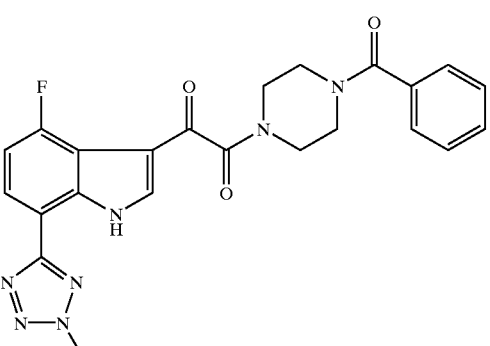

Example of Scheme 20. To a mixture of the tetrazole, intermediate 13, (20 mg, 98.4 μmol) in CH₃CN (1 mL) was added methyl bromoacetate (19 μL, 201 μmol) dropwise, followed by K₂CO₃ (16.3 mg, 118 μmol). The mixture was stirred at rt for 22 h and then evaporated in vacuo. The crude indole residue was then stirred in a solution of oxalyl chloride in CH₂Cl₂ (2.5 mL, 2 M) at rt for 21 h. After evaporation, the crude indole-3-glyoxyl chloride was dissolved in THF (1.0 mL), added excess hydrochloric acid (0.1 mL, 1 N aq. (or pyridine, 50 μl) and stirred at rt for 19 h. The reaction mixture was then diluted with water (10 mL), extracted with EtOAc (40 mL). The organic extract was washed with water (10 mL), dried (MgSO₄) and evaporated to give the crude indole-3-glyoxyl acid (36.6 mg). The glyoxyl acid was dissolved in DMF (1 mL) and to it was added intermediate 19 (35.5 mg, 0.157 mmol), DMAP (21.1 mg, 0.173 mmol), EDC (33.3 mg, 0.174 mmol) and NMM (37 μl, 0.337 mmol). The reaction mixture was stirred at rt for 20 h, and then diluted with water to induce precipitation. The precipitates were filtered, washed with hydrochloric acid (2×2 mL, 1 N aq.), followed by water, and dried under a stream of air for a short time. The crude material was purified by preparative TLC (EtOAc, 2×500 μm×20 cm×20 cm plates) to give the product shown above as a colorless glass (8.4 mg, 16% (4 steps from intermediate 13)). ¹H NMR (CDCl₃) δ 10.95 (b s, 1H), 8.22 (d, J=2.8, 1H), 8.12 (dd, J=8.3, 4.3, 1H), 7.43 (b s, 5H), 7.12 (app t, 1H), 5.55 (s, 2H), 4.05–3.40 (b m, 8H), 3.87 (s, 3H). LC/MS (ES+) m/z (M+H)⁺=520, HPLC R$_t$=1.317.

Example 23

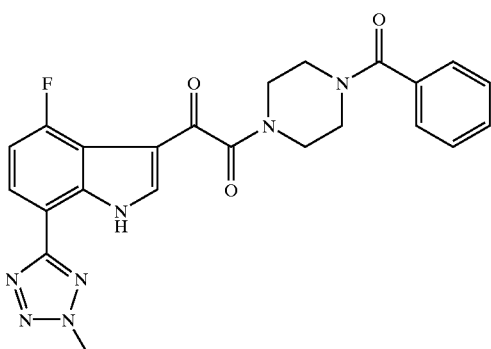

Prepared in the same manner of the compound of Example 22. ¹H NMR (CDCl₃) δ 11.04 (b s, 1H), 8.22 (d, J=3.1, 1H), 8.10 (dd, J=8.4, 4.4, 1H), 7.43 (b s, 5H), 7.12 (dd, J=10.2, 8.4, 1H), 4.79 (q, J=7.4, 2H), 4.05–3.40 (b m, 8H), 1.75 (t, J=7.4, 3H). LC/MS (ES+) m/z (M+H)⁺=476, HPLC R$_t$=1.407.

Example 24

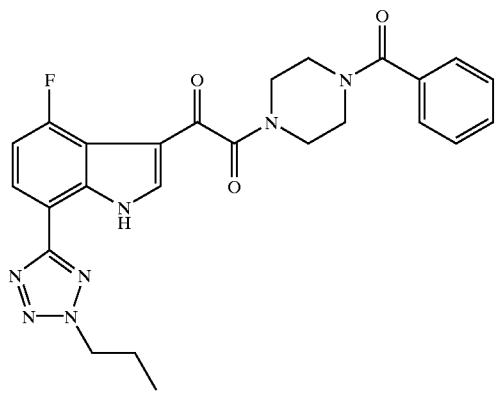

Prepared in the same manner as the compound of Example 22. ¹H NMR (CDCl₃) δ 10.52 (b s, 1H), 8.05 (dd, J=8.3, 4.6, 1H), 7.65 (d, J=2.5, 1H), 7.45 (b s, 5H), 7.00 (dd, J=10.2, 8.3, 1H), 4.69 (t, J=7.1, 2H), 4.05–3.35 (b m, 8H), 2.15 (qt, J=7.4, 7.1, 2H), 1.04 (t, J=7.4, 3H). LC/MS (ES+) m/z (M+H)⁺=490, HPLC R$_t$=1.530.

Example 25

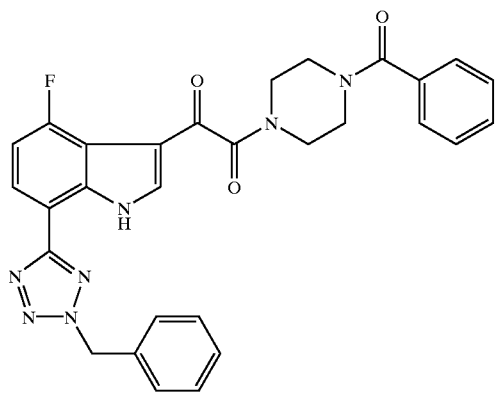

Prepared in the same manner as the compound of Example 22. ¹H NMR (CDCl₃) δ 10.97 (b s, 1H), 8.20 (b s, 1H), 8.09 (b dd, 1H), 7.44–7.40 and (b m, 10H), 7.09 (app t, 1H), 5.87 (s, 2H), 4.00–3.35 (b m, 8H). LC/MS (ES+) m/z (M+H)⁺=538, HPLC R$_t$=1.570.

Example 26

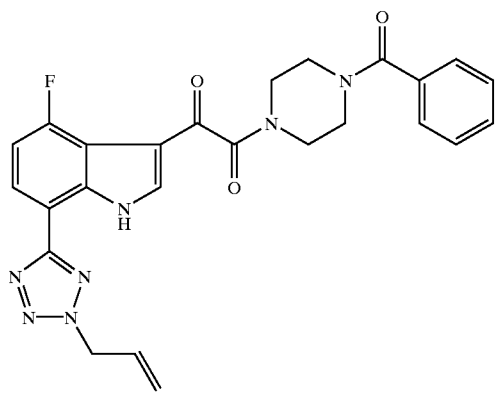

Prepared in the same manner as the compound of Example 22. The position of the allyl group at tetrazole N² was supported by H—N HMBC. $^1$H NMR (CDCl$_3$) δ 11.00 (b s, 1H), 8.22 (d, J=3.0, 1H), 8.11 (dd, J=8.0, 4.5, 1H), 7.43 (b s, 5H), 7.12 (app t, 1H), 6.16 (ddt, J=16.8, 10.5, 6.3, 1H), 5.48 (d, J=10.5, 1H), 5.47 (d, J=16.8, 1H), 5.34 (d, J=6.3, 1H), 4.00–3.35 (b m, 8H). LC/MS (ES+) m/z (M+H)$^+$=488, HPLC R$_t$=1.443.

Example 27

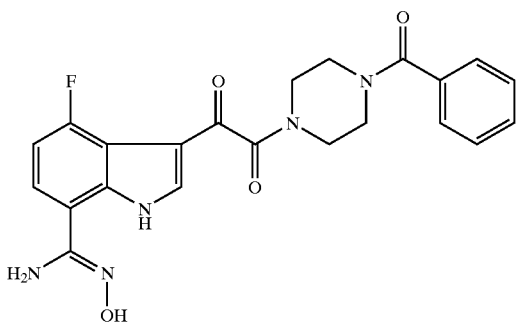

To the mixture of intermediate 12 (498 mg, 1.23 mmol) and hydroxylamine hydrochloride (128 mg, 1.85 mmol) in EtOH (10 mL) was added triethylamine (0.3 mL, 2.09 mmol). The resulting mixture was stirred at rt for 36 h. The precipitates were filtered, washed with excess EtOH, and dried under high vacuum to afford the product shown above as a white solid. The material was used for further transformations without further purification. $^1$H NMR (DMSO) δ 11.81 (s, 1H), 9.81 (s, 1H), 8.14 (app d, J=3.5, 1H), 7.66 (app dd, J=8.5, 4.0, 1H), 7.44 (b s, 5H), 7.08 (app t, J=9.5, 1H), 6.17 (s, 2H), 3.67–3.29 (b m, 8H). LC/MS (ES+) m/z (M+H)$^+$=438, HPLC R$_t$=0.923.

Example 28

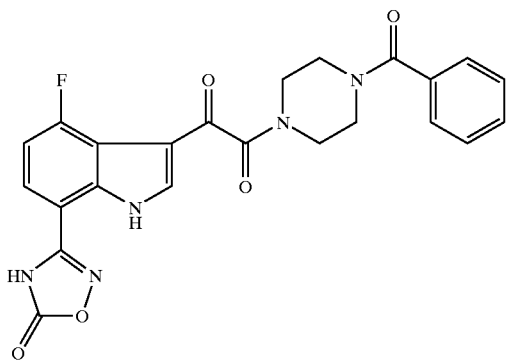

A mixture of the product compound of Example 27 (45 mg, 0.103 mmol) and phosgene (2 mL, 1.04 mmol, 1.92 M in toluene) in toluene (3 mL) was heated to reflux for 16 h, and then quenched with excess MeOH (1 mL) and concentrated in vacuo. Purification was performed by reverse phase preparative HPLC using the method: Start %B=30, Final %B=100, Gradient time=15 min, Flow Rate=35 ml/min, Column: YMC C18 S5 30×100 mm, Fraction Collection: 7.78–8.30 min. $^1$H NMR (DMSO) δ 13.23 (s, 1H), 12.26 (s, 1H), 8.13 (app d, J=3.4, 1H), 7.77 (app dd, J=3, 4.1, 1H), 7.44 (b s, 5H), 7.30 (app t, J=9.3 1H), 3.80–3.30 (b m, 8H). LC/MS (ES+) m/z (M+H)$^+$=464, HPLC R$_t$=1.220.

Example 29

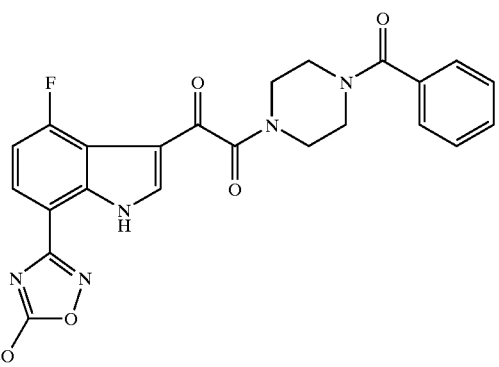

To a suspension of the product compound of Example 28 (23 mg, 0.05 mmol) in a mixture of MeOH (0.2 mL)/PhH (0.7 mL) was added (trimethylsilyl)diazomethane (0.05 mL, 0.10 mmol, 2 M in hexane). The resulting mixture was stirred at rt for 40 min., quenched with excess acetic acid and evaporated in vacuo. Purification was performed by reverse phase preparative HPLC using the method: Start %B=0, Final %B=100, Gradient time=15 min, Flow Rate=30 mL/min, Column: YMC C18 S5 20×50 mm, Fraction Collection: 10.48–11.08 min. The structure was supported by $^1$H-$^{13}$C HMBC NMR studies. $^1$H NMR (CDCl$_3$) δ 10.38 (s, 1H), 8.08 (s, 1H), 7.92 (app dd, J=8.3, 4.4, 1H), 7.33 (b s, 5H), 7.00 (app dd, J=9.9, 8.7, 1H), 4.24 (s, 3H), 3.85–3.39 (b m, 8H). LC/MS (ES+) m/z (M+H)$^+$=478, HPLC R$_t$=1.433.

Example 30

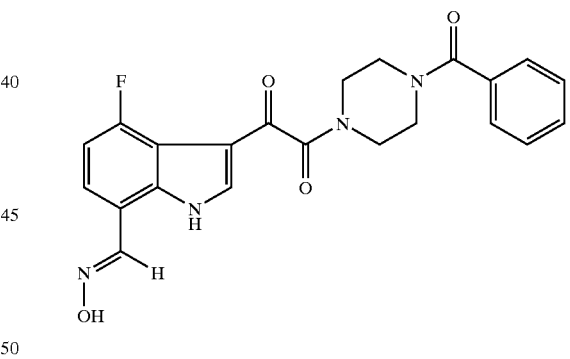

The indole carboxaldehyde, intermediate 10, (100 mg, 0.25 mmol) and hydroxylamine HCl (21 mg, 0.3 mmol) were suspended in MeOH (2 mL) while NaOMe (0.6 mL, 0.3 mmol, 0.5 M in MeOH) was added dropwise. The mixture was stirred at ambient temperature for 18 h and the volatile solvents removed in vacuo. The resulting gum was triturated with water and extracted into EtOAc. The EtOAc layers were dried (brine, MgSO$_4$) and concentrated in vacuo to give a gum that was triturated with ether. The resulting precipitate was filtered and washed with fresh ether to give the product shown above, (50 mg, 0.12 mmol, 47%). IR (KBr cm$^{-1}$) 3354 (br), 1636, 1514, 1433, 1264, 981, 710. $^1$H NMR (DMSO-d$_6$) δ 3.4 (m, 4H), 3.7 (m, 4H), 7.27 (t, J=5 Hz, 1H), 7.45 (m, 5H), 7.50 (m, 1H), 8.20 (d, J=1.8 Hz, 1H), 8.55 (s, 1H), 11.39 (s, 1H), 12.10 (br s, 1H). MS m/e 423.1 (MH$^+$).

Example 31

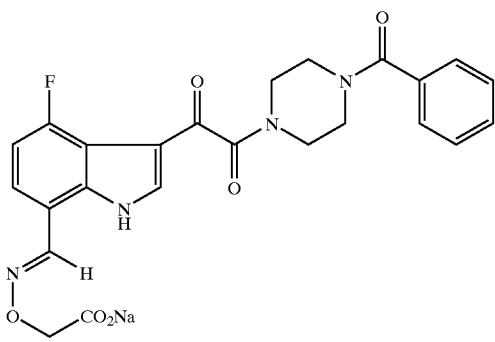

The indole carboxaldehyde, intermediate 10, (100 mg, 0.25 mmol) and carboxymethoxylamine HCl (30 mg, 0.14 mmol, MW=218.59) were suspended in EtOH (2 mL). The mixture was stirred at ambient temperature for 2 h at which time LC/MS indicated the reaction to be 95% done. The mixture was diluted with dry ether and the resulting precipitate was filtered and washed with fresh ether to give the product (compound of formula 37, $R_5$=$CH_2CO_2H$, $R_2$=F, $R_{1,3,4,6}$=H, Scheme 22) (80 mg, 0.17 mmol, 67%). The solid was treated with 0.5 M NaOMe in MeOH until the compound was completely in solution (pH approximately 8) and the volatile components were removed in vacuo to give the product as a sodium salt, shown above. IR (KBr cm$^{-1}$) 3336 (br), 1628, 1511, 1407, 1266, 927, 710. $^1$H NMR (DMSO-d$_6$) δ 3.4 (m, 4H), 3.7 (m, 4H), 5.04 (s, 1H), 7.30 (t, J=5 Hz, 1H), 7.60 (m, 5H), 7.70 (m, 1H), 8.32 (s, 1H), 8.83 (s, 1H), 12.20 (s, 1H), 13.0 (br s, 1H). MS m/e 481 (MH$^+$).

Example 32

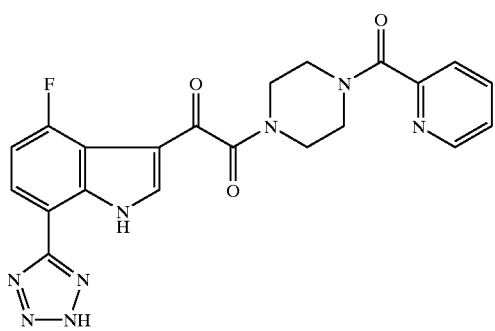

Prepared in the same manner as the compound of Example 20. Separation method: Start %B=20, Final %B=80, Gradient time=12 min, Flow Rate=25 mL/min, Column: YMC C18 S5 20×100 mm, Fraction Collection: 5.27–6.74 min. $^1$H NMR (mixture of conformers, CD$_3$OD) δ 8.66 & 8.58 (app, s & s, 1H), 8.27 (app, d, J=5.3, 1H), 7.98 (m, 2H), 7.69 (app, dd, J=13.3, 8.3, 1H), 7.55 (b m, 1H), 7.19 (m, 1H), 3.98–3.57 (b m, 8H); LC/MS (ES+) m/z (M+H)$^+$= 449, HPLC R$_t$=1.050.

Example 33

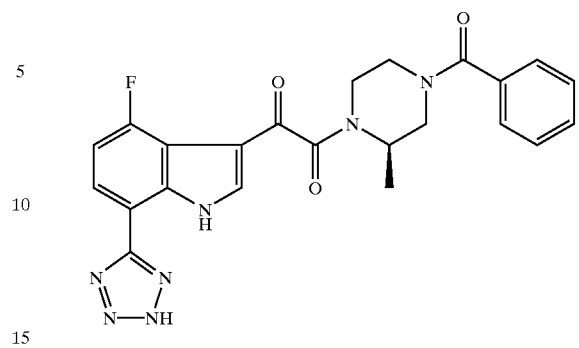

Prepared in the same manner as the compound of Example 20. Separation method: Start %B=20, Final %B=100, Gradient time=12 in, Flow Rate=35 ml/min, Column: YMC C18 S5 30×100 mm, Fraction Collection: 8.37–8.89 min. $^1$H NMR (mixture of conformers, CD$_3$OD) δ 8.28 and 8.23 (app s, 1H), 7.96 (b s, 1H), 7.46 (b s, 5H), 7.19 (app t, J=8.4, 1H), 4.95–3.05 (b m, 7H), 1.40–1.26 (b m, 3H); LC/MS (ES+) m/z (M+H)$^+$=462, HPLC R$_t$=1.247.

Example 34

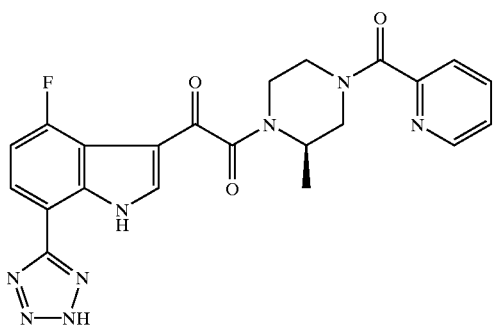

Prepared in the same manner as the compound of Example 20. Separation method: Start %B=0, Final %B=75, Gradient time=12 min, Flow Rate=30 ml/min, Column: YMC C18 S5 20×50 mm, Fraction Collection: 7.55–8.15 min. $^1$H NMR (CD$_3$OD) δ 8.66–8.54 (m, 1H), 8.30–8.21 (m, 1H), 8.05–7.90 (m, 2H), 7.73–7.66 (m, 1H), 7.60–7.48 (m, 1H), 7.20–7.09 (m, 1H), 4.35–3.12 (b m, 7H), 1.43–1.23 (b m, 3H); LC/MS (ES+) m/z (M+H)$^+$=463, HPLC R$_t$=1.123.

Example 35

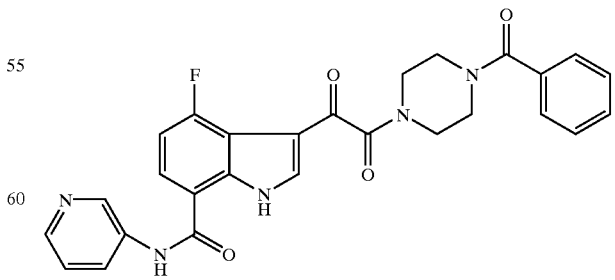

Example of Method 1:
To a mixture of the acid, intermediate 23, (50 mg, 0.12 mmol)], 3-aminopyridine (45 mg, 0.48 mmol) and DMAP (58 mg, 0.47 mmol) dissolved CH$_2$Cl$_2$ (1 mL) was added EDC (90 mg, 0.47 mmol). The resulting mixture was shaken at rt for 12 h, and then evaporated in vacuo. The residue was dissolved in MeOH, and subjected to preparative reverse phase HPLC purification. Separation method: Start %B=30, Final %B=80, Gradient time=15 min, Flow Rate=40 mL/min, Column: YMC C18 S5 30×100 mm, Fraction Collection: 6.57–7.02 min. $^1$H NMR (CD$_3$OD) δ 9.48 (s, 1H), 8.67 (d, J=8.6, 1H), 8.55 (d, J=4.8, 1H), 8.22 (s, 1H), 8.06 (dd, J=8.3, 4.0, 1H), 7.95 (dd, J=8.5, 5.4, 1H), 7.46 (b, s, 5H), 7.14 (app t, J=9.2, 1H), 4.00–3.45 (b m, 8H); LC/MS (ES+) m/z (M+H)$^+$=500, HPLC R$_t$=1.130.

Example 36

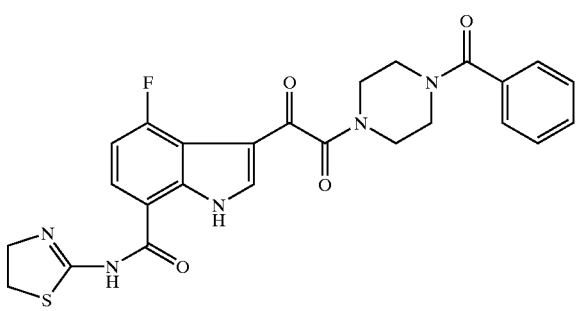

Prepared by Method 1 (as in Example 35) from the acid, intermediate 23, (50 mg, 0.12 mmol)], and 2-amino-2-thiazoline (49 mg, 0.48 mmol). Separation method: Start %B=20, Final %B=80, Gradient time=15 min, Flow Rate=30 mL/min, Column: YMC C18 S5 20×50 mm, Fraction Collection: 6.99–7.59 min. $^1$H NMR (CD$_3$OD) δ 8.14 (s, 1H), 8.08 (dd, J=8.4, 4.5, 1H), 7.42 (b, s, 5H), 7.03 (app t, J=9.2, 1H), 10 3.89 (t, J=8.0, 2H), 3.44 (t, J=8.0, 2H), 4.00–3.45 (b m, 8H); LC/MS (ES+) m/z (M+H)$^+$=508, HPLC R$_t$=1.210.

Example 37

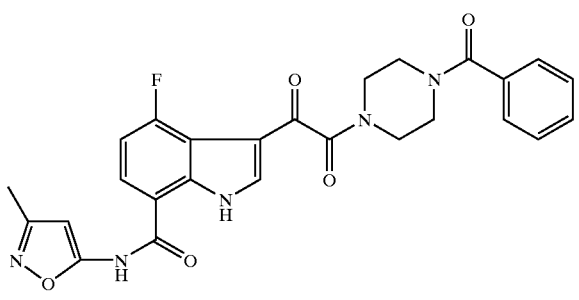

Prepared by Method 1 (as in Example 35) from the acid intermediate 23, (50 mg, 0.12 mmol)], and 5-amino-3-methyl isoxazole (49 mg, 0.48 mmol). Separation method: Start %B=20, Final %B=80, Gradient time=15 min, Flow Rate=30 mL/min, Column: YMC C18 S5 20×50 mm, Fraction Collection: 9.00–9.99 min. $^1$H NMR (CD$_3$OD) δ 8.20 (s, 1H), 7.99 (dd, J=8.2, 3.9, 1H), 7.46 (b, s, J=5H), 7.08 (app t, J=9.3, 1H), 6.46 (s, 1H), 4.00–3.45 (b m, 8H), 3.31 (s, 3H); LC/MS (ES+) m/z (M+H)$^+$=504, HPLC R$_t$=1.380.

Example 38

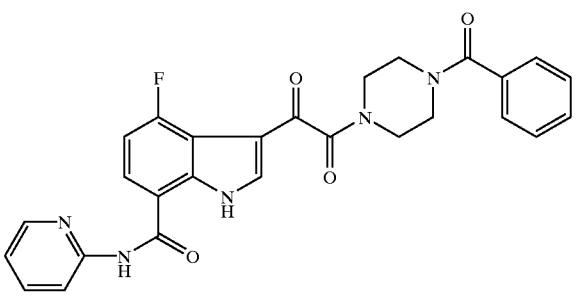

Prepared by Method 1 (as in Example 35) from the acid, intermediate 23, (50 mg, 0.12 mmol)], and 2-aminopyridine (45 mg, 0.48 mmol). Separation method: Start %B=20, Final %B=75, Gradient time=15 min, Flow Rate=30 mL/min, Column: YMC C18 S5 20×50 mm, Fraction Collection: 5.72–6.33 min. $^1$H NMR (CD30D) δ 8.44 (d, J=3.9, 1H), 8.30–8.24 (m, 2H), 8.10 (app t, J=3.9, 1H), 8.00 (d, J=8.6, 1H), 7.53–7.46 (m, 6H), 7.17–7.12 (m, 1H), 4.00–3.45 (b m, 8H); LC/MS (ES+) m/z (M+H)$^+$=500, HPLC R$_t$=1.143.

Example 39

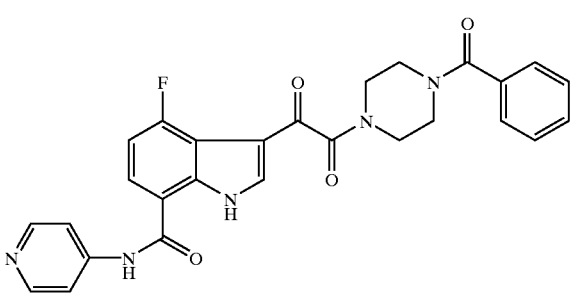

Prepared by Method 1 (as in Example 35) from the acid, intermediate 23, (50 mg, 0.12 mmol)], and 4-aminopyridine (45 mg, 0.48 mmol). Separation method: Start %B=20, Final %B=75, Gradient time=15 min, Flow Rate=30 mL/min, Column: YMC C18 S5 20×50 mm, Fraction Collection: 5.65–6.22 min. $^1$H NMR (CD$_3$OD) δ 8.68 (d, J=7.2, 2H), 8.43 (d, J=7.2, 2H), 8.24 (s, 1H), 8.12 (dd, J=8.3, 4.1, 1H), 7.46 (b s, 5H), 7.17 (app t, J=9.2, 1H), 4.00–3.45 (b m, 8H); LC/MS (ES+) m/z (M+H)$^+$=500, HPLC R$_t$=1.170.

Example 40

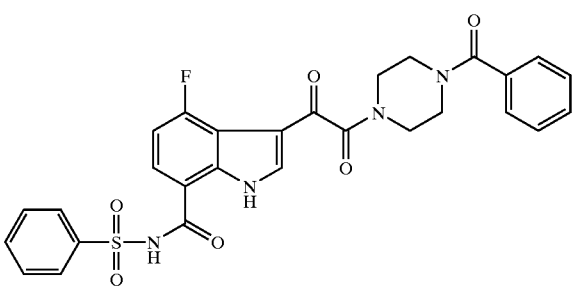

(TFA solvate) Prepared by Method 1 (as in Example 35) from the acid, intermediate 23, (50 mg, 0.12 mmol)], and benzenesulfonamide (75 mg, 0.48 mmol). Separation method: Start %B=30, Final %B=90, Gradient time=15 min, Flow Rate=30 mL/min, Column: YMC C18 S5 20×100 mm, Fraction Collection: 5.95–6.55 min. ¹H NMR (CD₃OD) δ 8.14 (m, 3H), 7.91 (m, 1H), 7.68 (m, 1H), 7.60 (m, 2H), 7.45 (b m, 5H), 7.07 (app, t, J=9.4, 1H), 3.82–3.44 (b m, 8H); LC/MS (ES+) m/z (M+H)⁺32 563, HPLC R$_t$=1.283.

Example 41

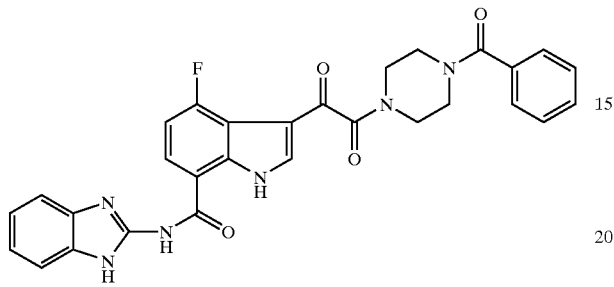

Example of Method 2:

To a mixture of 2-aminobenzimidazole (32 mg, 4 equiv., 0.24 mmol) and HOBT (16 mg, 0.12 mmol) in THF (0.5 mL) was added the acid, intermediate 23, (25 mg, 0.06 mmol)] and NMM (50 μl, 0.45 mmol), followed by EDC (23 mg, 0.12 mmol). The reaction mixture was shaken at rt for 12 h. The volatiles were evaporated in vacuo; and the residue dissolved in MeOH and subjected to preparative reverse phase HPLC purification. Separation method: Start %B=20, Final %B=70, Gradient time=15 min, Flow Rate=30 mL/min, Column: YMC C18 S5 20×0 mm, Fraction Collection: 10.35–10.95 min. ¹H NMR (CD₃OD) δ 8.28 s, 1H), 8.15 (m, 1H), 7.68 (dd, J=6.0, 3.2, 2H), 7.49 (m, 7H), 7.17 (app t, J=9.1, 1H), 4.00–3.45 (b m, 8H); LC/MS (ES+) m/z (M+H)⁺=539, HPLC R$_t$=1.323.

Example 42

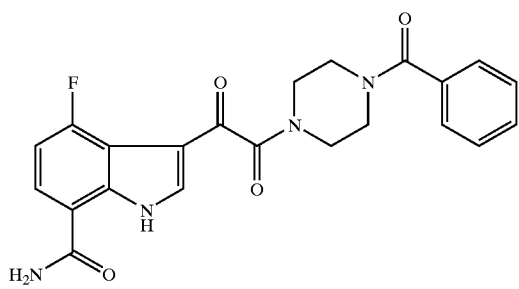

Prepared according to Method 2 as in Example 41 using excess ammonium chloride as the ammonia equivalent. Separation method: Start %B=0, Final %B=75, Gradient time=12 min, Flow Rate=30 mL/min, Column: YMC C18 S5 20×50 mm, Fraction Collection: 7.41–8.00 min. ¹H NMR (CD₃OD) δ 8.18 (s, 1H), 7.83 (dd, J=8.1, 4.2, 1H), 7.46 (b, s, 5H), 7.04 (app t, J=9.1, 1H), 3.95–3.40 (b m, 8H); LC/MS (ES+) m/z (M+H)⁺=423, HPLC R$_t$=1.150.

Example 43

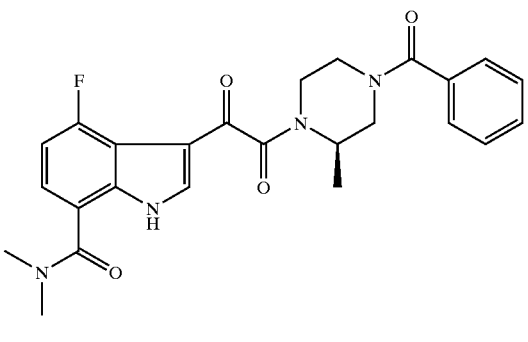

Prepared according to Method 2 as in Example 41 using dimethylamine as the amine component. Separation method: Start %B=0, Final %B=80, Gradient time=12 min, Flow Rate=30 mL/min, Column: YMC C18 S5 20×50 mm, Fraction Collection: 7.63–7.92 min. ¹H NMR (CD₃OD) δ 8.17 (s, 1H), 7.45 (b, s, 5H), 7.34 (dd, J=7.8, 4.2, 1H), 7.04 (app t, J=9.2, 1H), 3.95–3.40 (b m, 8H), 3.16 (s, 3H), 3.08 (s, 3H); LC/MS (ES+) m/z (M+H)⁺=451, HPLC R$_t$=1.167.

Example 44

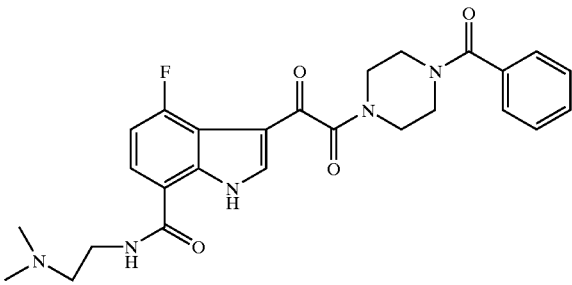

Prepared according to Method 2 as in Example 41 using N,N-dimethylethylenediamine as the amine component. Separation method: Start %B=0, Final %B=75, Gradient time=15 min, Flow Rate=30 mL/min, Column: YMC C18 S5 20×50 mm, Fraction Collection: 6.82–8.05 min. ¹H NMR (CD₃OD) δ 8.18 (s, 1H), 7.78 (dd, J=8.2, 4.1, 1H), 7.45 (b, s, 5H), 7.04 (app t, J=9.3, 1H), 3.95–3.40 (b m, 8H), 3.81 (t, J=5.6, 2H), 3.42 (t, J=5.6, 2H), 3.00 (s, 6H); LC/MS (ES+) m/z (M+H)⁺=494, HPLC R$_t$=1.043.

Example 45

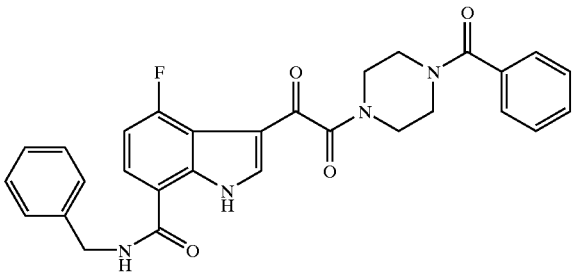

Prepared according to Method 2 as in Example 41 using benzylamine as the amine component. Separation method: Start %B=0, Final %B=90, Gradient time=15 min, Flow Rate=30 mL/min, Column: YMC C18 S5 20×50 mm, Fraction Collection: 10.95–12.18 min. $^1$H NMR (CD$_3$OD) δ 8.17 (s, 1H), 7.80 (dd, J=8.2, 4.1, 1H), 7.44 (b, s, 5H), 7.37 (d, J=7.5, 2H), 7.33–7.30 (m, 2H), 7.24 (t, J=7.3, 1H), 7.03 (app t, J=9.3, 1H), 4.63 (s, 2H), 3.95–3.40 (b m, 8H) LC/MS (ES+) m/z (M+H)$^+$=513, HPLC R$_t$=1.410.

Example 46

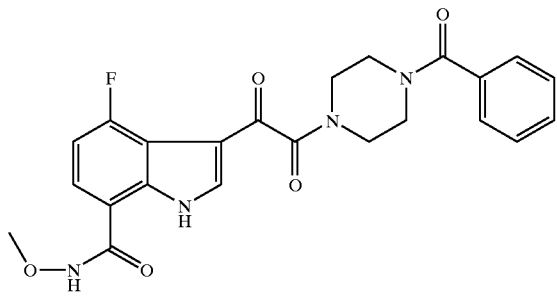

Example of Method 2. To a solution of acid, intermediate 23, (30.0 mg, 0.071 mmol) in DMF (1 mL) was added methoxylamine hydrochloride (11.8 mg, 0.14 mmol), HOBT (22.9 mg, 0.17 mmol). EDC (32.5 mg, 0.17 mmol), followed by NMM (42 μl, 0.38 mmol). The resulting mixture was stirred at rt for 14 h, and then evaporated in vacuo. The residue was treated with water (2 mL) to give precipitates, which were filtered and washed with HCl (2×3 mL, ~0.3 N aq.). The precipitates were further washed with water (2×2 mL) and dried under high vacuum to give the product shown above as a light pink solid. $^1$H NMR (CD$_3$OD) δ 8.19 (s, 1H), 7.64 (b dd, 1H), 7.47 (b, s, 5H), 7.03 (b t, J=9.2, 1H), 4.00–3.34 (b m, 8H), 3.85 (s, 3H); LC/MS (ES+) m/z (M+H)$^+$=453, HPLC R$_t$=1.150.

Example 47

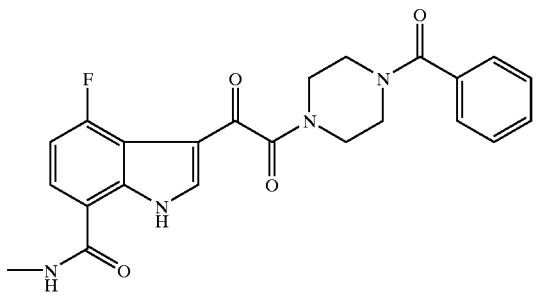

Prepared according to Method 2 as in Example 41 using methylamine as the amine component. Separation method: Start %B=0, Final %B=75, Gradient time=12 min, Flow Rate=30 mL/min, Column: YMC C18 S5 20×50 mm, Fraction Collection: 7.9–8.50 min. $^1$H NMR (CD$_3$OD) δ 8.17 (s, 1H), 7.71 (dd, J=8.1, 4.0, 1H), 7.45 (b, s, 5H), 7.01 (app t, J=9.2, 1H), 3.95–3.40 (b m, 8H), 2.96 (s, 3H); LC/MS (ES+) m/z (M+H)$^+$=437, HPLC R$_t$=1.123.

Alternatively, the compound of this example can be prepared as shown and described below.

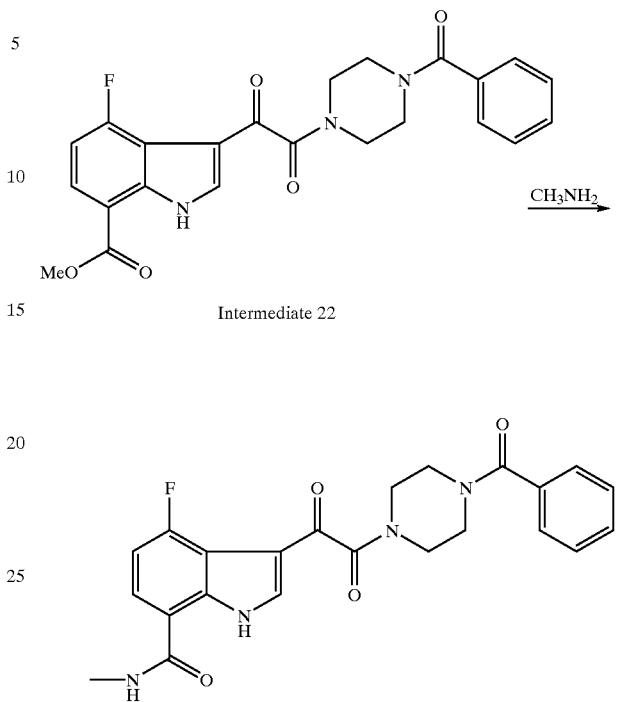

Intermediate 22

To the methyl ester intermediate 22, (60 mg, 0.137 mmol) was added a solution of methylamine in water (1.5 ml, 18 mmol, 40% aq.) and the resulting mixture stirred at rt for 52 h. Evaporation of the excess reagent in vacuo gave the product as a white solid (58 mg, 97%).

Example 48

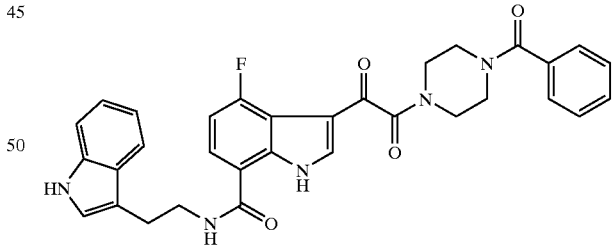

Prepared according to Method 2 as in Example 41 using 3-(2-aminoethyl)indole as the amine component. Separation method: Start %B=0, Final %B=100, Gradient time=12 min, Flow Rate=30 ml/min, Column: YMC C18 S5 20×50 mm, Fraction Collection: 8.84–9.44 min. $^1$H NMR (300M, CD$_3$OD) δ 8.20 (s, 1H), 7.72–7.63 (m, 2H), 7.48 (b, s, 5H), 7.40 (d, J=7.1, 1H), 7.12–6.96 (m, 4H), 3.95–3.40 (b m, 8H), 3.74 (t, J=7.4, 2H), 3.12 (t, J=7.4, 2H); LC/MS (ES+) m/z (M+H)$^+$=566, HPLC R$_t$=1.453.

Example 49

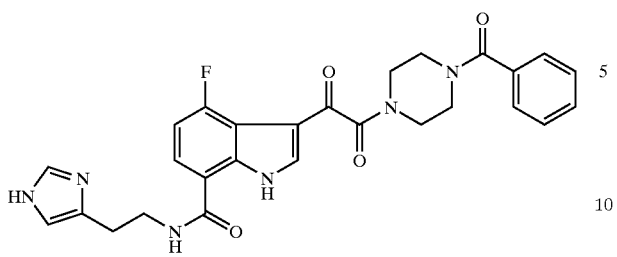

Prepared according to Method 2 as in Example 41 using 4-(2-aminoethyl)imidazole as the amine component. Separation method: Start %B=0, Final %B=80, Gradient time=12 min, Flow Rate=30 mL/min, Column: YMC C18 S5 20×50 mm, Fraction Collection: 6.42–7.02 min. $^1$H NMR (300 MHz, CD$_3$OD) δ 8.82 (s, 1H), 8.19 (s, 1H), 7.73 (dd, J=8.4, 4.3, 1H), 7.48 (b, s, 5H), 7.39 (s, 1H), 7.04 (dd, J=10.2, 8.5, 1H), 3.77 (t, J=6.7, 2H), 3.09 (t, J=6.7, 2H), 3.95–3.40 (b m, 8H); LC/MS (ES+) m/z (M+H)$^+$=517, HPLC R$_t$=1.083.

Example 50

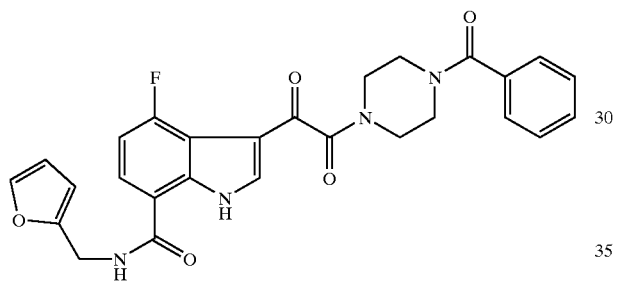

Prepared according to Method 2 as in Example 41 using 2-(aminomethyl)furan as the amine component. Separation method: Start %B=0, Final %B=90, Gradient time=10 min, Flow Rate=30 mL/min, Column: YMC C18 S5 20×50 mm, Fraction Collection: 7.42–8.03 min. $^1$H NMR (CD$_3$OD) δ 8.17 (s, 1H), 7.77 (dd, J=8.1, 4.1, 1H), 7.45 (b, s, 5H), 7.42 (s, 1H), 7.01 (app t, J=9.3, 1H), 6.35 (d, J=3.1, 1H), 6.31 (d, J=3.1, 1H), 4.60 (s, 2H), 3.95–3.40 (b m, 8H); LC/MS (ES+) m/z (M+H)$^+$=503, HPLC R$_t$=1.283.

Example 51

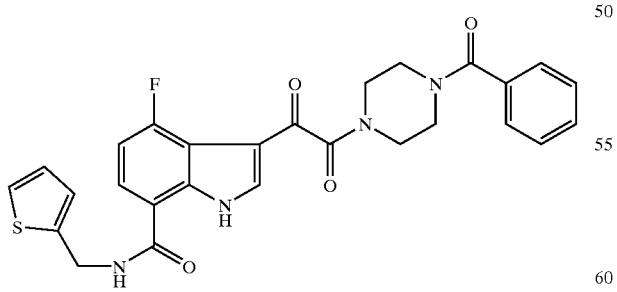

Prepared according to Method 2 as in Example 41 using 2-(aminomethyl)thiophene as the amine component. Separation method: Start %B=20, Final %B=90, Gradient time= 12 min, Flow Rate=30 mL/min, Column: YMC C18 S5 20×50 mm, Fraction Collection: 7.21–8.43 min. $^1$H NMR (CD$_3$OD) δ 8.18 (s, 1H), 7.76 (dd, J=7.8, 3.9, 1H), 7.45 (b, s, 5H), 7.27 (d, J=4.7, 1H), 7.06–7.00 (m, 2H), 6.94 (dd, J=5.0, 3.6, 1H), 4.78 (s, 2H), 3.95–3.40 (b m, 8H); LC/MS (ES+) m/z (M+H)$^+$=519, HPLC R$_t$=1.347.

Example 52

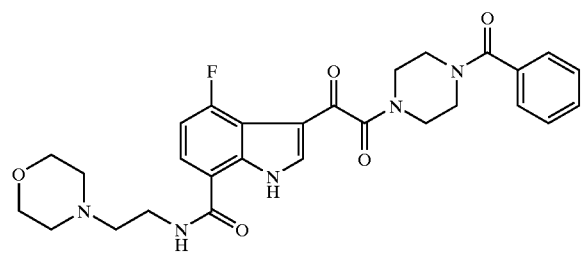

Prepared according to Method 2 as in Example 41 using 4-(2-aminoethyl)morpholine as the amine component. Separation method: Start %B=0, Final %B=75, Gradient time=12 min, Flow Rate=30 ml/min, Column: YMC C18 S5 20×50 mm, Fraction Collection: 6.39–6.99 min. $^1$H NMR (CD$_3$OD) δ 8.18 (s, 1H), 7.78 (dd, J=8.2, 4.0, 1H), 7.45 (b s, 5H), 7.04 (app t, J=9.2, 1H), 4.10–3.20 (b overlapping m, 16H), 3.84 (t, J=5.7, 2H), 3.45 (t, J=5.7, 2H); LC/MS (ES+) m/z (M+H)$^+$=536, HPLC R$_t$=1.030.

Example 53

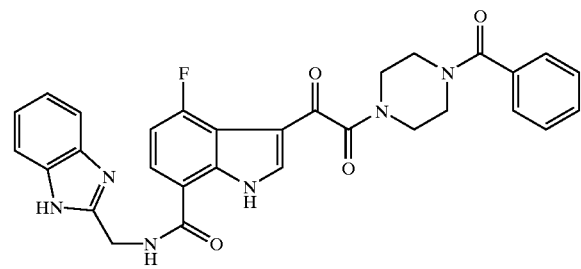

Prepared according to Method 2 as in Example 41 using 2-(aminomethyl)benzimidazole as the amine component. Separation method: Start %B=10, Final %B=75, Gradient time =15 min, Flow Rate=30 mL/min, Column: YMC C18 S5 20×50 mm, Fraction Collection: 7.73–8.34 min. $^1$H NMR (CD$_3$OD) δ 8.14 (s, 1H), 7.93 (dd, J=8.2, 4.5, 1H), 7.75–7.71 (m, 2H), 7.58–7.54 (m, 2H), 7.43 (b, s, 5H), 7.08 (app t, J=8.7, 1H), 5.08 (s, 2H), 3.95–3.40 (b m, 8H); LC/MS (ES+) m/z (M+H)$^+$=523, HPLC R$_t$=1.153.

Example 54

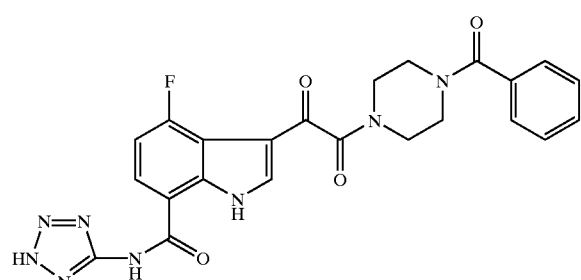

Example of Method 3:

To a mixture of the acid intermediate (compound of Example 23), (20 mg, 0.047 mmol) 5-aminotetrazole (4 equiv.) and DEPBT (prepared according to Li, H.; Jiang, X. Ye, Y.; Fan, C.; Todd, R.; Goodman, M. *Organic Letters* 1999, 1, 91; 21 mg, 0.071 mmol) in DMF (0.5 mL) was added TEA (0.03 mL, 0.22 mmol). The resulting mixture was shaken at rt for 12 h; and then diluted with MeOH (2 mL) and purified by preparative reverse phase HPLC. Separation method: Start %B=0, Final %B=80, Gradient time=15 min, Flow Rate=30 mL/min, Column: YMC C18 S5 20×50 mm, Fraction Collection: 8.24–10.09 min. $^1$H NMR (CD$_3$OD) δ 8.08 (s, 1H), 7.98 (dd, J=8.2, 4.0, 1H), 7.32 (b, 5H), 7.01 (app t, J=9.3, 1H), 3.95–3.40 (b m, 8H); LC/MS (ES+) m/z (M+H)$^+$=491, HPLC R$_t$=1.197.

Examples 55–59

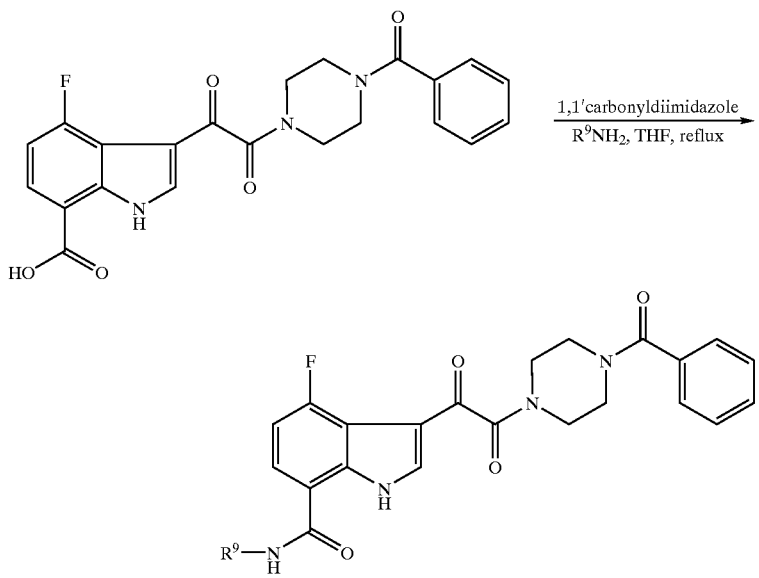

Example of Method 4. The compounds were prepared as follows: A mixture of an acid intermediate (shown above) (0.047 mmol) and 8.5 mg (0.052 mmol) of 1,1-carbonyldiimidazole in anhydrous THF (2 mL) was heated to reflux under nitrogen. After 2.5 h, 0.052 mmol of amine was added and heating continued. After an additional period of 3~20 h at reflux, the reaction mixture was cooled and concentrated in vacuo. The residue was purified by chromatography on silica gel to provide compounds of Formula I in the table below.

| $R^9$ ($X_1$ is point of attachment) | Ex. | HPLC retention time | mass obs. (M + H)+ |
|---|---|---|---|
| ethyl-pyrazole | 55 | 1.01 min | 517 |
| isoxazole | 56 | 1.02 min | 490 |
| thiazole | 57 | 1.37 min | 506 |
| thiadiazole | 58 | 1.03 min | 507 |
| benzothiazole | 59 | 1.77 min | 556 |

Example 60

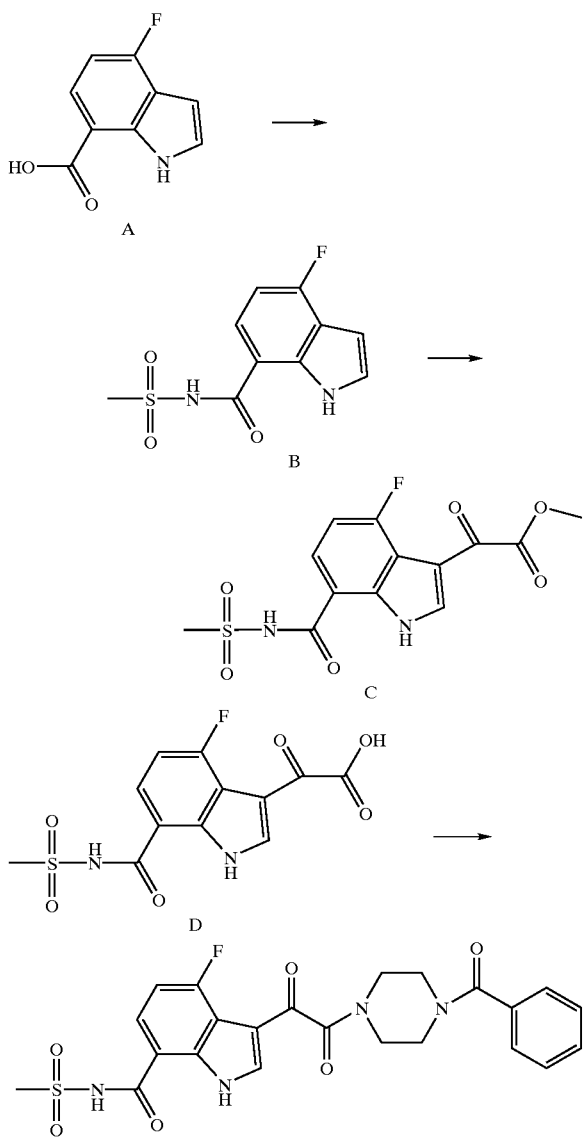

To a mixture of A (Reference 102, 50 mg, 0.279 mmol) and methanesulfonamide (32 mg, 0.34 mmol) in CH₂Cl₂ (1 mL), were added DMAP (47 mg, 0.385 mmol) and EDC (64 mg, 0.335 mmol). The resulting mixture was stirred at rt for 17 h. After which time, the mixture was diluted with CH₂Cl₂ (20 mL), washed with hydrochloric acid (3×20 mL, 1 N, aq.) followed by water (30 mL), dried (MgSO₄) and evaporated in vacuo to provide intermediate B as white solid. (66 mg, 92%) $^{1}$H NMR (300 MHz, CD$_3$OD) δ 7.76 (app, dd, J=8.4, 4.8, 1H), 7.41 (m, 1H), 6.84 (app, dd, J=9.9, 8.4, 1H), 6.64 (m, 1H), 3.44 (s, 3H).

To a solution of methyl chlorooxoacetate (0.04 ml, 0.435 mmol) in CH₂Cl₂ (2 mL) was added AlCl₃ (52 mg, 0.39 mmol). The resulting suspension was stirred at 4° C. for 20 min. before adding intermediate B (60 mg, 0.234 mmol). After stirring at rt for 15 h, the reaction mixture was quenched with hydrochloric acid (15 mL, ~5 N, aq.) and extracted with EtOAc (3×5 mL). The combined organic extracts were washed with water (30 mL), dried (MgSO₄) and evaporated in vacuo to give intermediate C as a brownish oil. The material was used without further purification.

To a solution of intermediate C in MeOH (0.5 ml) was added NaOH (0.6 ml, 0.6 mmol, 1 N aq.) and the resulting mixture was stirred at rt for 4.5 h. The mixture was then acidified with hydrochloric acid (1 N, aq.) to pH 3, and the precipitates were filtered. Evaporation of the filtrate under high vacuum afforded intermediate D as an off-white solid. The material was used without further purification.

To the solution of intermediate D and intermediate 19 (47 mg, 0.21 mmol) in CH₂Cl₂ was added DMAP (35 mg, 0.286 mmol) and EDC (38 mg, 0.319 mmol). The reaction mixture was stirred at rt for 27.5 h, and then evaporated in vacuo to afford a yellow oil, which was purified by preparative reverse phase HPLC using the method: Start %B=30, Final %B=100, Gradient time=8 min, Flow Rate=40 mL/min, Column: YMC C18 S5 30×100 mm, Fraction Collection: 4.52–4.98 min to provide the final product shown above. $^{1}$H NMR (300 MHz, CD$_3$OD) δ 8.23 (m, 1H), 7.93 (app, dd, J=8.8, 4.4, 1H), 7.48 (b s, 5H), 7.11 (app t, J=9.7, 1H), 3.90–3.40 (b m, 8H), 3.44 (s, 3H); LC/MS (ES+) m/z (M+H)$^{+}$=501, HPLC R$_t$=1.143.

Example 61

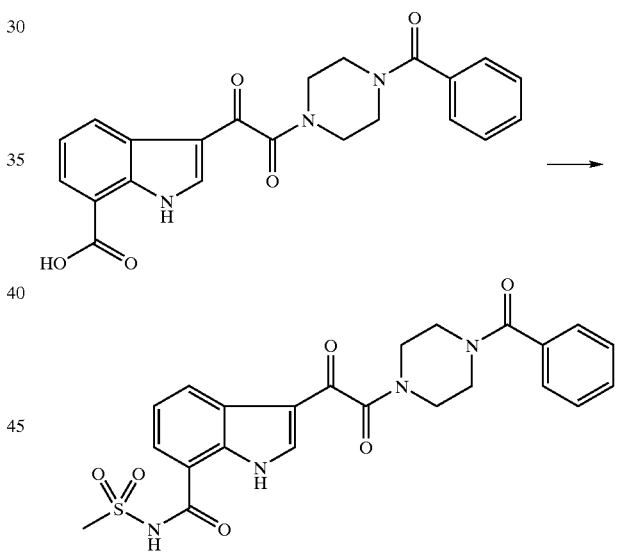

To a suspension of the acid (Reference 102, 30 mg, 0.074 mmol) and methylsulfonamide (0.296 mmol) in CH₂Cl₂ (1 mL), was added DMAP (36 mg, 0.295 mmol) and EDC (56 mg, 0.293 mmol). The resulting mixture was stirred at rt for 16 h, and then evaporated in vacuo. The residue was dissolved in MeOH, and subjected to preparative reverse phase HPLC purification to provide the product. Separation method: Start %B=0, Final %B=100, Gradient time=15 min, Flow Rate=25 mL/min, Column: YMC C18 S5 30×100 mm, Fraction Collection: 7.83–9.15 min. $^{1}$H NMR (300 MHz, CD$_3$OD) δ 8.50 (m, 1H), 8.1 0 (s, 1H), 7.84 (app, d, J=6.8, 1H), 7.40 (b m, 6H), 3.90–3.40 (b, m, 8H), 3.38 (s, 3H); LC/MS (ES+) m/z (M+H)$^{+}$=483, HPLC R$_t$=1.197.

Example 62

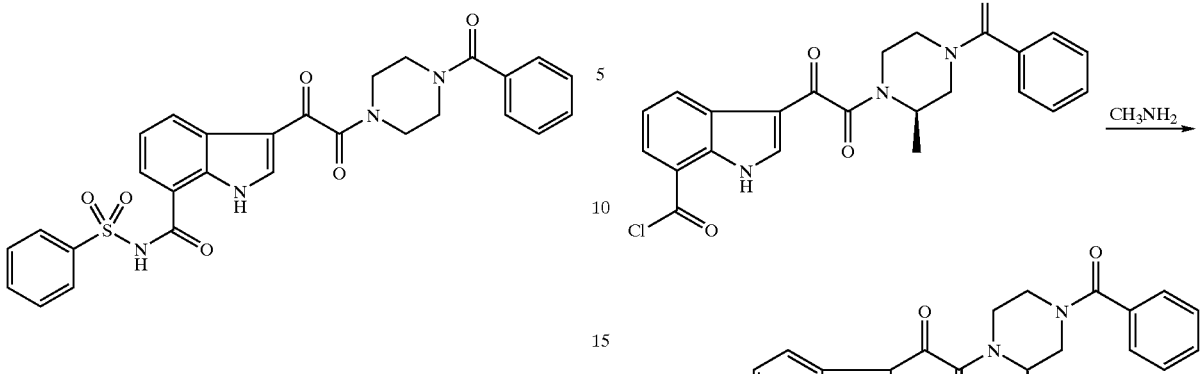

Example of Scheme 25A. Prepared as described above in Example 61 using benzenesulfonamide as the sulfonamide component. Purification was performed by flash chromatography using a gradient elution (100% EtOAc, to 2% to 10% MeOH/EtOAc) to give the product as a white solid. $^1$H NMR (300 MHz, CD$_3$OD) δ 8.30 (m, 1H), 8.06–7.84 (b m, H), 7.53–7.18 (b m, 9H), 3.93–3.33 (b m, 8H); LC/MS (ES+) m/z (M+H)$^+$=545, HPLC R$_t$=1.387.

Example 63

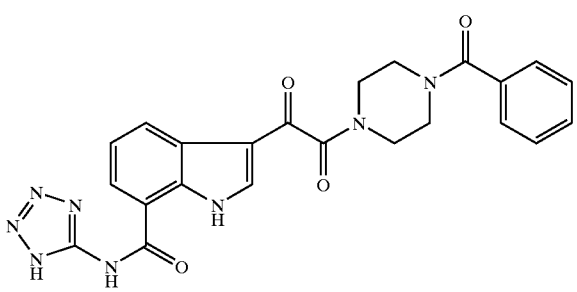

Example of Scheme 25A. Prepared as described above in Example 61 using 3-aminotetrazole as the amine component. Separation method: Start %B=30, Final %B=80, Gradient time =15 min, Flow Rate=25 mL/min, Column: YMC C18 S5 20×50 mm, Fraction Collection: 6.22–6.89 min. $^1$H NMR (300 MHz, CD$_3$OD) δ 8.50 (m, 1H), 8.16 (s, 1H), 8.06 (m, 1H), 7.57–7.27 (b m, 6H), 3.90–3.40 (b, m, 8H); LC/MS (ES+) m/z (M+H)$^+$=473, HPLC R$_t$=1.263.

Example 64

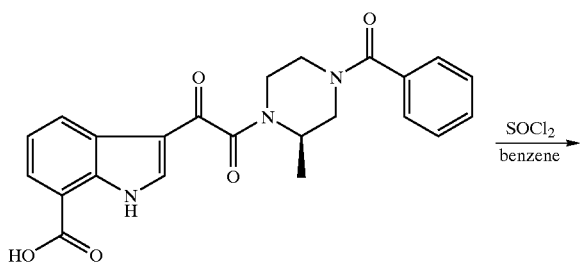

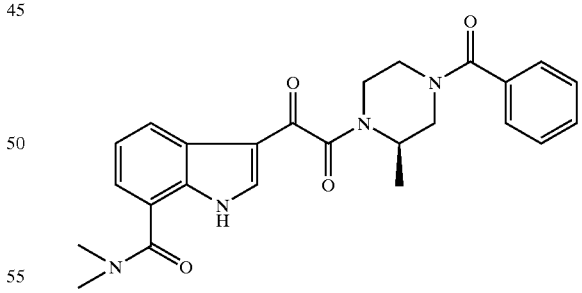

The crude acid chloride was obtained by refluxing a mixture of the acid shown and excess SOCl$_2$ (1.0 mL per 0.03 mmol of acid) in benzene (15 mL) for 3 h, followed by evaporation of the volatile. A mixture of the acid chloride (30.0 mg, 0.07 mmol) and excess amine (1.0 mL of a 2 M solution of methylamine in MeOH) in CH$_3$CN (7.0 mL) was stirred at rt for 10 min. After adding excess pyridine (1.0 mL, 12 mmol), the mixture was stirred overnight and then evaporated in vacuo to give a residue. The residue was dissolved in MeOH and subjected to purification by preparative reverse phase HPLC. Separation method: Start %B=30, Final %B=80, Gradient time=8 min, Flow Rate=25 mL/min, Column: YMC C18 S5 20×100 mm. $^1$H NMR (mixture of conformers, CD$_3$OD) δ 8.39 (app b s, 1H), 8.12 and 8.08 (s, 1H), 7.70 (app b s, 1H), 7.44 (b s, 5H), 7.34 (app b s, 1H), 5.00–3.00 (b m, 7H), 2.97 (s, 3H), 1.38–1.25 (b m, 3H); LC/MS (ES+) m/z (M+H)$^+$=433, HPLC R$_t$=1.240.

Example 65

Prepared as described above in Example 64 using dimethylamine as the amine component. Separation method: Start %B=40, Final %B=100, Gradient time=8 min, Flow Rate=25 mL/min, Column: YMC C18 S5 20×100 mm. $^1$H NMR (mixture of conformers, CD$_3$OD) δ 8.31 (app b s, 1H), 8.12 and 8.07 (s, 1H), 7.60–7.10 (b overlapping m, 7H), 5.10–3.00 (b m, 7H), 3.30 (s, 3H), 3.00 (s, 3H), 1.36–1.24 (b m, 3H); LC/MS (ES+) m/z (M+H)$^+$=447, HPCL R$_t$=1.260.

Example 66

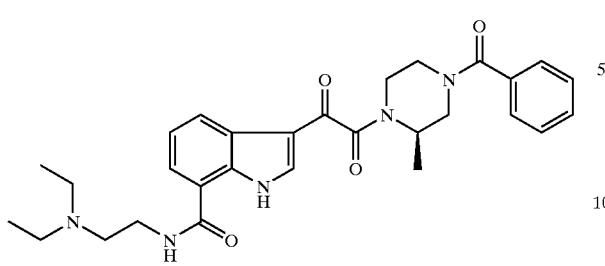

Prepared as described above in Example 64 using N,N-diethylethylenediamine as the amine component. Separation method: Start %B=30, Final %B=80, Gradient time=8 min, Flow Rate=25 ml/min, Column: YMC C18 S5 20×100 mm. $^1$H NMR (mixture of conformers, 300 MHz, CD$_3$OD) δ 8.47–8.45 (app b m, 1H), 8.15 and 8.12 (s, 1H), 7.82–7.79 (app b d, 1H), 7.47–7.37 (b overlapping m, 6H), 5.00–3.00 (b overlapping m, 7H), 3.84 (t, J=9.9, 2H), 3.45 (t, J=9.9, 2H), 3.33 (q, J=12.1, 4H), 1.39 (t, J=12.1, 6H), 1.10–1.45 (b m overlapped with t, 3H); LC/MS (ES+) m/z (M+H)$^+$=518, HPCL R$_t$=1.147.

Example 67

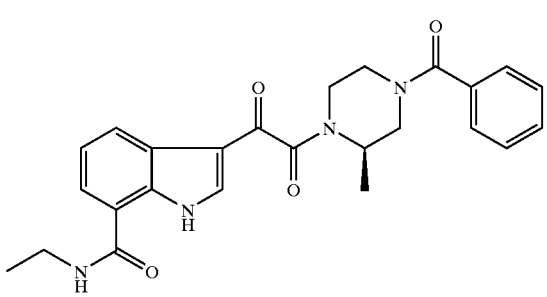

A mixture of the acid chloride (as shown in Example 64) (ca. 0.03 mmol) in neat ethylamine (0.5 ml, 7.6 mmol) was stirred at rt for 2 h. The excess amine was then removed by evaporation in vacuo to give a residue, which was dissolved in MeOH and subjected to purification by preparative reverse phase HPLC. Separation method: Start %B=30, Final %B=100, Gradient time=9 min, Flow Rate=25 mL/min, Column: YMC C18 S5 20×100 mm. $^1$H NMR (mixture of conformers, CDCl$_3$) δ 11.10 (b s, 1H), 8.50 (app b s, 1H), 8.052, 8.046 and 8.037 (s, 1H), 7.49–7.34 (b overlapping m, 6H), 6.49 (b s, 1H), 5.10–2.90 (b m, 7H), 3.59–3.53 (overlapping q, 2H), 1.50–1.10 (b m overlapped with t, 3H), 1.31 (t, J=7.3, 3H); LC/MS (ES+) m/z (M+H)$^+$=447, HPCL R$_t$=1.330.

Example 68

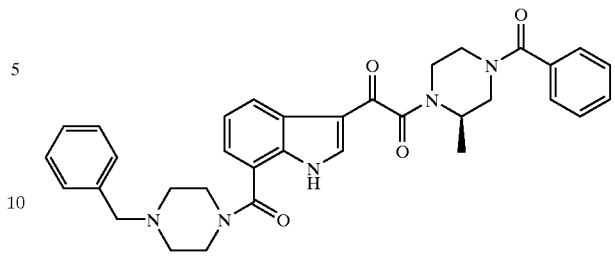

Prepared as described above in Example 64 using monobenzyl piperazine as the amine component. The product precipitated from a MeOH solution, and was filtered and washed with MeOH to provide a analytical pure sample; $^1$H NMR (mixture of conformers, CDCl$_3$) δ 11.7 (b s, 1H), 8.38, (app b s, 1H), 7.76–7.16 (overlapping m, 13H), 4.93–2.88 (overlapping m, 15H), 2.47 (s, 2H), 1.25 (b s, 3H); LC/MS (ES+) m/z (M+H)$^+$=578, HPCL R$_t$=1.210.

Example 69

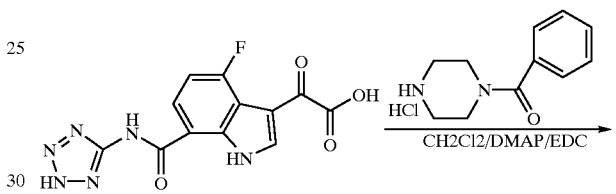

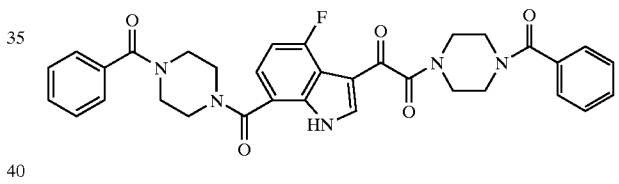

The product shown above was isolated as an unexpected product from the above reaction. Separation method: Start %B=30, Final %B=100, Gradient time=12 min, Flow Rate= 30 mL/min, Column: YMC C18 S5 20×50 mm, Fraction Collection: 4.89–5.42 min. $^1$H NMR (300 MHz, CD$_3$OD) δ 8.21 (s, 1H), 7.48 (b s, 10H), 7.39 (app, dd, J=7.8, 4.3, 1H), 7.06 (app, t, J=9.3, 1H), 4.10–3.36 (b m, 16H); LC/MS (ES+) m/z 5 (M+H)$^+$=596, HPCL R$_t$=1.330.

Example 70

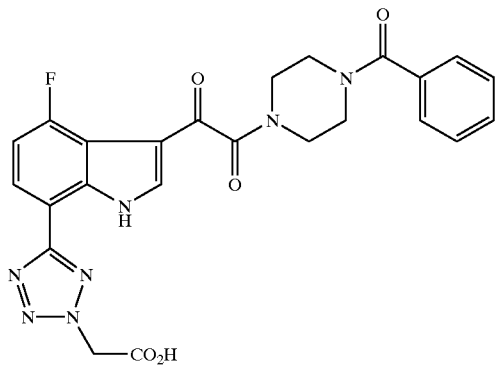

To a mixture of the methyl ester (Compound of Example 22), (100.0 mg, 0.193 mmol) in MeOH (1.5 mL) was added NaOH (0.4 mL, 0.4 mmol, 1 N, aq.). The resulting mixture was stirred at rt for 4 h and then concentrated under a stream of nitrogen. The residue was diluted with excess H$_2$O (~6 mL) and acidified to pH ~1 with HCl (1 N, aq.) to induce precipitation. The precipitates were filtered, washed with H$_2$O (3×1 mL) and dried under high vacuum to give the product as an off white solid (85.7 mg, 88%). $^1$H NMR (CD$_3$OD) δ 8.24 (s, 1H), 8.16 (b dd, 1H), 7.46 (b s, 5H), 7.16 (app t, 1H), 5.69 (s, 2H), 4.00–3.45 (b m, 8H); LC/MS (ES+) m/z (M+H)$^+$=506, HPCL R$_t$=1.320.

Example 71

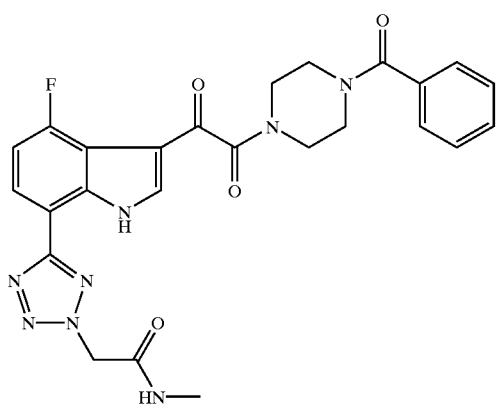

To a mixture of the acid (Compound of Example 70), (19.8 mg, 39.2 μmol) in DMF (1.0 mL) was added methylamine hydrochloride (17.0 mg, 0.252 mmol), HOBT (19.2 mg, 0.142 mmol), EDC (27.2 mg, 0.142 mmol) and NMM (35 μL, 0.318 mmol), and the resulting mixture stirred at rt for 24 h. The volatile was then evaporated under high vacuum to give a residue, which was diluted with H$_2$O (~5 mL) and acidified to pH ~1 with HCl (1 N, aq.). The precipitates were filtered, washed with H$_2$O (1 mL) and then HCl (1 mL, 1 N, aq.). The crude product was purified by preparative TLC (5% MeOH/CH$_2$Cl$_2$, 500 μm×20 cm×20 cm plate) to give the product as a white solid. $^1$H NMR (CDCl$_3$) δ 11.34 (s, 1H), 8.18 (d, J=2.4, 1H), 8.09 (dd, J=8.3, 4.3, 1H), 7.41 (b s, 5H), 7.09 (app t, 1H), 5.40 (s, 2H), 4.00–3.40 (b m, 8H), 2.85 (s, 3H); LC/MS (ES+) m/z (M+H)$^+$=519, HPCL R$_t$=1.203.

Example 72

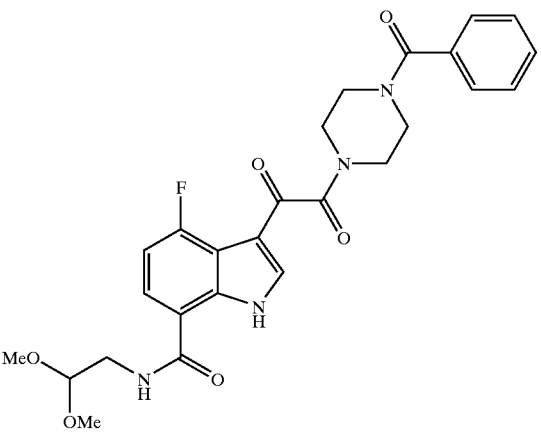

To a suspension of the acid, Intermediate 23, (250 mg, 0.590 mmol) in CH$_2$Cl$_2$ (5 mL), was added DMAP (116 mg, 0.949 mmol), aminoacetaldehyde dimethyl acetal (80 μl, 0.734 mmol) and EDC (136 mg, 1.142 mmol), and the resulting mixture stirred at rt for 16 h. The reaction mixture was then diluted with CH$_2$Cl$_2$ (40 mL), washed with HCl (3×20 mL, 1 N aq.), and then water (40 mL). The organic layer was dried (MgSO$_4$) and evaporated in vacuo to give the product as pale yellow solid (226 mg, purity: 90% HPLC), which was used for the next step without further purification. $^1$H NMR (CD$_3$OD) δ 8.17 (s, 1H), 7.77 (app t, J=9.2, 1H), 7.46 (b s, 5H), 7.02 (app dd, J=20.4, 11.6, 1H), 4.60 (t, J=5.3, 1H), 3.97–3.44 (b m, 10H, overlapped with singlets), 3.55 (s, 3H), 3.54 (s, 3H); LC/MS (ES+) m/z (M+H)$^+$=511, HPLC R$_t$=1.210.

Example 73

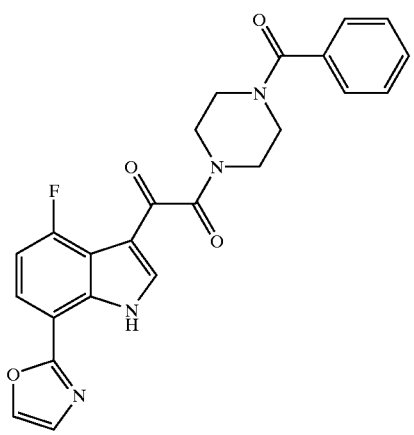

To the compound of Example 72 (75 mg, 0.147 mmol) was added the Eaton reagent (0.5 mL, freshly prepared by heating a suspension of phosphorous pentoxide (100 mg, 0.705 mmol) in methanesulfonic acid (1 mL, 0.015 mmol) at 90° C. for 3 h). The resulting mixture was stirred at 130° C. for 10.5 h. After cooling down to rt, the reaction mixture was added ice water (ca. 10 mL) while vigorously stirred. The solid residue was filtered, and dissolved in a mixture of DMF/MeOH for purification by reverse phase preparative HPLC using the method: Start %B=20, Final %B=90, Gradient time=15 min, Flow Rate=25 mL/min, Column: YMC C18 S5 20×100 mm, Fraction Collection: 11.03–11.59 min. $^1$H NMR (CD$_3$OD) δ 8.24 (s, 1H), 8.03 (app s, 1H), 7.95 (app dd, J=7.6, 4.1, 1H), 7.46 (b s, 5H), 7.42 (app s, 1H), 7.13 (app t, J=8.8, 1H), 3.96–3.44 (b m, 8H); LC/MS (ES+) m/z (M+H)$^+$=447, HPLC R$_t$=1.367.

Example 74

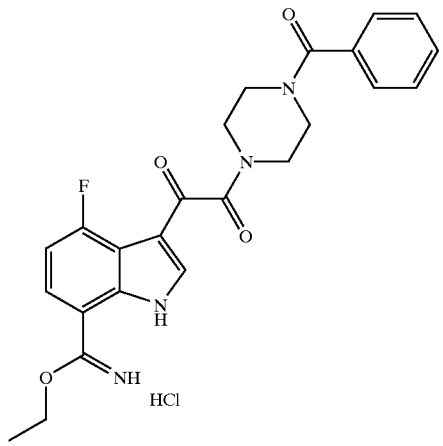

Intermediate 12, (100 mg, 0.247 mmol) was placed in a reusable sealed tube was dissolved in a solution of HCl in dioxane (3 mL, 4 M). To the solution was added EtOH (0.6 mL, 10.4 mmol, 200 proof, anhydrous, 99.5+% from Aldrich). The reaction mixture was cooled to −5° C. and bubbled with dry hydrochloride gas, while stirred, for 1 h. The reaction flask was then sealed and the reaction mixture stirred at rt for 17 h. Evaporation of the volatile in vacuo gave the product as a yellow oil, which was used without further purification. LC/MS (ES+) m/z (M+H)$^+$=451, HPLC R$_t$=1.093, purity: 91%.

Example 75

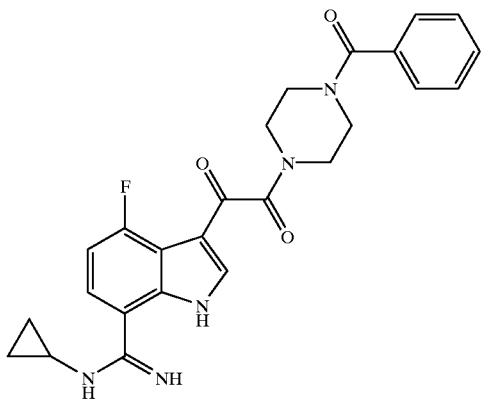

To a solution of the compound of Example 74 (ca. 0.06 mmol) in EtOH (0.5 mL) was added cyclopropylamine (14 µl, 0.20 mmol). After stirring at rt for 16 h, the reaction mixture was diluted with MeOH (2 mL), and subjected to purification by preparative HPLC using the method: Start %B=10, Final %B=75, Gradient time=15 min, Flow Rate=25 mL/min, Column: YMC C18 S5 20×100 mm, Fraction Collection: 7.44–8.17 min. $^1$H NMR (CD$_3$OD) δ 8.27 (s, 1H), 7.56 (app dd, J=8.3, 4.2, 1H), 7.46 (b s, 5H), 7.15, (app t, J=9.2, 1H), 3.96–3.35 (b m, 8H), 2.86 (m, 1H), 1.08 (m, 2H), 0.92 (m, 2H); LC/MS (ES+) m/z (M+H)$^+$=462, HPLC R$_t$=0.983.

Example 76

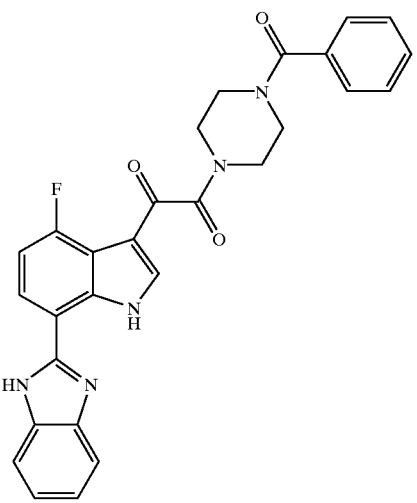

To a solution of the compound of Example 74 (ca. 0.083 mmol) in EtOH (0.5 mL) was added 1,2-phenylenediamine (26.0 mg, 0.24 mmol) and N,N-diisopropylethylamine (0.1 mL, 0.574 mmol). After stirring at 90° C. for 16 h, the reaction mixture was cooled to rt, diluted with MeOH (2 mL), and then subjected to purification by preparative HPLC using the method: Start %B=20, Final %B=75, Gradient time =15 min, Flow Rate=25 mL/min, Column: YMC C18 S5 20×100 mm, Fraction Collection: 10.33–11.05 min. $^1$H NMR (CD$_3$OD) δ 8.33 (s, 1H), 7.90 (app, t, J=3.8, 1H), 7.76 (app dd, J=6.0, 3.1, 2H), 7.46 (b s, 7H), 7.23 (app d, J=9.2, 1H), 3.90–3.44 (b m, 8H); LC/MS (ES+) m/z (M+H)$^+$=496, HPLC R$_t$=1.277.

Example 77

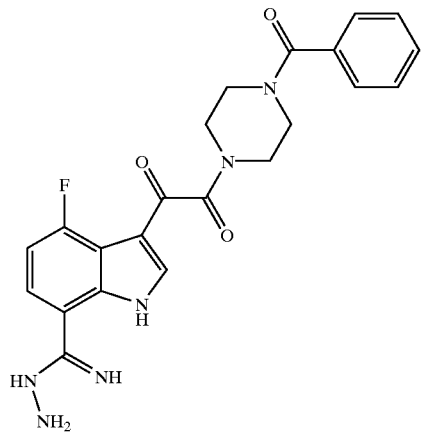

To a solution of the compound of Example 74 (ca. 0.166 mmol) in EtOH (0.5 ml) was added hydrazine (20 µl, 0.631 mmol, anhydrous) and N,N-diisopropylethylamine (0.1 mL, 0.574 mmol). The reaction mixture was stirred at rt for 16 h. Removal of solvent in vacuo afforded the product as a brown oil which was used for the next step without further purification. LC/MS (ES+) m/z (M+H)$^+$=437, HPLC R$_t$=0.913, purity: 50%.

Example 78

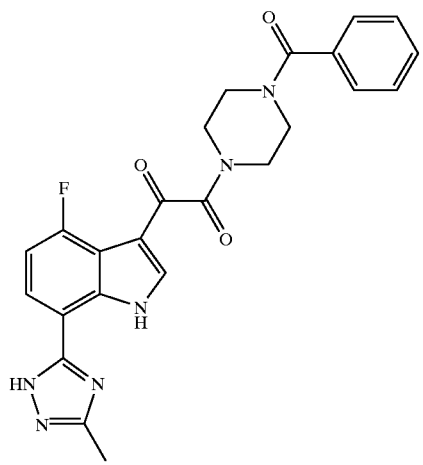

To a solution of the compound of Example 77 (ca. 0.083 mmol) in pyridine (0.5 mL) was added acetyl chloride (12 μl, 0.17 mmol). After stirring at 110° C. for 16 h, the reaction mixture was cooled to rt, diluted with MeOH (2 mL), and then subjected to purification by preparative reverse phase HPLC using the method: Start %B=20, Final %B=80, Gradient time=12 min, Flow Rate=25 mL/min, Column: YMC C18 S5 20×100 mm, Fraction Collection: 8.57–9.17 min. $^1$H NMR (CD$_3$OD) δ 8.21 (s, 1H), 7.96 (app d, J=7.9, 1H), 7.46 (b s, 5H), 7.09 (app t, J=9.0, 1H), 3.98–3.44 (b m, 8H), 2.57 (s, 3H); LC/MS (ES+) m/z (M+H)$^+$=461, HPLC R$_t$=1.270.

Example 79

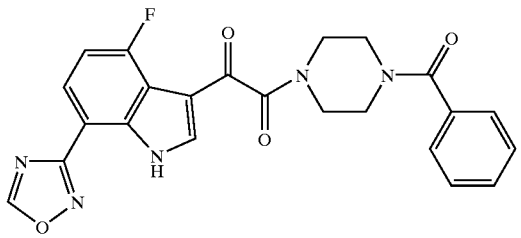

A suspension of the compound of Example 27 (32 mg, 0.073 mmol) in triethylorthoformate (0.5 mL, 3.0 mmol) was stirred at 105° C. for 16 h. After cooling down to rt, the reaction mixture was added to MeOH (2 mL), and then subjected to purification by preparative reverse phase HPLC using the method: Start %B=10, Final %B=80, Gradient time=15 min, Flow Rate=25 ml/min, Column: YMC C18 S5 20×100 mm, Fraction Collection: 11.49–12.29 min. $^1$H NMR (CD$_3$OD) δ 9.41 (s, 1H), 8.23 (s, 1H), 8.15 (app t, J=6.3, 1H), 7.46 (b s, 5H), 7.17 (app t, J=9.3, 1H), 3.91–3.44 (b m, 8H); LC/MS (ES+) m/z (M+H)$^+$=448, HPLC R$_t$=1.387.

Example 80

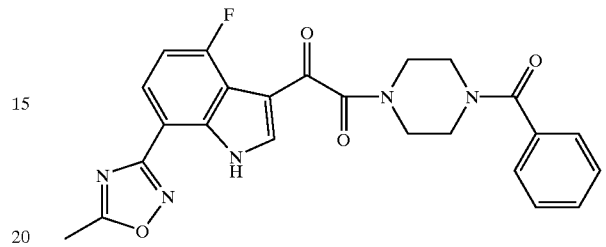

To a mixture of the compound of Example 27 (24 mg, 0.055 mmol) in pyridine (0.5 mL) was added acetyl chloride (9 μl, 0.121 mmol) and the resulting mixture stirred at 115° C. for 16 h. After cooling down to rt, the reaction mixture was added to MeOH (2 mL), and then subjected to purification by preparative reverse phase HPLC using the method: Start %B=10, Final %B=100, Gradient time=15 min, Flow Rate=25 mL/min, Column: YMC C18 S5 20×100 mm, Fraction Collection: 10.28–11.08 min. $^1$H NMR (CD$_3$OD) δ 8.22 (s, 1H), 8.06 (app d, J=5.0, 1H), 7.46 (b s, 5H), 7.15 (app t, J=8.6, 1H), 3.87–3.34 (b m, 8H), 2.72 (s, 3H); LC/MS (ES+) m/z (M+H)$^+$=462, HPLC R$_t$=1.453.

Example 81

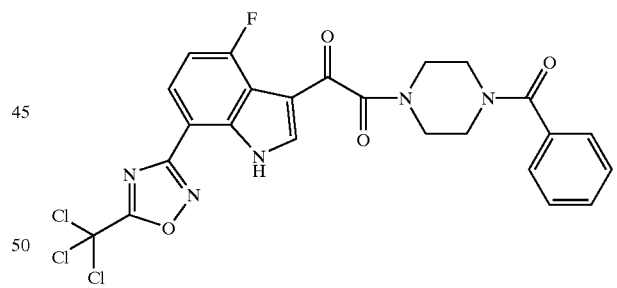

A suspension of the compound of Example 27 (100 mg, 0.229 mmol) in trichloroacetic anhydride (1 mL, 5.48 mmol) was stirred at 80° C. for 16 h. After cooling down to rt, the reaction mixture was poured into MeOH (20 mL) and left standing for 1 h. The precipitates were filtered, washed with MeOH (3×3 mL) and dried under high vacuum to give the product as a white solid (74 mg, 57%). Alternatively, after cooling down to rt, the reaction mixture was poured carefully into water and extracted with EtOAc (×3). The combined organic extracts were dried (MgSO$_4$) and evaporated in vacuo to give a yellow residue, which was purified by flash chromatography (Hexane then EtOAc/Hexane (50% to 60% to 70%)). $^1$H NMR (CDCl$_3$) δ 10.41 (s, 1H), 8.25 (d, J=3.1, 1H), 8.18 (app dd, J=8.4, 4.4, 1H), 7.47 (b s, 5H), 7.16 (app t, J=9.3, 1H), 3.87–3.34 (b m, 8H); LC/MS (ES+) m/z (M+H)$^+$=565, HPLC R$_f$=1.843.

Example 82

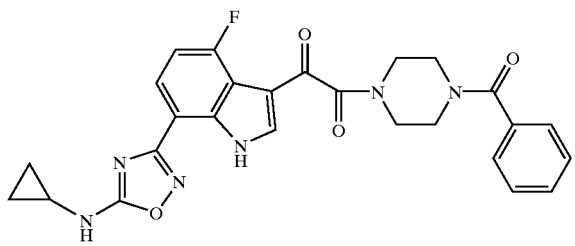

To a mixture of the compound of Example 81 (20 mg, 0.035 mmol) in DMF (0.5 mL) was added cyclopropylamine (0.1 mL, 1.426 mmol) and the resulting mixture stirred at rt for 16 h. Hydrochloric acid (1 N, aq.) was then added slowly to the reaction mixture until precipitates formed (pH about 6). The precipitates were filtered, washed three times with water, and dried under high vacuum to give the product as a white solid. (11 mg, 62%). $^1$H NMR (CDCl$_3$) δ 10.71 (s, 1H), 8.16 (d, J=3.0, 1H), 7.99 (app dd, J=8.3, 4.4, 1H), 7.47 (b s, 5H), 7.08 (app t, J=9.4, 1H), 5.73 (s, 1H), 3.83–3.49 (b m, 8H), 2.90 (b m, 1H), 0.94 (b m, 2H), 0.77 (b m, 2H); LC/MS (ES+) m/z (M+H)$^+$=503, HPLC R$_f$=1.513.

Example 83

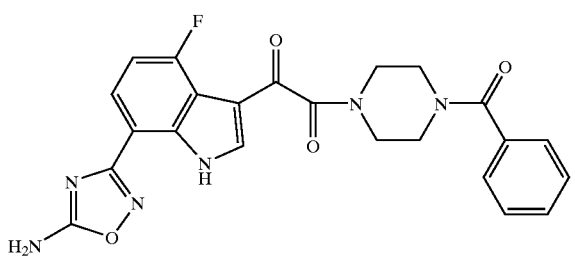

To a mixture of the compound of Example 81 (25 mg, 0.044 mmol) in DMF (0.3 mL) was added a saturated solution of ammonia in MeOH (0.2 mL) and the resulting mixture stirred at rt for 16 h. The reaction mixture was added to MeOH (2 mL), and then subjected to purification by preparative reverse phase HPLC using the method: Start %B=20, Final %B=100, Gradient time=12 min, Flow Rate= 40 mL/min, Column: YMC C18 S5 30×100 mm, Fraction Collection: 7.68–8.08 min. $^1$H NMR (CDCl$_3$) δ 10.61 (s, 1H), 8.17 (d, J=3.0, 1H), 7.93 (app dd, J=8.4, 4.4, 1H), 7.43 (b s, 5H), 7.09 (app t, J=9.7, 1H), 5.52 (s, 2H), 3.97–3.52 (b m, 8H); LC/MS (ES+) m/z (M+H)$^+$=463, HPLC R$_f$=1.303.

Example 84

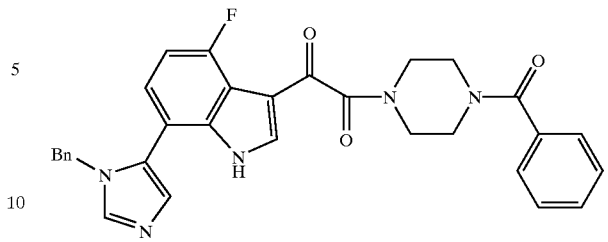

A mixture of the acid chloride intermediate 26 and benzoylpiperazine hydrochloride (24.9 mg, 0.110 mmol) in THF (2.0 ml) was added diisopropylethylamine (0.1 ml, 0.574 mmol) dropwise. After stirring for 5 hours, the reaction mixture, which contained mostly the acid of intermediate 26, was added EDC (21.1 mg, 0.110 mmol), DMAP (22.4 mg, 0.183 mmol) and DMF (1 ml), and then stirred for another 91 hours. The volatile was evaporated under a stream of nitrogen and the residue added excess water (about 10 ml) to induce precipitation. The off white solid was filtered, and washed with water (3×3 ml) and dried under a stream of air. The crude solid was purified by preparative TLC (5% MeOH/CH$_2$Cl$_2$, 1×500 m×20 cm×20 cm plate). The silica gel of the product band was removed from the plate, loaded onto a filter funnel, and washed with 10% MeOH/CH$_2$Cl$_2$ (3×5 ml). The combined washings were evaporated in vacuo to give the product as an off white solid (22.7 mg, 46% 2 steps). $^1$H NMR: (CDCl$_3$) δ 13,24 (b s, 1H), 8.13 (d, J=2.5, 1H), 7.43 (b s, 5H), 7.25–7.20 (overlapping m, 4H), 7.03–6.97 (overlapping m, 2H), 6.90 (s, 1H), 6.81 (d, J=7.4, 2H), 4.84 (s, 2H), 3.83–3.49 (b m, 8H); LC/MS: (ES+) m/z (M+H)$^+$=536, HPLC R$_f$=1.197.

Example 85

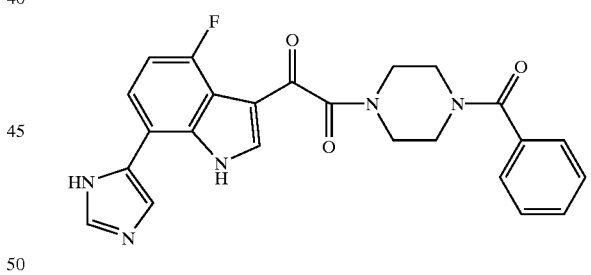

To a mixture of the compound prepared in Example 84 (12.0 mg, 22.4 μmol) in MeOH (2.0 ml) was added 10% Pd/C (25 mg). After stirring at room temperature for 24 hours, the 50% converted (based on LC/MS analysis) reaction mixture was filtered through a Whatman PDVF disc filter (0.45 μm). The residue obtained after evaporation of the filtrate was purified by preparative TLC (10% MeOH/ CH$_2$Cl$_2$, 2×500 m×20 cm×20 cm plates). The silica gel of the product band was removed from the plate, loaded onto a filter funnel, and washed with 10% MeOH/CH$_2$Cl$_2$ (3×5 ml). The combined washings were evaporated in vacuo to give the product as a white solid. $^1$H NMR: (CD$_3$OD/ CDCl$_3$) δ 8.02 (s, 1H), 7.76 (s, 1H), 7.45–7.30 (overlapping m, 7H), 6.85 (b s, 1H), 3.90–3.40 (b m, 8H); LC/MS: (ES+) m/z (M+H)$^+$=446, HPLC R$_f$=0.960.

Example 86

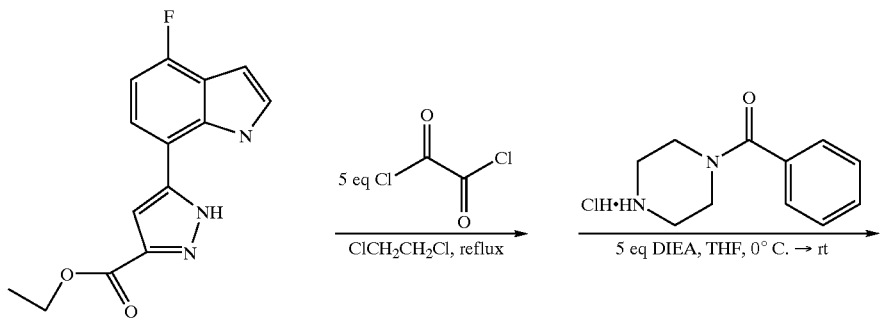

Intermediate 29

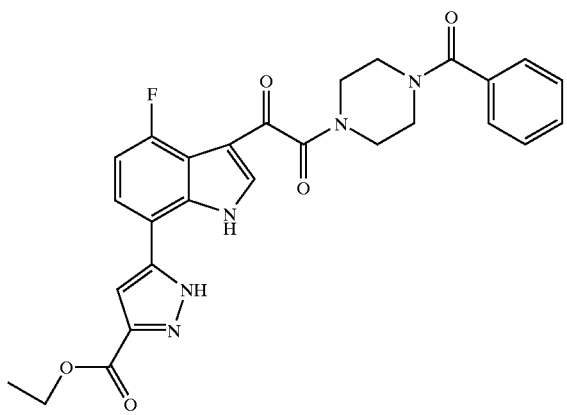

Example 86

An oven dried 50 ml flask was charged with the ethyl pyrrazole-3-carboxylate compound intermediate 29 (149 mg, 0.513 mmol) and 1,2-dichloroethane to give a solution, which at rt. was added neat oxalyl chloride (228 µl, 2.56 mmol) dropwise via a syringe. The reaction mixture was refluxed at about 85° C. for 2 h., cooled to rt, and the volatile evaporated in vacuo to give the crude indoleglyxoyl chloride. A mixture of the indoleglyxoyl chloride in dry THF (10 ml) at rt was added benzoylpiperazine hydrochloride (107 mg, 0.472 mmol), and then stirred for 10 min. N,N-diisopropylethylamine (447 µl, 2.56 mmol) was then added dropwise to the mixture cooled to 0° C. in an ice-water bath, and the resulting reaction mixture stirred for 10 min. The reaction mixture was warmed to rt and stirred for another 1 hr. After evaporation in vacuo to remove part of the solvent, the crude mixture was added MeOH (3 ml), and purified by preparative reverse phase HPLC to afford 102 mg of light solids. Recrystalization of the solids from hot MeOH gave, after drying, the product as (50 mg, 19%) of white solid. $^1$H NMR (CD$_3$OD) 8.21 (s, 1H), 7.68–7.74 (m, 1H), 7.41–7.54 (b s, 5H), 7.36 (s, 1H), 7.06 (m, 1H), 4.42 (q, J=7.1, 2H), 3.45–4.0 (b m, 8H), 1.42 (t, J=7.2, 3H); LC/MS: (ES+) m/z (M+H)$^+$=518, HPLC (0.2% H$_3$PO$_4$ buffer, gradient time=8 min, flow rate=2.5 ml/min) R$_t$=6.20.

Example 87

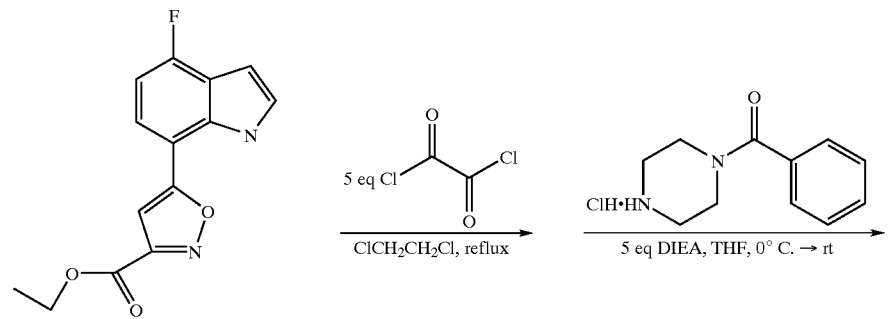

Intermediate 30

-continued

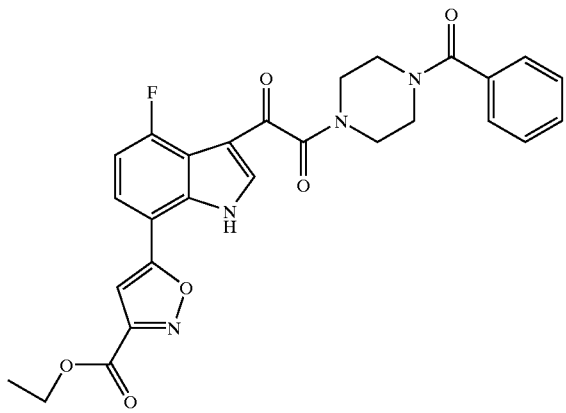

Example 87

An oven dried 20 ml flask was charged with the ethyl isoxazole-3-carboxylate compound intermediate 30 (56 mg, 0.204 mmol) and anhydrous 1,2-dichloroethane (3 ml). The mixture was stirred at rt for 5 min, added oxalyl chloride (89 µl, 1.02 mmol) and then refluxed at about 85° C. for 3 h. After cooling to rt, the volatile was evaporated in vacuo to give the crude indoleglyxoyl chloride. A mixture of the indoleglyxoyl chloride (40.8 mg, 0.112 mmol) in dry THF (4 ml) at rt was added benzoylpiperazine hydrochloride (23.4 mg, 0.103 mmol), and then stirred for 5 min. N,N-diisopropylethylamine (98 µl, 0.56 mmol) was then added dropwise to the mixture cooled to 0° C. in an ice-water bath, and the resulting reaction mixture stirred for 5 min. The reaction mixture was warmed to rt and stirred for another 1 hr. After evaporation in vacuo to remove part of the solvent, the crude mixture was added MeOH (3 ml), and purified by preparative reverse phase HPLC to give 28 mg of light yellow solids. Recrystallization of the solids from hot MeOH gave the product (17 mg, 16%) as a white solid. $^1$H NMR: (DMF-d$_7$, δ=8.22 ppm) 13.08 (s, 1H), 8.65 (d, J=3.5 1H), 8.3 (burried s, 1H), 7.82 (s, 1H), 7.68 (b s, 5H), 7.48 (t, J=9.5, 1H), 4.67 (q, J=7.2, 2H), 3.31–4.17 (b s, 8H), 1.59 (t, J=7.5, 3H); LC/MS: (ES+) m/z (M+H)$^+$=519, HPLC (0.2% H$_3$PO$_4$ buffer, gradient time=4 min, flow rate=2 ml/min) R$_t$=4.147.

Example 88

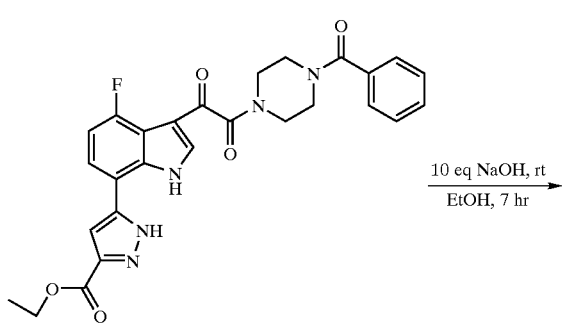

Example 86

10 eq NaOH, rt
EtOH, 7 hr

-continued

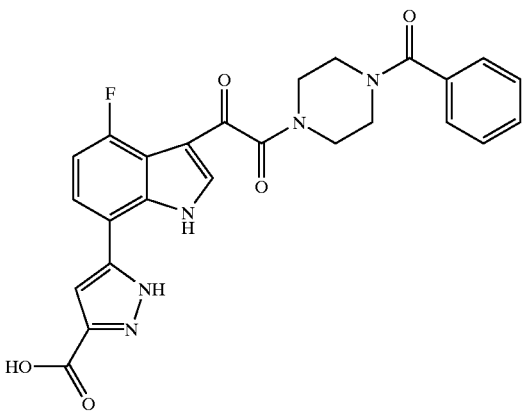

Example 88

To a mixture of the compound prepared in Example 86, (75 mg, 0.145 mmol) in EtOH (5 ml) at rt was added NaOH (0.145 ml, 1.45 mmol, 10 N, aq), and the reaction mixture stirred at rt for 7 h. The reaction mixture was then neutralized with 10 N hydrochloric acid, and the crude product purified by preparative reverse phase HPLC to afford the product (35.3 mg, 50%) as a light yellow solid. $^1$H NMR (CD$_3$OD) δ 8.14 (s, 1H), 7.59–7.66 (m, 1H), 7.32–7.48 (b s, 5H), 7.26 (s, 1H), 7.00 (app t, J=9.5, 1H), 3.35–3.95 (b m, 8H); LC/MS: (ES+) m/z (M+H)$^+$=490, HPLC (0.2% H$_3$PO$_4$ buffer, gradient time=4 min, flow rate =2 ml/min) R$_t$=3.987. This hydrolysis was also performed in MeOH using 5 equiv. of NaOH (1 N, aq).

Example 89

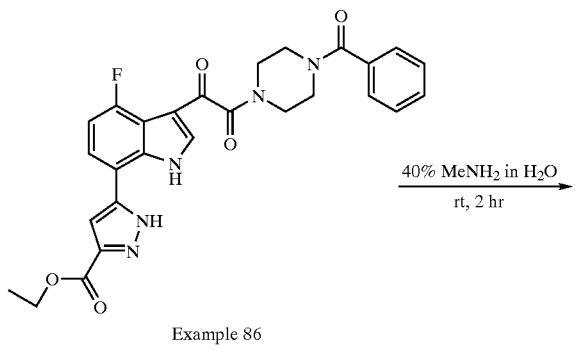

Example 90

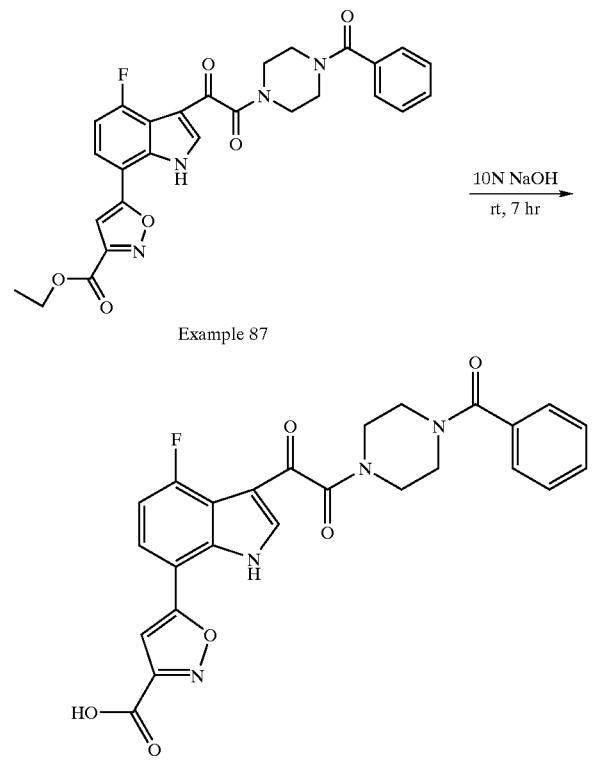

To a 2 ml vial was added the compound prepared in Example 86 (10 mg, 0.0193 mmol) and excess MeNH$_2$ (2 ml, 40% in H$_2$O), and the reaction mixture stirred at rt for 2 h. The crude product was then purified by reverse phase preparative HPLC to afford the product (5.2 mg, 54%). $^1$H NMR (CD$_3$OD) 8.14 (s, 1H), 7.54 (dd, J=4.2, 8.1, 1H), 7.31–7.48 (b s, 5H), 7.12 (s, 1H), 6.90 (overlapped dd, J=8.5, 10.2, 1H), 3.20–3.95 (b m, 8H), 2.88 (s, 3H); LC/MS: (ES+) m/z (M+H)$^+$=503, HPLC (0.2% H$_3$PO$_4$ buffer, gradient time=4 min, flow rate =2 ml/min) R$_t$=3.837.

To a mixture of the compound prepared in Example 87 (45 mg, 0.087 mmol) in EtOH (3 ml) at rt was added NaOH (0.09 ml, 0.87 mmol, 10 N, aq.), and the reaction mixture stirred for 7 h. The reaction mixture was then neutralized with 10 N hydrochloric acid, and the crude product purified by reverse phase preparative HPLC to afford the product (28.5 mg, 67%) as a light gray solid. $^1$H NMR (CD$_3$OD) 8.23 (s, 1H), 7.84 (dd, J=4.1, 8.5, 1H), 7.38–7.57 (b s, 5H), 7.29 (s, 1H), 7.15 (app t, J=9.3, 1H), 3.45–3.98 (b m, 8H); LC/MS: (ES+) m/z (M+H)$^+$=491, HPLC (0.2% H$_3$PO$_4$ buffer, gradient time=4 min, flow rate=2 ml/min) R$_t$=4.013.

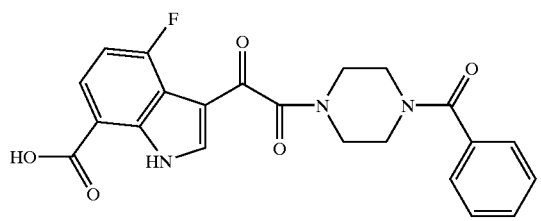

Intermediate 23

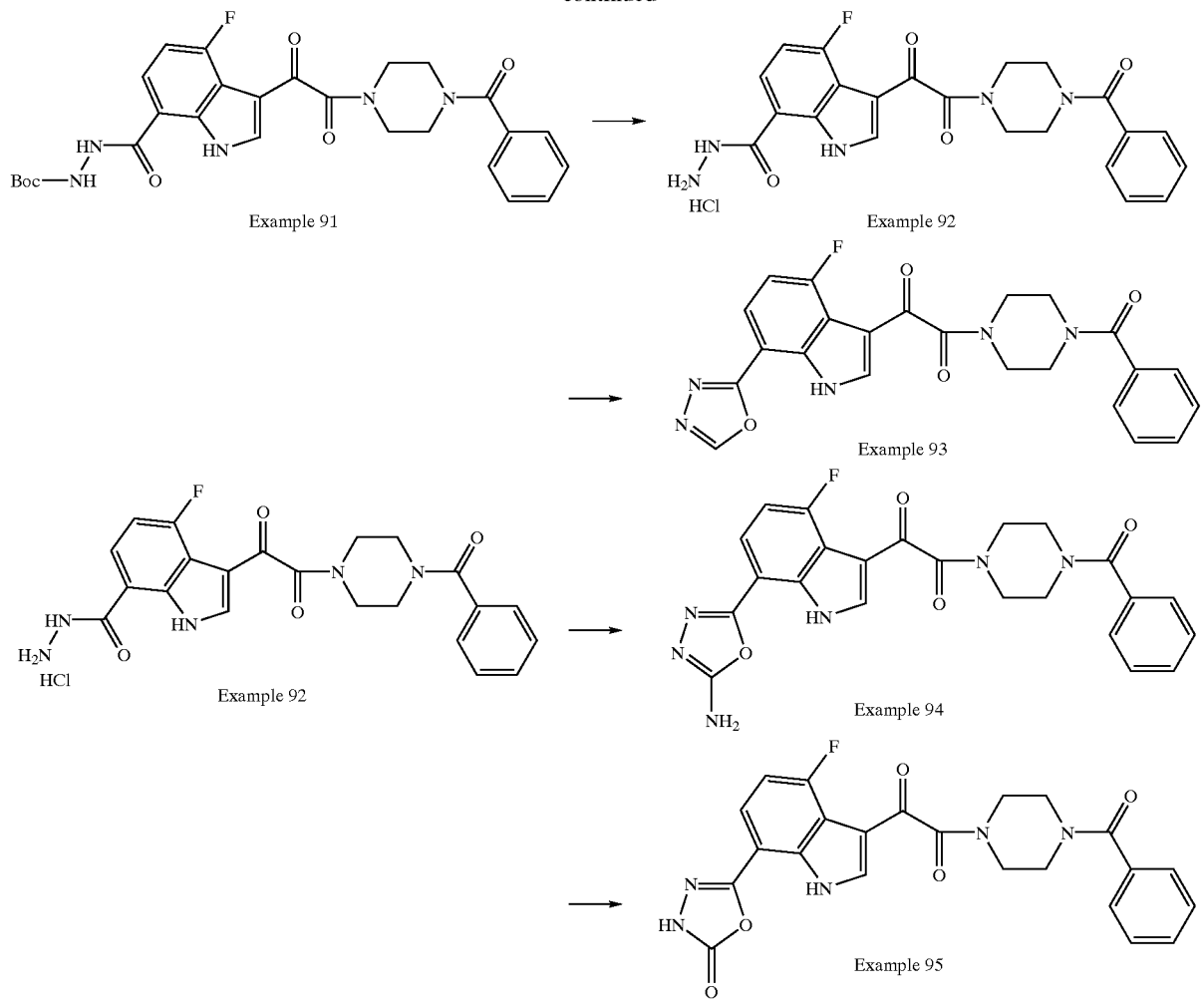

Example 91

To carboxylic acid Intermediate 23 (300 mg, 0.71 mmol) in $CH_2Cl_2$ (10 ml) was added tert-butylcarbazate (140 mg, 1.06 mmol), DMAP (130 mg, 1.06 mmol), and EDC (203 mg, 1.06 mmol). The reaction mixture was stirred at room temperature for 16 hours. After dilution with $CH_2Cl_2$ (40 ml), the organic mixture was washed with hydrochloric acid (60 ml, 1 N) and water (40 ml). Evaporation in vacuo gave a yellow solid which Was purified by flash chromatography using a gradient elution (hexane to 50% EtOAc/Hexane to EtOAc) to give the desired product as a pale yellow solid (300 mg, 79%). $^1$H NMR: ($CD_3OD$) δ 8.18 (s, 1H), 7.80 (b m, 1H), 7.46 (b s, 5H), 7.04 (app t, J=8.9, 1H), 3.85–3.51 (b m, 8H), 1.51 (s, 9H); LC/MS: (ES+) m/z $(M+H)^+$=538, HPLC $R_t$=1.343 min.

Example 92

To the compound prepared in Example 91 (300 mg, 0.558 mmol) was charged a solution of HCl in dioxane (3 ml, 12.0 mmol, 4 M), and the mixture stirred at room temperature for 4 hours. Removal of the excess reagent in vacuo afforded the hydrochloride salt of Example 92 as a yellow solid (100% conversion). $^1$H NMR: ($CD_3OD$) δ 8.21 (s, 1H), 7.81 (app, dd, J=8.4, 4.0, 1H), 7.46 (b s, 5H), 7.12 (app, t, J=9.2, 1H), 3.95–3.49 (b m, 8H); LC/MS: (ES+) m/z $(M+H)^+$=438, HPLC $R_t$=1.023 min.

Example 93

To the compound prepared in Example 92 (18 mg) was added triethylorthoformate (0.5 ml, 3.01 mmol) and the resulting suspension stirred at 105° C. for 16 hours. After cooling to room temperature, the reaction mixture was added MeOH (5 ml) and purified by reverse phase preparative HPLC using the method: Start %B=30, Final %B=90, Gradient time=20 min, Flow Rate=30 ml/min, Column: YMC C18 S5 30×100 mm, Fraction Collection: 11.00–11.60 min. $^1$H NMR: (DMSO) δ 12.56 (s, 1H), 9.48 (s, 1H), 8.18 (app d, J=3.0, 1H), 7.97 (app dd, J=8.3, 4.3, 1H), 7.44 (b s, 5H), 7.29 (app t, J=9.3, 1H), 3.69–3.20 (b, m, overlapped with the solvent peak, 8H); LC/MS: (ES+) m/z $(M+H)^+$= 448, HPLC $R_t$=1.317 min.

Example 94

To the compound prepared in Example 92 (15 mg) in dioxane (0.5 ml) was added a solution of cyanogen bomide in acetonitrile (0.1 ml, 0.5 mmol, 5.0 M) and a saturated aqueous solution of $NaHCO_3$ (0.1 ml). The resulting reaction mixture was stirred at room temperature for 16 hours. The reaction mixture was then added MeOH (2 ml) and purified by reverse phase preparative HPLC using the method: Start %B=20, Final %B=90, Gradient time=18 min, Flow Rate=30 ml/min, Column: YMC C18 S5 30×100 mm, Fraction Collection: 11.42–12.03 min. ¹H NMR: (CDCl₃) δ 10.65 (s, 1H), 8.22 (s, 1H), 7.67 (app dd, J=8.0, 4.1, 1H), 7.47 (b s, 5H), 7.10 (app t, J=9.3, 1H), 6.83 (b s, 2H), 3.98–3.47 (b m, 8H); LC/MS: (ES+) m/z (M+H)⁺=463, HPLC R$_t$=1.273 min.

Example 95

A solution of the compound of Example 92 (100 mg, 0.211 mmol) in EtOAc (50 ml) was washed with saturated aqueous NaHCO₃ solution (2×25 ml) and water (1×50 ml). After drying over MgSO₄, filtration, evaporation in vacuo and further dried under high vacuum, the resulting yellow solid was charged a solution of phosgene in toluene (5 ml, 1.92 M). The mixture was stirred at 110° C. for 16 hours, then cooled to room temperature and added MeOH (5 ml) carefully. After removal of solvent in vacuo, the residue was dissolved in MeOH (10 ml) and purified by reverse phase preparative HPLC using the method: Start %B=35, Final %B=90, Gradient time=15 min, Flow Rate=25 ml/min, Column: YMC C18 S5 30×100 mm, Fraction Collection: 6.66–7.23 min. ¹H NMR: (DMSO-d₆) δ 12.85 (s, 1H), 12.17 (s, 1H), 8.14 (app d, J=3.4, 1H), 7.73 (app dd, J=8.3, 4.1, 1H), 7.44 (b s, 5H), 7.22 (app t, J=9.4, 1H), 3.80–3.30 (b m, overlapped with solvent peak, 8H); LC/MS: (ES+) m/z (M+H)⁺=464, HPLC R$_t$=1.380 min.

Example 96

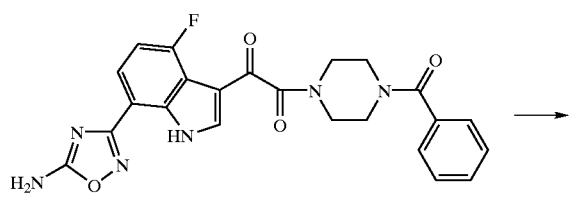

Example 83

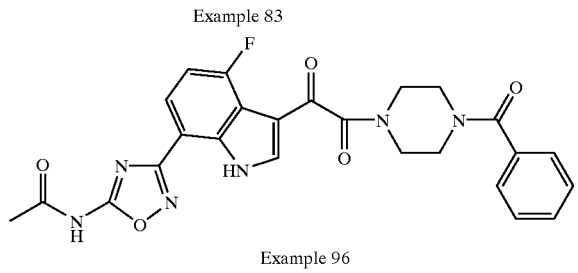

Example 96

To a suspension of the compound prepared in Example 83 (50 mg, 0.108 mmol) in toluene (1.0 ml) was added acetic anhydride (0.5 ml, 5.30 mmol). The resulting suspension was stirred at 110° C. for 20 hours. After cooling to room temperature, the reaction mixture was filtered, and the solid residue obtained washed with MeOH (30 ml) to afford the product as a white solid (27 mg, 50%). ¹H NMR: (DMSO-d₆) δ 12.36 (s, 1H), 12.16 (s, 1H), 8.16 (app d, J=3.0, 1H), 7.95 (app dd, J=8.3, 4.7, 1H), 7.44 (b s, 5H), 7.26 (app t, J=9.3, 1H), 3.69–3.20 (b m, 8H), 2.24 (s, 3H); LC/MS: (ES+) m/z (M+H)⁺=505, HPLC R$_t$=1.347 min.

Example 97

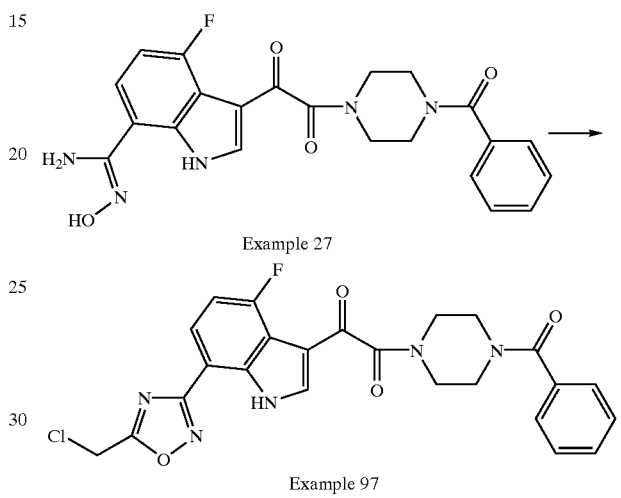

Example 27

Example 97

To the compound prepared in Example 27 (15 mg, 80% pure, 0.027 mmol) was added chloroacetyl chloride (0.5 ml, 6.28 mmol). The resulting mixture was stirred at 50° C. for 16 hours. After cooling to room temperature, the reaction mixture was added MeOH (4 ml) and purified by reverse phase preparative HPLC using the method: Start %B=25, Final %B=100, Gradient time=15 min, Flow Rate=35 ml/min, Column: YMC C18 S5 30×100 mm, Fraction Collection: 11.82–12.34 min. ¹H NMR: (CDCl₃) δ 10.56 (s, 1H), 8.22 (app d; J=3.0, 1H), 8.11 (app dd, J=8.3, 4.4, 1H), 7.47 (b s, 5H), 7.13 (app t, J=9.3, 1H), 4.8 (s, 2H), 3.98–3.50 (b, m, 8H); LC/MS: (ES+) m/z (M+H)⁺=496, HPLC R$_t$=1.507 min.

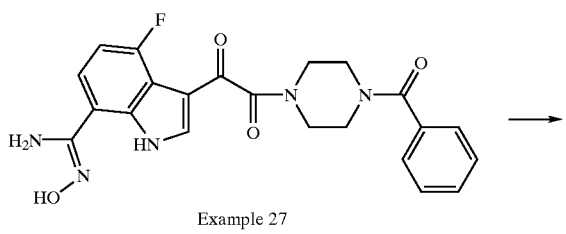

Example 27

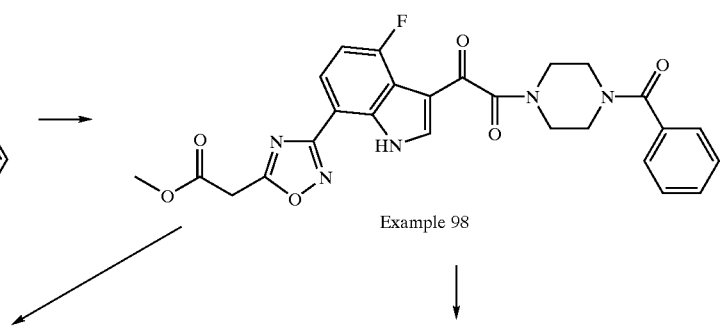

Example 98

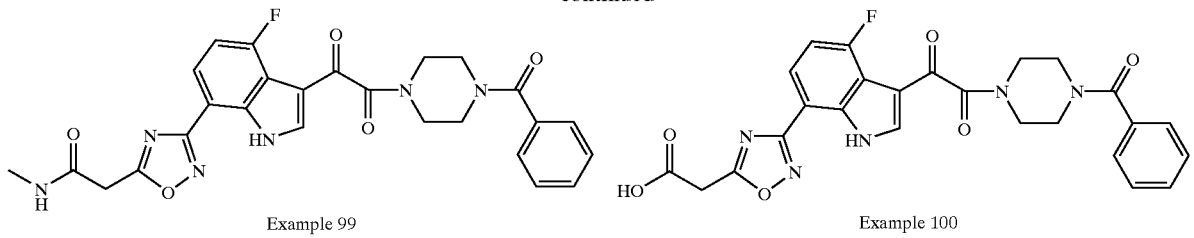

Example 99          Example 100

Example 98

To a solution of the compound prepared in Example 27 (100 mg, about 80% pure, 0.18 mmol) in pyridine (1 ml), was added methyl malonyl chloride (0.5 ml, 4.66 mmol). The resulting reaction mixture was stirred at 50° C. for 16 hours, then at 80° C. for another 16 hours to complete the reaction. After cooling to room temperature, the reaction mixture was added MeOH (4 ml) and purified by reverse phase preparative HPLC using the method: Start %B=20, Final %B=90, Gradient time=18 min, Flow Rate=35 ml/min, Column: YMC C18 S5 30×100 mm, Fraction Collection: 13.67–14.18 min. $^1$H NMR: (CDCl$_3$) δ 10.61 (s, 1H), 8.21 (app d, J=3.0, 1H), 8.10 (app dd, J=8.3, 4.4, 1H), 7.43 (b s, 5H), 7.12 (app t, J=9.4, 1H), 4.14 (s, 2H), 3.83 (s, 3H, overlapped with b m), 3.98–3.52 (b m, 8H); LC/MS: (ES+) m/z (M+H)$^+$=520, HPLC R$_t$=1.407 min.

Example 99

To the compound prepared in Example 98 (10 mg, 0.019 mmol) was charged a solution of methylamine in water (0.5 ml, 40%). The resulting mixture was stirred at room temperature for 16 hours. The reaction mixture was diluted with MeOH (2 ml) and purified by reverse phase preparative HPLC using the method: Start %B=25, Final %B=90, Gradient time=20 min, Flow Rate=35 ml/min, Column: YMC C18 S5 30×100 mm, Fraction Collection: 11.74–12.24 min. $^1$H NMR: (CDCl$_3$) δ 10.53 (s, 1H), 8.21 (s, 1H), 8.08 (app dd, J==8.2, 4.4, 1H), 7.43 (b s, 5H), 7.13 (app t, J=9.3, 1H), 6.69 (b s, 1H), 4.03 (s, 2H), 3.94–3.61 (b m, 8H), 2.94 (d, J=4.8, 3H); LC/MS: (ES+) m/z (M+H)$^+$=519, HPLC R$_t$=1.283 min.

Example 100

To a solution of the compound prepared in Example 98 (20 mg, 0.038 mmol) in MeOH (0.5 ml) was added an aqueous solution of NaOH (0.5 ml, 1 N). The resulting mixture was stirred at room temperature for 3 hours. After acidifying to pH about 2 using hydrochloric acid (1N), the reaction mixture was added MeOH (2 ml) and purified by reverse phase preparative HPLC using the method: Start %B=20, Final %B=80, Gradient time=15 min, Flow Rate= 35 ml/min, Column: YMC C18 S5 30×100 mm, Fraction Collection: 12.45–12.95 min. $^1$H NMR: (CD$_3$OD) δ 8.23 (s, 1H), 8.11 (app dd, J=7.7, 4.3, 1H), 7.47 (b s, 5H), 7.16 (app t, J==8.6, 1H), 4.22 (s, 2H), 3.87–3.44 (b m, 8H); LC/MS: (ES+) m/z (M+H)$^+$=506, HPLC R$_t$=1.340 min.

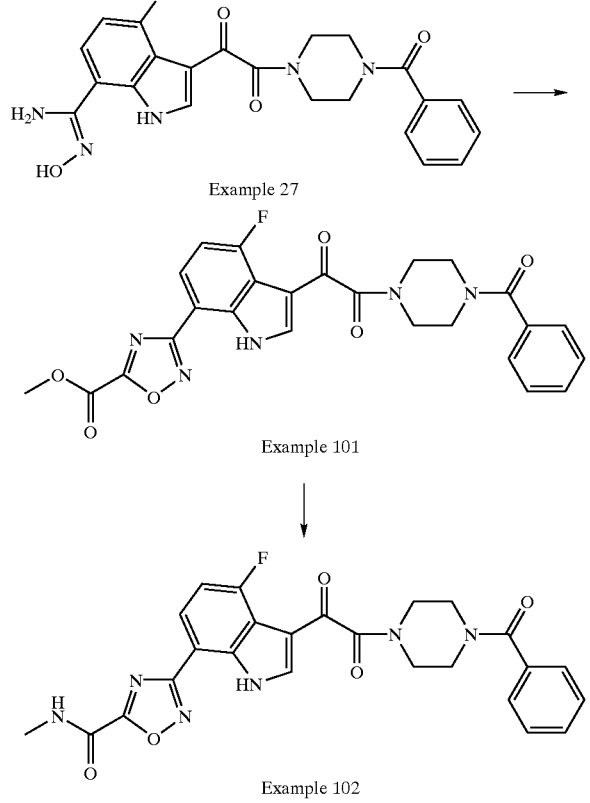

Example 27

Example 101

Example 102

Example 101

To a solution of the compound prepared in Example 27 (500 mg, about 80% pure, 0.91 mmol) in pyridine (8 ml), was added methyl chlorooxoacetate (2.0 ml, 21.7 mmol). The resulting mixture was stirred at room temperature for 16 hours. Addition of MeOH (5 ml) and evaporation in vacuo afforded a brownish oil, which was purified by flash chromatography using a gradient elution (hexane to 20% to 50% to 80% EtOAc/Hexane to EtOAc) to give the desired product as a white solid (188 mg, 41%). $^1$H NMR: (CDCl$_3$) δ 10.54 (s, 1H), 8.23 (app d, J=3.0, 1H), 8.20 (app dd, J=8.4, 4.4, 1H), 7.43 (b s, 5H), 7.15 (app t, J=9.3, 1H), 4.16 (s, 3H), 3.88–3.49 (b m, 8H); LC/MS: (ES+) m/z (M+H)$^+$=506, HPLC R$_t$=1.507 min.

Example 102

To the compound prepared in Example 101 (15 mg, 0.030 mmol) was charged a solution of methylamine in water (1.0 ml, 40%). The resulting mixture was stirred at room temperature for 16 hours. After concentration in vacuo, the residue was purified by flash chromatography using a gradient elution (hexane to 10% to 50% to 80% EtOAc/Hexane to EtOAc) to give a yellow solid. The solid was washed with MeOH (3 ml) to give the desired product as a white solid (4.1 mg, 27%). ¹H NMR: (CDCl₃) δ 10.51 (s, 1H), 8.22 (app d, J=3.0, 1H), 8.09 (app dd, J=8.3, 4.4, 1H), 7.43 (b s, 5H), 7.23 (m, 1H, overlapped with the solvent peak), 7.14 (app t, J=9.2, 1H), 3.88–3.49 (b m, 8H), 3.13 (d, J=5.1, 3H); LC/MS: (ES+) m/z (M+H)⁺=505, HPLC R$_t$=1.423 min.

Example 103

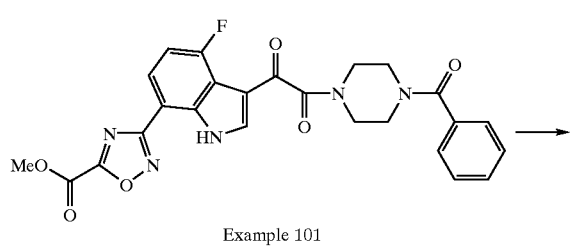

Example 101

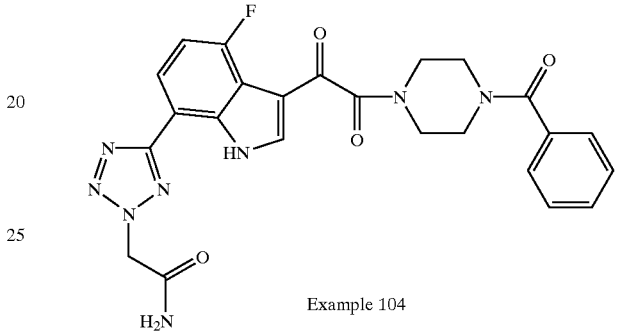

Example 103

A mixture of the compound prepared in Example 101 (25.0 mg, 49.5 mol) in THF (2.0 ml) in a reusable sealed tube was cooled to 0° C., and bubbled with ammonium gas for about 5 min. The sealed tube was closed tightly, and the reaction mixture stirred at room temperature for 3.5 hours. After which time, the volatile was evaporated under a stream of nitrogen, and water added to the residue. The white solid formed was filtered, washed with water (1 ml) and MeOH (2×0.5 ml), and dried to give a white solid (20.4 mg, 84%). ¹H NMR: (DMSO-d₆) δ 12.4 (s, 1H), 8.96 (s, 1H), 8.56 (s, 1H), 8.24 (d, J=3.0, 1H), 8.09 (dd, J=4.5, 8.5, 1H), 7.44 (b s, 5H), 7.30 (app t, 1H), 3.85–3.30 (b m, 8H); LC/MS: (ES+) m/z (M+H)⁺=491, HPLC R$_t$=1.363.

Example 104

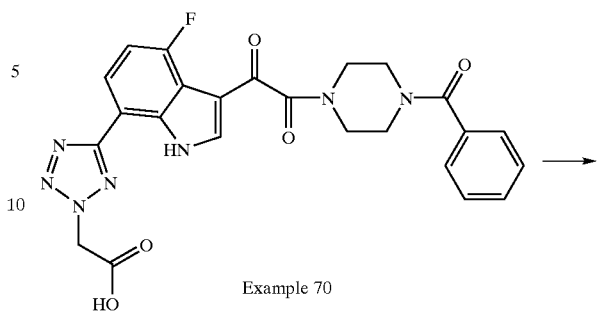

Example 70

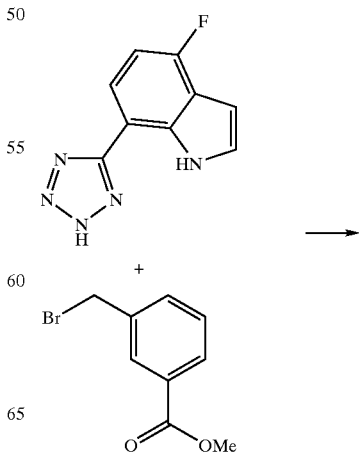

Example 104

To a mixture of the acid which is the product of Example 70 (130.1 mg, 0.257 mmol) in DMF (2.5 ml) was added ammonium chloride (57.2 mg, 1.07 mmol), HOBT (169.7 mg, 1.26 mmol), EDC (241.0 mg, 1.26 mmol) and NMM (0.3 ml, 2.73 mmol), and the resulting mixture stirred at room temperature for 24 hours. The volatile was then evaporated under high vacuum to give a residue, which was diluted with H₂O (~5 ml) and acidified to pH ~1 with HCl (1 N, aq.). The aqueous solution was decanted, and the residue washed with HCl (3×2 ml, 1 N, aq.) and dried under high vacuum. The dried residue was then added a minimun amount of MeOH (1.5 ml) to induce precipitation. The precipitates were filtered, and washed successively with MeOH (0.5 ml), H₂O (2×1 ml), HCl (2×1 ml, 1 N, aq.) and MeOH (3×0.5 ml) to give the product as a light beige solid (54.2 mg, 42%). ¹H NMR: (CD₃OD) δ 8.25 (s, 1H), 8.15 (dd, J==4.4, 8.0, 1H), 7.47 (b s, 5H), 7.16 (app t, 1H), 5.59 (s, 2H), 3.89–3.54 (b m, 8H); LC/MS: (ES+) m/z (M+H)⁺= 505, HPLC R$_t$=1.113.

-continued

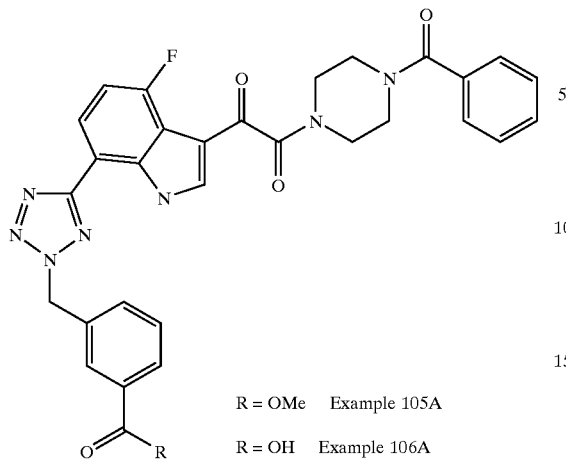

R = OMe   Example 105A
R = OH    Example 106A

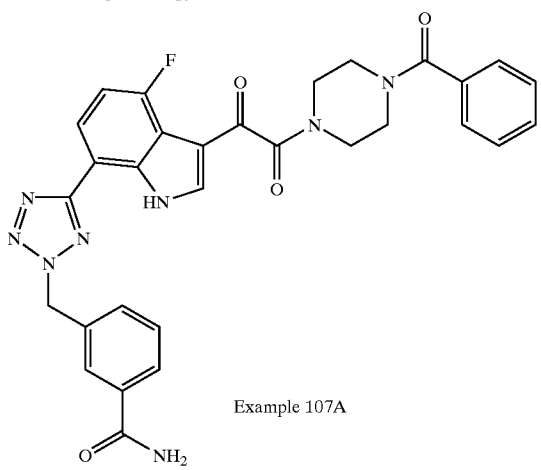

Example 107A

The products of Examples 105A, 106A, and 107A, and their ortho and para isomers were prepared analogously to those of Examples 22, 70, and 104 respectively. The corresponding benzyl bromide was prepared from bromination of methyl toluate using NBS/benzoyl peroxide in $CCl_4$.

Example 105A $^1$H NMR: ($CDCl_3$) δ 10.95 (b s, 1H), 8.21 (d, J==2.9, 1H), 8.17 (s, 1H), 8.11–8.07 (overlapping m, 2H), 7.64 (d, J=7.8, 1H), 7.51 (t, J=7.7, 1H), 7.43 (b s, 5H), 7.11 (app t, 1H), 5.92 (s, 2H), 4.00–3.45 (b m, 8H), 3.94 (s, 3H); LC/MS: (ES+) m/z $(M+H)^+$=596, HPLC $R_t$=1.703.

Example 106A $^1$H NMR: ($CD_3OD$) δ 8.24 (s, 1H), 8.14 (s, 1H), 8.12 (m, 1H), 8.03 (d, J=7.7, 1H), 7.71 (d, J=7.9, 1H), 7.53 (t, J==7.7, 1H), 7.46 (b s, 5H), 7.14 (app t, 1H), 6.07 (s, 2H), 4.00–3.45 (b m, 8H); LC/MS: (ES+) m/z $(M+H)^+$=582, HPLC $R_t$=1.627.

Example 107A $^1$H NMR: ($CD_3OD$) δ 8.24 (s, 1H), 8.11 (m, 1H), 8.01 (s, 1H), 7.88 (d, J=7.7, 1H), 7.67 (d, J=7.6, 1H), 7.52 (t, J==7.8, 1H), 7.46 (b s, 5H), 7.14 (app t, 1H), 6.06 (s, 2H), 3.95–3.45 (b m, 8H); LC/MS: (ES+) m/z $(M+H)^+$=581, HPLC $R_t$=1.463.

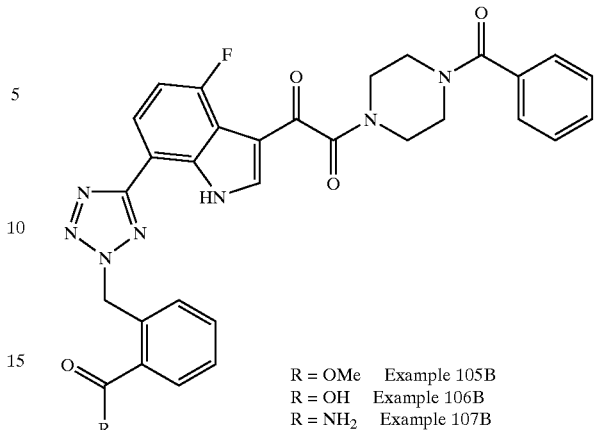

R = OMe   Example 105B
R = OH    Example 106B
R = $NH_2$   Example 107B

Example 105B $^1$H NMR: ($CDCl_3$) δ 10.95 (b s, 1H), 8.21 (d, J==3.1, 1H), 8.11–8.10 (overlapping m, 2H), 7.58–7.45 (m, 2H), 7.43 (b s, 5H), 7.10 (overlapping m, 2H), 6.38 (s, 2H), 3.96–3.50 (b m, 8H), 3.97 (s, 3H); LC/MS: (ES+) m/z $(M+H)^+$=596, HPLC $R_t$=1.707.

Example 106B $^1$H NMR: ($CD_3OD$) δ 8.13 (s, 1H), 8.08–8.04 (overlapping m, 2H), 7.50–7.30 (m overlapping with b s, 7H), 7.08 (d, J=7.7 1H), 7.04 (app t, 1H), 6.34 (s, 2H), 4.00–3.40 (b m, 8H); LC/MS: (ES+) m/z $(M+H)^+$582, HPLC $R_t$=1.627.

Example 107B $^1$H NMR: ($CD_3OD/CDCl_3$) δ 8.17 (s, 1H), 8.07 (dd, J=8.3, 4.4, 1H), 7.60 (d, J=7.2, 1H), 7.48–7.38 (m overlapping with b s, 7H), 7.30 (d, J=7.2, 1H), 7.05 (b dd, 1H), 6.20 (s, 2H), 3.95–3.40 (b m, 8H); LC/MS: (ES+) m/z $(M+H)^+$=581, HPLC $R_t$=1.470.

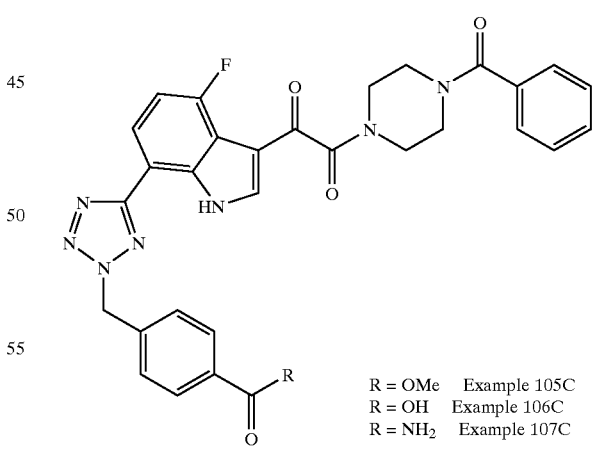

R = OMe   Example 105C
R = OH    Example 106C
R = $NH_2$   Example 107C

Example 105C $^1$H NMR: (CD $Cl_3$) δ 10.95 (b s, 1H), 8.21 (d, J=3.0, 1H), 8.10–8.07 (m overlapped d, 1H), 8.08 (d, J=8.3, 2H), 7.49 (d, J=8.3, 2H), 7.43 (b s, 5H), 7.10 (app t, 1H), 5.93 (s, 2H), 4.00–3.45 (b m, 8H), 3.92 (s, 3H); LC/MS: (ES+) m/z $(M+H)^+$=596, HPLC $R_t$=1.643.

Example 106C

¹H NMR: (DMSO-d₆) δ 13.09 (b s, 1H), 12.35 (b s, 1H), 8.18 (d, J=3.2, 1H), 8.05 (b m, 1H), 7.98 (d, J=8.1, 2H), 7.55 (d, J=8.1, 2H), 7.44 (b m, 5H), 7.25 (app t, 1H), 6.20 (s, 2H), 3.80–3.25 (b m, 8H); LC/MS: (ES+) m/z (M+H)⁺=582, HPLC R$_t$=1.530.

Example 107C

¹H NMR: (CD₃OD) δ 8.23 (s, 1H), 8.09 (dd, J=8.0, 4.3, 1H), 7.90 (d, J=8.3, 2H), 7.55 (d, J=8.3, 2H), 7.46 (b m, 5H), 7.12 (app t, 1H), 6.06 (s, 2H), 4.00–3.45 (b m, 8H); LC/MS: (ES+) m/z (M+H)⁺=581, HPLC R$_t$=1.380.

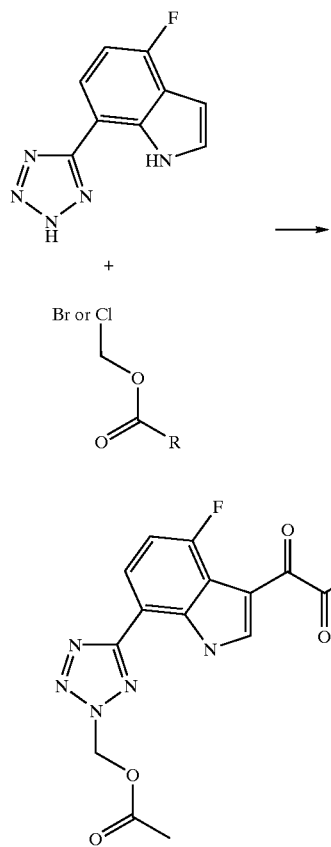

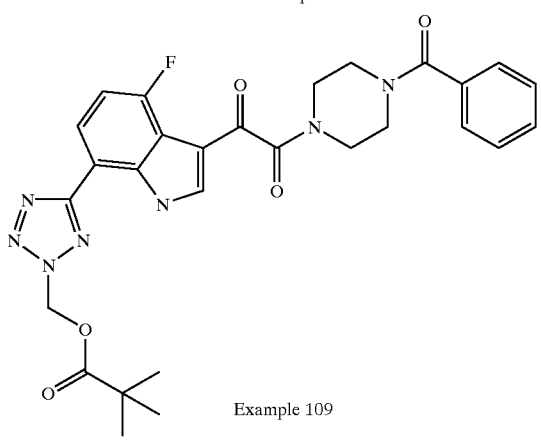

The products of Example 108 and Example 109 were prepared analogously to the product of Example 22.

Example 108

¹H NMR: (CDCl₃) δ 10.89 (b s, 1H), 8.24 (d, J=3.1, 1H), 8.17 (dd, J=4.4, 8.3, 1H), 7.43 (b s, 5H), 7.14 (app t, 1H), 6.59 (s, 2H), 4.00–3.45 (b m, 8H), 2.21 (s, 3H); LC/MS: (ES+) m/z (M+H)⁺=520, HPLC R$_t$=1.497.

Example 109

¹H NMR: (CDCl₃) δ 10.90 (b s, 1H), 8.24 (d, J=3.1, 1H), 8.17 (dd, J=4.3, 8.3, 1H), 7.43 (b s, 5H), 7.14 (app t, 1H), 6.59 (s, 2H), 4.00–3.45 (b m, 8H), 1.24 (s, 9H); LC/MS: (ES+) m/z (M+H)⁺=562, HPLC R$_t$=1.683.

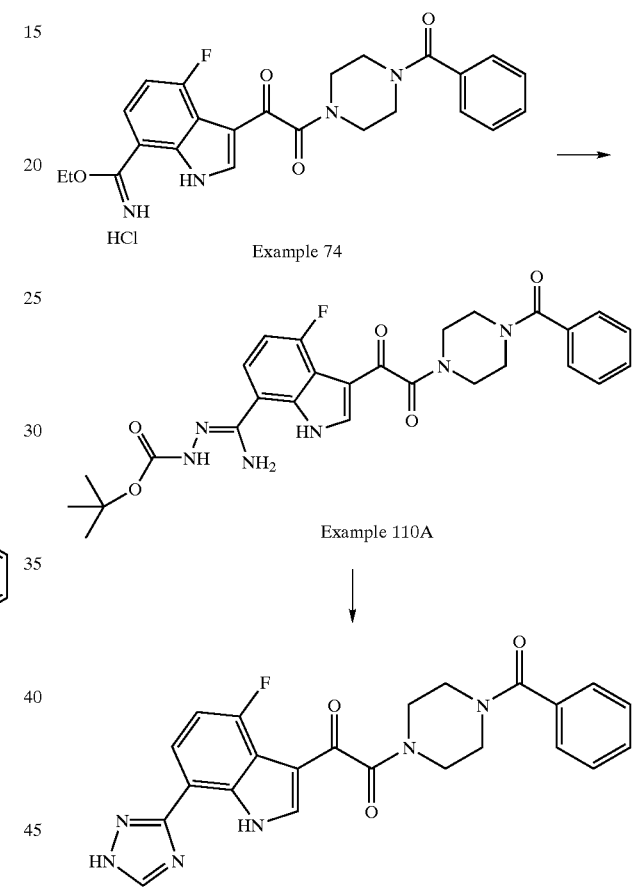

Example 110A

To compound from Example 74 (crude, 0.495 mmol) in EtOH (2 ml, 200 proof, anhydrous, 99.5+% from Aldrich) was added tert-butyl carbazate (196 mg, 1.485 mmol). The resulting mixture was stirred at room temperature for 3 hours. The reaction mixture was then added MeOH (4 ml) and purified by reverse phase preparative HPLC using the method: Start %B=25, Final %B=90, Gradient time=15 min, Flow Rate=25 ml/min, Column: YMC C18 S5 20×100 mm, Fraction Collection: 6.61–7.34 min.; ¹H NMR: (CD₃OD) δ 8.33 (s, 1H), 7.65 (app dd, J=7.8, 3.9, 1H), 7.47 (b s, 5H), 7.21 (app t, J=9.3, 1H), 3.97–3.40 (b m, 8H), 1.56 (s, 9H); LC/MS: (ES+) m/z (M+H)⁺=537, HPLC R$_t$=1.170 min. Fraction Collection of 11.62–12.43 min. gave compound of Example 110B. LC/MS: (ES+) m/z (M+H)⁺=652, HPLC R$_t$=1.417.

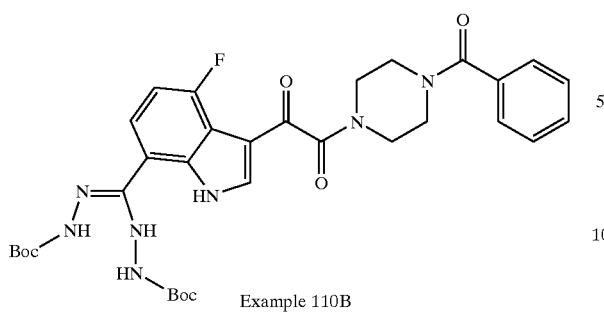

Example 110B

Example 111

To the compound of Example 110A (16 mg, 0.030 mmol) was charged triethylorthoformate (1 ml). The resulting mixture was heated at 110° C. for 16 hours. After cooled to room temperature, the reaction mixture was dissolved in MeOH (2 ml) and purified by reverse phase preparative HPLC using the method: Start %B=15, Final %B=75, Gradient time=16 min, Flow Rate=25 ml/min, Column: YMC C18 S5 20×100 mm, Fraction Collection: 10.72–11.52 min.; $^1$H NMR: (CDCl$_3$) δ 11.16 (b s, 1H), 8.39 (s, 1H), 8.12 (s, 1H), 7.87 (app dd, J=8.0, 4.1, 1H), 7.44 (b s, 5H), 7.01 (app t, J=9.4, 1H), 3.98–3.51 (b, m, 8H); LC/MS: (ES+) m/z (M+H)$^+$=447, HPLC R$_t$=1.257 min.

Alternatively, compound of Example 111 was prepared directly from compound of Example 74 by the following procedure: To a solution of compound of Example 74 (100 mg, 0.205 mmol) in EtOH (2 ml) was charged N,N-diisopropylethylamine (0.1 ml, 0.57 mmol) and formic hydrazide (57 mg, 0.95 mmol). The resulting mixture was heated at 60° C. for 16 hours. After cooled to room temperature, the reaction mixture was dissolved in MeOH (4 ml) and purified by preparative reverse phase HPLC using the same method as above.

Example 112

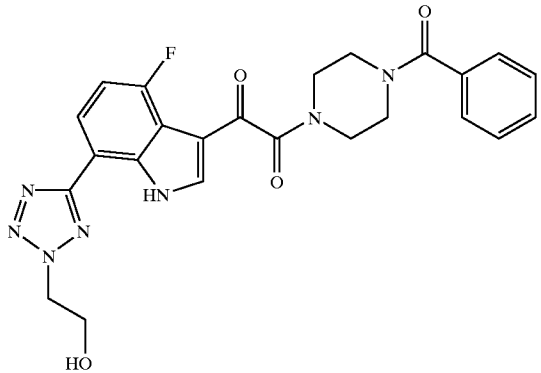

Compound of Example 112 was prepared by the reduction of compound of Example 22 using NaBH$_4$ in EtOH/THF (1:2) at rt. $^1$H NMR: (CDCl$_3$) δ 10.30 9b s, 1H), 8.01 (b m, 1H), 7.47–7.32 (b m, 6H), 6.97 (b m, 1H), 5.84 (b s, 1H), 4.88 (t, J=5.0, 2H), 4.29 (t, J=5.0, 2H), 4.00–3.00 (b m, 8H); LC/MS: (ES+) m/z (M+H)$^+$=492, HPLC R$_t$=1.250.

Example 113

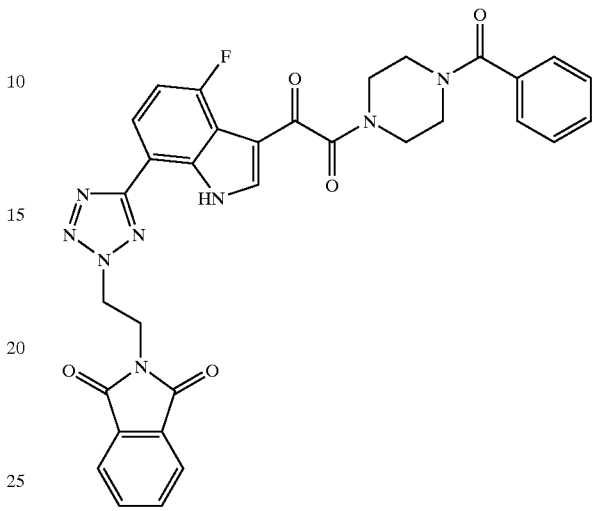

Compound of Example 113 was prepared analogously to compound of Example 22. $^1$H NMR: (CDCl$_3$) δ 10.96 (b s, 1H), 8.21 (d, J=3.2, 1H), 7.97 (dd, J=8.4, 4.4, 1H), 7.85–7.80 (overlapping m, 2H), 7.76–7.72 (overlapping m, 2H), 7.43 (b s, 5H), 7.06 (dd, J=10.2, 8.4, 1H), 5.08 (t, J=5.6, 2H), 4.40 (t, J=5.6, 2H), 4.05–3.40 (b m, 8H); LC/MS: (ES+) m/z (M+H)$^+$=621, HPLC R$_t$=1.557.

Example 114

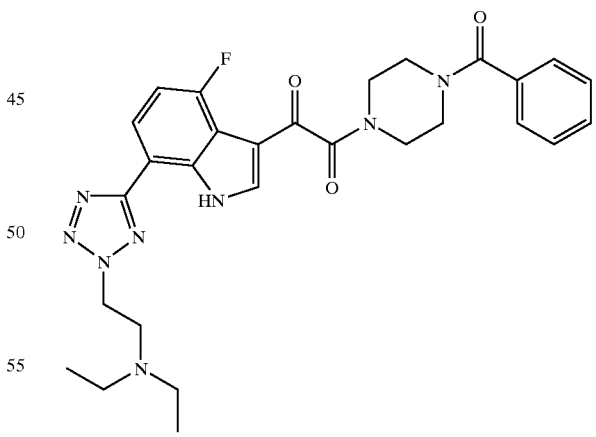

Compound of Example 114 was prepared analogously to compound of Example 22. $^1$H NMR: (CD$_3$OD) δ 8.25 (s, 1H), 8.13 (b dd, 1H), 7.47 (b s, 5H), 7.16 (b app t, 1H), 4.87 (buried t, 2H), 4.00–3.45 (b m, 8H), 3.20 (t, J=6.4, 2H), 2.62 (q, J=7.1, 4H), 1.00 (t, J=7.1, 6H); LC/MS: (ES+) m/z (M+H)$^+$=547, HPLC R$_t$=1.143.

Example 115

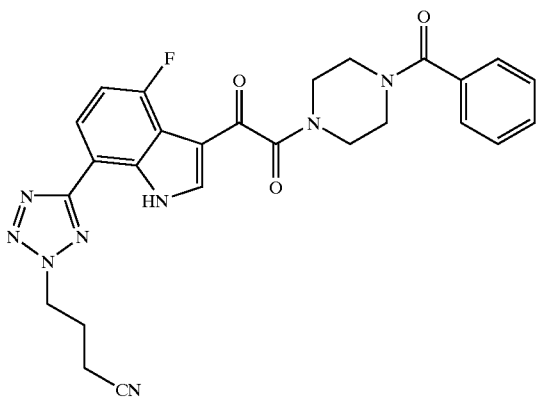

Compound of Example 115 was prepared analogously to compound of Example 22. $^1$H NMR: (CDCl$_3$) δ 10.98 (b s, 1H), 8.22 (d, J=3.0, 1H), 8.09 (dd, J=8.3, 4.4, 1H), 7.43 (b s, 5H), 7.13 (app t, 1H), 4.92 (t, J=6.4, 2H), 4.00–3.40 (b m, 8H), 2.59–2.48 (overlapping m, 4H); LC/MS: (ES+) m/z (M+H)$^+$=515, HPLC R$_t$=1.350.

Example 116

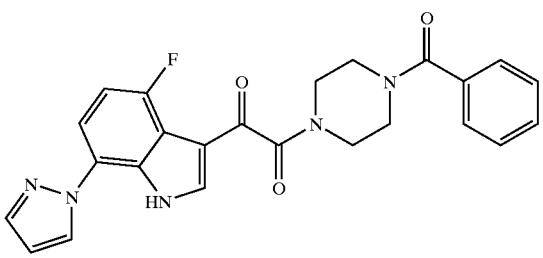

A mixture of intermediate 34a (c.a. 0.149 mmol) and the hydrochloride salt of intermediate 19 (52.0 mg, 0.229 mmol) in THF (1.0 ml) was added NMM (0.1 ml, 0.910 mmol), and the resulting mixture stirred at rt for 22 h. The mixture was then added intermediate 19 (43.0 mg, 0.190 mmol), DMAP (30.4 mg, 0.249 mmol), EDC (48.0 mg, 0.250 mmol), NMM (0.1 ml, 0.910 mmol), and DMF (1.5 ml), and stirred for a further 24 h to complete the reaction. The volatile was then evaporated to give a residue, which was diluted with excess H$_2$O and acidified to pH ~1 with HCl (1 N, aq.). The precipitates were filtered and washed with H$_2$O (2 ml) and dried. The crude solid was purified by preparative TLC (5% MeOH/CH$_2$Cl$_2$, two of 500 μm×20 cm×20 cm plates) to give the product of Example 116. $^1$H NMR: (CDCl$_3$) δ 11.47 (b s, 1H), 8.15 (d, J=3.1, 1H), 8.09 (d, J=2.5, 1H), 7.80 (d, J=1.8, 1H), 7.43 (b s, 5H), 7.33 (dd, J=8.6, 3.5, 1H), 7.01 (app t, 1H), 6.55 (t, J=2.2, 1H), 4.10–3.40 (b m, 8H); LC/MS: (ES+) m/z (M+H)$^+$=446, HPLC R$_t$=1.363.

Example 117

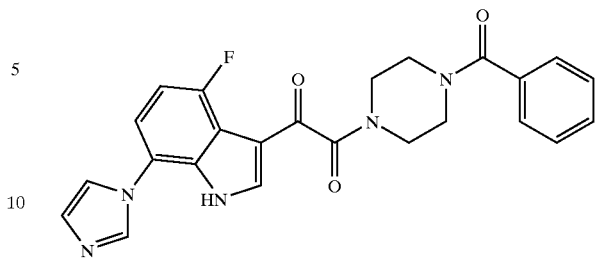

Compound of Example 117 was prepared analogously to compound of Example 116, except that only DMF was used as the solvent and the crude material was purified by reverse phase preparative HPLC. $^1$H NMR: (CD$_3$OD) δ 9.45 (s, 1H), 8.28 (s, 1H), 7.98 (s, 1H), 7.86 (s, 1H), 7.54 (dd, J=8.4, 3.4, 1H), 7.46 (b s, 5H), 7.18 (app t, 1H), 4.00–3.45 (b m, 8H); LC/MS: (ES+) m/z (M+H)$^+$=446, HPLC R$_t$=0.967.

Example 118

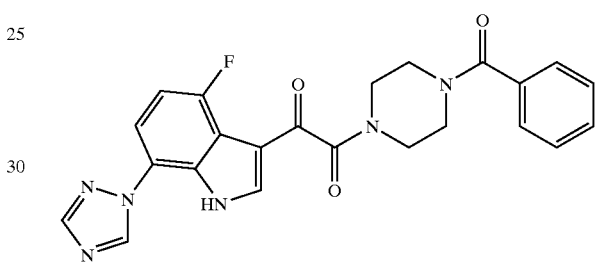

Compound of Example 118 was prepared analogously to compound of Example 116, except that only DMF was used as the solvent. $^1$H NMR: (CDCl$_3$) δ 10.95 (b s, 1H), 8.76 (s, 1H), 8.24 (s, 1H), 8.19 (d, J=3.1, 1H), 7.49–7.43 (dd overlapped with b s, 6H), 7.08 (app t, 1H), 4.00–3.40 (b m, 8H); LC/MS: (ES+) m/z (M+H)$^+$=447, HPLC R$_t$=1.187.

Example 119

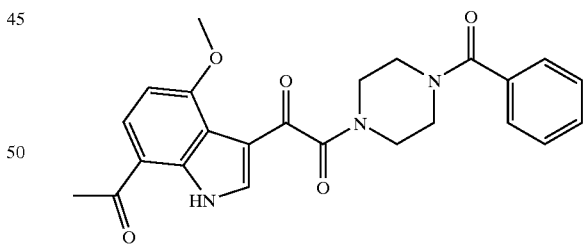

A mixture of intermediate 38 (c.a. 0.109 mmol) and the hydrochloride salt of intermediate 19 (38.0 mg, 0.168 mmol) in DMF (2.0 ml) was added DMAP (25.0 mg, 0.205 mmol), EDC (38.3 mg, 0.2 mmol) and NMM (55 μl, 0.5 mmol), and the resulting mixture stirred at rt for 22 h. The mixture was then added another amount of the amine (38.0 mg, 0.168 mmol) followed by DMF (1.5 ml), and stirred for 24 h. After which time, DMAP (25.0 mg, 0.205 mmol), EDC (38.3 mg, 0.2 mmol) and NMM (55 μl, 0.55 mmol) were added again to the reaction mixture, which was then stirred for a further 24 h to complete the reaction. The volatile was then evaporated under high vacuum to give a residue, which was diluted with H₂O (~15 m l) and acidified to pH ~1 with HCl (1 N, aq.). The resulting mixture was extracted with EtOAc (40 ml), and the organic extract washed with HCl (25 ml, t N, aq.) and evaporated to give a crude product. The crude material was purified by preparative TLC (5% MeOH/ CH₂Cl₂, 500 μm×20 cm×20 cm plates) to give the product as a yellow glass, which was then treated with MeOH (2×0.5 ml) and the methanolic layer removed by pipet to give the solid of Example 119 ¹H NMR: (CDCl₃) δ 8.07 (s, 1H), 7.86 (d, J=8.4, 1H), 7.43 (b s, 5H), 6.73 (d, J=8.4, 1H), 4.04 (s, 3H), 4.00–3.40 (b s, 8H), 2.67 (s, 3H); LC/MS: (ES+) m/z (M+H)⁺=456, HPLC R$_t$=1.227.

Example 120

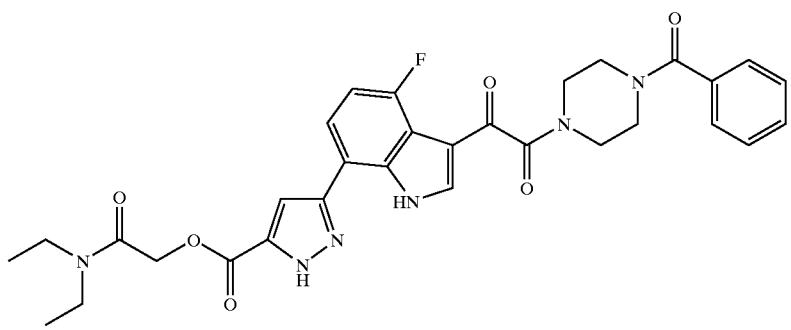

To a mixture of the compound prepared in Example 88 (13.7 mg, 0.028 mmol) and 2-chloro-N,N-diethylacetamide (5.0 mg, 0.033 mmol) in DMF (1.0 ml) was added triethylamine (10 μl, 0.036 mmol), and the resulting mixture stirred at rt for 24 h. NaI (one pipet tip), 2-chloro-N,N-diethylacetamide (5.0 mg, 0.033 mmol) and triethylamine (10 μl, 0.036 mmol) were then added successively to the reaction mixture. After stirring at rt for another 21 h, the three reagents were added again in the same order to the reaction mixture. The resulting mixture was stirred for another 20 h to complete the reaction and then evaporated under high vacuum to give a residue, which was purified by preparative TLC (5% MeOH/CH₂Cl₂, 1×500 μm×20 cm×20 cm plate) to give the product as a white solid. ¹H NMR: (CDCl₃) δ 12.35 (b s, 1H), 11.26, (b s, 1H), 8.14 (s, 1H), 7.43 (b s, 6H), 6.97 (app t, 1H), 5.02 (s, 2H), 4.00–3.40 (b m, 8H), 3.46 (q, J=7.1, 2H), 3.33 (q, J=7.1, 2H), 1.29 (t, J=7.1, 3H), 1.18 (t, J=7.1, 3H); LC/MS: (ES+) m/z (M+H)⁺=603, HPLC R$_t$=1.530.

Example 121

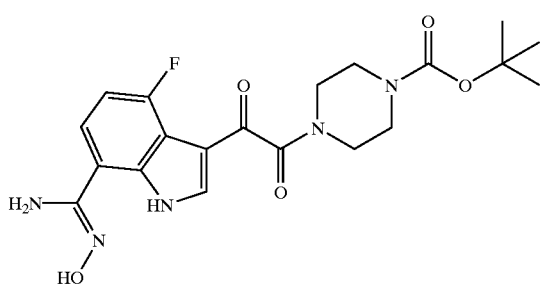

Compound of Example 121 was prepared from intermediate 39 analogously to Example 27, and purified by preparative TLC (10% MeOH/CH₂Cl₂, 500 μm×20 cm×20 cm plates). ¹H NMR: (CD₃OD) δ 8.12 (s, 1H), 7.59 (dd, J=8.4, 4.3, 1H), 7.02 (dd, J=10.5, 8.4, 1H), 3.72 (b m, 2H), 3.57 (b s, 2H), 3.46 (b s, 4H), 1.46 (s, 9H); LC/MS: (ES+) m/z (M+H)⁺=434, HPLC R$_t$=1.137.

Example 122

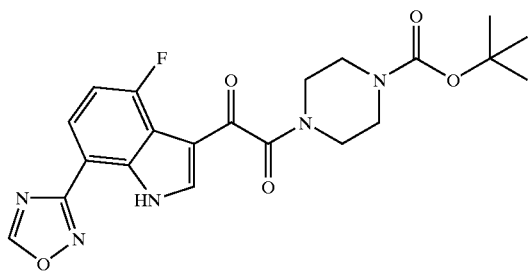

Compound of Example 122 was prepared from compound of Example 121 analogously to Example 79, and purified by preparative TLC (5% MeOH/CH₂Cl₂, 500 μm×20 cm×20 cm plate). ¹H NMR: (CDCl₃) δ 8.87 (s, 1H), 8.20 (d, J=3.1, 1H), 8.15 (dd, J=8.4, 4.5, 1H), 7.15 (dd, J=10.2, 8.4, 1H), 3.74 (app t, 2H), 3.57 (app t, 2H), 3.51 (m, 4H), 1.48 (s, 9H); LC/MS: (ES+) m/z (M+Na)⁺=466, HPLC R$_t$=1.537.

Example 123

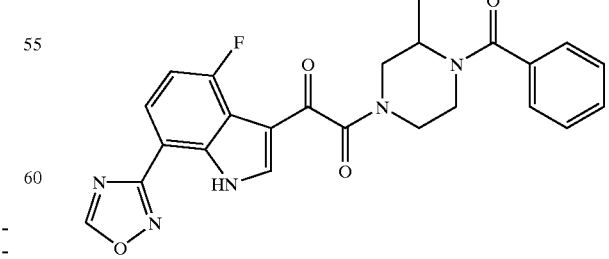

To a mixture of intermediate 50 (100 mg, 0.493 mmol) in DMF (2.0 ml) was added 2-methylpiperazine (54.3 mg, 0.542 mmol), and NMM (60 μl, 0.546 mmol), and the resulting mixture stirred at rt for 20 h. After which time, LC/MS analysis showed the formation of a monoamide and the hydrolyzed side product of intermediate 50 (ketoacid). The reaction mixture was then added 2-methylpiperazine (54.3 mg, 0.542 mmol), EDC (104 mg, 0.542 mmol), DMAP (66.3 mg, 0.543 mmol) and NMM (120 μl, 1.09 mmol) and stirred for 21 h to complete the formation of the monoamide. Benzoic acid (66.0 mg, 0.540 mmol), followed by EDC (104 mg, 0.542 mmol), DMAP (66.3 mg, 0.543 mmol) and NMM (120 μl, 1.09 mmol) were added to the reaction mixture, which was stirred for another 27 h. The mixture was diluted with water (about 10 ml) and acidified with HCl (1 N, aq.) to induce precipitation. The precipitates were filtered, washed HCl (3×2 ml, 1 N, aq.) and dried. The crude was purified by preparative TLC (5% MeOH/CH$_2$Cl$_2$, 500μm× 20 cm×20 cm plate) to give the product as a white solid. The position of the piperazine methyl group was supported by H-H NOESY studies. $^1$H NMR: (a ~1:1 mixture of 2 conformational isomers) (CDCl$_3$) δ 10.60 (b s, 1H), 8.86 (s, 1H), 8.21 (app t, 1H), 8.15 (m, 1H), 7.42 (b m, 5H), 7.14 (m, 1H), 4.65, 4.47, 3.95 and 3.76 (app b d, 4H), 3.50–2.90 (overlapping b m, 3H), 1.37 and 1.32 (d, J=6.7, 3H); LC/MS: (ES+) m/z (M+H)$^+$462, HPLC R$_t$=1.407.

Example 124

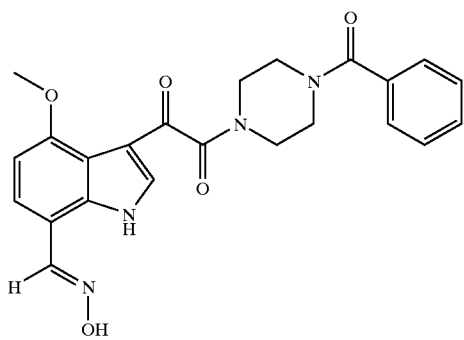

To the aldehyde intermediate 42 (20 mg, 0.048 mmol) in EtOH (2 ml) at rt. was added hydroxyamine (0.5 ml, 50% in H$_2$O), and the mixture stirred overnight. The crude mixture was then purified by reverse phase preparative HPLC to give compound of Example 124 (15.9 mg, 77%). $^1$H NMR: (CD$_3$OD) δ 8.25 (s, 1H), 8.11 (s, 1H), 7.38–7.57 (b s, 5H), 7.27 (d, J=8.2 Hz, 1H), 6.79 (d, J=8.2 Hz, 1H), 3.93 (s, 3H), 3.38–3.95 (m, 8H); LC/MS: (ES+) m/z (M+H)$^+$=435, HPLC (YMC C18 S7 3×50 mm, Flow Rate 4 ml/min, Gradient Time 2 min) R$_t$=1.263.

Example 125

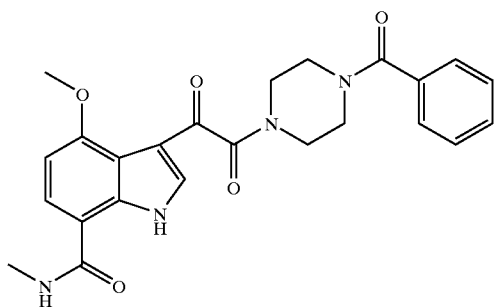

To the ester intermediate 45 (17 mg, 0.056 mmol) in EtOH (5 ml) was added 10 N NaOH (0.028 ml, 0.28 mmol), and the reaction mixture stirred for 28 hr at rt. The solvent was removed in vacuo and the residue dried overnight under high vacuum. The crude sodium salt in DMF (5 ml) at rt., after adding N,N-diisopropylethylamine (36.2 mg, 0.049 ml, 0.28 mmol) and 3-(diethoxyphosphoryloxy)-1,2,3-benzotriazo-4(3H)-one (18.4 mg, 0062 mmol), was treated with the benzoylpiperazine hydrochloride salt (16.5 mg, 0.073 mmol) The reaction mixture was then stirred at rt. for 48 hr before the solvent partially removed in vacuo. The crude mixture was dissolved in MeOH and purified by reverse phase preparative HPLC to afford compound of Example 125 (10 mg, 40% two steps). $^1$H NMR: (300 MHz, CD$_3$OD) δ 8.13 (s, 1H), 7.69 (d, J=8.4 Hz, 1H), 7.46 (b s, 5H), 6.81 (d, J=8.4 Hz, 1H), 3.78 (s, 3H), 3.20–3.98 (m, 8H), 2.94 (s, 3H); LC/MS: (ES+) m/z (M+H)$^+$=449, HPLC (YMC C18 S7 3×50 mm, Flow Rate 4 ml/min, Gradient Time 2 min) R$_t$=1.180.

Example 126

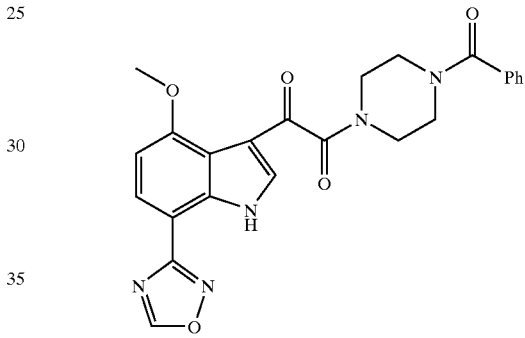

Intermediate 46 (120 mg, 0.288 mmol) was dissolved in hot EtOH (6 ml). After cooling to rt., the mixture was added dropwise NH$_2$OH (0.5 ml, 50% in H$_2$O) and then stirred at rt. for 3 hr. The crude material was purified by reverse phase preparative HPLC to afford a 4:1 mixture (72 mg) of the desired hydroxyaminidine (I) and its oxime side product (II), which was submitted to the cyclization reaction without further purification. LC/MS: (ES+) m/z (M+H)$^+$=450 (I) and 465 (II), HPLC (YMC C18 S7 3×50 mm, Flow Rate 4 ml/min, Gradient Time 2 min) R$_t$=0.890 (I and II). To the above 4:1 mixture (72 mg) of I and II in a 10 ml-flask was added anhydrous triethyl orthoformate (4 ml) and the resulting mixture stirred at 110° C. for 3 hr. After cooling to rt., the crude mixture was purified by reverse phase preparative HPLC to give compound of Example 126 (15 mg). The mixture was further purified by preparative TLC (5% MeOH/CH$_2$Cl$_2$, one 500 μm×20 cm×20 cm plate) to remove the side product. $^1$H NMR: (CD$_3$OD) δ 9.32 (s, 1H), 8.17 (s, 1H), 8.08 (d, J=8.4 Hz, 1H), 7.47 (b s, 5H), 6.95 (d, J=8.4 Hz, 1H), 4.07–3.42 (m, 8H), 4.00 (s, 3H); LC/MS: (ES+) m/z (M+H)$^+$=460, HPLC (YMC C18 S7 3×50 mm, Flow Rate 4 ml/min, Gradient Time 3 min) R$_t$=1.770.

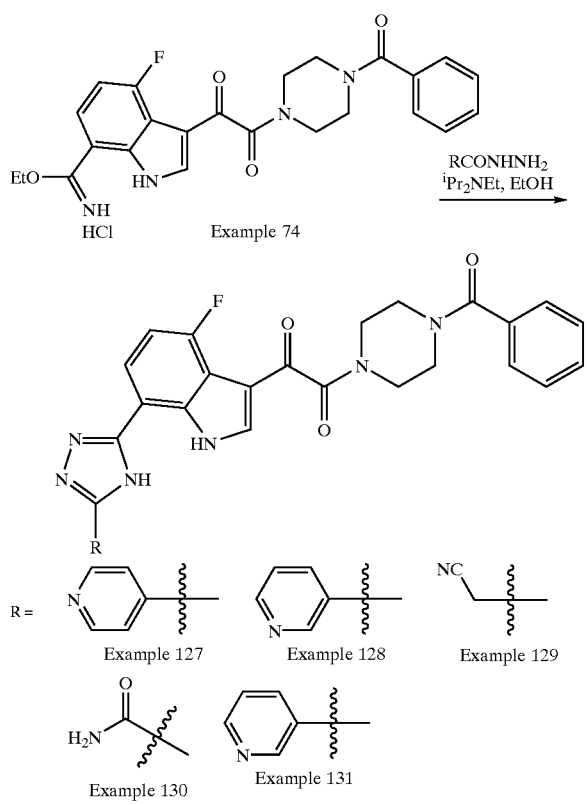

Example 127

Compound of Example 127 was prepared in the same manner as the alternative method of Example 111. Purification was performed preparative by reverse phase preparative HPLC using the method: Start %B=30, Final %B=90, Gradient time=15 min, Flow Rate=40 ml/min, Column: YMC C18 S5 30×100 mm, Fraction Collection: 7.16–7.62 min. $^1$H NMR: (CD$_3$OD) δ 8.84 (overlapping doublets, 4H), 8.31 (b s, 1H), 7.96 (b s, 1H), 7.47 (b s, 5H), 7.17 (app t, J=9.2, 1H), 3.97–3.38 (b, m, 8H); LC/MS: (ES+) m/z (M+H)$^+$=524, HPLC R$_t$=1.717.

Example 128

Compound of Example 128 was prepared in the same manner as compound of Example 127. $^1$H NMR: (CD$_3$OD) δ 9.54 (b m, 1H), 9.08 (b m, 1H), 8.81 (b s, 1H), 8.30 (s, 1H), 7.98 (b m, 2H), 7.47 (b s, 5H), 7.17 (app t, J=8.7, 1H), 3.98–3.44 (b m, 8H); LC/MS: (ES+) m/z (M+H)$^+$=524, HPLC R$_t$=1.763.

Example 129

Compound of Example 129 was prepared in the same manner as compound of Example 127. Purification was performed by preparative reverse phase HPLC using the method: Start %B=30, Final %B=90, Gradient time=15 min, Flow Rate=40 ml/min, Column: YMC C18 S5 30×100 mm, Fraction Collection: 7.58–8.03 min. $^1$H NMR: (CD$_3$OD) δ 8.25 (s, 1H), 7.92 (b s, 1H), 7.46 (b s, 5H), 7.12 (app t, J=8.5, 1H), 4.20 (s, 2H), 3.97–3.44 (b m, 8H); LC/MS: (ES+) m/z (M+H)$^+$=524, HPLC R$_t$=1.753.

Example 130

Compound of Example 130 was prepared in the same manner as compound of Example 127, except that the reaction temperature was 100° C. Purification was performed by preparative reverse phase HPLC using the method: Start %B=30, Final %B=90, Gradient time=15 min, Flow Rate=40 ml/min, Column: YMC C18 S5 30×100 mm, Fraction Collection: 7.63–8.08 min. $^1$H NMR: (DMSO-d$_6$) δ 12.50 (s, 1H), 8.67 (s, 1H), 8.20 (d, J=3.0, 1H), 8.03 (app dd, J=8.0, 4.3, 1H), 7.44 (b s, 5H), 7.21 (app t, J=9.1, 1H), 3.91–3.31 (overlapping with broad water peak, 8H); LC/MS: (ES+) m/z (M+H)$^+$=490, HPLC R$_t$=1.777.

Example 131

Compound of Example 131 was prepared (using hydrazide intermediate 47) in the same manner as compound of Example 127, except that the reaction temperature was 78° C. $^1$H NMR: (CD$_3$OD) δ 9.59 (s, 1H), 8.74 (overlapping doublets, 2H), 8.29 (s, 1H), 8.07 (b s, 1H), 7.47 (b s, 5H), 7.14 (app t, J=8.4, 1H), 3.99–3.44 (b m, 8H); LC/MS: (ES+) m/z (M+H)$^+$=525, HPLC R$_t$=1.447.

Example 132

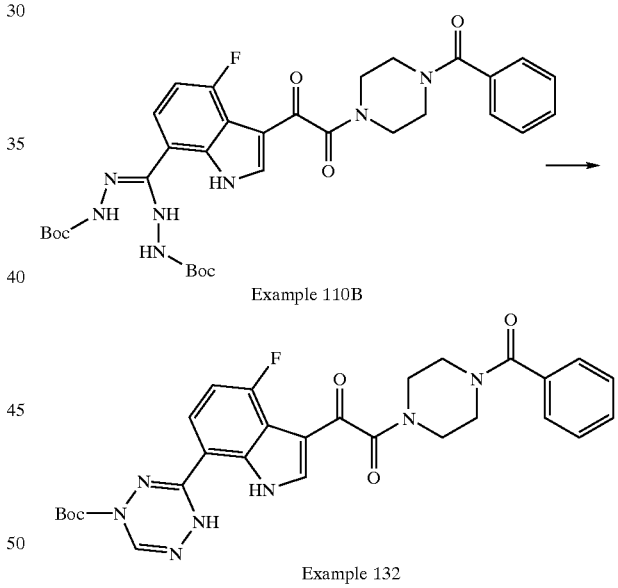

To compound of Example 110B (crude, 20 mg, 0.031 mmol) was charged triethylorthoformate (1 ml). The resulting mixture was heated at 110° C. for 16 hours. After cooled to room temperature, the mixture was dissolved in MeOH (2 ml) and purified by preparative reverse phase HPLC using the method: Start %B=30, Final %B=80, Gradient time=16 min, Flow Rate=25 ml/min, Column: YMC C18 S5 20×100 mm, Fraction Collection: 10.50–11.08 min. $^1$H NMR: (CD$_3$OD) δ 8.81 (s, 1H), 8.19 (s, 1H), 7.77 (b, s, 1H), 7.46 (b s, 5H), 7.15 (app t, J=8.9, 1H), 3.88–3.44 (b m, 8H), 1.37 (b s, 9H); LC/MS: (ES+) m/z (M+H)$^+$=562, HPLC R$_t$=1.370.

Example 133

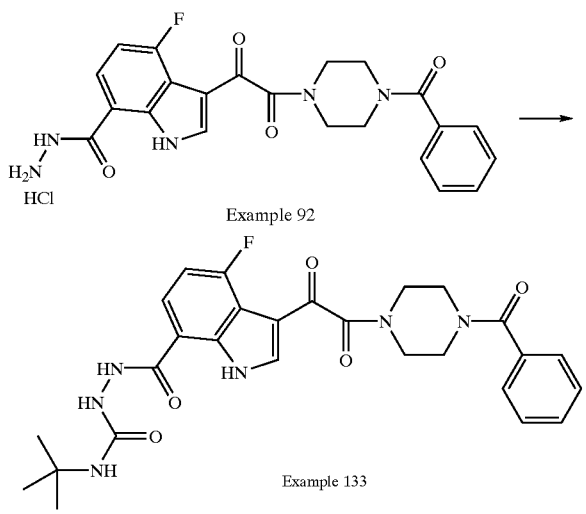

Example 92

Example 133

To a solution of compound of Example 92 (100 mg, 0.211 mmol) in EtOH (2 ml), was added N,N-diisopropylethylamine (0.1 ml) and tert-butylisocyanate (50 μl, 0.438 mmol). The reaction mixture was stirred at room temperature for 16 hours and then filtered. The filtrate was purified by preparative reverse phase HPLC using the method: Start %B=30, Final %B=100, Gradient time=15 min, Flow Rate=40 ml/min, Column: YMC C18 S5 30×100 mm, Fraction Collection: 7.79–8.24 min. $^1$H NMR: (CD$_3$OD) δ 8.19 (s, 1H), 7.82 (app dd, J=8.1, 4.2, 1H), 7.46 (b s, 5H), 7.03 (app t, J=9.0, 1H), 3.99–3.43 (b m, 8H), 1.35 (b, s, 9H); LC/MS: (ES+) m/z (M+H)$^+$=537, HPLC R$_t$=1.790.

Example 134

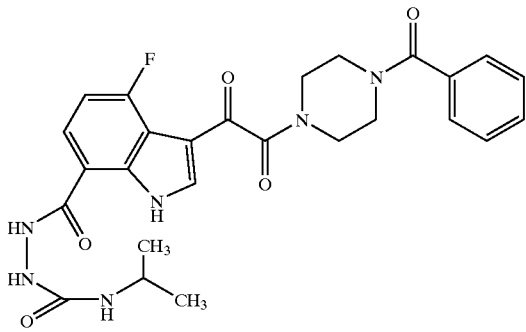

Compound of Example 134 was prepared in the same manner as compound of Example 133. Purification was performed by reverse phase preparative HPLC using the method: Start %B=30, Final %B=80, Gradient time=12 min, Flow Rate=40 ml/min, Column: YMC C18 S5 30×100 mm, Fraction Collection: 6.74–7.07 min. $^1$H NMR (CD$_3$OD) δ 8.13 (s, 1H), 7.76 (b m, 1H), 7.43 (b s, 5H), 6.99 (app t, J=8.8, 1H), 3.88 (app, dd, overlapping with b m, J=13.0, 6.5, 1H); 3.95–3.49 (b m, 8H), 1.13 (d, J=6.5, 6H); LC/MS (ES+) m/z (M+H)$^+$=523, HPLC R$_t$=1.607.

Example 135

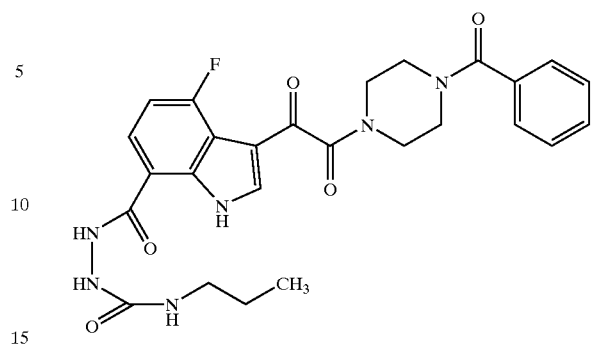

Compound of Example 135 was prepared in the same manner as compound of Example 133. Purification was performed by reverse phase preparative HPLC using the method: Start %B=30, Final %B=95, Gradient time=16 min, Flow Rate=40 ml/min, Column: YMC C18 S5 30×100 mm, Fraction Collection: 6.57–7.50 min. $^1$H NMR (CD$_3$OD) δ 8.18 (s, 1H), 7.86 (b m, 1H), 7.46 (b s, 5H), 7.04 (app, t, J=9.2, 1H), 3.97–3.38 (b m, 8H), 3.14 (app dd, J=13.1, 5.5, 2H), 1.53 (m, 2H), 0.92 (t, J=7.4, 3H); LC/MS (ES+) m/z (M+H)$^+$=523, HPLC R$_t$=1.593.

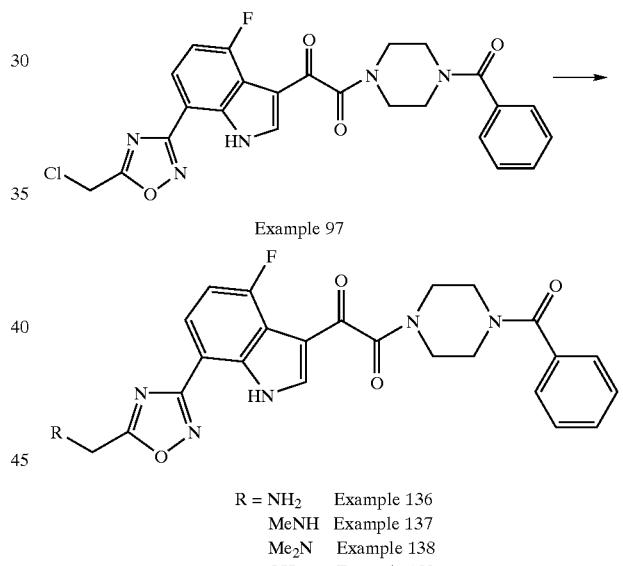

Example 97

| R = NH$_2$ | Example 136 |
| MeNH | Example 137 |
| Me$_2$N | Example 138 |
| OH | Example 139 |

Example 136

To a solution of compound of Example 97 (13 mg, 0.026 mmol) in THF (2 ml) in a reusable sealed tube at −78° C. was bubbled ammonia for one hour. The tube was tightly sealed, and the reaction mixture was stirred at room temperature for 16 hours. After removal of most of the solvent, the resulting residue was added MeOH (2 ml) and purified by preparative reverse phase HPLC using the method: Start %B=10, Final %B=80, Gradient time=15 min, Flow Rate= 40 ml/min, Column: YMC C18 S5 30×100 mm, Fraction Collection: 12.98–13.48 min. $^1$H NMR: (DMSO-d$_6$) δ 12.33 (s, 1H), 8.85 (s, 2H), 8.22 (d, J=3.2, 1H), 8.05 (app dd, J=8.2, 4.4, 1H), 7.44 (b s, 5H), 7.31 (app t, J=9.2, 1H), 4.69 (s, 2H), 3.87–3.30 (b, m, 8H); LC/MS: (ES+) m/z (M+H)$^+$=476, HPLC R$_t$=1.117.

Example 137

To compound of Example 97 (30 mg, 0.060 mmol) was added an aqueous solution of methylamine (1 ml, 40 wt. %). The reaction mixture was stirred at room temperature for 16 hours. After removal of most of the solvent, the resulting residue was added MeOH (4 ml) and purified by preparative reverse phase HPLC using the method: Start %B=10, Final %B=80, Gradient time=15 min, Flow Rate=40 ml/min, Column: YMC C18 S5 30×100 mm, Fraction Collection: 9.67–10.18 min. $^1$H NMR: (CD$_3$OD) δ 8.25 (s, 1H), 8.15 (app dd, J=8.2, 4.3, 1H), 7.46 (b s, 5H), 7.18 (app t, J=9.0, 1H), 4.80 (s, 2H), 3.99–3.43 (b, m, 8H), 2.98 (s, 3H); LC/MS: (ES+) m/z (M+H)$^+$=491, HPLC R$_t$=1.120.

Example 138

To compound Example 97 (10 mg, 0.020 mmol) was added an aqueous solution of dimethylamine (0.5 ml, 40 wt. %). The reaction mixture was stirred at room temperature for 16 hours. After removal of most of the solvent, the resulting residue was added MeOH (4 ml) and purified by preparative reverse phase HPLC using the method: Start %B=10, Final %B=80, Gradient time=10 min, Flow Rate=40 ml/min, Column: YMC C18 S5 30×100 mm, Fraction Collection: 7.37–7.83 min. $^1$H NMR: (CD$_3$OD) δ 8.24 (s, 1H), 8.16 (app dd, J=8.1, 4.4, 1H), 7.47 (b s, 5H), 7.19 (app t, J=9.2, 1H), 4.96 (s, 2H), 3.85–3.43 (b, m, 8H), 3.16 (s, 6H); LC/MS: (ES+) m/z (M+H)$^+$=505, HPLC R$_t$=1.110.

Example 139

To a solution of compound Example 97 (10 mg, 0.020 mmol) in MeOH (0.5 ml) was added an aqueous solution of NaOH (0.2 ml, 1 N). The reaction mixture was stirred at room temperature for 4 hours. After removal of most of the solvent, the resulting residue was added MeOH (2 ml) and purified by preparative reverse phase HPLC using the method: Start %B=20, Final %B=100, Gradient time=15 min, Flow Rate=40 ml/min, Column: YMC C18 S5 30×100 mm, Fraction Collection: 10.26–10.76 min. $^1$H NMR: (CD$_3$OD) δ 8.20 (s, 1H), 8.09 (app dd, J=8.0, 4.4, 1H), 7.46 (b s, 5H), 7.03 (app t, J=9.0, 1H), 4.83 (s, 2H), 3.99–3.45 (b m, 8H); LC/MS: (ES+) m/z (M+H)$^+$=478, HPLC R$_t$=1.983.

Example 140

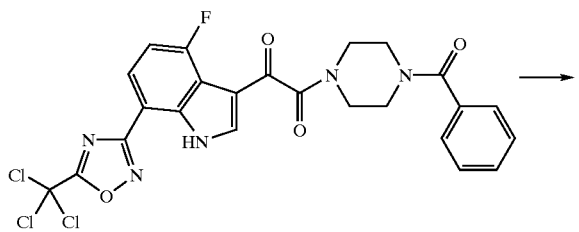

Example 81

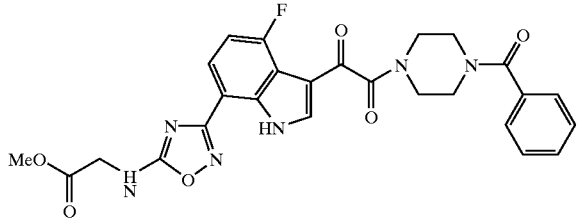

Example 140

To a solution of compound Example 81 (30 mg, 0.053 mmol) in THF (1 ml) was added glycine methyl ester hydrochloride (33 mg, 0.265 mmol) and Hunig's base (0.3 ml). The reaction mixture was stirred at room temperature for 16 hours. After removal of most of the solvent, the residue was added MeOH (4 ml) and purified by preparative reverse phase HPLC using the method: Start %B=20, Final %B=90, Gradient time=15 min, Flow Rate=40 ml/min, Column: YMC C18 S5 30×100 mm, Fraction Collection: 10.45–11.02 min. $^1$H NMR: (CDCl$_3$, two isomers) δ 10.60 (b s, 1H), 8.20 & 8.15 (d, J=2.8, 1H), 8.09 & 7.92 (app dd, J=8.2, 4.3, 1H), 7.43 (b s, 5H), 7.12 & 7.06 (app t, J=9.2, 1H), 7.84 & 6.25 (b s, 1H), 4.31 (overlapping doublets, J=4.6, 2H), 3.98–3.49 (b m, 8H), 3.86 (s, overlapping with b m, 3H); LC/MS: (ES+) m/z (M+H)$^+$=535 HPLC R$_t$=1.397.

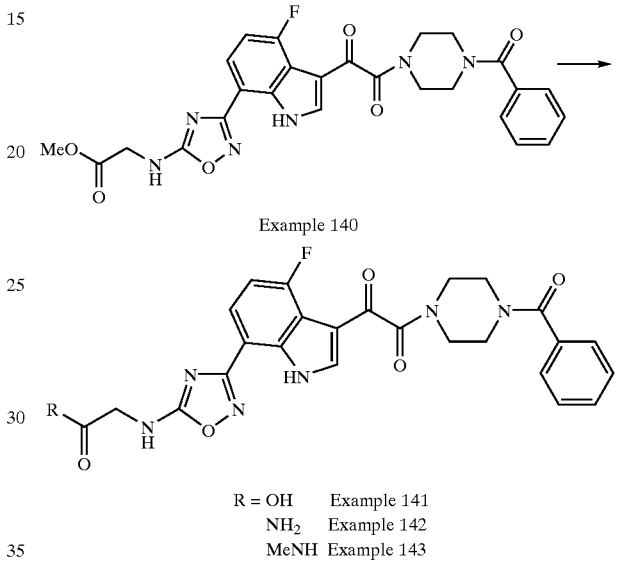

R = OH  Example 141
NH$_2$  Example 142
MeNH  Example 143

Example 141

To a solution of compound of Example 140 (16 mg, 0.03 mmol) in MeOH (0.5 ml) was added an aqueous solution of NaOH (0.1 ml, 0.1 mmol, 1 N). The reaction mixture was stirred at room temperature for 4 hours. After adjusting the pH to about 2 using hydrochloric acid (1 N), the reaction mixture was added MeOH (2 ml) and purified by preparative reverse phase HPLC using the method: Start %B=20, Final %B=90, Gradient time=20 min, Flow Rate=35 ml/min, Column: YMC C18 S5 30×100 mm, Fraction Collection: 13.00–13.52 min. $^1$H NMR: (CD$_3$OD) δ 8.18 (s, 1H), 7.95 (app dd, J=8.1, 4.4, 1H), 7.46 (b s, 5H), 7.08 (app t, J=9.2, 1H), 4.23 (s, 2H), 3.98–3.45 (b m, 8H); LC/MS: (ES+) m/z (M+H)$^+$=521, HPLC R$_t$=1.330.

Example 142

To a solution of compound of Example 140 (15 mg, 0.028 mmol) in THF (1 ml) in a reusable sealed tube at −78° C. was bubbled ammonia for one hour. The tube was tightly sealed, and the reaction mixture stirred at room temperature for 16 hours. After removal of most of the solvent, the resulting residue was added MeOH (2 ml) and purified by preparative reverse phase HPLC to afford the product as a TFA salt. HPLC method: Start %B=25, Final %B=80, Gradient time=20 min, Flow Rate=35 ml/min, Column: YMC C18 S5 30×100 mm, Fraction Collection: 11.77–12.29 min. $^1$H NMR: (CD$_3$OD) δ 8.19 (s, 1H), 7.97 (app dd, J=8.0, 4.0, 1H), 7.46 (b s, 5H), 7.10 (app t, J=9.2, 1H), 4.15 (s, 2H), 3.98–3.44 (b m, 8H); LC/MS: (ES+) m/z (M+H)$^+$=520, HPLC R$_t$=1.217.

Example 143

To compound of Example 140 (20 mg, 0.037 mmol) was added an aqueous solution of methylamine (0.5 ml, 40 wt. %). The resulting mixture was stirred at room temperature for 16 hours. After removal of most of the solvent, the resulting residue was added MeOH (2 ml) and purified by preparative reverse phase HPLC using the method: Start %B=20, Final %B=85, Gradient time=15 min, Flow Rate= 35 ml/min, Column: YMC C18 S5 30×100 mm, Fraction Collection: 10.62–11.14 min. $^1$H NMR: (CD$_3$OD) δ 8.19 (s, 1H), 7.96 (app dd, J=8.0, 4.3, 1H), 7.46 (b s, 5H), 7.10 (app t, J=9.2, 1H), 4.13 (s, 2H), 3.86–3.45 (b m, 8H), 2.78 (s, 3H); LC/MS: (ES+) m/z (M+H)$^+$=478, HPLC R$_t$=1.983.

Example 144

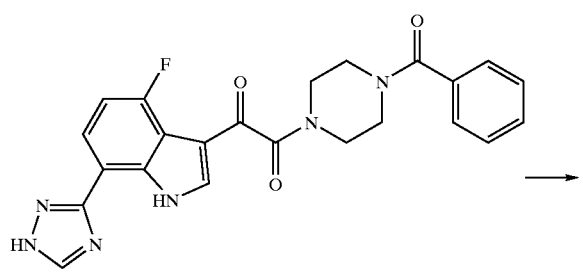

Example 111

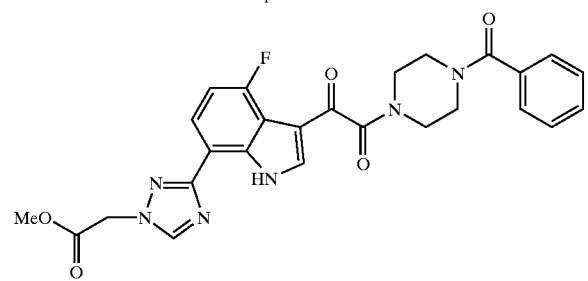

Example 144

To a mixture of compound of Example 111 (100 mg, 0.224 mmol) in THF (2 ml) was added Cs$_2$CO$_3$ (80 mg, 0.246 mmol) and methyl bromoacetate (25 μl, 0.23 mmol). The reaction mixture was stirred at room temperature for 16 hours, and was then added additional portions of Cs$_2$CO$_3$ (200 mg, 0.614 mmol) and ethyl bromoacetate (0.1 ml, 0.90 mmol). The reaction mixture was stirred for a further 16 more hours, and added MeOH (4 ml), followed by filtration. The filtrate was purified by preparative reverse phase HPLC using the method: Start %B=20, Final %B=80, Gradient time=12 min, Flow Rate=40 ml/min, Column: Xterra MS C-18 5 μm 30×100 mm, Fraction Collection: 8.71–9.16 min. The position of the methyl acetate group at triazole N$^1$ was supported by H-C HMBC and H-H NOESY. $^1$H NMR: (DMSO-d$_6$) δ 12.12 (s, 1H), 8.80 (s, 1H), 8.15 (d, J=3.3, 1H), 7.98 (app dd, J=8.2, 4.3, 1H), 7.44 (b s, 5H), 7.16 (app t, J=9.2, 1H), 5.36 (s, 2H), 3.80–3.30 (b m, 8H), 3.75 (s, overlapping with b m, 3H); LC/MS: (ES+) m/z (M+H)$^+$= 519, HPLC R$_t$=1.283.

Example 145

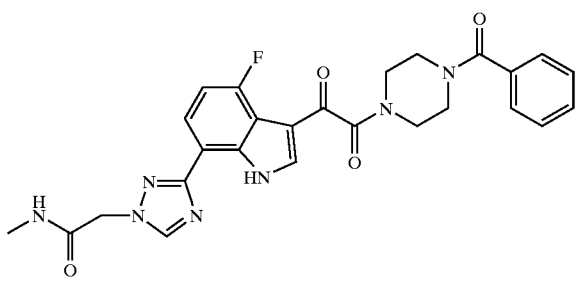

Compound of example 145 was prepared in the same manner as compound of example 143. Purification was performed by reverse phase preparative HPLC using the method: Start %B=10, Final %B=100, Gradient time=15 min, Flow Rate=40 ml/min, Column: Xterra MS C-18 5μm 30×100 mm, Fraction Collection: 8.70–9.15 min. $^1$H NMR (CD$_3$OD) δ 8.52 (s, 1H), 8.12 (s, 1H), 7.95 (app, dd, J=7.8, 4.4, 1H), 7.36 (b s, 5H), 7.01 (app, t, J=8.9, 1H), 4.93 (s, 2H), 3.85–3.34 (b m, 8H), 2.77 (s, 3H); LC/MS (ES+) m/z (M+H)$^+$=518, HPLC R$_t$=1.207.

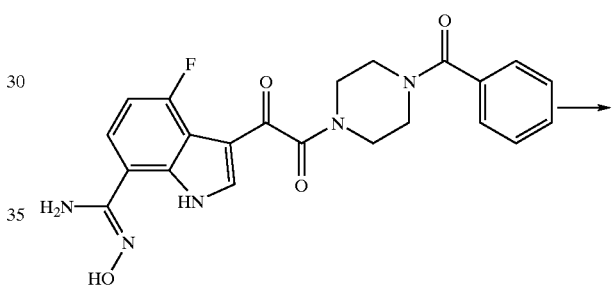

Example 27

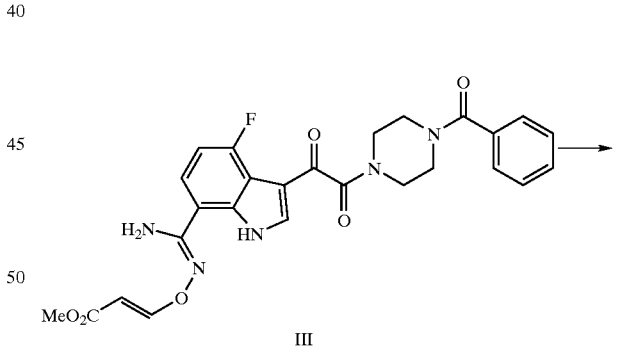

III

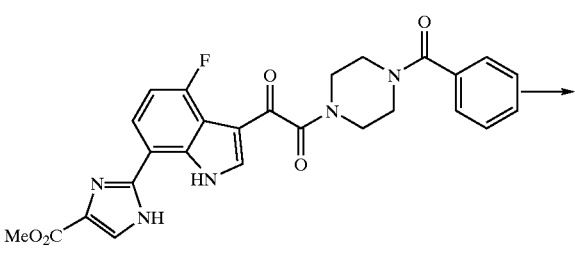

Example 146

161
-continued

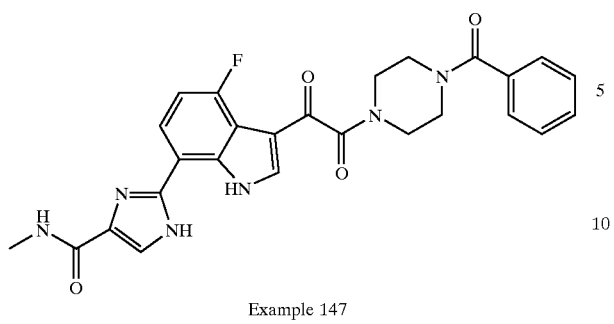

Example 147

Example 146

To the solution of compound of example 27 (crude, ca. 0.549 mmol) in MeOH (3 ml) in a reusable sealed tube was added methyl propiolate (0.3 ml, 3.37 mmol) and triethylamine (0.2 ml). The tube was tightly sealed and the reaction mixture was heated at 75° C. for 2 hours. After cooled to room temperature, the crude material was purified by preparative TLC (4:1 EtOAc/Hexane, 2×500 μm×20 cm×20 cm plates) to give intermediate III as an off-white solid, which was directly used in the following reaction without further purification. A mixture of intermediate III (47 mg, 0.09 mmol) and phenyl ether (210 mg, 1.23 mmol) was heated to maintain gentle reflux for 10 minutes. The resulting black residue was added MeOH (4 ml) and filtered. The filtrate was purified by reverse phase HPLC using the method: Start %B=30, Final %B=100, Gradient time=16 min, Flow Rate= 40 ml/min, Column: YMC C18 S5 30×100 mm, Fraction Collection: 8.50–9.00 min. $^1$H NMR: (CD$_3$OD) δ 8.25 (s, 1H), 7.96 (s, 1H), 7.75 (app dd, J=8.3, 3.9, 1H), 7.46 (b s, 5H), 7.09 (app t, J=9.6, 1H), 3.94 (s, overlapping with b m, 3H), 3.97–3.46 (b, m, 8H); LC/MS: (ES+) m/z (M+H)$^+$= 504, HPLC R$_t$=1.350.

Example 147

To compound of Example 146 (15 mg, 0.030 mmol) was added an aqueous solution of methylamine (0.5 ml, 40 wt. %). The resulting mixture was stirred at room temperature for 16 hours. After removal of most of the solvent, the resulting residue was added MeOH (2 ml) and purified by preparative reverse phase HPLC using the method: Start %B=20, Final %B=85, Gradient time=10 min, Flow Rate= 40 ml/min, Column: YMC C18 S5 30×100 mm, Fraction Collection: 7.16–7.67 min. $^1$H NMR: (CD$_3$OD) δ 8.22 (s, 1H), 7.75 (s, overlapping with b m, 1H), 7.77 (b, m, 1H), 7.46 (b s, 5H), 7.09 (app t, J=9.3, 1H), 3.97–3.45 (b m, 8H), 2.99 (s, 3H); LC/MS: (ES+) m/z (M+H)$^+$=503, HPLC R$_t$=1.223.

162

Example 148

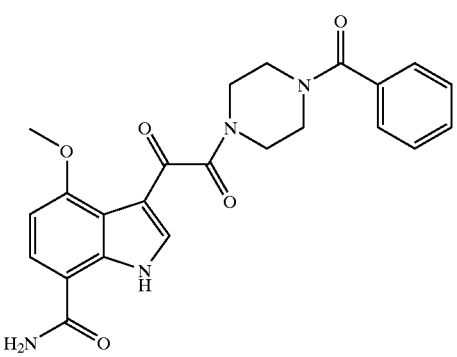

Compound of Example 148 was isolated as a minor product from the following reaction to prepare hydroxyamidine: To an oven dried pressure tube was added intermediate 46 (130 mg, 0.313 mmol), hydroxyamine hydrochloride (65.3 mg, 0939 mmol), EtOH (5 ml) and triethylamine (142.5 mg, 0.196 ml, 1.41 mmol), and the resulting mixture stirred at 110° C. for 4 hr. After cooling to rt., the mixture was purified reverse phase preparative HPLC to isolate the amide of Example 148 (10.5 mg, 8%) as a minor product, which was contaminated with 15% (based on $^1$H—NMR) of its oxime derivative. $^1$H NMR: (CD$_3$OD) δ 8.13 (s, 1H), 7.80 (d, J=8.4 Hz, 1H), 7.47 (b s, 5H), 6.83 (d, J=8.3 Hz, 1H), 3.98 (s, 3H), 3.45–4.07 (m, 8H); LC/MS: (ES+) m/z (M+H)$^+$=435, HPLC (YMC C18 S7 3×50 mm, Flow Rate 4 ml/min, Gradient Time 2 min) R$_t$=1.057.

Example 149

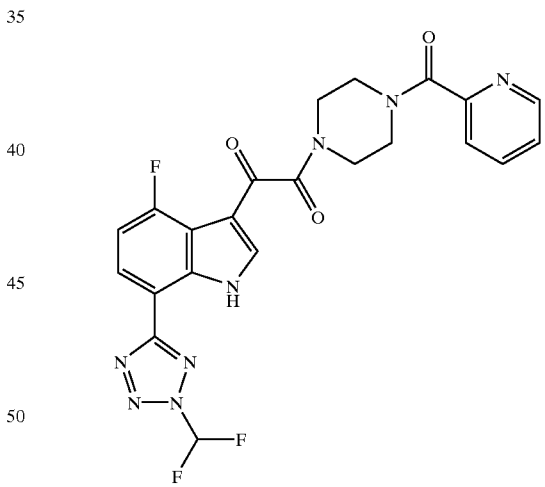

To a mixture of 18-Crown-6 (12 mg, 0.045 mmol), KF (3.7 mg, 0.064 mmol) and the tetrazole of Example 32 (26 mg, 0.058 mmol) in 2-methoxyethyl ether (0.5 ml) was added methyl 2-chloro-2,2-difluoroacetate (6.1 μl, 0.058 mmol). The reaction mixture was heated at 85° C. for 5 hours, and was added more portions of KF (7 mg, 0.12 mmol) and methyl 2-chloro-2,2-difluoroacetate (6 μl, 0.057 mmol) and heated for 8 more hours. The reaction mixture was then added MeOH (2 ml), filtered and purified by reverse phase preparative HPLC using the method: Start %B=40, Final %B=75, Gradient time=15 min, Flow Rate= 25 ml/min, Column: YMC C18 S5 20×100 mm, Fraction Collection: 8.03–8.75 min $^1$H NMR (CD$_3$OD) δ 8.64 and 8.56 (s, 1H), 8.42–8.20 (b m, 3H), 8.00 and 7.95 (t, J=7.5, 1H), 7.67 (m, 1H), 7.55 and 7.49 (t, J=5.9, 1H), 7.20 (dd, J=20.2, 10.2, 1H), 3.94–3.58 (b m, 8H); LC/MS (ES+) m/z (M+H)⁺=499, HPLC R$_f$=1.327.

Example 150A

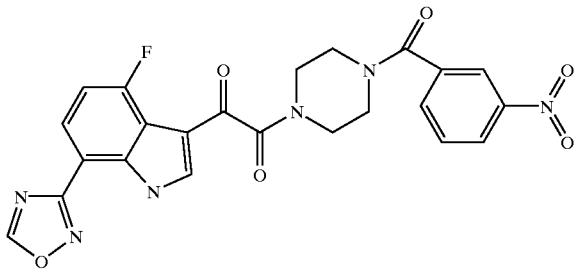

To a solution of intermediate 50 (ca. 0.644 mmol) in THF (6 ml) was added N,N-diisopropylethylamine (0.5 ml) and intermediate 48 (210 mg, 0.77 mmol). The reaction mixture was stirred at room temperature for 16 hours. After concentrated in vacuo, the residue was added MeOH (6 ml) and purified by reverse phase preparative HPLC using the method: Start %B=20, Final %B=90, Gradient time=12 min, Flow Rate=40 ml/min, Column: YMC C18 S5 30×100 mm, Fraction Collection: 8.44–8.89 min. ¹H NMR (DMSO-d$_6$) δ 12.31 (s, 1H), 9.88 (s, 1H), 8.30 (b m, 2H), 8.11 (app d, J=3.0, 1H), 8.09 (b m, 1H), 7.89 (b m, 1H), 7.77 (b m, 1H), 7.27 (b m, 1H), 3.77–3.40 (b m, overlapping with broad water peak, 8H); LC/MS (ES+) m/z (M+H)⁺=493, HPLC R$_f$=1.340.

Example 150B

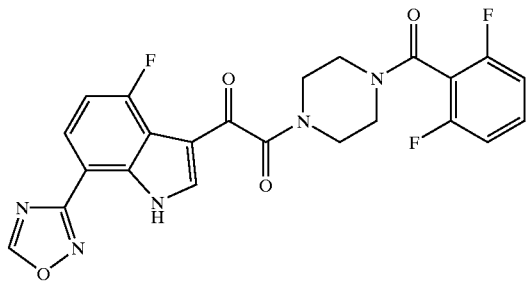

Compound of Example 150B was prepared in ther same manner as compound of Example 150A. Purification was performed by preparative reverse phase HPLC using the method: Start %B=20, Final %B=90, Gradient time=15 min, Flow Rate=40 ml/min, Column: Xterra MS C18 S5 30×100 mm, Fraction Collection: 9.88–10.34 min. ¹H NMR (CDCl$_3$) δ 10.62 & 10.60 (b overlapping s, 1H), 8.871 and 8.866 (s, 1H), 8.22 (t, J=3.0, 1H), 8.16 (b m, 1H), 7.40 (b m, 1H), 7.16 (b m, 1H), 7. 00 (t, J=7.8, 1H), 6.95 (t, J=7.8, 1H), 3.99 (m, 1H), 3.92 (m, 2H), 3.79 (m, 1H), 3.67 (m, 1H), 3.58 (m, 1H), 3.48 (m, 1H), 3.42 (m, 1H); LC/MS (ES+) m/z (M+H)⁺=484, HPLC R$_f$ -1.777.

Example 150C

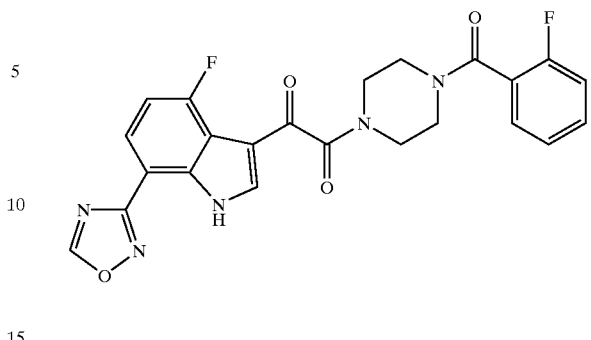

Compound of Example 150C was prepared in the same manner as compound of Example 150A. Purification was performed by preparative reverse phase HPLC using the method: Start %B=30, Final %B =90, Gradient time=15 min, Flow Rate=40 ml/min, Column: Xterra MS C18 S5 30×100 mm, Fraction Collection: 8.58–9.03 min. ¹H NMR (CDCl$_3$) δ 10.66 & 10.63 (b overlapping s, 1H), 8.874 and 8.869 (s, 1H), 8.22 (d, J=3.0, 1H), 8.16 (b m, 1H), 7.46 (b m, 2H), 7.28–7.07 (b m, 3H), 3.98–3.44 (b m, 8H); LC/MS (ES+) m/z (M+H)⁺=466, HPLC R$_f$=1.910.

Example 151

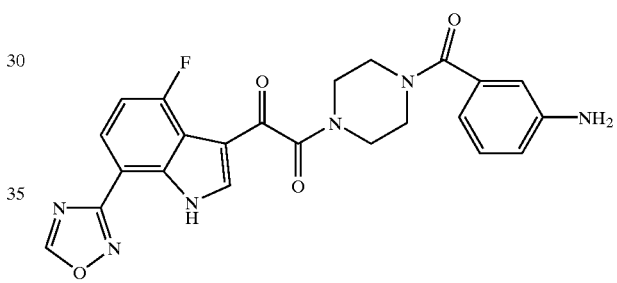

To compound of Example 150 (50 mg, 0.102 mmol) in MeOH (3 ml) was added palladium on activated carbon (36 mg, 10%). The reaction mixture was stirred at room temperature under a hydrogen atmosphere for 16 hours. After passing through a short Celite®545 pad, the filtrate was purified by reverse phase HPLC using the method: Start %B=15, Final %B=85, Gradient time=12 min, Flow Rate= 40 ml/min, Column XTerra MS C-18 5 μm 30×100 mm, Fraction Collection: 6.65–7.10 min. ¹H NMR (CD$_3$OD) δ 9.27 (s, 1H), 8.21 (s, 1H), 8.12 (b m, 1H), 7.35 (b m, 1H), 7.14–7.06 (b m, 4H), 3.87–3.51 (b m, 8H); LC/MS (ES+) m/z (M+H)⁺=463, HPLC R$_f$=1.033.

Example 152

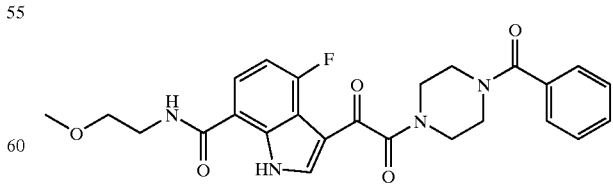

Compound of Example 152 was prepared in the same manner as compound of Example 64, except that THF was used as the solvent for coupling of the acid chloride of intermediate 23 to excess 2-methoxyethylamine in the absence of pyridine. The crude residue obtained after evaporation of the volatile was purified by preparative TLC (5% MeOH/CH$_2$Cl$_2$, 50 m×20 cm×20 cm plate). $^1$H NMR: (CD$_3$OD) δ 8.17 (s, 1H), 7.77 (dd, J=8.1, 4.0, 1H), 7.46 (b m, 5H), 7.03 (app t, 1H), 4.00–3.45 (b m, 8H), 3.62–3.60 (m overlapped with b m, 4H), 3.39 (s, 3H); LC/MS: (ES+) m/z (M+H)$^+$=481, HPLC R$_t$=1.253.

Example 153

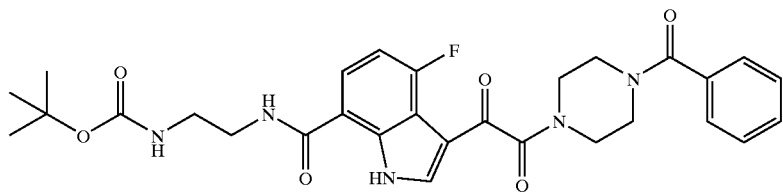

Compound of Example 153 was prepared in the same manner as compound of Example 152. $^1$H NMR: (CDCl$_3$) δ 11.40 (b s, 1H), 8.13 (d, J=3.0, 1H), 7.86 (b s, 1H), 7.59 (dd, J=8.0, 3.5, 1H), 7.43 (b m, 5H), 6.99 (app t, 1H), 5.04 (b s, 1H), 4.00–3.25 (b overlapping m, 12H), 1.44 (s, 9H); LC/MS: (ES+) m/z (M+H)$^+$=566, HPLC R$_t$=1.340.

Example 154

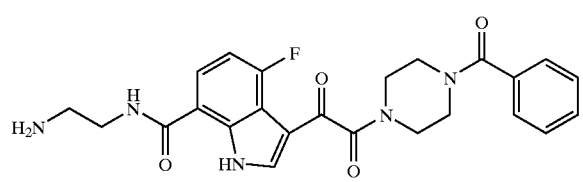

The hydrochloride salt of Example 154 was prepared by treating compound of Example 153 with an excess of a solution of HCl in dioxane (4 M). $^1$H NMR: (300 MHz, CD$_3$OD) δ 8.21 (s, 1H), 7.84 (b dd, 1H), 7.48 (b m, 5H), 7.08 (b app t, 1H), 4.00–3.45 (b overlapping m, 12H); LC/MS: (ES+) m/z (M+H)$^+$=466, HPLC R$_t$=0.920.

Example 155

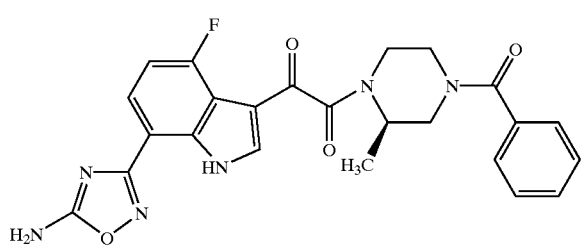

Compound of Example 155 was prepared in the same manner as compound of Example 83. Purification was performed by preparative reverse phase HPLC using the method: Start %B=20, Final %B=100, Gradient time=12 min, Flow Rate=40 ml/min, Column: YMC C18 S5 30×100 mm, Fraction Collection: 8.04–8.49 min. $^1$H NMR (CDCl$_3$) δ 10.58 (s, 1H), 8.14 (s, 1H), 7.87 (b m, 1H), 7.43 (b m, 5H), 7.08 (app t, J=9.2, 1H), 5.92(s, 2H), 5.05–3.07 (b m, 7H), 1.39–1.15 (b m, 3H); LC/MS (ES+) m/z (M+H)$^+$=477, HPLC R$_t$=1.356.

Compound of Examples 156 to 162 were prepared analogously to compound of Example 82.

Example 156

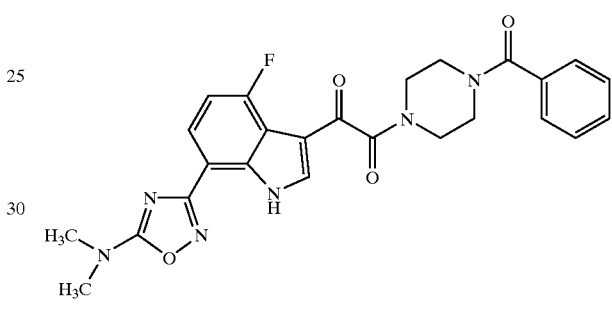

Purification was performed by preparative reverse phase HPLC using the method: Start %B=20, Final %B=100, Gradient time=12 min, Flow Rate=25 ml/min, Column: YMC C18 S5 20×100 mm, Fraction Collection: 10.52–11.24 min. $^1$H NMR (CDCl$_3$) δ 10.72(s, 1H), 8.16 (s, 1H), 7.99 (app dd, J=8.2, 4.3, 1H), 7.43 (b s, 5H), 7.07 (app t, J=9.3, 1H), 3.85–3.40 (b m, 8H), 3.26 (s, 6H); LC/MS (ES+) m/z (M+H)$^+$=491, HPLC R$_t$=1.503.

Example 157

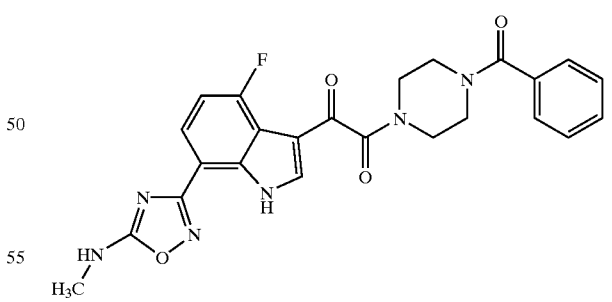

Purification was performed by preparative reverse phase HPLC using the method: Start %B=10, Final %B=100, Gradient time=12 min, Flow Rate=25 ml/min, Column: YMC C18 S5 20×100 mm, Fraction Collection: 9.47–9.82 min. $^1$H NMR (CDCl$_3$) δ 10.66(s, 1H), 8.17 (d, J=2.7, 1H), 7.97 (app dd, J=8.2, 4.2, 1H), 7.43 (b s, 5H), 7.09 (app t, J=9.3, 1H), 5.59 (b s, 1H), 3.85–3.50 (b m, 8H), 3.20 (d, J=5.0, 3H); LC/MS (ES+) m/z (M+H)$^+$=477, HPLC R$_t$=1.360.

Example 158

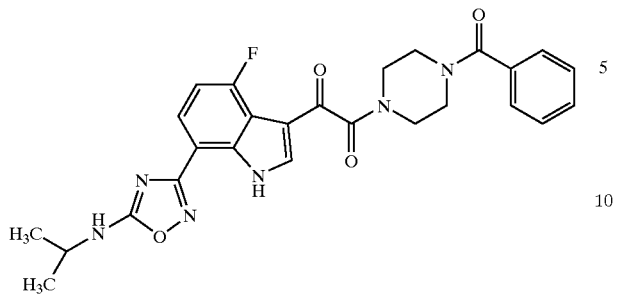

Purification was performed by preparative reverse phase HPLC using the similar method as that of compound of Example 157. $^1$H NMR (300 MHz, CDCl$_3$) δ 10.70 (s, 1H), 8.18 (s, 1H), 8.01 (app dd, J=8.3, 4.6, 1H), 7.45 (b s, 5H), 7.09 (app t J=9.4, 1H), 5.24 (d, J=7.4, 1H), 4.09 (app, dd, J=13.3, 6.7, 1H), 3.81–3.51 (b m, 8H), 1.39 (d, J=6.5, 6H); LC/MS (ES+) m/z (M+H)$^+$=505, HPLC R$_t$=1.587.

Example 159

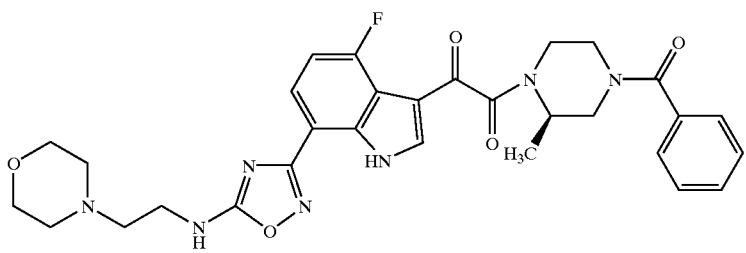

Purification was performed by preparative reverse phase HPLC using the method: Start %B=20, Final %B=90, Gradient time=15 min, Flow Rate=40 ml/min, Column: YMC C18 S5 30×100 mm, Fraction Collection: 8.71–9.17 min. $^1$H NMR (CDCl$_3$) δ 10.81 (d, J=11.5, 1H), 8.10 (d, J=6.2,1H), 7.77 (b m, 1H), 7.42 (b s, 5H), 6.95 (app t, J=8.3, 1H), 5.00–2.47 (broad overlapping m, 20H), 1.40–1.22 (b m, 3H); LC/MS (ES+) m/z (M+H)$^+$=590, HPLC R$_t$=1.226.

Example 160

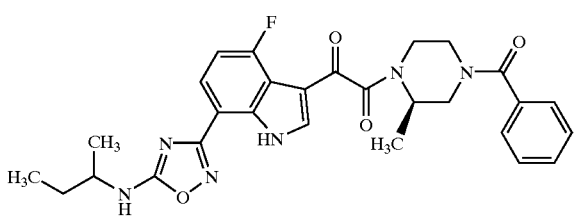

Purification was performed by preparative reverse phase HPLC using a similar method as that of compound of Example 159. $^1$H NMR (CDCl$_3$) δ 10.69 (s, 1H), 8.12 (app dd, J=4.7, 3.3, 1H), 7.98 (app dd, J=7.5, 4.5, 1H), 7.43 (b s, 5H), 7.07 (app t, J=10.5, 1H), 5.12 (d, J=9.0, 1H), 3.88 (m, overlapping with b m, 1H), 5.00–2.96 (b m, 7H), 1.69 (m, 2H), 1.36 (overlapping b m, 6H), 1.00 (m, 3H); LC/MS (ES+) m/z (M+H)$^+$=533, HPLC R$_t$=1.689.

Example 161

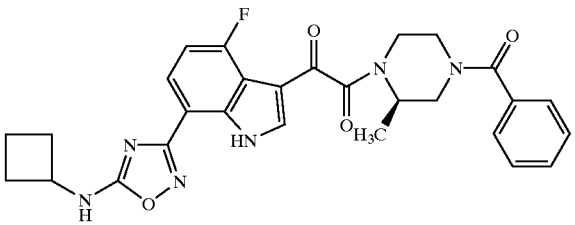

Purification was performed by preparative reverse phase HPLC using a similar method as that of compound of Example 159. $^1$H NMR (CDCl$_3$) δ 10.69 (s, 1H), 8.12 (app dd, J=5.2, 3.3,1H), 7.96 (app dd, J=8.0, 4.0,1H), 7.42 (b s, 5H), 7.05 (app t, J=8.5, 1H), 5.55 (dd, J=7.3, 3.8, 1H), 4.35 (app, dd, overlapping with b m, J=16.2, 7.8,1H), 5.10–2.88 (b m, 7H), 2.34 (m, 2H), 2.07 (m, 2H), 1.82 (m, 2H), 1.39–1.20 (b m, 3H); LC/MS (ES+) m/z (M+H)$^+$=531, HPLC R$_t$=1.676.

Example 162

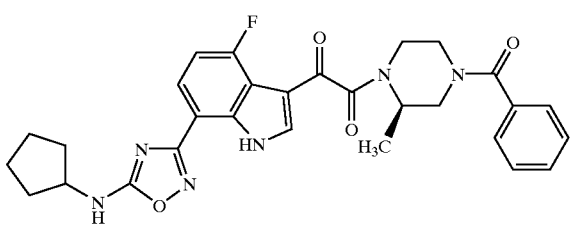

Purification was performed by preparative reverse phase HPLC using a similar method as that of compound of Example 159. $^1$H NMR (CODCl$_3$) δ 10.71 (s, 1H), 8.12 (b m, 1H), 7.97 (app dd, J=7.8, 4.3, 1H), 7.42 (b s, 5H), 7.07 (app t, J=8.5, 1H), 5.31 (d, J=6.5, 1H), 4.81–2.88 (broad overlapping m, 8H), 2.18–1.26 (broad overlapping m, 11H); LC/MS (ES+) m/z (M+H)$^+$=545, HPLC R$_t$=1.729.

Compound of Examples 163 to 165 were prepared analogously to compound of Example 76.

Example 163

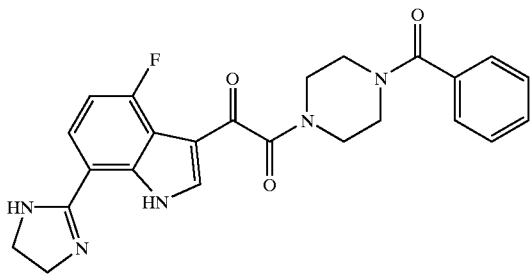

Purification was performed by preparative reverse phase HPLC using the method: Start %B=0, Final %B=75, Gradient time=15 min, Flow Rate=25 ml/min, Column: YMC C18 S5 20×100 mm, Fraction Collection: 8.79–9.18 min. $^1$H NMR (CD$_3$OD) δ 8.31 (s, 1H), 7.70 (app dd, J=8.2, 4.1, 1H), 7.47 (b s, 5H), 7.20 (app t, J=9.4, 1H), 4.17 (s, 4H), 3.79–3.34 (b m, 8H); LC/MS (ES+) m/z (M+H)$^+$=448, HPLC R$_t$=0.983.

Example 164

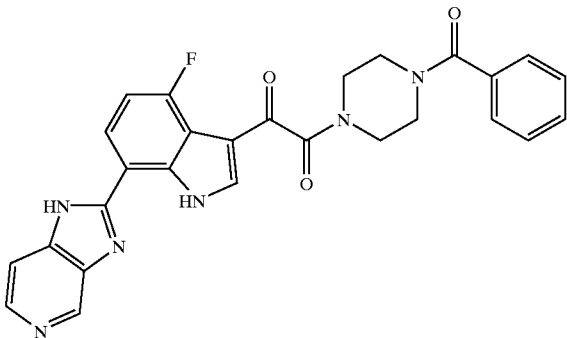

Purification was performed by preparative reverse phase HPLC using the method: Start %B=20, Final %B=75, Gradient time=15 min, Flow Rate=25 ml/min, Column: YMC C18 S5 20×100 mm, Fraction Collection: 8.79–9.42 min. $^1$H NMR (CD$_3$OD) δ 9.29 (b s, 1H), 8.57 (d, J=6.5, 1H), 8.34 (s, 1H), 8.16 (b m, 2H), 7.47 (b s, 5H), 7.27 (app t, J=9.3, 1H), 3.98–3.44 (b m, 8H); LC/MS (ES+) m/z (M+H)$^+$=497, HPLC R$_t$=1.200.

Example 165

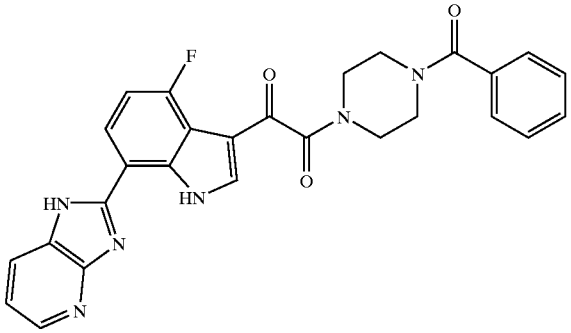

Purification was performed by preparative HPLC using the method: Start %B 20 Final%B=80, Gradient time=14 min. Flow Rate=25 ml/min, Column:YMC C18 S5 20×100 mm, Fraction Collection: 11.89–12.34 min. $^1$H NMR (CD$_3$OD) δ 8.51 (d, J=4.9, 1H), 8.34 (b s, 2H), 8.08 (b m, 1H), 7.55 (app, dd, J=13.5, 8.3, 1H), 7.47 (b s, 5H), 7.22(app, t, J=8.5, 1H), 3.81–3.44 (b m, 8H); LC/MS (ES+) m/z (M+H)$^+$=497, HPLC R$_t$=1.227.

Example 166

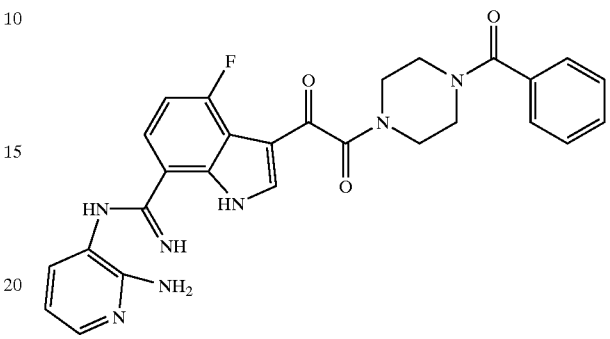

Compound of Example 166 was isolated as a side product in the preparation of compound of Example 165. Purification was performed by preparative reverse phase HPLC using the method: Start %B=20, Final %B=80, Gradient time=14 min. Flow Rate=25 ml/min, Column: YMC C18 S5 20×100 mm, Fraction Collection: 7.88–8.16 min. $^1$H NMR (CD$_3$OD) δ 8.20 (s, 1H), 7.89 (b m, 1H), 7.73 (b m, 2H), 7.47 (b s, 5H), 7.15 (b m, 1H), 6.95 (b m, 1H), 3.89–3.44 (b m, 8H); LC/MS (ES+) m/z (M+H)$^+$=514, HPLC R$_t$=0.913.

Methods of the preparation of compounds of Examples 167 to 193 can be found in the analogous Examples described above.

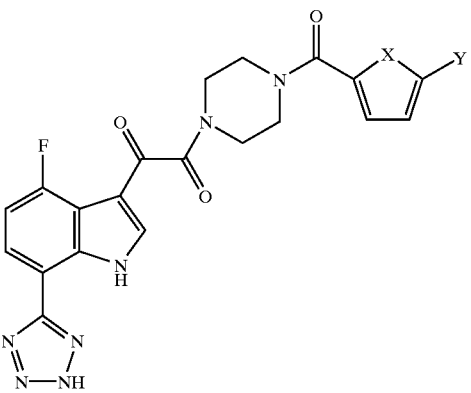

Example 167, X = O, Y = H
Example 168, X = O, Y = Cl
Example 169, X = O, Y = Br
Example 170, X = S, Y = H

Example 167

Separation method: Start %B=10, Final %B=75, Gradient time=12 min. Flow Rate=30 ml/min, Column: YMC C18 S5 20×50 mm, Fraction Collection: 6.93–8.06 min. $^1$H NMR: (DMSO-d$_6$) δ 12.52 (s, 1H), 8.41 (app d, J=3.3, 1H), 7.99 (app dd, J=8.3, 4.2, 1H), 7.86 (app s, 1H), 7.33 (app dd, J=10.3, 8.4, 1H), 7.04 (app d, J=3.2, 1H), 6.64 (app B, 1H), 3.81–3.47 (b m, 8H); LC/MS: (ES+) m/z (M+H)$^+$=438, (2M+H)$^+$=875, HPLC R$_t$=1.123.

Example 168

Separation method: Start %B=20, Final %B=85, Gradient time=12 min, Flow Rate=30 ml/min, Column: YMC C18 S5 20×50 mm, Fraction Collection: 7.01–7.62 min. $^1$H NMR: (DMSO) δ 12.53 (s, 1H), 8.20 (s, 1H), 7.98 (app dd, J=8.1, 3.9, 1H), 7.32 (app dd, J=10.3, 8.4, 1H), 7.13 (d, J=3.4, 1H), 6.70 (d, J=3.4, 1H), 3.73–3.47 (b m, 8H); LC/MS: (ES+) m/z (M+H)$^+$=472, HPLC R$_t$=1.267.

Example 169

Separation method: Start %B=0, Final %B=100, Gradient time=10 min, Flow Rate=30 ml/min, Column YMC C18 S5 20×50 mm, Fraction Collection: 6.90–7.15 min. $^1$H NMR: (DMSO) δ 12.53 (s, 1H), 8.20 (s, 1H), 7.98 (app dd, J=8.0, 4.0, 1H), 7.32 (app dd, J=10.2, 8.2, 1H), 7.08 (d, J=3.5, 1H), 6.78 (d, J=3.5, 1H), 3.79–3.42 (b m, 8H); LC/MS: (ES+) m/z (M+H)$^+$=517, HPLC R$_t$=1.293.

Example 170

Separation method: Start %B=20, Final %B=75, Gradient time=14 min, Flow Rate=30 ml/min, Column: YMC C18 S5 20×50 mm, Fraction Collection: 6.85–8.07 min. $^1$H NMR: (DMSO) δ 12.53 (s, 1H), 8.20 (app d, J=3.2, 1H), 7.98 (app dd, J=8.4, 4.2, 1H), 7.79 (app dd, J=5.0, 0.90, 1H), 7.46 (d, J=3.2, 1H), 7.32 (app dd, J=10.3, 8.4, 1H), 7.14 (app t, J=4.2, 1H), 3.80–3.66 (b m, 8H); LC/MS: (ES+) m/z (M+H)$^+$=454, HPLC R$_t$=1.170.

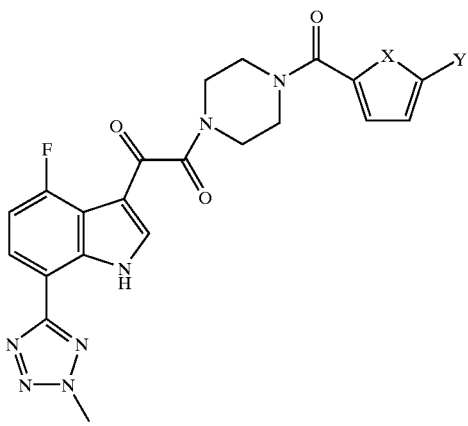

Example 171, X = O, Y = H
Example 172, X = O, Y = Cl
Example 173, X = O, Y = Br
Example 174, X = S, Y = H

Example 171

Separation method: Start %B=30, Final %B=100, Gradient time=15 min, Flow Rate=35 ml/min, Column: YMC C18 S5 30×100 mm, Fraction Collection: 8.30–8.82 min. $^1$H NMR: (CDCl$_3$) δ 11.03 (s, 1H), 8.24 (app d, J=3.1, 1H), 8.09 (app dd, J=8.4, 4.4, 1H), 7.53 (app s, 1H), 7.13 (m, 2H), 6.53 (app dd, J=3.3, 1.6, 1H), 4.49 (s, 3H), 4.00–3.87 (b m, 6H), 3.68 (m, 2H); LC/MS: (ES+) m/z (M+H)$^+$=452, HPLC R$_t$=1.240.

Example 172

Separation method: Start %B=20, Final %B=100, Gradient time=12 min, Flow Rate=30 ml/min, Column: YMC C18 S5 30×100 mm, Fraction Collection: 7.17–7.34 min. $^1$H NMR: (TFA solvate, CDCl$_3$) δ 11.01 (s, 1H), 8.24 (app d, J=3.1, 1H), 8.09 (app dd, J=8.3, 4.4, 1H), 7.13 (app dd, J=10.4, 8.3, 1H), 7.08 (d, J=3.6, 1H), 6.31 (d, J=3.6, 1H), 4.49 (s, 3H), 3.95–3.86 (b m, 6H), 3.66 (m, 2H); LC/MS: (ES+) m/z (M+H)+=486, HPLC R$_t$=1.383.

Example 173

Separation method: Start %B=20, Final %B=100, Gradient time=12 min, Flow Rate=35 ml/min, Column: YMC C18 S5 30×100 mm, Fraction Collection: 9.76–10.24 min. $^1$H NMR: (CDCl$_3$) δ 11.01 (s, 1H), 8.23 (app d, J=3.1, 1H), 8.10 (app dd, J=8.4, 4.4, 1H), 7.13 (app dd, J=10.4, 8.3, 1H), 7.05 (d, J=3.5, 1H), 6.45 (d, J=3.5, 1H), 4.49 (s, 3H), 3.88–3.86 (b m, 6H), 3.66 (m, 2H); LC/MS: (ES+) m/z (M+H)$^+$=531, HPLC R$_t$=1.397.

Example 174

Separation method: Start %B=30, Final %B=100, Gradient time=12 min, Flow Rate=35 ml/min, Column: YMC C18 S5 30×100 mm, Fraction Collection: 7.92–8.45 min. $^1$H NMR: (CDCl$_3$) δ 11.02 (s, 1H), 8.23 (app d, J=3.1, 1H), 8.10 (app dd, J=8.4, 4.4, 1H), 7.50 (app dd, J=5.0, 1.0, 1H), 7.34 (app dd, J=3.6, 0.95, 1H), 7.12 (app dd, J=10.4, 8.4, 1H), 7.08 (app dd, J=5.0, 3.7, 1H), 4.49 (s, 3H), 3.93 (m, 2H), 3.85 (m, 4H), 3.64 (m, 2H); LC/MS: (ES+) m/z (M+H)$^+$=468, HPLC R$_t$=1.287.

Example 175

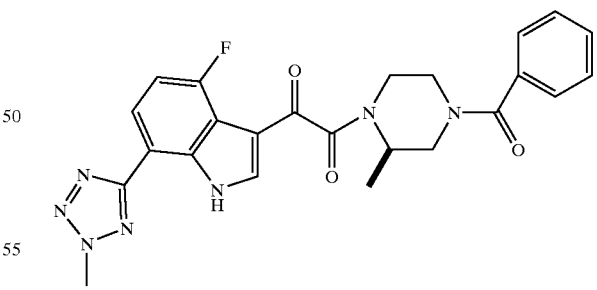

Separation method Start %B=30, Final %B=100, Gradient time=8 min, Flow Rate=25 ml/min, Column: YMC C18 S5 20×50 mm, Fraction Collection: 4.71–5.41 min. $^1$H NMR: (CD$_3$OD) δ 8.25 and 8.21 (s, 1H), 8.13 (b s, 1H), 7.46 (b m, 5H), 7.15 (b s, 1H), 4.49 (2, 3H), 3.0–4.80 (very b m, 7H), 1.15–1.45 (b m, 3H); LC/MS: (ES+) m/z (M+H)$^+$=476, HPLC R$_t$=1.353.

Example 176

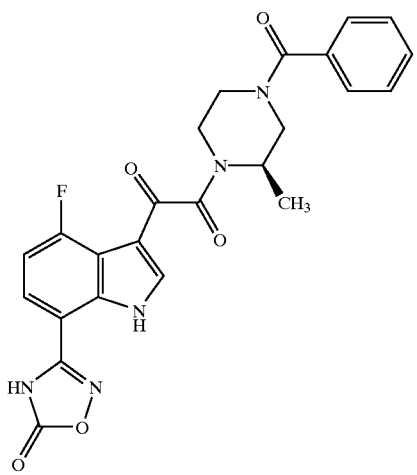

Purification was performed by preparative HPLC using the method: Start %B=30, Final %B=100, Gradient time=14 min, Flow Rate=25 ml/min, Column: YMC C18 S5 20×100 mm, Fraction Collection: 6.73–8.20 min. $^1$H NMR (mixture of conformers, CD$_3$OD) δ 8.26 and 8.17 (s, 1H), 7.66 (b m, 1H), 7.46 (b s, 5H), 7.16 (b m, 1H), 4.73–2.99 (b m, 7H), 1.46–1.24 (b m, 3H); LC/MS (ES+) m/z (M+H)$^+$=478, HPLC R$_t$=1.237.

Example 177

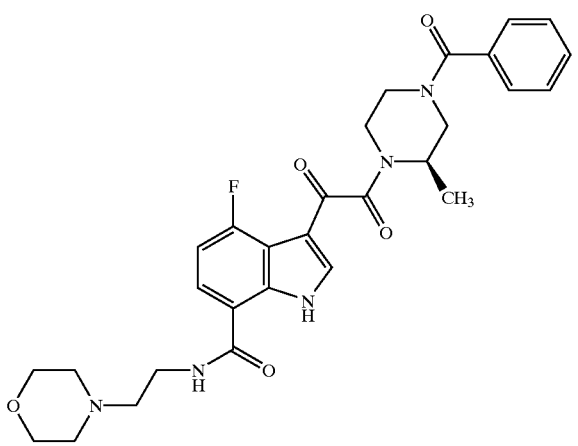

Purification was performed by preparative HPLC using the method: Start %B=10, Final %B=80, Gradient time=12 min, Flow Rate=25 ml/min, Column: YMC C18 S5 20×100 mm, Fraction Collection: 7.17–7.90 min. $^1$H NMR (mixture of conformers, CD$_3$OD) δ 8.19 and 8.15 (s, 1H), 7.80 (b m, 1H), 7.48 (b s, 5H), 7.07 (app t, J=8.1, 1H), 3.84 (t, overlapping with b m, J=5.6, 2H), 3.45 (t, overlapping with b m, J=5.6, 2H), 4.84–3.09 (b overlapping m, 15H), 1.37–1.25 (b m, 3H); LC/MS (ES+) m/z (M+H)$^+$=550, HPLC R$_t$=1.040.

Example 178

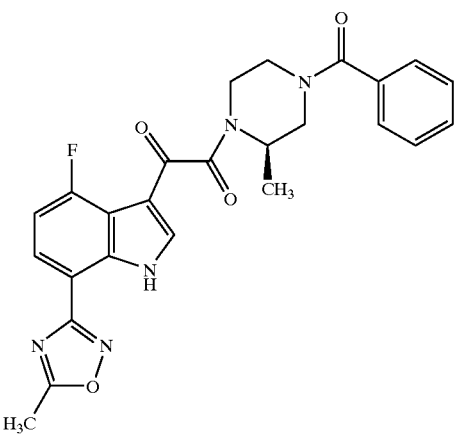

Purification was performed by preparative HPLC using the method: Start %B=20, Final %B=90, Gradient time=15 min, Flow Rate=25 ml/min, Column: YMC C18 S5 20×100 mm, Fraction Collection: 11.55–12.27 min. $^1$H NMR (mixture of conformers, CD$_3$OD) δ 8.22 and 8.18 (s, 1H), 8.07 (b m, 1H), 7.46 (b s, 5H), 7.15 (b m, 1H), 4.82–3.10 (b m, 7H), 2.72 (s, 3H), 1.39–1.25 (b m, 3H); LC/MS (ES+) m/z (M+H)$^+$=476, HPLC R$_t$=1.403.

Example 179

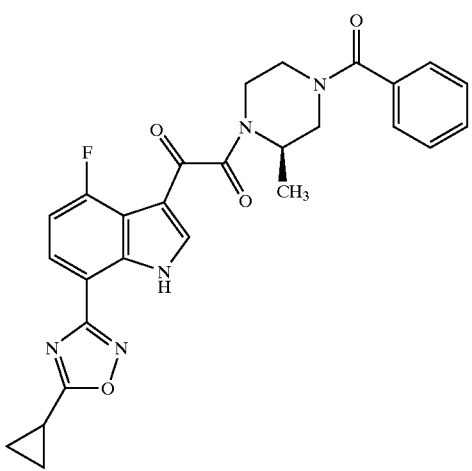

Purification was performed by preparative HPLC using the method: Start %B=30, Final %B=100, Gradient time=14 min, Flow Rate=25 ml/min, Column: YMC C18 S5 20×100 mm, Fraction Collection: 11.05–11.77 min. $^1$H NMR (mixture of conformers, CD$_3$OD) δ 8.21 and 8.17 (s, 1H), 8.04 (b m, 1H), 7.46 (b s, 5H), 7.13 (b m, 1H), 4.80–3.11 (b m, 7H), 2.40 (m, 1H), 1.38–1.25 (overlapping b m, 7H); LC/MS (ES+) m/z (M+H)$^+$=502, HPLC R$_t$=1.520.

Example 180

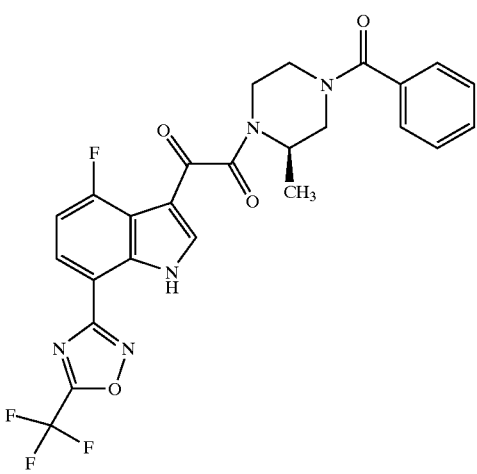

Purification was performed by preparative HPLC using the method: Start %B=30, Final %B=100, Gradient time=14 min, Flow Rate=25 ml/min, Column: YMC C18 S5 20×100 mm, Fraction Collection: 12.05–12.77 min. $^1$H NMR (CDCl$_3$) δ 10.36 (s, 1H), 8.22 (d, J=4.2, 1H), 8.17 (app, dd, J=7.8, 4.1, 1H), 7.43 (b s, 5H), 7.17 (app t, J=9.3, 1H), 4.90–3.00 (b m, 7H), 1.40–1.29 (b m, 3H); LC/MS (ES+) m/z (M+H)$^+$=530, HPLC R$_t$=1.613.

Example 181

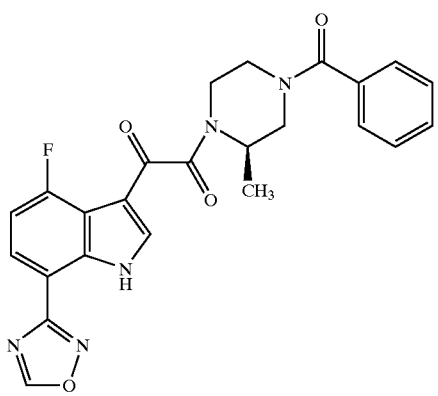

Purification was performed by preparative HPLC using the method: Start %B=30, Final %B=100, Gradient time=15 min, Flow Rate=30 ml/min, Column: YMC C18 S5 20×100 mm, Fraction Collection: 6.32–6.93 min. $^1$H NMR (CD$_3$OD) δ 9.41(s, 1H), 8.23 and 8.20 (s, 1H), 8.15 (b m, 1H), 7.46 (b s, 5H), 7.18 (b m, 1H), 4.79–3.07 (b m, 7H), 1.39–1.18 (b m, 3H); LC/MS (ES+) m/z (M+H)$^+$=462, HPLC R$_t$=1.350.

Example 182

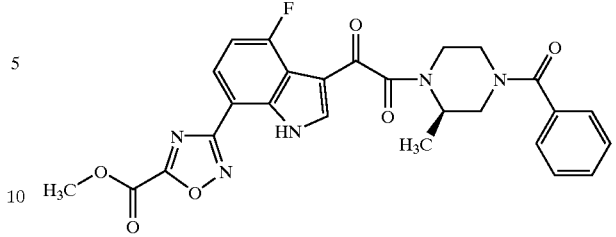

Purification was performed by preparative HPLC using the method: Start %B=20, Final %B=80, Gradient time=15 min, Flow Rate=40 ml/min, Column: YMC C18 S5 30×100 mm, Fraction Collection: 13.60–14.04 min. $^1$H NMR (CDCl$_3$) δ 10.56 (s, 1H), 8.21 (overlapping m, 2H), 7.26 (b m, 5H), 7.15 (app t, J=9.3, 1H), 4.16(s, overlapping with b m, 3H), 5.10–3.00 (b m, 7H), 1.50–1.20 (b m, 3H); LC/MS (ES+) m/z (M+H)$^+$=520, HPLC R$_t$=1.500.

Example 183

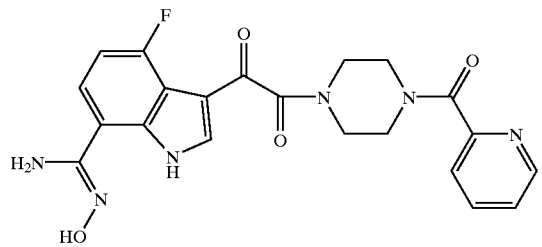

Purification was performed by preparative HPLC using the method: Start %B=0, Final %B=75, Gradient time=10 min, Flow Rate=40 ml/min, Column: YMC C18 S5 30×100 mm, Fraction Collection: 4.34–5.06 min. $^1$H NMR (DMSO-d$_6$) δ 13.97 (d, J=15.0, 1H), 10.47 (b, s, 2H), 9.17 (b s, 1H), 8.64 and 8.54 (d, J=4.5,1H), 8.39 (t, J=3.3, 1H), 7.96 (m, 1H), 7.65–7.46 (b m, 3H), 7.22 (b m, 1H), 3.83 (app d, J=5.5, 1H), 3.75 (app d, J=5.3, 1H), 3.66 (app d, J=3.4, 2H), 3.61 (app t, J=2.6, 1H), 3.48 (app t, J=4.8, 1H), 3.44 (app t, J=2.8, 1H), 3.90 (app d, J=5.2, 1H); LC/MS (ES+) m/z (M+H)$^+$= 439, HPLC R$_t$=0.740.

Example 184

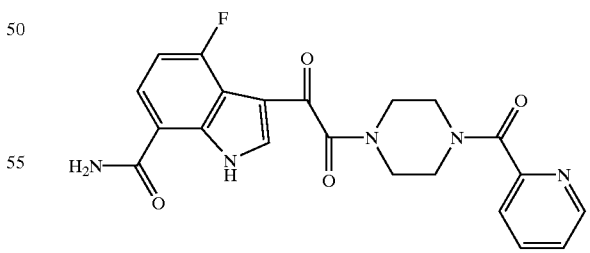

Purification was performed by preparative HPLC using the method: Start %B=0, Final %B=75, Gradient time=10 min, Flow Rate=40 ml/min. Column: YMC C18 S5 30×100 mm, Fraction Collection: 6.43–7.15 min. $^1$H NMR (DMSO-d$_6$) δ 12.39 (d, J=12.0, 1H), 8.63 and 8.54 (d, J=4.5, 1H), 8.24 (b s, 1H), 8.08 (d, J=2.9, 1H), 7.99–7.87(b m, 2H), 7.63 (m, 2H), 7.52 and 7.46 (app dd, J=7.0, 5.2, 1H), 7.10 (b m, 1H), 3.79 (app t, J=2.8, 1H), 3.74 (app d, J=5.5, 1H), 3.65 (app d, J=2.7, 2H), 3.57 (app d, J=5.4, 1H), 3.48 (app d, J=4.9, 1H), 3.42 (app d, J=5.7, 1H), 3.39 (app d, J=5.4, 1H); LC/MS (ES+) m/z (M+H)$^+$=424, HPLC R$_t$=0.903.

Example 185A

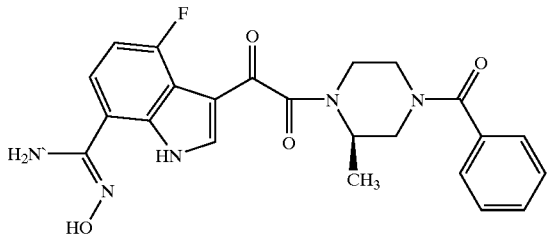

Purification was performed by preparative HPLC using the method: Start %B=10, Final %B=80, Gradient time=12 min, Flow Rate=25 ml/min, Column: YMC C18 S5 20×100 mm, Fraction Collection: 5.82–7.28 min. $^1$H NMR (CD$_3$OD) δ 8.26 and 8.21 (s, 1H), 7.56 (b m, 1H), 7.46 (b s, 5H), 7.15 (b m, 1H), 4.83–3.11 (b m, 7H), 1.37–1.16 (b m, 3H); LC/MS (ES+) m/z (M+H)$^+$=452, HPLC R$_t$=0.937.

Example 185B

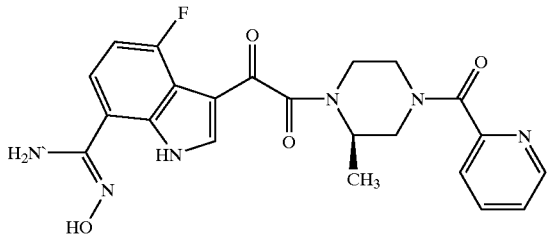

Purification was performed by preparative HPLC using the method: Start %B=0, Final %B=100, Gradient time=15 min, Flow Rate=40 ml/min, Column: YMC C18 S5 30×100 mm, Fraction Collection: 5.80–5.06 min. $^1$H NMR (DMSO-d$_6$) δ 12.71 (b s, 1H), 11.10 (b, s, 1H), 8.64 and 8.54 (app dd, J=9.6, 4.7,1H), 8.36–8.26 (b m, 1H), 7.99–7.95 (b m, 1H), 7.67–7.46 (b m, 3H), 7.23–7.17 (b m, 1H), 6.10 (b s, 2H), 4.81–2.91 (b m, 7H), 1.29–1.11 (b m, 3H); LC/MS (ES+) m/z (M+H)$^+$=453, HPLC R$_t$=0.793.

Example 186A

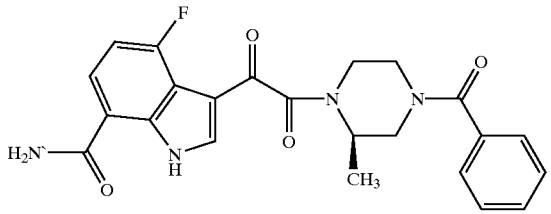

Purification was performed by preparative HPLC using the method: Start %B=10, Final %B=80, Gradient time=12 min, Flow Rate=25 ml/min, Column: YMC C18 S5 20×100 mm, Fraction Collection: 8.10–8.83 min. $^1$H NMR (CD$_3$OD) δ 8.18 and 8.14 (s, 1H), 7.83 (b m, 1H), 7.46 (b s, 5H), 7.04 (b m, 1H), 4.83–3.11 (b m, 7H), 1.38–1.25 (b m, 3H); LC/MS (ES+) m/z(M+H)$^+$=437, HPLC R$_t$=1.113.

Example 186B

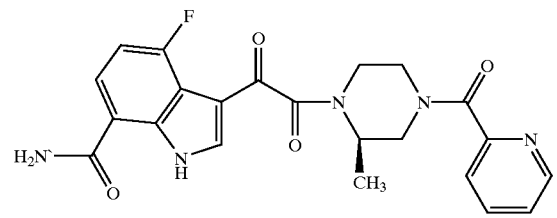

Purification was performed by preparative HPLC using the method: Start %B=0, Final %B=100, Gradient time=15 min, Flow Rate=40 ml/min, Column: YMC C18 S5 30×100 mm, Fraction Collection: 7.94–8.39 min. $^1$H NMR (DMSO-d$_6$) δ 12.37 (b m, 1H), 8.64 and 88.54 (app dd, J=10.6, 4.7, 1H), 8.23 (app d, J=6.4, 1H), 8.08–7.88 (b m, 3H), 7.66–7.46 (b m, 3H), 7.15–7.08 (b m, 1H), 4.98–2.89 (b m, 7H), 1.27–1.10 (b m, 3H); LC/MS (ES+) m/z (M+H)$^+$=438, HPLC R$_t$=0.960.

Example 187

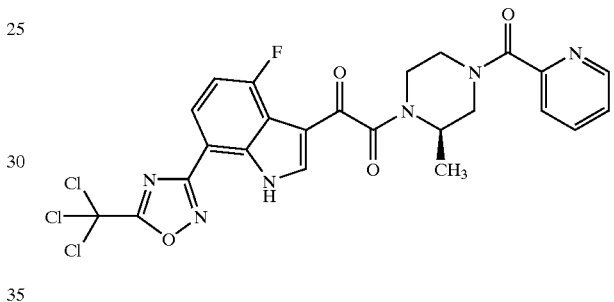

Purification was performed by preparative HPLC using the method: Start %B=30, Final %B=100, Gradient time=16 min, Flow Rate=30 ml/min, Column: YMC C18 S5 30×100 mm, Fraction Collection: 14.81–15.37 min. $^1$H NMR (CDCl$_3$) δ 10.43 (d, J=8.0, 1H), 8.71–8.58 (b m, 1H), 8.21–8.16 (b m, 2H), 7.95–7.86 (b m, 1H), 7.73 (b s, 1H), 7.49–7.43 (b m, 1H), 7.18–7.12 (b m, 1H), 5.05–3.08 (b m, 7H), 1.45 and 1.29 (b m, 3H); LC/MS (ES+) m/z (M+H)$^+$= 580, HPLC R$_t$=1.773.

Example 188

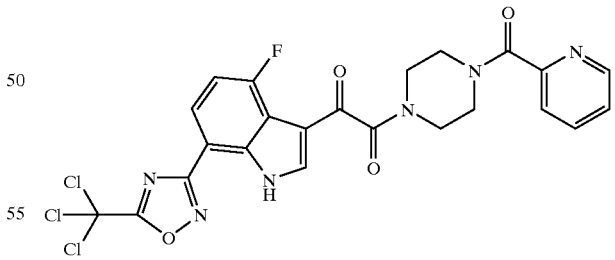

Purification was performed by preparative HPLC using the method: Start %B=10, Final %B=100, Gradient time=12 min, Flow Rate=40 ml/min, Column: YMC C18 S5 30×100 mm, Fraction Collection: 12.77–13.37 min. $^1$H NMR (CDCl$_3$) δ 10.47 (b s, 1H), 8.77 and 8.69 (b s, 1H), 8.25 (app d, J=2.8,1H), 8.18 (b s, 1H), 8.04(b m, 1H), 7.74 (b s, 1H), 7.62–7.57 (b m, 1H), 7.15 (app dd, J=17.9, 8.6, 1H), 3.98–3.59 (b m, 8H); LC/MS (ES+) m/z (M+H)$^+$=566, HPLC R$_t$=1.750.

Example 189

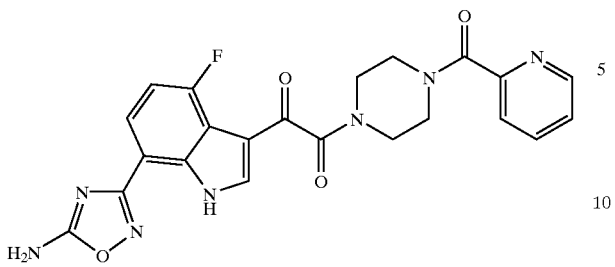

Purification was performed by preparative HPLC using a similar method as that of compound of Example 190. $^1$H NMR (DMSO-$d_6$) δ 12.00 (d, J=12.0,1H), 8.64 and 8.54 (app d, J=5.0, 1H), 8.13 (b s, 3H), 7.98–7.85 (b m, 2H), 7.62 (app dd, J=14.0, 8.0, 1H), 7.52 and 7.46 (b m, 1H), 7.19 (b m, 1H), 3.80 (app d, J=6.0, 1H), 3.75 (app d, J=6.0, 1H), 3.65 (app d, J=3.0, 2H), 3.5 8 (app d, J=5.5, 1H), 3.49 (app d, J=5.0, 1H), 3.42 (app d, J=7.5, 2H); LC/MS (ES+) m/z (M+H)$^+$=464, HPLC R$_t$=1.123.

Example 190

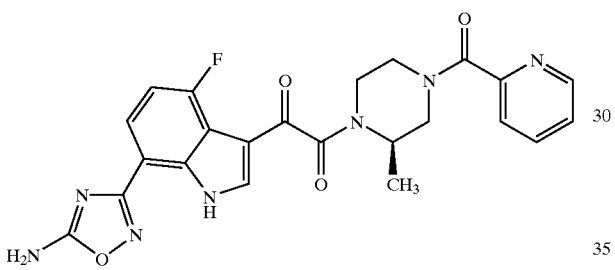

Purification was performed by preparative HPLC using the method: Start %B=20, Final %B=100, Gradient time=15 min, Flow Rate=30 ml/min, Column: YMC C18 S5 30×100 mm, Fraction Collection: 8.96–8.98 min. $^1$H NMR (CD$_3$OD) δ 8.65–8.52 (b m, 1H), 8.24 (m, 1H), 7.99–7.91 (b m, 2H), 7.67 (m, 1H), 7.56–7.47 (b m, 1H), 7.10 (b m, 1H), 4.69–3.06 (b m, 7H), 1.40 and 1.26 (b m, 3H); LC/MS (ES+) m/z (M+H)$^+$=478, HPLC R$_t$=1.173.

Example 191

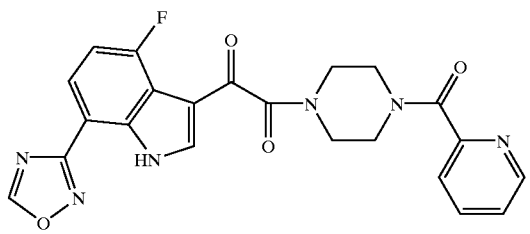

Purification was performed by preparative HPLC using the method: Start %B=10, Final %B=90, Gradient time=15 min, Flow Rate=40 ml/min, Column: YMC C18 S5 30×100 mm, Fraction Collection: 9.79–10.25 min. $^1$H NMR (CDCl$_3$) δ 10.66 (b s, 1H), 8.87 (s, 1H), 8.70 and 8.53 (b s, 1H), 8.22 (app d, J=3.1, 1H), 8.15 (b m, 1H), 7.94 (b m, 1H), 7.73 (b s, 1H), 7.48 (b m, 1H), 7.13 (app dd, J=18.8, 9.9, 1H), 3.98–3.50 (b m, 8H); LC/MS (ES+) m/z (M+H)$^+$=449, HPLC R$_t$=1.220.

Example 192

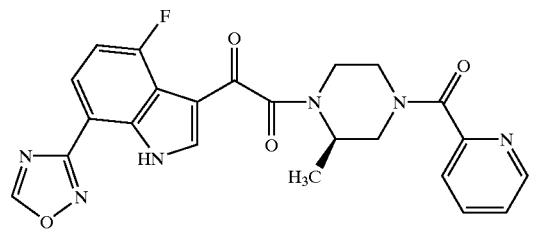

Purification was performed by preparative HPLC using the method: Start %B=10, Final %B=90, Gradient time=15 min, Flow Rate=40 ml/min, Column: YMC C18 S5 30×100 mm, Fraction Collection: 10.26–10.71 min. $^1$H NMR (CD$_3$OD) δ 9.40 (d, J=3.5, 1H), 8.67–8.56 (b, m, 1H), 8.25–8.53 (b m, 1H), 8.25–8.18 (b m, 1H), 8.12 (b m, 1H), 8.03 (b m, 1H), 7.72 (b m, 1H), 7.60 (b m, 1H), 4.87–3.15 (b m, 7H), 1.42 and 1.27 (b m, 3H); LC/MS (ES+) m/z (M+H)$^+$=463, HPLC R$_t$=1.263.

Example 193

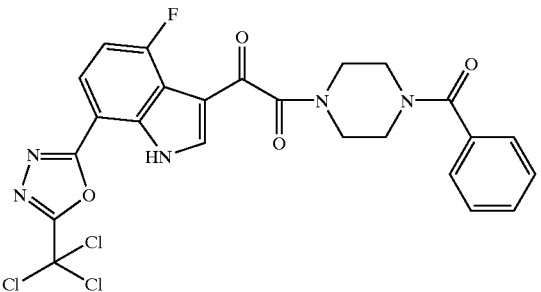

Purification was performed by preparative HPLC using the method: Start %B=30, Final %B=100, Gradient time=18 min, Flow Rate=40 ml/min, Column: YMC C18 S5 30×100 mm, Fraction Collection: 15.58–16.18 min. $^1$H NMR (CDCl$_3$) δ 10.92 (s, 1H), 8.29 (d, J=3.0, 1H), 7.99 (app dd, J=8.0, 4.0, 1H), 7.44 (b s, 5H), 7.18 (app t, J=9.0, 1H), 3.98–3.52 (b m, 8H); LC/MS (ES+) m/z (M+H)$^+$=565, HPLC R$_t$=1.750.

Example 194

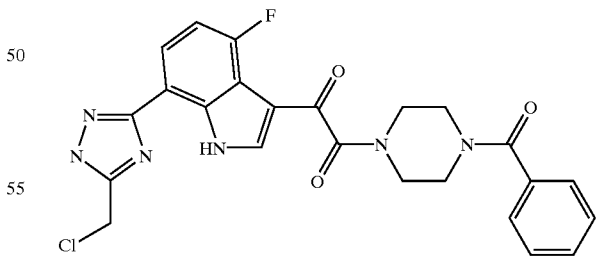

Purification was performed by preparative HPLC using the method: Start %B=20, Final %B=80, Gradient time=15 min, Flow Rate=40 ml/min, Column: YMC C18 S5 30×100 mm, Fraction Collection: 11.57–11.87 min. $^1$H NMR (CDCl$_3$) δ 11.17 (s, 1H), 8.03 (s, 1H), 7.67 (app dd, J=7.6, 3.9, 1H), 7.44 (b s, 5H), 6.88 (app t, J=9.3, 1H), 4.77 (s, 2H), 3.87–3.45 (b m, overlapping with broad water peak, 8H); LC/MS (ES+) m/z (M+H)$^+$=495. HPLC R$_t$=1.380.

Examples 195–214 and 219–284

Compounds of Examples 195 to 214 and Examples 219 to 284 were prepared according to the method described in Scheme 25D and are of the general formula below.

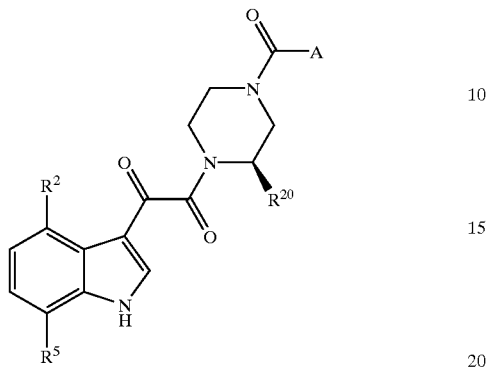

| EXAMPLE | R² | R⁵ | R²⁰ | A | HPLC R_t (min) | (M + H)⁺ |
|---|---|---|---|---|---|---|
| 195 | F | (1,2,4-oxadiazole with X₂, CH₂SO₂CH₂-furan) | H | X₄-phenyl | 1.57 | 606.37 |
| 196 | F | (1,2,4-oxadiazole with X₂, CH₂S-thiophene) | H | X₄-phenyl | 1.742 | 576.32 |
| 197 | F | (1,2,4-oxadiazole with X₂, phenyl) | H | X₄-phenyl | 1.428 | 524.25 |
| 198 | F | (1,2,4-oxadiazole with X₂, CH₂S-pyridine) | H | X₄-phenyl | 1.563 | 571.36 |
| 199 | F | (1,2,4-oxadiazole with X₂, 4-fluorophenyl) | H | X₄-phenyl | 1.527 | 542.15 |
| 200 | F | (1,2,4-oxadiazole with X₂, CH₂C(O)-pyrrolidine) | H | X₄-phenyl | 1.308 | 559.43 |

-continued
| EXAMPLE | R² | R⁵ | R²⁰ | A | HPLC R$_t$ (min) | (M + H)⁺ |
|---|---|---|---|---|---|---|
| 201 | F | 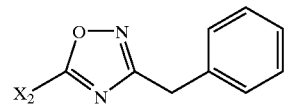 | H | 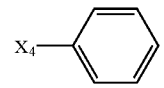 | 1.744 | 538.38 |
| 202 | F | 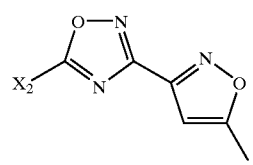 | H | 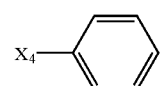 | 1.360 | 529.14 |
| 203 | F | 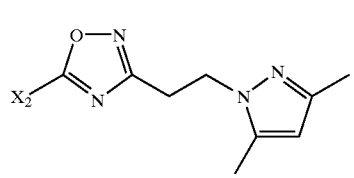 | H | 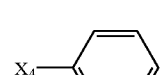 | 1.344 | 570.43 |
| 204 | F | 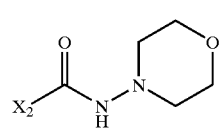 | H | 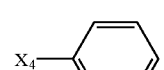 | 1.036 | 508.21 |
| 205 | F | 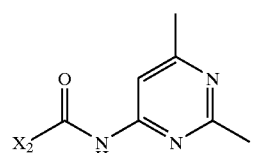 | H | 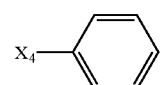 | 0.979 | 529.41 |
| 206 | F | 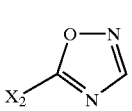 | H | 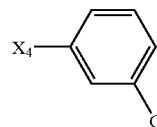 | 1.461 | 482.27 |
| 207 | F | 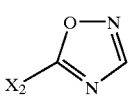 | H | 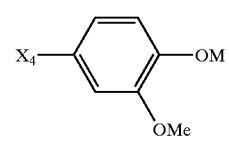 | 0.984 | 508.26 |
| 208 | F |  | H | 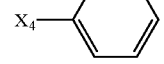 | 1.392 | 586.16 |
| 209 | F | 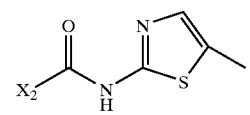 | H | 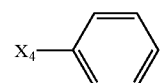 | 1.235 | 520.14 |
| 210 | F | 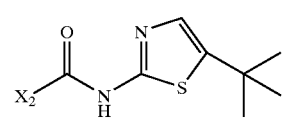 | H | 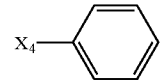 | 1.496 | 562.21 |

-continued
| EXAMPLE | R² | R⁵ | R²⁰ | A | HPLC R_t (min) | (M + H)⁺ |
|---|---|---|---|---|---|---|
| 211 | F | 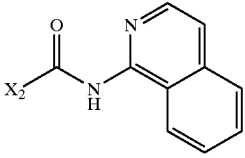 | H | 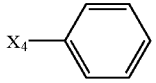 | 1.214 | 550.23 |
| 212 | F | 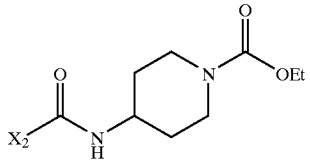 | H | 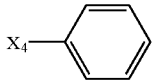 | 1.237 | 578.25 |
| 213 | F | 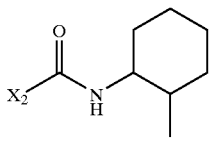 | H | 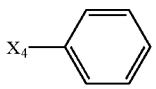 | 1.391 | 519.25 |
| 214 | F | 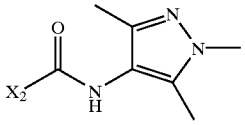 | H | 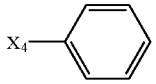 | 1.102 | 531.22 |
| 219 | F | 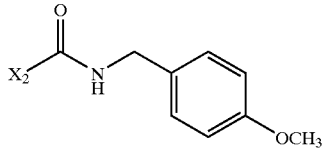 | H | 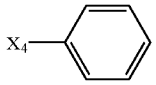 | 5.54 | 543.31 (51%) |
| 220 | F | 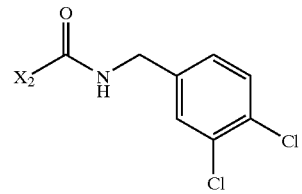 | H | 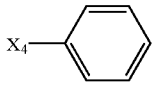 | 6.89 | 581.13/ 583.12 (100%) |
| 221 | F | 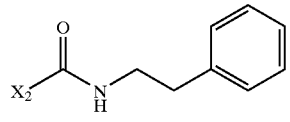 | H | 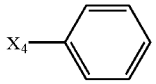 | 6.41 | 527.21 (100%) |
| 222 | F | 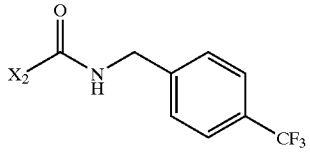 | H | 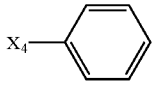 | 6.80 | 581.18 (100%) |
| 223 | F | 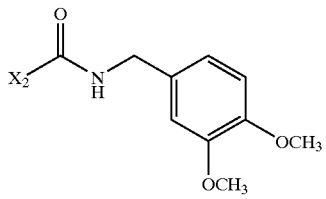 | H | 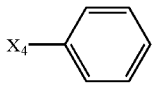 | 5.70 | 573.27 (100%) |

-continued

| EXAMPLE | R² | R⁵ | R²⁰ | A | HPLC Rₜ (min) | (M + H)⁺ |
|---|---|---|---|---|---|---|
| 224 | F | X₂-C(O)-NH-CH₂CH₂CH₂-N(pyrrolidin-2-one) | H | X₄-phenyl | 4.07 | 548.31 (100%) |
| 225 | F | X₂-C(O)-NH-CH₂-CN | H | X₄-phenyl | 5.93 | 461.41 (100%) |
| 226 | F | X₂-C(O)-NH-(4-methylthiazol-2-yl) | H | X₄-(3-CF₃-phenyl) | 5.81 | 588.25 (71%) |
| 227 | F | X₂-C(O)-NH-CH₂CH₂-(thiophen-2-yl) | H | X₄-phenyl | 6.24 | 533.17 (100%) |
| 228 | F | X₂-C(O)-NH-CH₂CH₂-O-phenyl | H | X₄-phenyl | 6.36 | 543.19 (96%) |
| 229 | F | X₂-C(O)-NH-CH₂-CH(phenyl)₂ | H | X₄-phenyl | 7.01 | 603.24 (100%) |
| 230 | F | X₂-C(O)-NH-CH₂-(pyridin-2-yl) | H | X₄-phenyl | 3.80 | 514.35 (24%) |
| 231 | F | X₂-C(O)-NH-(4-methylthiazol-2-yl) | H | X₄-morpholinyl | 4.36 | 529.28 (11%) |
| 232 | F | X₂-C(O)-NH-CH₂-(pyridin-3-yl) | H | X₄-phenyl | 5.06 | 514.47 (92%) |
| 233 | F | X₂-C(O)-NH-(4-methylthiazol-2-yl) | H | X₄-(3-OCH₃-phenyl) | 5.13 | 550.29 (53%) |

-continued
| EXAMPLE | R² | R⁵ | R²⁰ | A | HPLC R_f (min) | (M + H)⁺ |
|---|---|---|---|---|---|---|
| 234 | F | 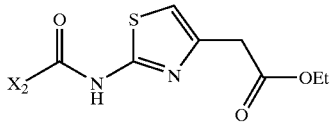 | H | 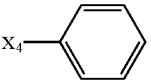 | 5.49 | 592.34 (47%) |
| 235 | F | 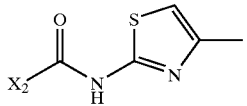 | H | 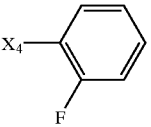 | 5.20 | 538.26 (74%) |
| 236 | F | 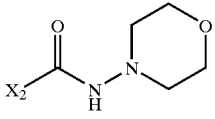 | H | 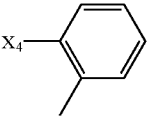 | 4.33 | 522.32 (7%) |
| 237 | F | 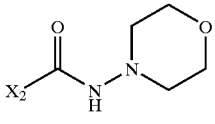 | H | 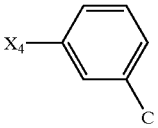 | 4.10 | 533.32 (5%) |
| 238 | F | 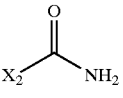 | H | 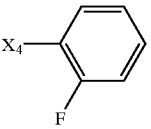 | 4.31 | 441.26 (34%) |
| 239 | F | 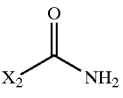 | H | 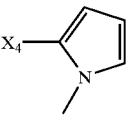 | 3.56 | 426.16 (100%) |
| 240 | F | 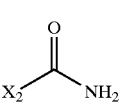 | H | 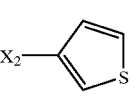 | 4.01 | 429.22 (34%) |
| 241 | F | 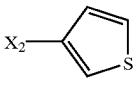 | H | 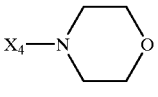 | 6.10 | 471.36 (100%) |
| 242 | F | 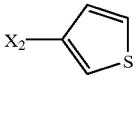 | H | 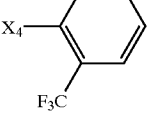 | 6.24 | 530.21 (66%) |
| 243 | F | 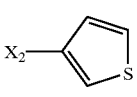 | H | 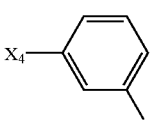 | 6.22 | 496.17 (65%) |
| 244 | F | 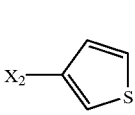 | H | 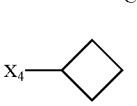 | 5.68 | 440.18 (86%) |

-continued
| EXAMPLE | R² | R⁵ | R²⁰ | A | HPLC R$_t$ (min) | (M + H)⁺ |
|---|---|---|---|---|---|---|
| 245 | F | 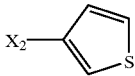 | H | 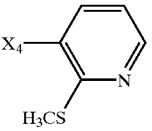 | 5.66 | 509.20 (85%) |
| 246 | F | 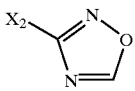 | H | 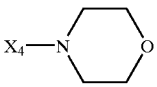 | 4.30 | 457.68 (29%) |
| 247 | F | 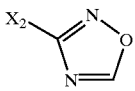 | H | 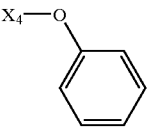 | 5.79 | 464.66 (15%) |
| 248 | F | 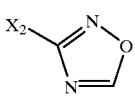 | H | 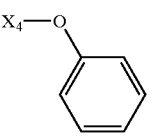 | | |
| 249 | F | 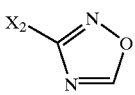 | H | 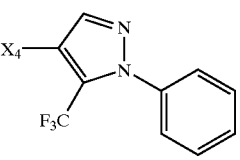 | 5.95 | 582.76 (42%) |
| 250 | F | 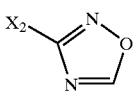 | H | 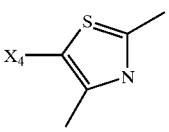 | 4.42 | 483.66 (39%) |
| 251 | F | 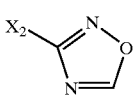 | H | 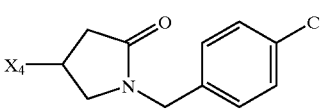 | 5.39 | 579.76 (24%) |
| 252 | F | 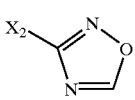 | H | 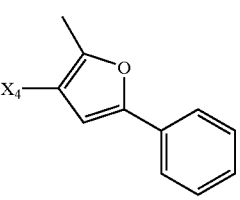 | 6.18 | 528.72 (23%) |
| 253 | F | 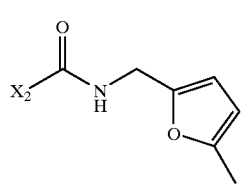 | H | 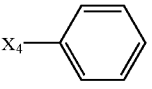 | 5.51 | 517.28 (19%) |
| 254 | F | 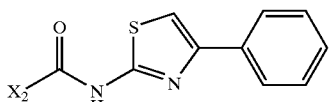 | H | 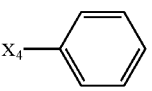 | 6.23 | 582.24 (37%) |

-continued

| EXAMPLE | R² | R⁵ | R²⁰ | A | HPLC R_t (min) | (M + H)⁺ |
|---|---|---|---|---|---|---|
| 255 | F | 5-acetyl-4-methyl-thiazol-2-yl-NH-C(O)-X₂ | H | X₄-phenyl | 5.25 | 562.24 (5%) |
| 256 | F | X₂-thiophen-3-yl | H | X₄-(3-methoxy-4-SCH)phenyl | 6.14 | 538.23 (42%) |
| 257 | F | X₂-thiophen-3-yl | H | X₄-(2,3-dimethyl)phenyl | 6.18 | 490.24 (26%) |
| 258 | F | X₂-thiophen-3-yl | H | X₄-CH₂-phenyl | 5.96 | 476.24 (89%) |
| 259 | F | morpholin-4-yl-NH-C(O)-X₂ | H | X₄-(2-SCH₃)pyridin-3-yl | 3.93 | 555.32 (9%) |
| 260 | F | morpholin-4-yl-NH-C(O)-X₂ | H | X₄-(2,6-difluoro)phenyl | 4.35 | 544.34 (21%) |
| 261 | F | morpholin-4-yl-NH-C(O)-X₂ | H | X₄-O-phenyl | 4.80 | 524.32 (11%) |
| 262 | F | 4-methyl-thiazol-2-yl-NH-C(O)-X₂ | H | X₄-(2-methyl)phenyl | 5.28 | 534.28 (48%) |
| 263 | F | 4-methyl-thiazol-2-yl-NH-C(O)-X₂ | H | X₄-(3-fluoro)phenyl | 5.27 | 538.24 (46%) |

-continued

| EXAMPLE | R² | R⁵ | R²⁰ | A | HPLC R_t (min) | (M + H)⁺ |
|---|---|---|---|---|---|---|
| 264 | F | thiazole-methyl amide | H | 2,6-difluorophenyl | 5.35 | 556.25 (62%) |
| 265 | F | morpholine hydrazide | H | 3-Cl-phenyl | 4.63 | 542.32/ 544.26 (17%) |
| 266 | F | 5-methylisothiazole amide | H | 2-CF₃-phenyl | 5.52 | 588.26 (34%) |
| 267 | F | 5-methylisothiazole amide | H | 4-OC, 3-OCH₃-phenyl | 4.87 | 580.29 (22%) |
| 268 | F | 5-methylisothiazole amide | H | 2-OCH₃-phenyl | 5.09 | 550.29 (18%) |
| 269 | F | 5-methylisothiazole amide | H | 2-F-phenyl | 5.18 | 538.26 (13%) |
| 270 | F | 5-methylisothiazole amide | H | 2-SCH₃-pyridyl | 4.93 | 567.26 (31%) |
| 271 | F | 1,3-dimethylpyrazole amide | H | 2-CF₃-phenyl | 4.68 | 599.30 (31%) |
| 272 | F | 1,3-dimethylpyrazole amide | H | 2-F-phenyl | 4.32 | 549.34 (33%) |
| 273 | F | 1,3-dimethylpyrazole amide | H | 2-methylphenyl | 4.40 | 545.37 (23%) |

-continued

| EXAMPLE | R² | R⁵ | R²⁰ | A | HPLC R$_t$ (min) | (M + H)⁺ |
|---|---|---|---|---|---|---|
| 274 | F | 3-methyl-1-methyl-pyrazol-4-yl carboxamide | H | 3-(methylthio)pyridin-2-yl | 4.07 | 578.34 (6%) |
| 275 | F | morpholin-4-yl-NH-C(O)- | H | 2,6-dimethoxypyridin-3-yl | 4.39 | 569.34 (5%) |
| 276 | F | 4-methyl-thiazol-2-yl carboxamide | H | phenoxy | 5.72 | 536.25 (67%) |
| 277 | F | 4-methyl-thiazol-2-yl carboxamide | H | 1-methyl-pyrrol-2-yl | 5.06 | 523.25 (53%) |
| 278 | F | 4-methyl-thiazol-2-yl carboxamide | H | 2,6-dimethoxypyridin-3-yl | 5.30 | 581.29 (26%) |
| 279 | F | 4-methyl-thiazol-2-yl carboxamide | H | 2-(trifluoromethyl)phenyl | 5.59 | 588.24 (92%) |
| 280 | F | 5-methyl-thiazol-2-yl carboxamide | H | phenyl | 5.27 | 534.29 (15%) |
| 281 | F | 5-methyl-thiazol-2-yl carboxamide | H | phenoxy | 5.66 | 536.26 (38%) |
| 282 | F | 1,3,5-trimethyl-pyrazol-4-yl carboxamide | H | 4-methoxy-3-methoxyphenyl | 4.03 | 591.35 (11%) |
| 283 | F | 1,3,5-trimethyl-pyrazol-4-yl carboxamide | H | 2-methoxyphenyl | 4.27 | 561.38 (14%) |

-continued

| EXAMPLE | R[2] | R[5] | R[20] | A | HPLC R$_t$ (min) | (M + H)+ |
|---|---|---|---|---|---|---|
| 284 | F | ![pyrazole carboxamide] | H | X$_4$—O—phenyl | 4.81 | 547.34 (34%) |

Example 215

Special Procedures:

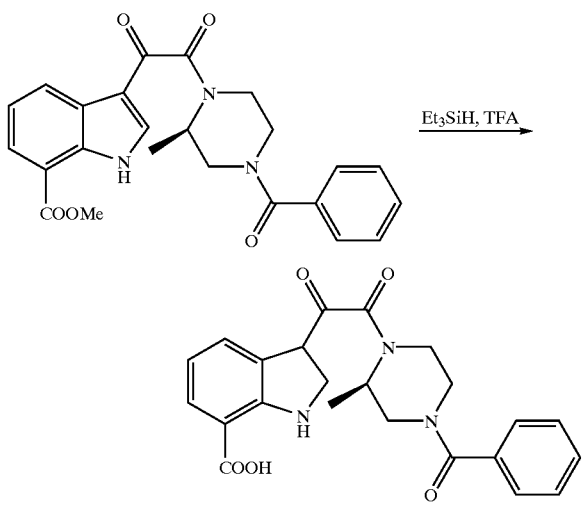

Preparation of 1-(benzoyl)-3-(R)-Methyl-4-[(7-hydoxycarbonyl-indolin-3-yl)-2-oxoacetyl]piperazine: 1-(benzoyl)-3-(R)-methyl4-[(7-(methoxycarbonyl)indol-3-yl)-2-oxoacetyl]piperazine (50 mg) was dissolved in a solution of triethylsilane (Et$_3$SiH, 0.5 mL) in TFA (5 mL). The reaction was stirred for 10 hours. Solvents were removed under vaccum, and the residue was purified using Shimadzu automated preparative HPLC System to give 1-benzoyl-3-(R)-methyl-4-[(7-carboxyindolin-3-yl)-2-oxoacetyl]piperazine (5.5 mg).

Example 216

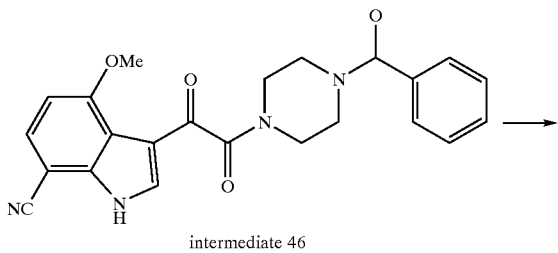

intermediate 46

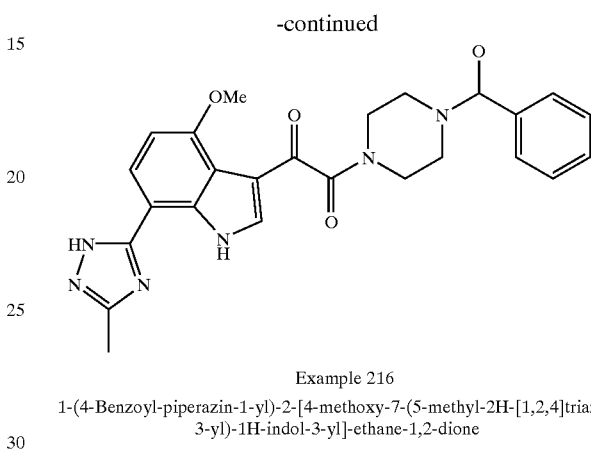

Example 216
1-(4-Benzoyl-piperazin-1-yl)-2-[4-methoxy-7-(5-methyl-2H-[1,2,4]triazol 3-yl)-1H-indol-3-yl]-ethane-1,2-dione A mixture of intermediate 46 (100 mg, 0.24 mmol) in anhydrous MeOH (1.5 ml) at 0° C. in a re-usable sealed tube was bubbled hydrogen chloride gas for 20 min. The sealed tube was tightly closed, and the reaction mixture stirred at r.t. overnight. After transferring to a round bottom flask, the mixture was evaporated in vacuo and the residue dried under high vacuum to give the methyl imidate (LC/MS: (ES+) m/z (M+H)+=449; HPLC R$_t$=0.997). To a mixture of the methyl imidate in absolute EtOH (1.5 ml) was added acetic hydrazide (89 mg, 1.2 mmol, dried under high vacuum before use) and N,N-diisopropylethylamine (126 µl, 0.72 mmol). The resulting mixture was stirred at 130° C. for 3 h, then at 150° C. for 8 h, and filtered to give a solid residue. LC/MS analysis showed that this solid material contained a major product (LC/MS: (ES+) m/z (M+H)+=491; HPLC R$_t$=0.820), which presumably was the uncyclized condensation intermediate of the reaction between methyl imidate and acetic hydrazide. To a mixture of the solid in absolute EtOH (1.5 ml) was added methanolic sodium methoxide (55 µl, 0.24 mmol, 25 wt. %, d=0.945), and the resulting mixture refluxed at 110° C. for 45 min. After cooling to r.t. and evaporated in vacuo, the residue was treated with a small amount of water and added hydrochloric acid (3 drops, 1 N aq.) dropwise via a pipet to give precipitates. The precipitates were collected by filtration and purified by preparative thin layer chromatography (5% MeOH/CH$_2$Cl$_2$) to give the compound of Example 216. $^1$H NMR: (CDCl$_3$) δ 11.13 (b s, 1H), 8.00 (s, 1H), 7.82 (b d, 1H), 7.43 (b s, 5H), 6.66 (d, J=8.3, 1H), 4.05–3.40 (b m, 8H), 3.95 (s, 3H), 2.47 (s, 3H); LC/MS: (ES+) m/z (M+H)+=473; HPLC R$_t$=1.070.

Example 217

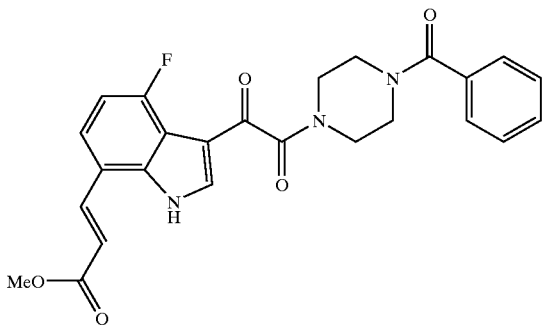

A mixture of intermediate 4 (1 g, 2.18 mmol), methyl acrylate (282 mg, 3.27 mmol), palladium acetate (27 mg, 0.120 mmol), tri-o-tolylphosphine (100 mg, 0.329 mmol) and triethylamine (264 mg, 2.61 mmol) in DMF (5 ml) was heated at 100° C. in a sealed tube for 48 h. The mixture was then cooled to r.t, diluted with water and extracted with EtOAc (3 times). Evaporation of the combined organic extracts in vacuo and crystallization of the resulting residue from MeOH gave the compound of Example 217 as a yellowish brown solid. $^1$H NMR: (CDCl$_3$ +drop of DMSO-d$_6$, 300 MHz) δ 8.16 (d, J=15.9, 1H), 8.03 (d, J=3.3, 1H), 7.50 (dd, 1H), 7.39 (b s, 5H), 6.94 (dd, 1H), 6.50 (d, J=15.9, 1H), 3.90–3.40 (b m, 8H), 3.79 (s, 3H); LC/MS: (ES+) m/z (M+H)$^+$=464; HPLC R$_t$=1.467.

Another aspect of the present invention are the compounds P-217 through P-280 in Table P-1 of the following general formula which may be prepared by the methods described herein.

TABLE P-1

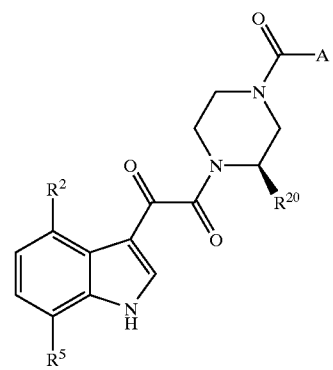

| Compound | R$^2$ | R$^5$ | R$^{20}$ | A |
|---|---|---|---|---|
| P-217 | Cl | 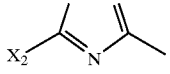 | H | 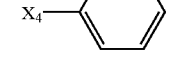 |
| P-218 | F | 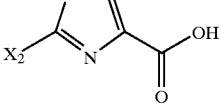 | H | 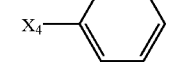 |
| P-219 | OCH$_3$ | 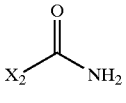 | CH$_3$ | 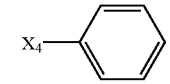 |
| P-220 | F | 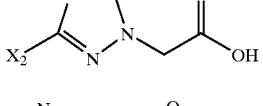 | H | 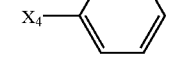 |
| P-221 | F | 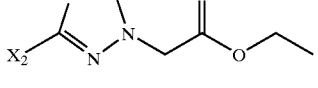 | H | 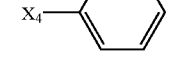 |
| P-222 | F | 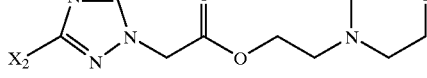 | H | 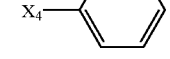 |
| P-223 | F | 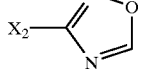 | H | 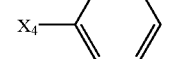 |

-continued
| Compound | R² | R⁵ | R²⁰ | A |
|---|---|---|---|---|
| P-224 | F | 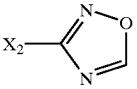 | H | 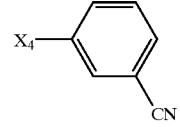 |
| P-225 | F | 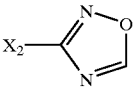 | H | 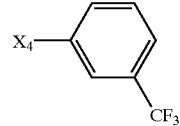 |
| P-226 | OCH₃ | 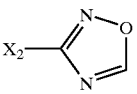 | H | 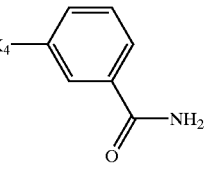 |
| P-227 | OCH₃ | 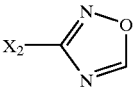 | H | 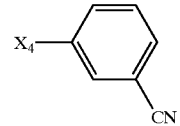 |
| P-228 | OCH₃ | 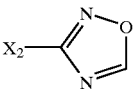 | H | 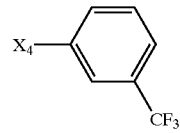 |
| P-229 | OCH₃ | 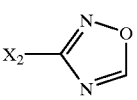 | H | 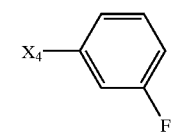 |
| P-230 | F | 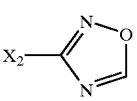 | H | 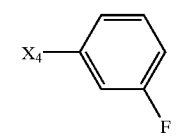 |
| P-231 | OCH₃ | 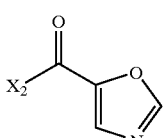 | H | 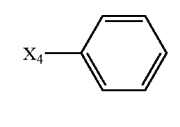 |
| P-232 | OCH₃ | 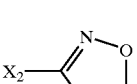 | H | 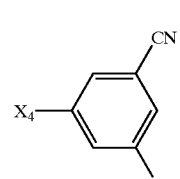 |
| P-233 | F | 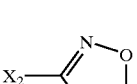 | H | 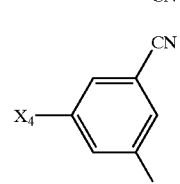 |

-continued
| Compound | R² | R⁵ | R²⁰ | A |
|---|---|---|---|---|
| P-234 | OCH₃ | 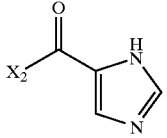 | H | 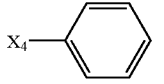 |
| P-235 | OCH₃ | 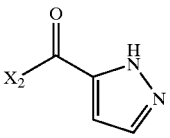 | H | 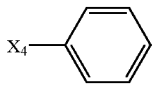 |
| P-236 | OCH₃ | 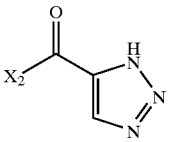 | H | 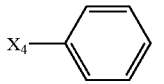 |
| P-237 | OCH₃ | 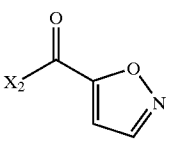 | H | 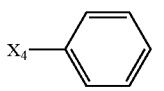 |
| P-238 | OCH₃ | 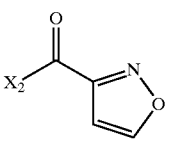 | H | 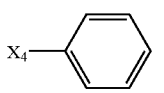 |
| P-239 | OCH₃ | 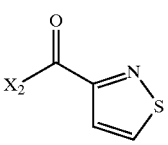 | H | 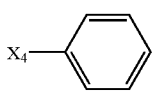 |
| P-240 | OCH₃ | 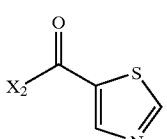 | H | 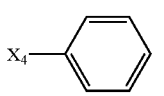 |
| P-241 | OCH₃ | 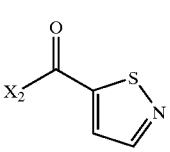 | H | 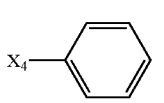 |
| P-242 | OCH₃ | 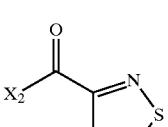 | H | 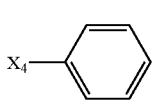 |
| P-243 | OCH₃ | 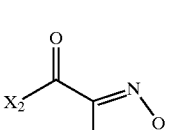 | H | 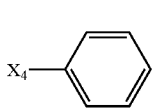 |

-continued

| Compound | R² | R⁵ | R²⁰ | A |
|---|---|---|---|---|
| P-244 | OCH₃ | ![structure: X₂-C(=O)-pyrazine] | H | X₄-phenyl |
| P-245 | OCH₃ | ![structure: X₂-C(=O)-pyrimidine] | H | X₄-phenyl |
| P-246 | OCH₃ | ![structure: X₂-C(=O)-pyridine-2-yl] | H | X₄-phenyl |
| P-247 | OCH₃ | ![structure: X₂-C(=O)-(1H-pyrazole)-C(=O)OtBu] | H | X₄-phenyl |
| P-248 | OCH₃ | ![structure: X₂-C(=O)-(1H-pyrazole)-C(=O)OMe] | H | X₄-phenyl |
| P-249 | OCH₃ | ![structure: X₂-C(=O)-(1H-pyrazole)-C(=O)OPr] | H | X₄-phenyl |
| P-250 | OCH₃ | ![structure: X₂-C(=O)-(1H-pyrazole)-C(=O)OiPr] | H | X₄-phenyl |
| P-251 | OCH₃ | ![structure: X₂-C(=O)-(1H-pyrazole)-C(=O)OnBu] | H | X₄-phenyl |

-continued

| Compound | R² | R⁵ | R²⁰ | A |
|---|---|---|---|---|
| P-252 | F | pyrazole-C(O)X₂ / C(O)OtBu | H | X₄—phenyl |
| P-253 | F | pyrazole-C(O)X₂ / C(O)OMe | H | X₄—phenyl |
| P-254 | F | pyrazole-C(O)X₂ / C(O)OPr | H | X₄—phenyl |
| P-255 | F | pyrazole-C(O)X₂ / C(O)OiPr | H | X₄—phenyl |
| P-256 | F | pyrazole-C(O)X₂ / C(O)OnBu | H | X₄—phenyl |
| P-257 | F | pyrazole-C(O)X₂ / C(O)OEt | H | X₄—phenyl |
| P-258 | OCH₃ | pyrazole-C(O)X₂ / C(O)OEt | H | X₄—phenyl |

-continued
| Compound | R² | R⁵ | R²⁰ | A |
|---|---|---|---|---|
| P-259 | OCH₃ | 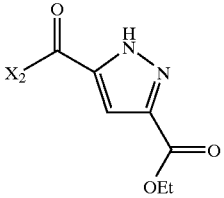 | H | 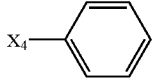 |
| P-260 | OCH₃ | 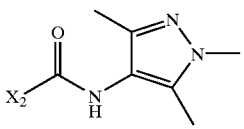 | H | 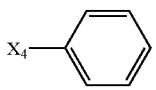 |
| P-261 | OCH₃ | 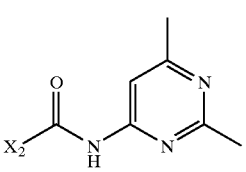 | H | 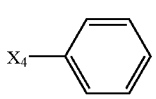 |
| P-262 | OCH₃ | 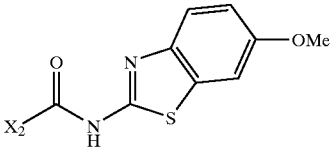 | H | 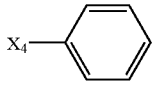 |
| P-263 | OCH₃ | 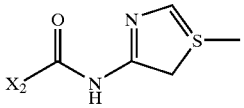 | H | 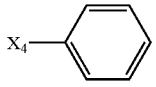 |
| P-264 | OCH₃ | 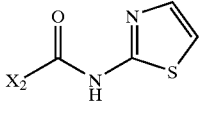 | H | 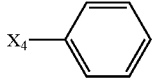 |
| P-265 | OCH₃ | 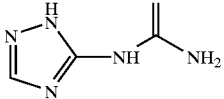 | H | 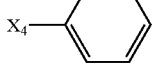 |
| P-266 | OCH₃ | 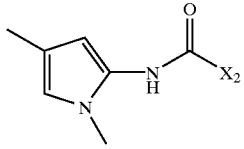 | H | 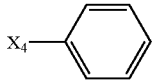 |
| P-267 | OCH₃ | 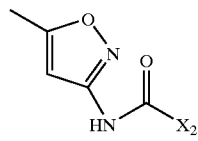 | H | 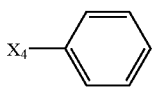 |
| P-268 | OCH₃ | 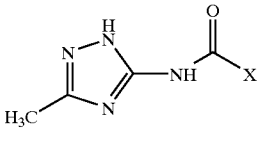 | H | 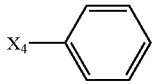 |

-continued

| Compound | R² | R⁵ | R²⁰ | A |
|---|---|---|---|---|
| P-269 | OCH₃ | (1,2,3,4-thiadiazol-5-yl)NHC(O)X₂ | H | X₄-phenyl |
| P-270 | OCH₃ | (1H-1,2,4-triazol-3-yl)NHC(O)X₂ | H | X₄-phenyl |
| P-271 | OCH₃ | (1,2,4,5-tetrazin-3-yl)NHC(O)X₂ | H | X₄-phenyl |
| P-272 | F | (1H-1,2,4-triazol-3-yl)NHC(O)X₂ | H | X₄-phenyl |
| P-273 | OCH₃ | (5-methyl-1H-1,2,4-triazol-3-yl)NHC(O)X | H | X₄-phenyl |
| P-274 | F | (5-methyl-1H-1,2,4-triazol-3-yl)NHC(O)X₂ | H | X₄-phenyl |
| P-275 | F | (1,3-dimethyl-1H-pyrazol-5-yl)NHC(O)X | H | X₄-phenyl |
| P-276 | F | (5-methylisoxazol-3-yl)NHC(O)X | H | X₄-phenyl |
| P-277 | F | (5-methyl-1H-1,2,4-triazol-3-yl)NHC(O)X | H | X₄-phenyl |
| P-278 | F | (1,2,3,4-thiadiazol-5-yl)NHC(O)X₂ | H | X₄-phenyl |
| P-279 | F | (1H-1,2,4-triazol-3-yl)NHC(O)X₂ | H | X₄-phenyl |

-continued

| Compound | R² | R⁵ | R²⁰ | A |
|---|---|---|---|---|
| P-280 | F | [structure: triazinyl-NH-C(=O)-X₂] | H | [structure: X₄-phenyl] |

Experimental Procedures

Biology

In Table I and hereafter, the following definitions apply.

"$\mu$M" means micromolar;

"ml" means milliliter;

"$\mu$l" means microliter;

"mg" means milligram;

The materials and experimental procedures used to obtain the results reported in Table I are described below.

Cells

Virus production-Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).

Virus infection-Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis , Mo.) and supplemented with 0.2 mg/ml Geneticin (Life Technologies, Gaithersburg, Md.) and 0.4 mg/ml Zeocin (Invitrogen, Carlsbad, Calif.). Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 30b). Transfections were performed using lipofectAMINE PLUS reagent as described by the manufacturer (Life Technologies, Gaithersburg, Md.).

Experiment

1. Compound was added to HeLa CD4 CCR5 cells plated in 96 well plates at a cell density of 5×104 cells per well in 100 $\mu$l Dulbecco's Modified Eagle Medium containing 10% fetal Bovine serum at a concentration of <20 $\mu$M.
2. 100 $\mu$l of single-round infectious reporter virus in Dulbecco's Modified Eagle Medium was then added to the plated cells and compound at an approximate multiplicity of infection (MOI) of 0.01, resulting in a final volume of 200 $\mu$l per well and a final compound concentration of <10 $\mu$M.
3. Samples were harvested 72 hours after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 $\mu$l of Dulbecco's Modified Eagle Medium (without phenol red) and 50 $\mu$l of luciferase assay reagent reconstituted as described by the manufacturer (Roche Molecular Biochemicals, Indianapolis, Ind. were added per well. Luciferase activity was then quantified by measuring luminescence using a Wallac microbeta scintillation counter.
5. The percent inhibition for each compound was calculated by quantifying the level of luciferase expression in cells infected in the presence of each compound as a percentage of that observed for cells infected in the absence of compound and subtracting such a determined value from 100.
6. An $EC_{50}$ provides a method for comparing the antiviral potency of the compounds of this invention. The effective concentration for fifty percent inhibition ($EC_{50}$) was calculated with the Microsoft Excel XLfit curve fitting software. For each compound, curves were generated from percent inhibition calculated at 10 different concentrations by using a four paramenter logistic model (model 205). The $EC_{50}$ data for the compounds is shown in Table 2. Table 1 is the key for the data in Table 2.

Results

TABLE 1

Biological Data Key for $EC_{50}$s

| Compounds* with $EC_{50}$s > 5 $\mu$M | Compounds with $EC_{50}$s > 1 $\mu$M but <5 $\mu$M | Compounds with EC50 < 1 $\mu$M |
|---|---|---|
| Group C | Group B | Group A |

*Some of these compounds may have been tested at a concentration lower than their $EC_{50}$ but showed some ability to cause inhibition and thus should be evaluated at a higher concentration to determine the exact $EC_{50}$.

In Table 2, $X_1$, $X_2$, $X_4$ etc. indicates the point of attachment.

TABLE 2

[Structure: indole with R² at 4-position, R⁵ at 7-position, substituted at 3-position with -C(O)-C(O)-N(piperazine with R²⁰)-C(O)-A]

| Table Entry (Example number) | R² | R⁵ | R²⁰ | A | EC₅₀ Group from Table 1 |
|---|---|---|---|---|---|
| 1 (Example 1) | F | X₂-phenyl | H | X₄-phenyl | A |
| 2 (Example 14) | F | X₂-thiazol-2-yl (S,N) | H | X₄-phenyl | A |
| 3 (Example 12) | F | X₂-thien-2-yl | H | X₄-phenyl | A |
| 4 (Example 5) | F | X₂-pyridin-2-yl | H | X₄-phenyl | A |
| 5 (Example 9) | F | X₂-pyrimidin-5-yl | H | X₄-phenyl | A |
| 6 (Example 16) | F | X₂-(5-chloro)thien-2-yl | H | X₄-phenyl | A |
| 7 (Example 15) | OCH₃ (X₁) | X₂-thiazol-2-yl | H | X₄-phenyl | A |
| 8 (Example 7) | OCH₃ (X₁) | X₂-pyridin-2-yl | H | X₄-phenyl | A |
| 9 (Example 10) | OCH₃ (X₁) | X₂-pyrimidin-5-yl | H | X₄-phenyl | A |

TABLE 2-continued
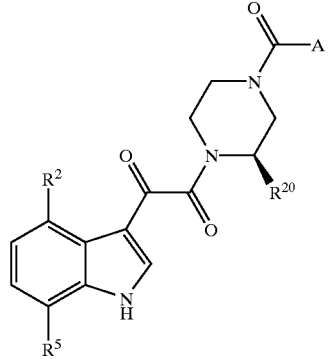
| Table Entry (Example number) | R² | R⁵ | R²⁰ | A | EC₅₀ Group from Table 1 |
|---|---|---|---|---|---|
| 10 (Example 8) |  | 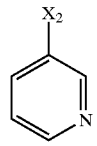 | H | 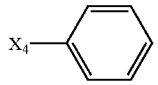 | A |
| 11 (Example 18) | F | 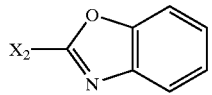 | H | 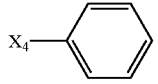 | A |
| 12 (Example 29) | F | 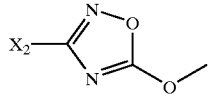 | H | 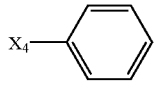 | A |
| 13 (Example 34) | F | 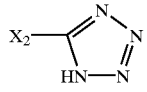 | CH₃ | 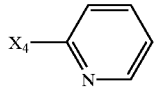 | A |
| 14 (Example 21) | F | 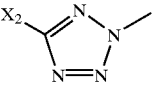 | H | 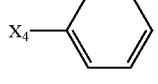 | A |
| 15 (Example 19) |  | 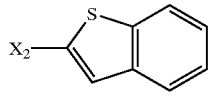 | H | 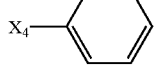 | A |
| 16 (Example 6) | F | 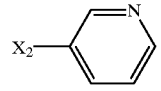 | H | 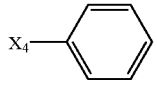 | A |
| 17 (Example 11) |  | 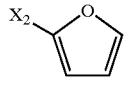 | H | 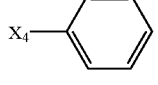 | A |
| 18 (Example 17) | F | 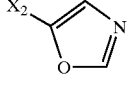 | H | 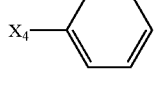 | A |
| 19 (Example 30) | F | 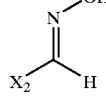 | H | 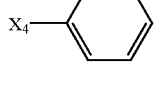 | A |

TABLE 2-continued
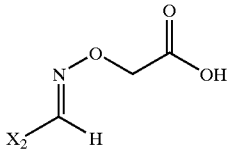
| Table Entry (Example number) | R² | R⁵ | R²⁰ | A | EC₅₀ Group from Table 1 |
|---|---|---|---|---|---|
| 20 (Example 31) | F | 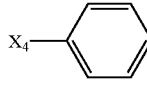 | H |  | A |
| 21 (Example 4) | F | 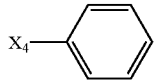 | H | 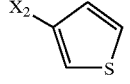 | A |
| 22 (Example 13) | F | 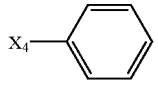 | H | 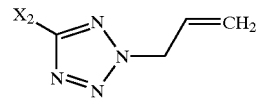 | A |
| 23 (Example 26) | F | 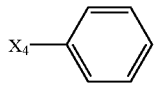 | H |  | A |
| 24 (Example 3) |  | 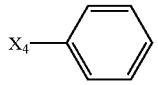 | H | 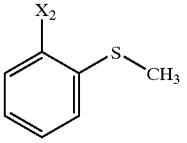 | A |
| 25 (Example 2) | F | 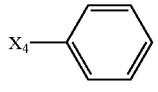 | H | 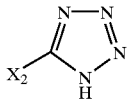 | A |
| 26 (Example 167) | F | 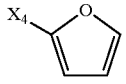 | H | 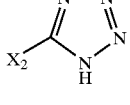 | A |
| 27 (Example 170) | F | 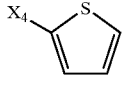 | H | 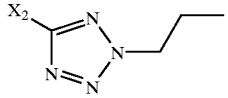 | A |
| 28 (Example 24) | F | 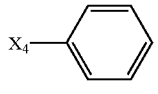 | H |  | A |

TABLE 2-continued

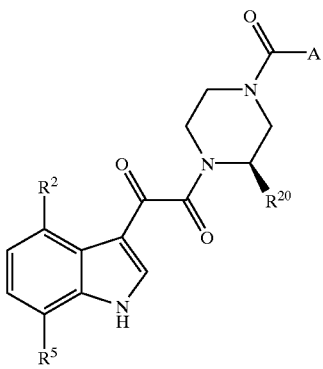

| Table Entry (Example number) | R² | R⁵ | R²⁰ | A | EC₅₀ Group from Table 1 |
|---|---|---|---|---|---|
| 29 (Example 23) | F | X₂-tetrazole-N-ethyl | H | X₄-phenyl | A |
| 30 (Example 25) | F | X₂-tetrazole-N-benzyl | H | X₄-phenyl | A |
| 31 (Example 22) | F | X₂-tetrazole-N-CH₂C(O)OCH₃ | H | X₄-phenyl | A |
| 32 (Example 173) | F | X₂-tetrazole-N-CH₃ | H | X₄-(5-bromofuran-2-yl) | A |
| 33 (Example 172) | F | X₂-tetrazole-N-CH₃ | H | X₄-(5-chlorofuran-2-yl) | A |
| 34 (Example 171) | F | X₂-tetrazole-N-CH₃ | H | X₄-(furan-2-yl) | A |
| 35 (Example 174) | F | X₂-tetrazole-N-CH₃ | H | X₄-(thiophen-2-yl) | A |
| 36 (Example 40) | F | phenylsulfonyl-NH-C(O)-X₂ | H | X₄-phenyl | A |
| 37 (Example 32) | F | X₂-(1H-tetrazol-5-yl) | H | X₄-(pyridin-2-yl) | A |

TABLE 2-continued
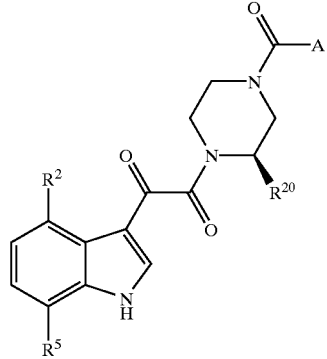
| Table Entry (Example number) | R² | R⁵ | R²⁰ | A | EC₅₀ Group from Table 1 |
|---|---|---|---|---|---|
| 38 (Example 185A) | F | 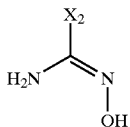 | CH₃ | 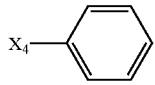 | A |
| 39 (Example 186A) | F | 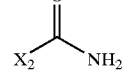 | CH₃ | 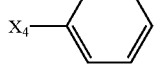 | A |
| 40 (Example 49) | F | 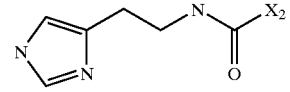 | H | 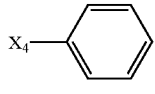 | A |
| 41 (Example 48) | F | 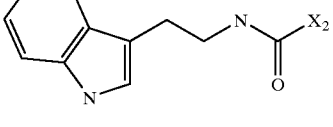 | H | 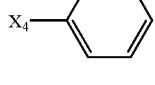 | A |
| 42 (Example 50) | F | 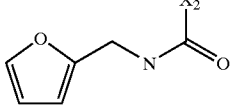 | H | 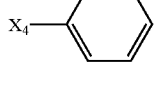 | A |
| 43 (Example 51) | F | 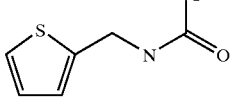 | H | 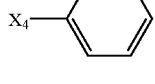 | A |
| 44 (Example 52) | F | 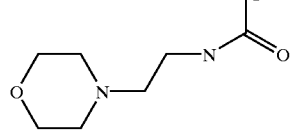 | H | 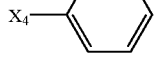 | A |
| 45 (Example 168) | F | 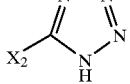 | H | 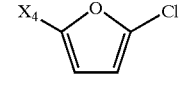 | A |
| 46 (Example) | F | 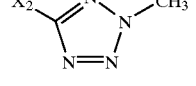 | CH₃ | 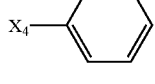 | A |

TABLE 2-continued

| Table Entry (Example number) | R² | R⁵ | R²⁰ | A | EC₅₀ Group from Table 1 |
|---|---|---|---|---|---|
| 47 (Example 169) | F | tetrazol-5-yl (X₂ attached, NH) | H | 5-bromofuran-2-yl (X₄) | A |
| 48 (Example 35) | F | pyridin-3-yl-NH-C(O)- (X₂) | H | phenyl (X₄) | A |
| 49 (Example 36) | F | 4,5-dihydrothiazol-2-yl-NH-C(O)- (X₂) | H | phenyl (X₄) | A |
| 50 (Example 37) | F | 3-methylisoxazol-5-yl-NH-C(O)- (X₂) | H | phenyl (X₄) | A |
| 51 (Example 41) | F | benzimidazol-2-yl-NH-C(O)- (X₂) | H | phenyl (X₄) | A |
| 52 (Example 38) | F | pyridin-2-yl-NH-C(O)- (X₂) | H | phenyl (X₄) | A |
| 53 (Example 42) | F | H₂N-C(O)- (X₂) | H | phenyl (X₄) | A |
| 54 (Example 43) | F | (CH₃)₂N-C(O)- (X₂) | H | phenyl (X₄) | A |
| 55 (Example 44) | F | (CH₃)₂N-CH₂CH₂-N(CH₃)-C(O)- (X₂) | H | phenyl (X₄) | A |

TABLE 2-continued

| Table Entry (Example number) | R² | R⁵ | R²⁰ | A | EC₅₀ Group from Table 1 |
|---|---|---|---|---|---|
| 56 (Example 39) | F | 4-pyridyl-NH-C(=O)-X₂ | H | X₄-phenyl | A |
| 57 (Example 45) | F | benzyl-NH-C(=O)-X₂ | H | X₄-phenyl | A |
| 58 (Example 46) | F | H₃C-O-N(H)-C(=O)-X₂ | H | X₄-phenyl | A |
| 59 (Example 33) | F | X₂-(1H-tetrazol-5-yl) | CH₃ | X₄-phenyl | A |
| 60 (Example 47) | F | H₃C-NH-C(=O)-X₂ | H | X₄-phenyl | A |
| 61 (Example 54) | F | X₂-C(=O)-NH-(1H-tetrazol-5-yl) | H | X₄-phenyl | A |
| 62 (Example 62) | H | PhSO₂-N(H)-C(=O)-X₂ | H | X₄-phenyl | B |
| 63 (Example 61) | H | H₃C-S(=O)₂-N(H)-C(=O)-X₂ | H | X₄-phenyl | B |
| 64 (Example 63) | H | (1H-tetrazol-5-yl)-NH-C(=O)-X₂ | H | X₄-phenyl | A |

TABLE 2-continued

| Table Entry (Example number) | R² | R⁵ | R²⁰ | A | EC₅₀ Group from Table 1 |
|---|---|---|---|---|---|
| 65 (Example 20) | F | tetrazole-X₂ | H | X₄–phenyl | A |
| 66 (Example 28) | F | 1,3,4-oxadiazol-2(3H)-one-X₂ | H | X₄–phenyl | A |
| 67 (Example 60) | F | H₃C-S(O)₂-NH-C(O)-X₂ | H | X₄–phenyl | A |
| 68 (Example 27) | F | H₂N-C(=N-OH)-X₂ | H | X₄–phenyl | A |
| 69 (Example 69) | F | X₂-C(O)-N(piperazine)N-C(O)-phenyl | H | X₄–phenyl | A |
| 70 (Example 64) | H | CH₃-NH-C(O)-X₂ | CH₃ | X₄–phenyl | A |
| 71 (Example 65) | H | (CH₃)₂N-C(O)-X₂ | CH₃ | X₄–phenyl | A |
| 72 (Example 67) | H | Et-NH-C(O)-X₂ | CH₃ | X₄–phenyl | A |
| 73 (Example 66) | H | (Et)₂N-CH₂CH₂-NH-C(O)-X₂ | CH₃ | X₄–phenyl | A |

TABLE 2-continued
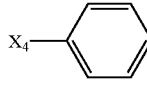
| Table Entry (Example number) | R² | R⁵ | R²⁰ | A | EC₅₀ Group from Table 1 |
|---|---|---|---|---|---|
| 74 (Example 68) | H | 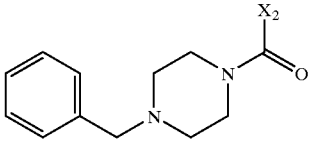 | CH₃ | 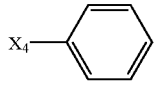 | A |
| 75 (Example 73) | F | 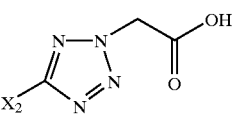 | H | 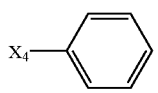 | A |
| 76 (Example 70) | F | 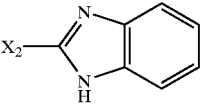 | H | 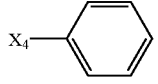 | A |
| 77 (Example 76) | F | 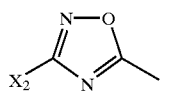 | H | 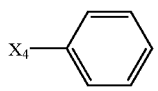 | A |
| 78 (Example 80) | F | 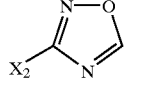 | H | 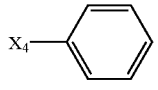 | A |
| 79 (Example 79) | F | 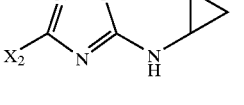 | H | 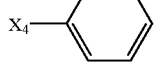 | A |
| 80 (Example 82) | F | 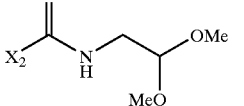 | H | 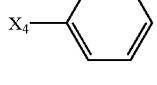 | A |
| 81 (Example 72) | F | 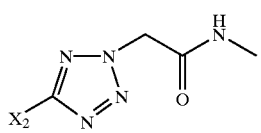 | H | 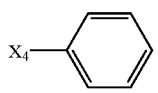 | A |
| 82 (Example 71) | F | | H | | A |

TABLE 2-continued

| Table Entry (Example number) | R² | R⁵ | R²⁰ | A | EC₅₀ Group from Table 1 |
|---|---|---|---|---|---|
| 83 (Example 78) | F | 3-methyl-1H-1,2,4-triazol-5-yl (X₂ at 5-position) | H | X₄-phenyl | A |
| 84 (Example 75) | F | N-cyclopropylcarbamimidoyl (X₂-C(=NH)NH-cyclopropyl) | H | X₄-phenyl | A |
| 85 (Example 83) | F | 5-amino-1,2,4-oxadiazol-3-yl (X₂ at 3-position, NH₂ at 5) | H | X₄-phenyl | A |
| 86 (Example 84) | F | 1-benzyl-1H-imidazol-5-yl (X₂ at 5-position, Bn on N1) | H | X₄-phenyl | A |
| 87 (Example 85) | F | 1H-imidazol-5-yl (X₂ at 5-position) | H | X₄-phenyl | A |
| 88 (Example 86) | F | ethyl 1H-pyrazole-3-carboxylate-5-yl (X₂ at 5, CO₂Et at 3) | H | X₄-phenyl | A |
| 89 (Example 87) | F | ethyl isoxazole-3-carboxylate-5-yl (X₂ at 5, CO₂Et at 3) | H | X₄-phenyl | A |
| 90 (Example 88) | F | 1H-pyrazole-3-carboxylic acid-5-yl (X₂ at 5, CO₂H at 3) | H | X₄-phenyl | A |
| 91 (Example 89) | F | N-methyl-1H-pyrazole-3-carboxamide-5-yl (X₂ at 5, C(O)NHCH₃ at 3) | H | X₄-phenyl | A |

TABLE 2-continued
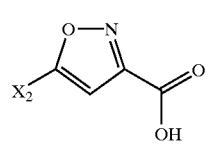
| Table Entry (Example number) | R² | R⁵ | R²⁰ | A | EC₅₀ Group from Table 1 |
|---|---|---|---|---|---|
| 92 (Example 90) | F | 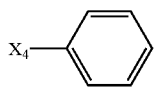 | H | 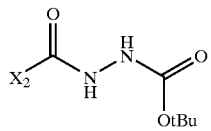 | A |
| 93 (Example 91) | F | 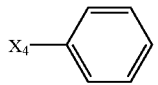 | H | 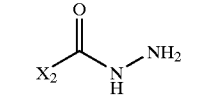 | A |
| 94 (Example 92) | F | 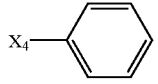 | H | 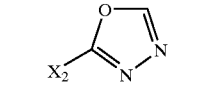 | A |
| 95 (Example 93) | F | 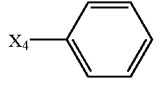 | H | 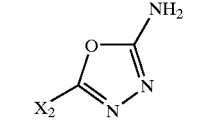 | A |
| 96 (Example 94) | F | 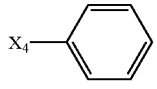 | H | 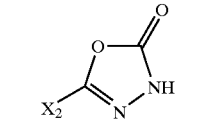 | A |
| 97 (Example 95) | F | 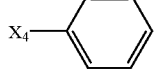 | H | 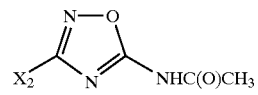 | A |
| 98 (Example 96) | F | 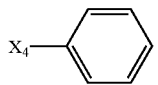 | H | 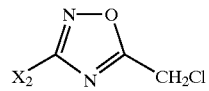 | A |
| 99 (Example 97) | F | 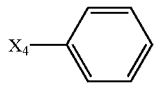 | H | 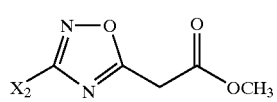 | A |
| 100 (Example 98) | F | 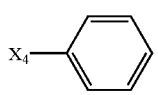 | H | | A |

TABLE 2-continued

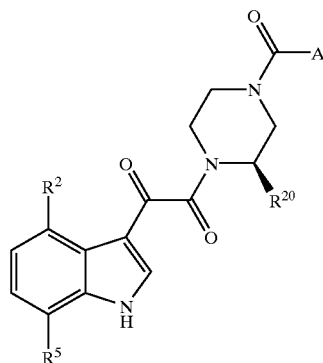

| Table Entry (Example number) | R² | R⁵ | R²⁰ | A | EC₅₀ Group from Table 1 |
|---|---|---|---|---|---|
| 101 (Example 99) | F | X₂-[1,2,4-oxadiazole]-CH₂-C(=O)-OCH₃ | H | X₄-phenyl | A |
| 102 (Example 100) | F | X₂-[1,2,4-oxadiazole]-CH₂-C(=O)-NHCH₃ | H | X₄-phenyl | A |
| 103 (Example 101) | F | X₂-[1,2,4-oxadiazole]-CH₂-C(=O)-OH | H | X₄-phenyl | A |
| 104 (Example 102) | F | X₂-[1,2,4-oxadiazole]-C(=O)-NHCH₃ | H | X₄-phenyl | A |
| 105 (Example 103) | F | X₂-[1,2,4-oxadiazole]-C(=O)-NH₂ | H | X₄-phenyl | A |
| 106 (Example 104) | F | X₂-tetrazole-CH₂-C(=O)-NH₂ | H | X₄-phenyl | A |
| 107 (Example 105A) | F | X₂-tetrazole-CH₂-(3-C(=O)OMe-phenyl) | H | X₄-phenyl | A |
| 108 (Example 106A) | F | X₂-tetrazole-CH₂-(3-C(=O)OH-phenyl) | H | X₄-phenyl | A |

TABLE 2-continued
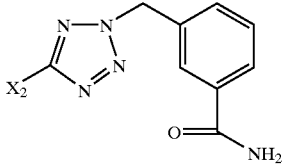
| Table Entry (Example number) | R² | R⁵ | R²⁰ | A | EC₅₀ Group from Table 1 |
|---|---|---|---|---|---|
| 109 (Example 107A) | F | 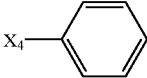 | H | 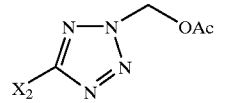 | A |
| 110 (Example 108) | F | 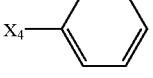 | H | 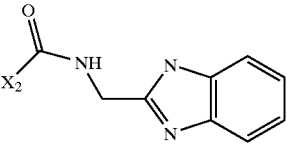 | A |
| 111 (Example 53) | F | 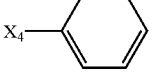 | H | 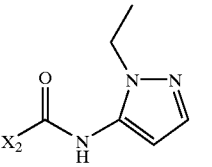 | A |
| 112 (Example 55) | F | 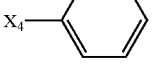 | H | 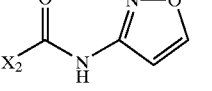 | A |
| 113 (Example 56) | F | 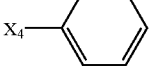 | H | 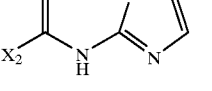 | A |
| 114 (Example 57) | F | 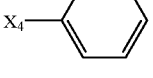 | H | 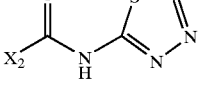 | A |
| 115 (Example 58) | F | 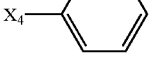 | H | 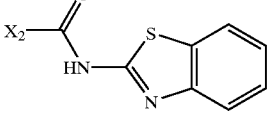 | A |
| 116 (Example 59) | F | 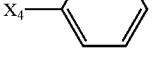 | H | | A |

TABLE 2-continued

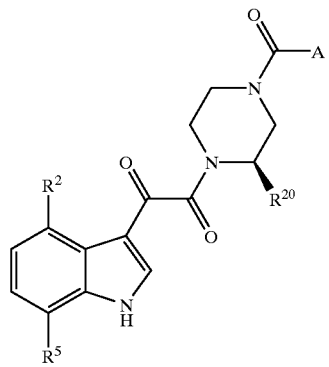

| Table Entry (Example number) | R² | R⁵ | R²⁰ | A | EC₅₀ Group from Table 1 |
|---|---|---|---|---|---|
| 117 (Example 72) | F | X₂—C(=O)—NH—CH(OMe)₂ attached via CH₂ | H | X₄—phenyl | A |
| 118 (Example 81) | F | 1,2,4-oxadiazole with X₂ and CCl₃ | H | X₄—phenyl | A |
| 119 (Example 111) | F | 1,2,4-triazole with X₂ and NH | H | X₄—phenyl | A |
| 120 (Example 176) | F | 1,2,4-oxadiazol-5(4H)-one with X₂ | CH₃ | X₄—phenyl | A |
| 121 (Example 177) | F | morpholino-ethyl-NH-C(=O)-X₂ | CH₃ | X₄—phenyl | A |
| 122 (Example 178) | F | 1,2,4-oxadiazole with X₂ and CH₃ | CH₃ | X₄—phenyl | A |
| 123 (Example 114) | F | tetrazole with X₂ and CH₂CH₂N(Et)₂ | H | X₄—phenyl | A |
| 124 (Example 113) | F | tetrazole with X₂ and CH₂CH₂-phthalimide | H | X₄—phenyl | A |

TABLE 2-continued

| Table Entry (Example number) | R² | R⁵ | R²⁰ | A | EC₅₀ Group from Table 1 |
|---|---|---|---|---|---|
| 125 (Example 179) | F | X₂-(5-cyclopropyl-1,2,4-oxadiazol-3-yl) | CH₃ | X₄-phenyl | A |
| 126 (Example 149) | F | X₂-(2-(difluoromethyl)tetrazol-5-yl) | H | X₄-phenyl | A |
| 127 (Example 180) | F | X₂-(5-(trifluoromethyl)-1,2,4-oxadiazol-3-yl) | CH₃ | X₄-phenyl | A |
| 128 (Example 153) | F | BocNH-CH₂CH₂-NH-C(O)-X₂ | H | X₄-phenyl | A |
| 129 (Example 154) | F | H₂N-CH₂CH₂-NH-C(O)-X₂ | H | X₄-phenyl | A |
| 130 (Example 181) | F | X₂-(1,2,4-oxadiazol-3-yl) | CH₃ | X₄-phenyl | A |
| 131 (Example 152) | F | MeO-CH₂CH₂-NH-C(O)-X₂ | H | X₄-phenyl | A |
| 132 (Example 112) | F | X₂-(2-(2-hydroxyethyl)tetrazol-5-yl) | H | X₄-phenyl | A |
| 133 (Example 163) | F | X₂-(4,5-dihydro-1H-imidazol-2-yl) | H | X₄-phenyl | A |

TABLE 2-continued

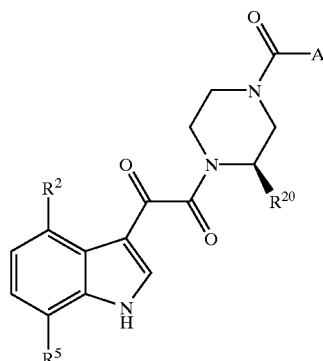

| Table Entry (Example number) | R² | R⁵ | R²⁰ | A | EC₅₀ Group from Table 1 |
|---|---|---|---|---|---|
| 134 (Example 164) | F | X₂-[imidazo-pyridine] | H | X₄-phenyl | A |
| 135 (Example 156) | F | X₂-[oxadiazole-N(CH₃)₂] | H | X₄-phenyl | A |
| 136 (Example 157) | F | X₂-[oxadiazole-NHCH₃] | H | X₄-phenyl | A |
| 137 (Example 158) | F | X₂-[oxadiazole-NH-iPr] | H | X₄-phenyl | A |
| 138 (Example 166) | F | X₂-C(=NH)NH-[2-aminopyridin-3-yl] | H | X₄-phenyl | A |
| 139 (Example 165) | F | X₂-[imidazo[4,5-b]pyridine] | H | X₄-phenyl | A |
| 140 (Example 115) | F | X₂-[tetrazole-CH₂CH₂CN] | H | X₄-phenyl | A |
| 141 (Example 155) | F | X₂-[oxadiazole-NH₂] | CH₃ | X₄-phenyl | A |
| 142 (Example 160) | F | X₂-[oxadiazole-NH-sBu] | CH₃ | X₄-phenyl | A |

TABLE 2-continued

| Table Entry (Example number) | R² | R⁵ | R²⁰ | A | EC₅₀ Group from Table 1 |
|---|---|---|---|---|---|
| 143 (Example 159) | F | X₂-[1,2,4-oxadiazole]-NH-CH₂CH₂-morpholine | CH₃ | X₄-phenyl | A |
| 144 (Example 161) | F | X₂-[1,2,4-oxadiazole]-NH-cyclobutyl | CH₃ | X₄-phenyl | A |
| 145 (Example 162) | F | X₂-[1,2,4-oxadiazole]-NH-cyclopentyl | CH₃ | X₄-phenyl | A |
| 146 (Example 182) | F | X₂-[1,2,4-oxadiazole]-C(O)OCH₃ | CH₃ | X₄-phenyl | A |
| 147 (Example 183) | F | X₂-C(NH₂)=N-OH | H | X₄-pyridyl | A |
| 148 (Example 184) | F | X₂-C(O)NH₂ | H | X₄-pyridyl | A |
| 149 (Example 185B) | F | X₂-C(NH₂)=N-OH | CH₃ | X₄-pyridyl | A |
| 150 (Example 186B) | F | X₂-C(O)NH₂ | CH₃ | X₄-pyridyl | A |
| 151 (Example 187) | F | X₂-[1,2,4-oxadiazole]-CCl₃ | CH₃ | X₄-pyridyl | A |

TABLE 2-continued
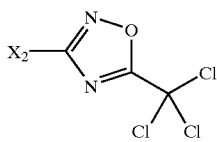
| Table Entry (Example number) | R² | R⁵ | R²⁰ | A | EC₅₀ Group from Table 1 |
|---|---|---|---|---|---|
| 152 (Example 188) | F | 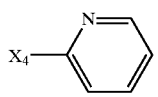 | H | 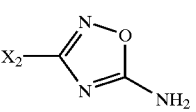 | A |
| 153 (Example 189) | F | 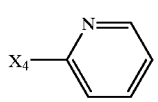 | H | 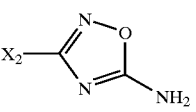 | A |
| 154 (Example 190) | F | 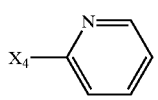 | CH₃ | 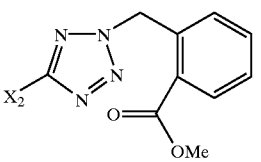 | A |
| 155 (Example 105B) | F | 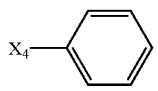 | H | 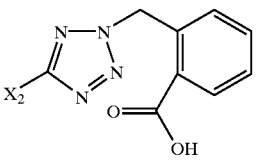 | A |
| 156 (Example 106B) | F | 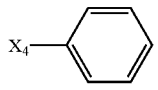 | H | 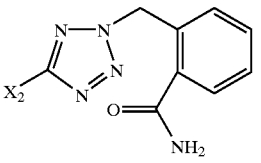 | A |
| 157 (Example 107B) | F | 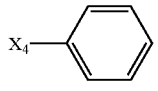 | H | 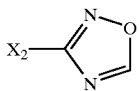 | A |
| 158 (Example 191) | F | 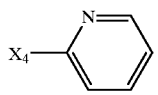 | H | 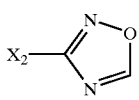 | A |
| 159 (Example 192) | F | 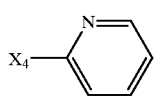 | CH₃ | | A |

TABLE 2-continued

| Table Entry (Example number) | R² | R⁵ | R²⁰ | A | EC₅₀ Group from Table 1 |
|---|---|---|---|---|---|
| 160 (Example 193) | F | X₂-(1,3,4-oxadiazol-2-yl)-CCl₃ | H | X₄-phenyl | A |
| 161 (Example 125) | OCH₃ (X₁) | H₃C-N(X₂)-C(=O)- | H | X₄-phenyl | A |
| 162 (Example 140) | F | X₂-(1,2,4-oxadiazol-3-yl)-NH-CH₂-C(=O)OMe | H | X₄-phenyl | A |
| 163 (Example 124) | OCH₃ (X₁) | X₂-CH=N-OH | H | X₄-phenyl | A |
| 164 (Example 106C) | F | X₂-tetrazol-5-yl-N2-CH₂-(4-carboxyphenyl) | H | X₄-phenyl | A |
| 165 (Example 105C) | F | X₂-tetrazol-5-yl-N2-CH₂-(4-methoxycarbonylphenyl) | H | X₄-phenyl | A |
| 166 (Example 107C) | F | X₂-tetrazol-5-yl-N2-CH₂-(4-carbamoylphenyl) | H | X₄-phenyl | A |
| 167 (Example 141) | F | X₂-(1,2,4-oxadiazol-3-yl)-NH-CH₂-C(=O)OH | H | X₄-phenyl | A |

TABLE 2-continued

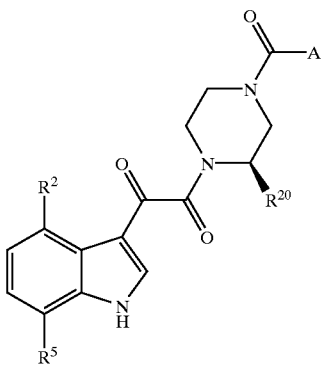

| Table Entry (Example number) | $R^2$ | $R^5$ | $R^{20}$ | A | $EC_{50}$ Group from Table 1 |
|---|---|---|---|---|---|
| 168 (Example 142) | F | $X_2$-[1,2,4-oxadiazole]-NH-CH$_2$-C(O)NH$_2$ | H | $X_4$-phenyl | A |
| 169 (Example 143) | F | $X_2$-[1,2,4-oxadiazole]-NH-CH$_2$-C(O)NHCH$_3$ | H | $X_4$-phenyl | A |
| 170 (Example 121) | F | $H_2N$-C(=N-OH)-$X_2$ | H | $X_4$-O-C(CH$_3$)$_3$ | A |
| 171 (Example 136) | F | $X_2$-[1,2,4-oxadiazole]-CH$_2$NH$_2$ | H | $X_4$-phenyl | A |
| 172 (Example 137) | F | $X_2$-[1,2,4-oxadiazole]-CH$_2$NHCH$_3$ | H | $X_4$-phenyl | A |
| 173 (Example 122) | F | $X_2$-[1,2,4-oxadiazole] | H | $X_4$-O-C(CH$_3$)$_3$ | A |
| 174 (Example 148) | $X_1$-O-CH$_3$ | $X_2$-C(O)NH$_2$ | H | $X_4$-phenyl | A |
| 175 (Example 138) | F | $X_2$-[1,2,4-oxadiazole]-CH$_2$-N(CH$_3$)$_2$ | H | $X_4$-phenyl | A |
| 176 (Example 110A) | F | $X_2$-C(NH$_2$)=N-NH-C(O)-O-C(CH$_3$)$_3$ | H | $X_4$-phenyl | A |

TABLE 2-continued

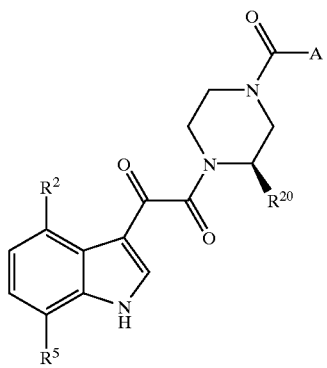

| Table Entry (Example number) | R² | R⁵ | R²⁰ | A | EC₅₀ Group from Table 1 |
|---|---|---|---|---|---|
| 177 (Example 139) | F | X₂–(1,2,4-oxadiazole)–CH₂OH | H | X₄–phenyl | A |
| 178 (Example 132) | F | X₂–(tetrazine)–N–C(O)O–tBu | H | X₄–phenyl | A |
| 179 (Example 194) | F | X₂–(1,2,4-triazole)–CH₂Cl | H | X₄–phenyl | A |
| 180 (Example 146) | F | X₂–(imidazole)–C(O)OMe | H | X₄–phenyl | A |
| 181 (Example 126) | X₁–O–CH₃ | X₂–(1,2,4-oxadiazole) | H | X₄–phenyl | A |
| 182 (Example 134) | F | X₂–C(O)–NH–NH–C(O)–NH–iPr | H | X₄–phenyl | A |
| 183 (Example 135) | F | X₂–C(O)–NH–NH–C(O)–NH–propyl | H | X₄–phenyl | A |
| 184 (Example 133) | F | X₂–C(O)–NH–NH–C(O)–NH–tBu | H | X₄–phenyl | A |

TABLE 2-continued

| Table Entry (Example number) | R² | R⁵ | R²⁰ | A | EC₅₀ Group from Table 1 |
|---|---|---|---|---|---|
| 185 (Example 129) | F | 1H-triazole with CH₂CN substituent, attached via X₂ | H | X₄-phenyl | A |
| 186 (Example 127) | F | 1H-triazole with 4-pyridyl substituent, attached via X₂ | H | X₄-phenyl | A |
| 187 (Example 130) | F | 1H-triazole with C(O)NH₂ substituent, attached via X₂ | H | X₄-phenyl | A |
| 188 (Example 147) | F | 1H-imidazole with C(O)NHCH₃ substituent, attached via X₂ | H | X₄-phenyl | A |
| 189 (Example 128) | F | 1H-triazole with 3-pyridyl substituent, attached via X₂ | H | X₄-phenyl | A |
| 190 (Example 119) | OCH₃ attached via X₁ | C(O)CH₃ attached via X₂ | H | X₄-phenyl | A |
| 191 (Example 120) | F | 1H-pyrazole-C(O)O-CH₂-C(O)-N(Et)₂, attached via X₂ | H | X₄-phenyl | A |
| 192 (Example 116) | F | pyrazol-1-yl attached via X₂ | H | X₄-phenyl | A |
| 193 (Example 117) | F | imidazol-1-yl attached via X₂ | H | X₄-phenyl | A |

TABLE 2-continued

| Table Entry (Example number) | R² | R⁵ | R²⁰ | A | EC₅₀ Group from Table 1 |
|---|---|---|---|---|---|
| 194 (Example 131) | F | (HN-triazole-pyrazine with X₂) | H | X₄-phenyl | A |
| 195 (Example 118) | F | (1,2,4-triazole with X₂) | H | X₄-phenyl | A |
| 196 (Example 144) | F | (triazole-CH₂C(O)OMe with X₂) | H | X₄-phenyl | A |
| 197 (Example 150A) | F | (1,2,4-oxadiazole with X₂) | H | X₄-phenyl-NO₂ (meta) | A |
| 198 (Example 195) | F | (oxadiazole-CH₂-SO₂-CH₂-furan with X₂) | H | X₄-phenyl | A |
| 199 (Example 196) | F | (oxadiazole-CH₂-S-thiophene with X₂) | H | X₄-phenyl | A |
| 200 (Example 197) | F | (oxadiazole-phenyl with X₂) | H | X₄-phenyl | A |
| 201 (Example 198) | F | (oxadiazole-CH₂-S-pyridine with X₂) | H | X₄-phenyl | A |

TABLE 2-continued

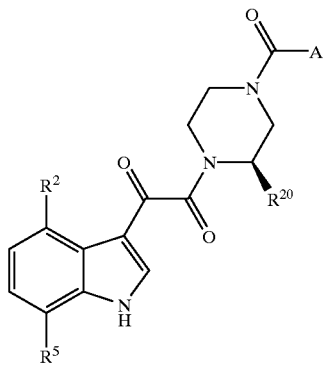

| Table Entry (Example number) | $R^2$ | $R^5$ | $R^{20}$ | A | $EC_{50}$ Group from Table 1 |
|---|---|---|---|---|---|
| 202 (Example 199) | F | $X_2$—[1,2,4-oxadiazole-3-yl(4-fluorophenyl)] | H | $X_4$—phenyl | A |
| 203 (Example 200) | F | $X_2$—[1,2,4-oxadiazole-3-yl-CH2-C(O)-pyrrolidine] | H | $X_4$—phenyl | A |
| 204 (Example 201) | F | $X_2$—[1,2,4-oxadiazole-3-yl-CH2-phenyl] | H | $X_4$—phenyl | A |
| 205 (Example 202) | F | $X_2$—[1,2,4-oxadiazole-3-yl(5-methylisoxazole-3-yl)] | H | $X_4$—phenyl | A |
| 206 (Example 203) | F | $X_2$—[1,2,4-oxadiazole-3-yl-CH2CH2-(3,5-dimethylpyrazol-1-yl)] | H | $X_4$—phenyl | A |
| 207 (Example 204) | F | $X_2$—C(O)NH-morpholine | H | $X_4$—phenyl | A |
| 208 (Example 205) | F | $X_2$—C(O)NH-(2,6-dimethylpyrimidin-4-yl) | H | $X_4$—phenyl | A |

TABLE 2-continued

| Table Entry (Example number) | R² | R⁵ | R²⁰ | A | EC₅₀ Group from Table 1 |
|---|---|---|---|---|---|
| 209 (Example 206) | F | 1,2,4-oxadiazol-5-yl (X₂ attached) | H | 3-chlorophenyl (X₄) | A |
| 210 (Example 207) | F | 1,2,4-oxadiazol-5-yl (X₂ attached) | H | 3,4-dimethoxyphenyl (X₄) | A |
| 211 (Example 208) | F | X₂-C(O)NH-(6-methoxybenzothiazol-2-yl) | H | phenyl (X₄) | A |
| 212 (Example 209) | F | X₂-C(O)NH-(5-methylthiazol-2-yl) | H | phenyl (X₄) | A |
| 213 (Example 210) | F | X₂-C(O)NH-(5-tert-butylthiazol-2-yl) | H | phenyl (X₄) | A |
| 214 (Example 211) | F | X₂-C(O)NH-(isoquinolin-1-yl) | H | phenyl (X₄) | A |
| 215 (Example 212) | F | X₂-C(O)NH-(1-ethoxycarbonylpiperidin-4-yl) | H | phenyl (X₄) | A |
| 216 (Example 213) | F | X₂-C(O)NH-(2-methylcyclohexyl) | H | phenyl (X₄) | A |

TABLE 2-continued

| Table Entry (Example number) | R² | R⁵ | R²⁰ | A | EC₅₀ Group from Table 1 |
|---|---|---|---|---|---|
| 217 (Example 214) | F | 1,3,5-trimethylpyrazol-4-yl-NHC(O)-X₂ | H | X₄-phenyl | |
| 219 (Example 145) | F | 3-(1-methylcarbamoylmethyl)-1,2,4-triazol-5-yl-X₂ | H | X₄-phenyl | A |
| 220 (Example 151) | F | 1,2,4-oxadiazol-3-yl-X₂ | H | X₄-(3-aminophenyl) | A |
| 221 (Example 216) | OMe | 5-methyl-1,2,4-triazol-3-yl-X₂ | H | X₄-phenyl | A |
| 222 (Example 217) | F | X₂-CH=CH-C(O)OCH₃ | H | X₄-phenyl | A |
| 223 (Example 150B) | F | 1,2,4-oxadiazol-3-yl-X₂ | H | X₄-(2,6-difluorophenyl) | A |
| 224 (Example 150C) | F | 1,2,4-oxadiazol-3-yl-X₂ | H | X₄-(2-fluorophenyl) | A |
| 225 (Example 219) | F | X₂-C(O)NH-CH₂-(4-methoxyphenyl) | H | X₄-phenyl | |

TABLE 2-continued
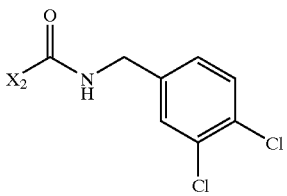
| Table Entry (Example number) | R² | R⁵ | R²⁰ | A | EC₅₀ Group from Table 1 |
|---|---|---|---|---|---|
| 226 (Example 220) | F | 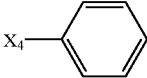 | H | 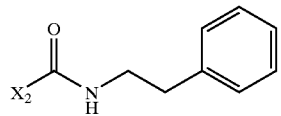 | A |
| 227 (Example 221) | F | 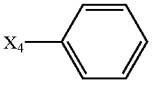 | H | 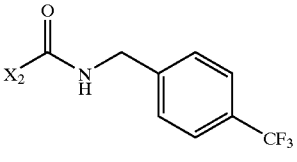 | A |
| 228 (Example 222) | F | 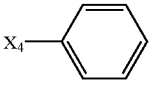 | H | 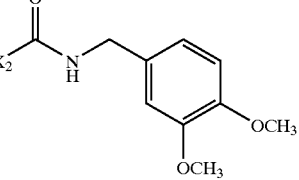 | A |
| 228 (Example 223) | F | 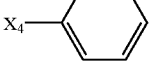 | H | 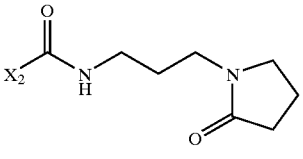 | A |
| 230 (Example 224) | F | 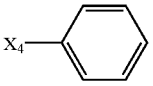 | H | 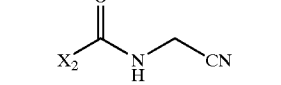 | A |
| 231 (Example 225) | F | 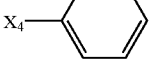 | H | 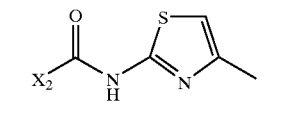 | A |
| 232 (Example 226) | F | 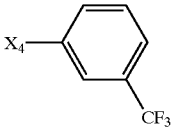 | H |  | A |

TABLE 2-continued

| Table Entry (Example number) | R² | R⁵ | R²⁰ | A | EC₅₀ Group from Table 1 |
|---|---|---|---|---|---|
| 233 (Example 227) | F | X₂-C(O)-NH-CH₂CH₂-(2-thienyl) | H | X₄-phenyl | A |
| 234 (Example 228) | F | X₂-C(O)-NH-CH₂CH₂-O-phenyl | H | X₄-phenyl | A |
| 235 (Example 229) | F | X₂-C(O)-NH-CH₂-CH(phenyl)₂ | H | X₄-phenyl | A |
| 236 (Example 230) | F | X₂-C(O)-NH-CH₂-(2-pyridyl) | H | X₄-phenyl | A |
| 237 (Example 231) | F | X₂-C(O)-NH-(4-methylthiazol-2-yl) | H | X₄-N-morpholino | A |
| 238 (Example 232) | F | X₂-C(O)-NH-CH₂-(3-pyridyl) | H | X₄-phenyl | A |
| 239 (Example 233) | F | X₂-C(O)-NH-(4-methylthiazol-2-yl) | H | X₄-(2-methoxyphenyl) | A |

TABLE 2-continued

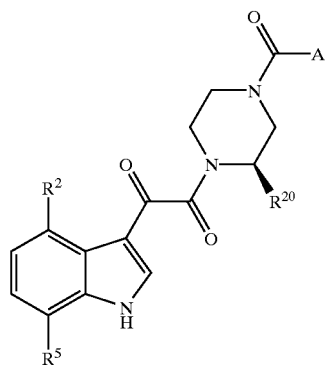

| Table Entry (Example number) | R² | R⁵ | R²⁰ | A | EC₅₀ Group from Table 1 |
|---|---|---|---|---|---|
| 240 (Example 234) | F | X₂-C(O)NH-thiazole-CH₂C(O)OEt | H | X₄-phenyl | A |
| 241 (Example 235) | F | X₂-C(O)NH-(4-methylthiazole) | H | X₄-(2-fluorophenyl) | A |
| 242 (Example 236) | F | X₂-C(O)NH-N-morpholine | H | X₄-(2-methylphenyl) | C |
| 243 (Example 237) | F | X₂-C(O)NH-N-morpholine | H | X₄-(3-cyanophenyl) | C |
| 244 (Example 238) | F | X₂-C(O)NH₂ | H | X₄-(2-fluorophenyl) | B |
| 245 (Example 239) | F | X₂-C(O)NH₂ | H | X₄-(N-methylpyrrol-2-yl) | B |
| 246 (Example 240) | F | X₂-C(O)NH₂ | H | X₄-(thien-3-yl) | A |
| 247 (Example 241) | F | X₄-(thien-3-yl) | H | X₄-N-morpholine | A |
| 248 (Example 242) | F | X₄-(thien-3-yl) | H | X₄-(2-trifluoromethylphenyl) | B |

TABLE 2-continued

[Structure: indole with R² at 4-position, R⁵ at 7-position, and at 3-position a -C(O)-C(O)- linker to a piperazine bearing R²⁰, with the distal piperazine nitrogen acylated by -C(O)-A]

| Table Entry (Example number) | R² | R⁵ | R²⁰ | A | EC₅₀ Group from Table 1 |
|---|---|---|---|---|---|
| 249 (Example 243) | F | X₄-(thiophen-3-yl) | H | X₄-(3-chlorophenyl) | A |
| 250 (Example 244) | F | X₄-(thiophen-3-yl) | H | X₄-cyclobutyl | A |
| 251 (Example 245) | F | X₄-(thiophen-3-yl) | H | X₄-(2-methylthio-pyridin-3-yl) | A |
| 252 (Example 246) | F | X₂-(1,2,4-oxadiazol-3-yl) | H | X₄-morpholin-4-yl | A |
| 253 (Example 247) | F | X₂-(1,2,4-oxadiazol-3-yl) | H | X₄-O-phenyl | B |
| 254 (Example 248) | F | X₂-(1,2,4-oxadiazol-3-yl) | H | X₄-O-phenyl | B |
| 255 (Example 249) | F | X₂-(1,2,4-oxadiazol-3-yl) | H | X₄-(5-trifluoromethyl-1-phenyl-pyrazol-4-yl) | C |
| 256 (Example 250) | F | X₂-(1,2,4-oxadiazol-3-yl) | H | X₄-(2,4-dimethylthiazol-5-yl) | C |

TABLE 2-continued

[Structure: indole with R² at 4-position, R⁵ at 7-position, and at 3-position a -C(O)-C(O)- linker to a piperazine bearing R²⁰, with the distal piperazine N acylated by -C(O)-A]

| Table Entry (Example number) | R² | R⁵ | R²⁰ | A | EC₅₀ Group from Table 1 |
|---|---|---|---|---|---|
| 257 (Example 251) | F | X₂-(1,2,4-oxadiazol-3-yl) | H | X₄-(1-(4-chlorobenzyl)-5-oxopyrrolidin-3-yl) | C |
| 258 (Example 252) | F | X₂-(1,2,4-oxadiazol-3-yl) | H | X₄-(2-methyl-5-phenylfuran-3-yl) | C |
| 259 (Example 253) | F | X₂-C(O)NH-CH₂-(5-methylfuran-2-yl) | H | X₄-phenyl | A |
| 260 (Example 254) | F | X₂-C(O)NH-(4-phenylthiazol-2-yl) | H | X₄-phenyl | A |
| 261 (Example 255) | F | X₂-C(O)NH-(5-acetyl-4-methylthiazol-2-yl) | H | X₄-phenyl | A |
| 262 (Example 256) | F | X₄-(thiophen-3-yl) | H | X₄-(3-methoxy-4-(methylthio)phenyl) | A |
| 263 (Example 257) | F | X₄-(thiophen-3-yl) | H | X₄-(2,6-dimethylphenyl) | A |

TABLE 2-continued
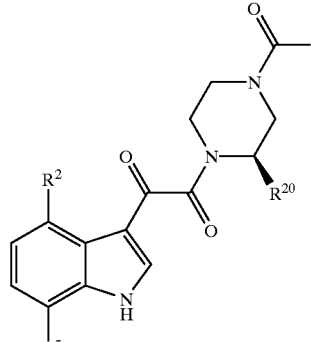
| Table Entry (Example number) | R² | R⁵ | R²⁰ | A | EC₅₀ Group from Table 1 |
|---|---|---|---|---|---|
| 264 (Example 258) | F | 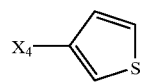 | H | 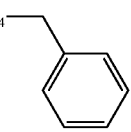 | A |
| 265 (Example 259) | F | 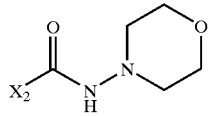 | H | 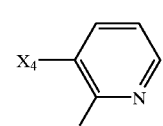 | C |
| 266 (Example 260) | F | 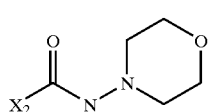 | H | 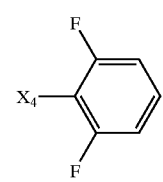 | A |
| 267 (Example 261) | F | 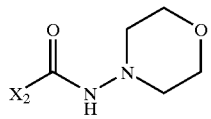 | H | 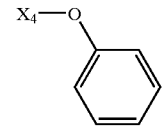 | A |
| 268 (Example 262) | F | 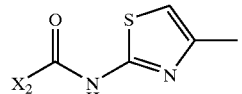 | H | 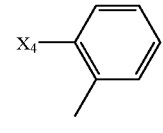 | A |
| 269 (Example 263) | F | 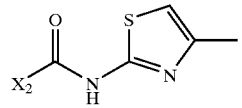 | H | 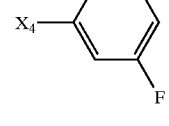 | A |
| 270 (Example 264) | F | 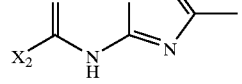 | H | 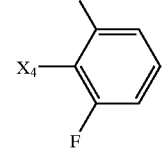 | A |

TABLE 2-continued

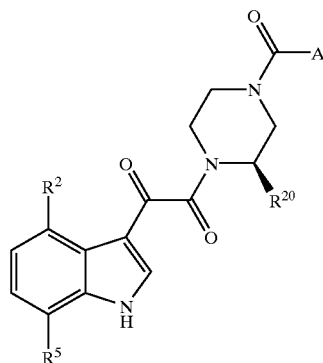

| Table Entry (Example number) | R² | R⁵ | R²⁰ | A | EC₅₀ Group from Table 1 |
|---|---|---|---|---|---|
| 271 (Example 265) | F | X₂-C(O)-NH-N(morpholine) | H | X₄-(3-chlorophenyl) | A |
| 272 (Example 266) | F | X₂-C(O)-NH-(5-methylthiazol-2-yl) | H | X₄-(2-trifluoromethylphenyl) | B |
| 273 (Example 267) | F | X₂-C(O)-NH-(5-methylthiazol-2-yl) | H | X₄-(3,4-dimethoxyphenyl) | A |
| 274 (Example 268) | F | X₂-C(O)-NH-(5-methylthiazol-2-yl) | H | X₄-(2-methoxyphenyl) | A |
| 275 (Example 269) | F | X₂-C(O)-NH-(5-methylthiazol-2-yl) | H | X₄-(2-fluorophenyl) | A |
| 276 (Example 270) | F | X₂-C(O)-NH-(4-methylthiazol-2-yl) | H | X₄-(2-methylthiopyridin-3-yl) | A |
| 277 (Example 271) | F | X₂-C(O)-NH-(1,3,5-trimethylpyrazol-4-yl) | H | X₄-(2-trifluoromethylphenyl) | C |

TABLE 2-continued

| Table Entry (Example number) | R² | R⁵ | R²⁰ | A | EC₅₀ Group from Table 1 |
|---|---|---|---|---|---|
| 278 (Example 272) | F | X₂-C(O)NH-(1,3,5-trimethylpyrazol-4-yl) | H | X₄-(2-fluorophenyl) | B |
| 279 (Example 273) | F | X₂-C(O)NH-(1,3,5-trimethylpyrazol-4-yl) | H | X₄-(2-methylphenyl) | A |
| 280 (Example 274) | F | X₂-C(O)NH-(1,3,5-trimethylpyrazol-4-yl) | H | X₄-(2-methylthiopyridin-3-yl) | A |
| 281 (Example 275) | F | X₂-C(O)NH-(morpholin-4-yl) | H | X₄-(2,6-dimethoxypyridin-3-yl) | C |
| 282 (Example 276) | F | X₂-C(O)NH-(4-methylthiazol-2-yl) | H | X₄-O-phenyl | A |
| 283 (Example 277) | F | X₂-C(O)NH-(4-methylthiazol-2-yl) | H | X₄-(1-methylpyrrol-2-yl) | A |
| 284 (Example 278) | F | X₂-C(O)NH-(4-methylthiazol-2-yl) | H | X₄-(2,6-dimethoxypyridin-3-yl) | A |
| 285 (Example 279) | F | X₂-C(O)NH-(4-methylthiazol-2-yl) | H | X₄-(3-trifluoromethylphenyl) | A |

TABLE 2-continued
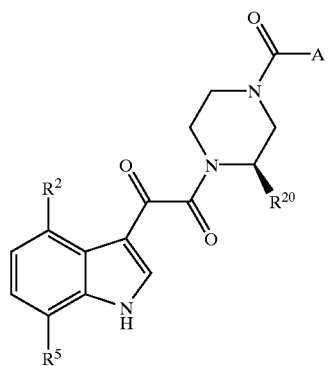
| Table Entry (Example number) | R² | R⁵ | R²⁰ | A | EC₅₀ Group from Table 1 |
|---|---|---|---|---|---|
| 286 (Example 280) | F | 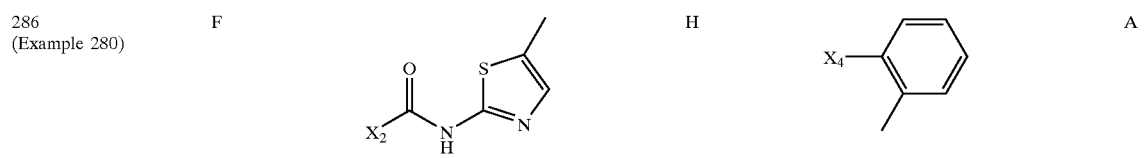 | H | | A |
| 287 (Example 281) | F | 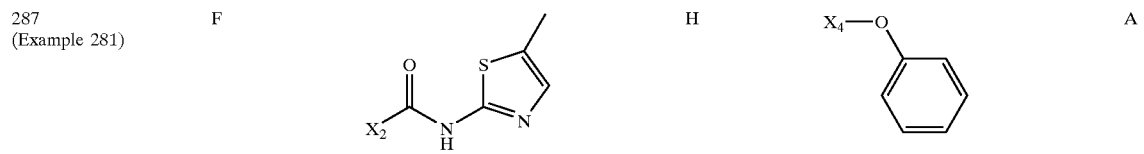 | H | | A |
| 288 (Example 282) | F | 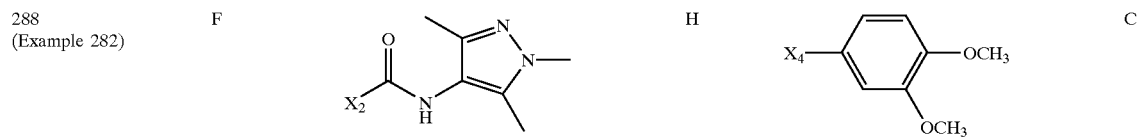 | H | | C |
| 289 (Example 283) | F | 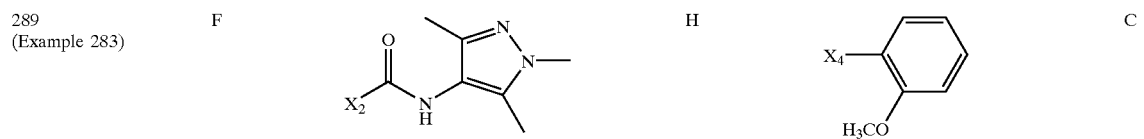 | H | | C |

TABLE 2-continued

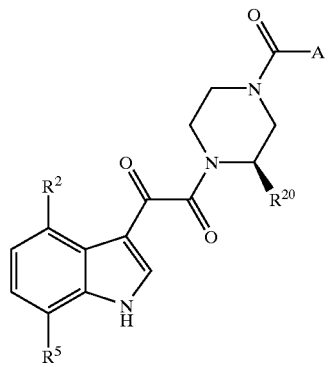

| Table Entry (Example number) | R² | R⁵ | R²⁰ | A | EC₅₀ Group from Table 1 |
|---|---|---|---|---|---|
| 290 (Example 284) | F | (pyrazole-carboxamide group, X₂ attachment) | H | X₄—O—(phenyl) | A |
| 291 (Example 123) | | (full structure drawn) | | | A |
| 292 (Example 215) | | (full structure drawn) | | | A |

**Note for table entries 291 and 292, the entire structure was drawn rather than using columns for R², R⁵, R²⁰, and A The compounds of Table 3 below were all found to be very potent in the assay described above using % inhibition as a criteria. In Table 3, $X_2$, $X_4$ etc. indicates the point of attachment. The vast majority of the compounds exhibited greater than 98% inhibition at a concentration of 10 uM. The data at 10 $\mu$M was calculated in the following manner:

Method for Extrapolating % Inhibition at 10 $\mu$M

The data in Table 3 was obtained using the general procedures above and by the following methods. Data is not reported for all compounds since data for all the compounds is reported by the alternate method in Table 2. The percent inhibition for each compound was calculated by quantifying the level of luciferase expression in cells infected in the presence of compound as a percentage of that observed for cells infected in the absence of compound and subtracting such a determined value from 100. For compounds tested at concentrations less than 10 $\mu$M, the percent inhibition at 10 $\mu$M was determined by extrapolation using the XLfit curve fitting feature of the Microsoft Excel spreadsheet software. Curves were obtained from 10 data points (% inhibition determined at 10 concentrations of compound) by using a four parameter logistic model (XLfit model 205: $y=A+((B-A)/(1+((C/x)^D)))$, where, A=minimum y, B=maximum y, C=logEC$_{50}$, D=slope factor, and x and y are known data values. Extrapolations were performed with the A and B parameters unlocked.

Thus the compounds of this invention are all potent antiviral inhibitors based on this assay.

TABLE 3
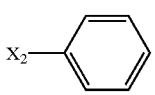
| Table Entry (Example number) | R1 | R2 | R3 | R4 | % Inhibition @ 10 uM |
|---|---|---|---|---|---|
| 1 (Example 1) | F | 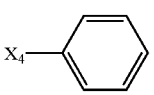 | H | 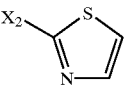 | >98 |
| 2 (Example 14) | F | 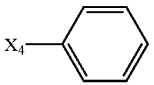 | H | 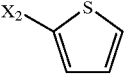 | >98 |
| 3 (Example 12) | F | 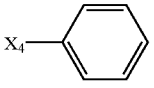 | H | 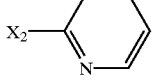 | >98 |
| 4 (Example 5) | F | 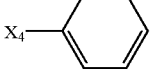 | H | 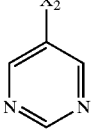 | >98 |
| 5 (Example 9) | F | 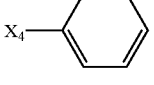 | H | 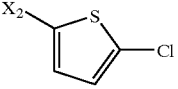 | >98 |
| 6 (Example 16) | F | 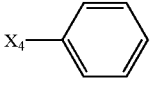 | H |  | >98 |
| 7 (Example 15) | 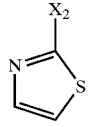 | 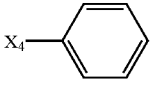 | H |  | >98 |
| 8 (Example 7) | 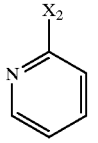 | 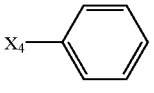 | H |  | >98 |
| 9 (Example 10) | 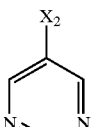 | 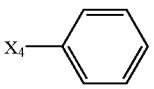 | H | | >98 |

TABLE 3-continued
| Table Entry (Example number) | R1 | R2 | R3 | R4 | % Inhibition @ 10 uM |
|---|---|---|---|---|---|
| 10 (Example 8) | 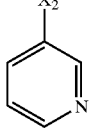 | 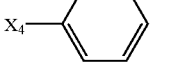 | H | 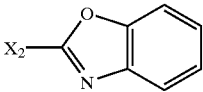 | >98 |
| 11 (Example 18) | F | 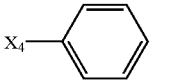 | H | 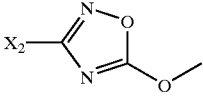 | >98 |
| 12 (Example 29) | F | 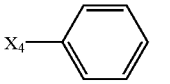 | H | 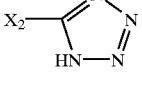 | >98 |
| 13 (Example 34) | F | 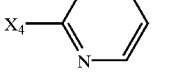 | $CH_3$ | 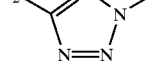 | >98 |
| 14 (Example 21) | F | 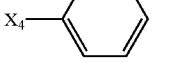 | H |  | >98 |
| 15 (Example 19) | 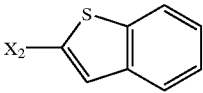 | 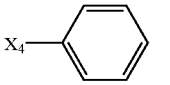 | H | 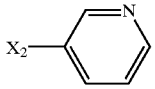 | >98 |
| 16 (Example 6) | F | 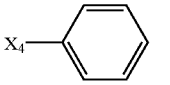 | H |  | >98 |
| 17 (Example 11) | 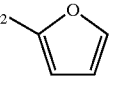 | 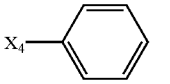 | H | 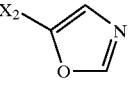 | >98 |
| 18 (Example 17) | F | 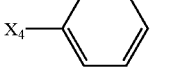 | H | 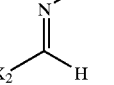 | >98 |
| 19 (Example 30) | F | 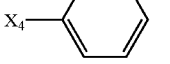 | H |  | >98 |

TABLE 3-continued

| Table Entry (Example number) | R1 | R2 | R3 | R4 | % Inhibition @ 10 uM |
|---|---|---|---|---|---|
| 20 (Example 31) | F | X₂–CH=N–O–CH₂–C(O)OH | H | X₄–phenyl | >98 |
| 21 (Example 4) | F | X₂–(4-methoxyphenyl) | H | X₄–phenyl | >98 |
| 22 (Example 13) | F | X₂–(3-thienyl) | H | X₄–phenyl | >98 |
| 23 (Example 26) | F | X₂–(2-allyl-tetrazol-5-yl) | H | X₄–phenyl | >98 |
| 24 (Example 3) | O(CH₃)–X₁ | X₂–(4-fluorophenyl) | H | X₄–phenyl | >98 |
| 25 (Example 2) | F | X₂–(2-(methylthio)phenyl) | H | X₄–phenyl | >98 |
| 26 (Example 167) | F | X₂–(1H-tetrazol-5-yl) | H | X₄–(2-furyl) | >98 |
| 27 (Example 170) | F | X₂–(1H-tetrazol-5-yl) | H | X₄–(2-thienyl) | >98 |
| 28 (Example 24) | F | X₂–(2-propyl-tetrazol-5-yl) | H | X₄–phenyl | >98 |
| 29 (Example 23) | F | X₂–(2-ethyl-tetrazol-5-yl) | H | X₄–phenyl | >98 |

TABLE 3-continued

| Table Entry (Example number) | R1 | R2 | R3 | R4 | % Inhibition @ 10 uM |
|---|---|---|---|---|---|
| 30 (Example 25) | F | $X_2$-tetrazole-N-benzyl | H | $X_4$-phenyl | >98 |
| 31 (Example 22) | F | $X_2$-tetrazole-N-CH$_2$CO$_2$CH$_3$ | H | $X_4$-phenyl | >98 |
| 32 (Example 173) | F | $X_2$-tetrazole-N-CH$_3$ | H | $X_4$-(5-bromofuran-2-yl) | >98 |
| 33 (Example 172) | F | $X_2$-tetrazole-N-CH$_3$ | H | $X_4$-(5-chlorofuran-2-yl) | >98 |
| 34 (Example 171) | F | $X_2$-tetrazole-N-CH$_3$ | H | $X_4$-(furan-2-yl) | >98 |
| 35 (Example 174) | F | $X_2$-tetrazole-N-CH$_3$ | H | $X_4$-(thien-2-yl) | >98 |
| 36 (Example 40) | F | phenylsulfonyl-NH-C(O)-$X_2$ | H | $X_4$-phenyl | >98 |
| 37 (Example 32) | F | $X_2$-tetrazole-NH | H | $X_4$-(pyridin-2-yl) | >98 |
| 38 (Example 185A) | F | $X_2$-C(=N-OH)-NH$_2$ | CH$_3$ | $X_4$-phenyl | >98 |
| 39 (Example 186A) | F | $X_2$-C(O)NH$_2$ | CH$_3$ | $X_4$-phenyl | >98 |

TABLE 3-continued

| Table Entry (Example number) | R1 | R2 | R3 | R4 | % Inhibition @ 10 uM |
|---|---|---|---|---|---|
| 40 (Example 49) | F | imidazol-4-yl-CH₂CH₂-NH-C(=O)-X₂ | H | X₄-phenyl | >98 |
| 41 (Example 48) | F | indol-3-yl-CH₂CH₂-NH-C(=O)-X₂ | H | X₄-phenyl | >98 |
| 42 (Example 50) | F | furan-2-yl-CH₂-NH-C(=O)-X₂ | H | X₄-phenyl | >98 |
| 43 (Example 51) | F | thien-2-yl-CH₂-NH-C(=O)-X₂ | H | X₄-phenyl | >98 |
| 44 (Example 52) | F | morpholin-4-yl-CH₂CH₂-NH-C(=O)-X₂ | H | X₄-phenyl | >98 |
| 45 (Example 168) | F | X₂-(1H-tetrazol-5-yl) | H | X₄-(5-chlorofuran-2-yl) | >98 |
| 46 (Example 175) | F | X₂-(2-methyl-2H-tetrazol-5-yl) | CH₃ | X₄-phenyl | >98 |
| 47 (Example 169) | F | X₂-(1H-tetrazol-5-yl) | H | X₄-(5-bromofuran-2-yl) | >98 |
| 48 (Example 35) | F | pyridin-3-yl-NH-C(=O)-X₂ | H | X₄-phenyl | >98 |

TABLE 3-continued

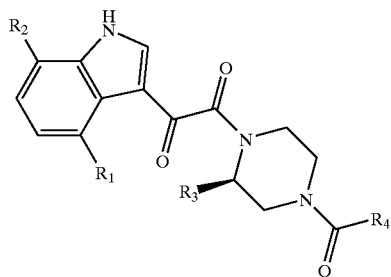

| Table Entry (Example number) | R1 | R2 | R3 | R4 | % Inhibition @ 10 uM |
|---|---|---|---|---|---|
| 49 (Example 36) | F | 4,5-dihydrothiazol-2-yl-NH-C(=O)-$X_2$ | H | phenyl-$X_4$ | >98 |
| 50 (Example 37) | F | 3-methylisoxazol-5-yl-NH-C(=O)-$X_2$ | H | phenyl-$X_4$ | >98 |
| 51 (Example 41) | F | benzimidazol-2-yl-NH-C(=O)-$X_2$ | H | phenyl-$X_4$ | >98 |
| 52 (Example 38) | F | pyridin-2-yl-NH-C(=O)-$X_2$ | H | phenyl-$X_4$ | >98 |
| 53 (Example 42) | F | $H_2N$-C(=O)-$X_2$ | H | phenyl-$X_4$ | >98 |
| 54 (Example 43) | F | $(H_3C)_2N$-C(=O)-$X_2$ | H | phenyl-$X_4$ | 89 |
| 55 (Example 44) | F | $(H_3C)_2N$-CH$_2$CH$_2$-N(CH$_3$)-C(=O)-$X_2$ | H | phenyl-$X_4$ | 97 |
| 56 (Example 39) | F | pyridin-4-yl-NH-C(=O)-$X_2$ | H | phenyl-$X_4$ | >98 |
| 57 (Example 45) | F | benzyl-NH-C(=O)-$X_2$ | H | phenyl-$X_4$ | >98 |
| 58 (Example 46) | F | $H_3C$-O-NH-C(=O)-$X_2$ | H | phenyl-$X_4$ | >98 |

TABLE 3-continued
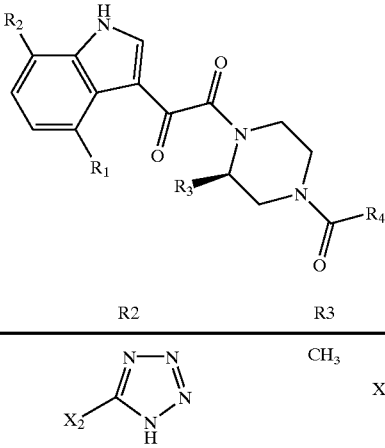
| Table Entry (Example number) | R1 | R2 | R3 | R4 | % Inhibition @ 10 uM |
|---|---|---|---|---|---|
| 59 (Example 33) | F | 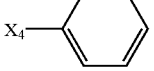 | $CH_3$ | 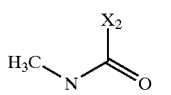 | >98 |
| 60 (Example 47) | F | 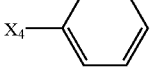 | H | 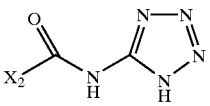 | >98 |
| 61 (Example 54) | F | 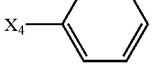 | H | 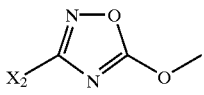 | >98 |
| 62 (Example 29) | F | 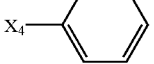 | H | 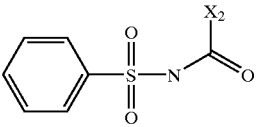 | >98 |
| 63 (Example 62) | H | 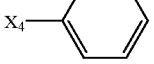 | H | 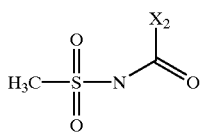 | 74 |
| 64 (Example 61) | H | 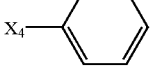 | H | 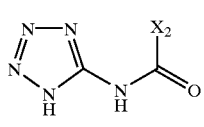 | 75 |
| 65 (Example 63) | H | 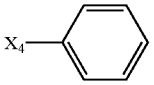 | H | 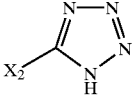 | 96 |
| 66 (Example 20) | F | 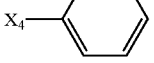 | H | 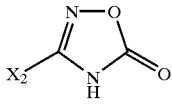 | >98 |
| 67 (Example 28) | F | 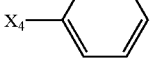 | H | 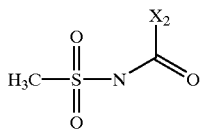 | >98 |
| 68 (Example 60) | F | 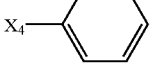 | H | | >98 |

TABLE 3-continued

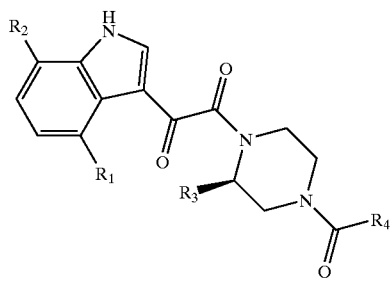

| Table Entry (Example number) | R1 | R2 | R3 | R4 | % Inhibition @ 10 uM |
|---|---|---|---|---|---|
| 69 (Example 27) | F | H₂N–C(=N–OH)–X₂ | H | X₄–phenyl | >98 |
| 70 (Example 69) | F | X₂–C(O)–piperazine–C(O)–phenyl | H | X₄–phenyl | >98 |
| 71 (Example 64) | H | CH₃–NH–C(O)–X₂ | CH₃ | X₄–phenyl | >98 |
| 72 (Example 65) | H | (CH₃)₂N–C(O)–X₂ | CH₃ | X₄–phenyl | 70 |
| 73 (Example 67) | H | Et–NH–C(O)–X₂ | CH₃ | X₄–phenyl | >98 |
| 74 (Example 66) | H | Et₂N–CH₂CH₂–NH–C(O)–X₂ | CH₃ | X₄–phenyl | 98 |
| 75 (Example 68) | H | benzyl–piperazine–C(O)–X₂ | CH₃ | X₄–phenyl | >98 |
| 76 (Example 73) | F | X₂–oxazol-2-yl | H | X₄–phenyl | >98 |
| 77 (Example 70) | F | X₂–tetrazol-5-yl, N2-CH₂COOH | H | X₄–phenyl | >98 |
| 78 (Example 76) | F | X₂–benzimidazol-2-yl | H | X₄–phenyl | >98 |

TABLE 3-continued

| Table Entry (Example number) | R1 | R2 | R3 | R4 | % Inhibition @ 10 uM |
|---|---|---|---|---|---|
| 79 (Example 80) | F | 3-methyl-1,2,4-oxadiazol-5-yl (X₂-attached) | H | phenyl (X₄-) | >98 |
| 80 (Example 79) | F | 1,2,4-oxadiazol-3-yl (X₂-attached) | H | phenyl (X₄-) | >98 |
| 81 (Example 82) | F | 5-(cyclopropylamino)-1,2,4-oxadiazol-3-yl (X₂-attached) | H | phenyl (X₄-) | >98 |
| 82 (Example 72) | F | $X_2$-C(O)NH-CH$_2$-CH(OMe)$_2$ | H | phenyl (X₄-) | >98 |
| 83 (Example 71) | F | tetrazol-5-yl-CH$_2$-C(O)NHMe (X₂-attached) | H | phenyl (X₄-) | >98 |
| 84 (Example 77) | F | 3-methyl-1H-1,2,4-triazol-5-yl (X₂-attached) | H | phenyl (X₄-) | >98 |
| 85 (Example 75) | F | $X_2$-C(=NH)NH-cyclopropyl | H | phenyl (X₄-) | >98 |
| 86 (Example 83) | F | 5-amino-1,2,4-oxadiazol-3-yl (X₂-attached) | H | phenyl (X₄-) | >98 |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound of Formula I, including pharmaceutically acceptable salts thereof,

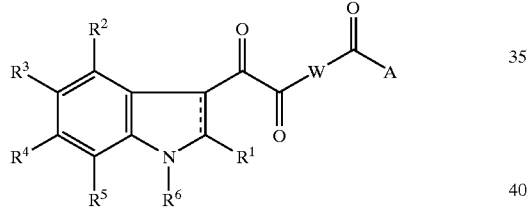

I wherein:

A is selected from the group consisting of $C_{1-6}$alkoxy, aryl and heteroaryl; in which said aryl is phenyl or napthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl; and said aryl or heteroaryl is optionally substituted with one or two of the same or different amino, nitro, cyano, $C_{1-6}$alkoxy, —C(O)NH$_2$, halogen or trifluoromethyl;

—W— is

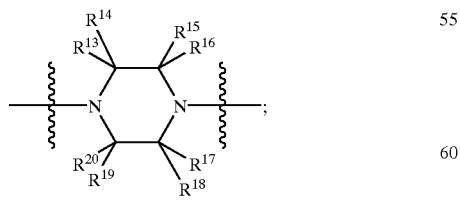

— may represent a carbon-carbon bond;

$R^1$ is hydrogen;

$R^2$, $R^3$, $R^4$, and $R^5$ are each independently selected from the group (a)–(r) consisting of:

(a) hydrogen,
(b) halogen,
(c) cyano,
(d) nitro,
(e) amino,
(f) $C_{1-4}$alkylamino,
(g) di($C_{1-4}$alkyl)amino,
(h) hydroxy,
(i) $C_{1-6}$alkyl optionally substituted with one to three same or different halogen, hydroxy, $C_{1-6}$alkoxy, amino, $C_{1-4}$alkylamino, di($C_{1-4}$alkyl)amino, cyano or nitro,
(j) $C_{3-7}$cycloalkyl optionally substituted with one to three same or different halogen, hydroxy, $C_{1-6}$alkoxy, amino, $C_{1-4}$alkylamino, di($C_{1-4}$alkyl)amino, cyano or nitro,
(k) $C_{1-6}$alkoxy,
(l) —C(O)OR$^7$,
(m) —C(O)R$^8$,
(n) —C(O)NR$^9$R$^{10}$,
(o) —C(=NR$^{12}$)(R$^{11}$),
(p) aryl, said aryl is phenyl or napthyl, and said aryl is optionally substituted with one to two of the same or different amino, $C_{1-4}$alkylamino, di($C_{1-4}$alkyl)amino, cyano, C-amido, N-amido, $C_{1-6}$ alkoxy, $C_{1-6}$thioalkoxy or halogen,
(q) heteroaryl, said heteroaryl is selected from the group consisting of pyridinyl, pyrazinyl, pyridazinyl, pyrimidinyl, furanyl, thienyl, benzothienyl, thiazolyl, isothiazolyl, oxazolyl, benzooxazolyl, isoxazolyl, imidazolyl, benzoimidazolyl, 1H-imidazo[4,5-b]pyridin-2-yl, 1H-imidazo[4,5-c]pyridin-2-yl, oxadiazolyl, thiadiazolyl, pyrazolyl, tetrazolyl, tetrazinyl, triazinyl and triazolyl, and said heteroaryl is optionally substituted with one to two same or different groups selected from (aa)–(pp) consisting of: (aa) halogen, (bb) $C_{1-6}$ alkyl, said $C_{1-6}$ alkyl optionally substituted with one to three same or different halogen, hydroxy, cyano, amino, $C_{1-4}$alkylamino or di($C_{1-4}$alkyl)amino, (cc) $C_{3-6}$alkenyl, (dd) $C_{1-6}$alkoxy, (ee) phenyl optionally substituted with one or two same or different halogen, (ff) heteroaryl, said heteroaryl selected from the group consisting of pyridinyl, pyrimidinyl, furanyl, thienyl, oxazolyl, isoxazolyl, pyrazolyl, triazolyl and tetrazolyl, and said heteroaryl optionally substituted with one or two same or different $C_{1-4}$alkyl, $C_{1-4}$alkoxy, halogen, amino, $C_{1-4}$alkylamino and di($C_{1-4}$alkyl)amino, (gg) heteroaryl$C_{1-6}$alkyl-, in which the heteroaryl of said heteroaryl $C_{1-6}$alkyl- is selected from the group consisting of pyridinyl, furanyl, thienyl and pyrazolyl, the heteroaryl of said heteroaryl$C_{1-6}$alkyl- is optionally substituted with one or two same or different $C_{1-4}$alkyl, halogen or amino, and in which a carbon of the $C_{1-6}$alkyl of said heteroaryl$C_{1-6}$alkyl- is optionally replaced by one sulfur or sulfonyl, (hh) amino, (ii) $C_{1-4}$alkylamino, in which the $C_{1-4}$alkyl of said $C_{1-4}$alkylamino is optionally substituted with amino, $C_{1-4}$alkylamino, di($C_{1-4}$alkyl)amino, morpholinyl, piperazinyl or piperidinyl, (jj) di($C_{1-4}$alkyl)amino, (kk) $C_{3-7}$cycloalkylamino, (ll) —(CH$_2$)$_q{}^a$C(O)R$^{23}$, (mm) —CH$_2$OC(O)C$_{1-6}$alkyl, (nn) —NH—(CH$_2$)$_q{}^b$C(O)R$^{24}$, (oo) —CO$_2$CH$_2$C(O)R$^{25}$, (pp) phenylmethyl, in which the phenyl of said phenylmethyl is optionally substituted with a —(CH$_2$)$_q{}^c$C(O)R$^{26}$; and (r) heteroalicyclic, said heteroalicyclic selected from the group consisting of piperazinyl, piperidinyl, morpholinyl, 5-oxo-4,5-dihydro-[1,2,4]oxadiazol-3-yl, 4,5-dihydro-thiazol-2-yl, 5-oxo4,5-dihydro-[1,3,4]oxadiazol-2-yl and 4,5-dihydro-1H-imidazol-2-yl, and said heteroalicyclic is optionally substituted with one or two same or different $C_{1-4}$alkyl, $C_{1-4}$alkoxy, hydroxy, cyano or amino;

$R^6$ and $R^7$ are each independently selected from hydrogen or $C_{1-6}$ alkyl;

$R^8$ is selected from the group consisting of $C_{1-6}$alkyl, phenyl and heteroaryl in which said heteroaryl is selected from the group consisting of oxazolyl, isoxazolyl, imidazolyl, pyrazolyl, thiazolyl, isothiazolyl, oxadiazolyl, thiadiazolyl, pyridinyl, and pyrimidinyl and said heteroaryl is optionally substituted with one to two of the same or different $C_{1-6}$alkyl, amino, $CO_2H$ or $CO_2C_{1-6}$alkyl;

$R^9$ and $R^{10}$ are each independently selected from the group (a)–(l) consisting of:
(a) hydrogen,
(b) $C_{1-6}$alkyl, said $C_{1-6}$alkyl is optionally substituted with in one to two of the same or different amino, di($C_{1-6}$alkyl)amino or $C_{1-6}$alkoxy,
(c) $C_{1-6}$alkoxy,
(d) heteroaryl, in which said heteroaryl is selected from the group consisting of pyridinyl, isoxazolyl, benzoimidazolyl, tetrazolyl, pyrazolyl, thiazolyl, oxadiazolyl, thiadiazolyl, benzothiazolyl, pyrimidinyl and isoquinolinyl and said heteroaryl is optionally substituted with one to two of the same or different $C_{1-6}$alkyl or $C_{1-6}$alkoxy,
(e) heteroaryl-$C_{1-6}$alkyl-, in which said heteroaryl is selected from the group consisting of indolyl, imidazolyl, benzoimidazolyl, pyridinyl, pyrimidinyl, thiazolyl, triazolyl, tetrazolyl, furanyl and thienyl,
(f) heteroalicyclic, in which said heteroalicyclic is morpholinyl, piperazinyl or dihydrothiazolyl, and said heteroalicyclic is optionally substituted with a $C_{1-6}$alkoxycarbonyl,
(g) morpholin-4-ylethyl,
(h) phenylsulfonyl,
(i) $C_{1-4}$alkylsulfonyl,
(j) amino,
(k) ($C_{1-6}$alkoxy)-C(O)NH—, and
(l) ($C_{1-6}$alkyl)-NHC(O)NH; or $R^9$ and $R^{10}$ taken together with the nitrogen to which they are attached are 4-benzylpiperazin-1-yl or 4-benzoylpiperazin-1-yl;

$R^{11}$ is selected from the group consisting of hydrogen, $C_{1-6}$alkoxy and $NR^{21}R^{22}$;

$R^{12}$ is selected from the group consisting of hydrogen, hydroxy, $NHCO_2$ $C_{1-6}$alkyl and $C_{1-6}$alkoxy, said $C_{1-6}$alkoxy optionally substituted with one $CO_2H$ or $CO_2C_{1-6}$alkyl;

$R^{13}$, $R^{14}$, $R^{15}$, $R^{16}$, $R^{17}$, $R^{18}$, $R^{19}$ and $R^{20}$ are each independently selected from hydrogen or $C_{1-6}$alkyl;

$R^{21}$ and $R^{22}$ are each independently selected from the group consisting of hydrogen, amino, $C_{1-6}$alkyl, $C_{3-7}$cycloalkyl and $NHCO_2C_{1-6}$alkyl;

$R^{23}$, $R^{24}$, $R^{25}$ and $R^{26}$ are each independently selected from the group consisting of hydroxy, $C_{1-4}$alkyl, $C_{1-4}$alkoxy optionally substituted with morpholin-4-yl or di($C_{1-4}$alkyl)amino, amino, pyrolidin-1-yl, ($C_{1-4}$alkyl)amino and di($C_{1-4}$alkyl)amino;

$q^a$, $q^b$ and $q^c$ are each independently 0 or 1; and provided that at least one of $R^2$, $R^3$, $R^4$, and $R^5$ is selected from the group consisting of —$C(O)R^8$, —$C(O)NR^9R^{10}$, —$C(=NR^{12})(R^{11})$, aryl, heteroaryl, and heteroalicyclic when—represents a carbon-carbon bond.

2. A compound of claim 1, including pharmaceutically acceptable salts thereof, wherein:

A is selected from the group consisting of $C_{1-6}$alkoxy, phenyl and heteroaryl in which said heteroaryl is selected from pyridinyl, furanyl and thienyl, and said phenyl or said heteroaryl is optionally substituted with one to two of the same or different amino, nitro, cyano, $C_{1-6}$alkoxy, —$C(O)NH_2$, halogen or trifluoromethyl;

— represents a carbon-carbon bond;

$R^6$ is hydrogen;

$R^{13}$, $R^{14}$, $R^{16}$, $R^{17}$ and $R^{18}$ are each hydrogen; and $R^{15}$, $R^{19}$ and $R^{20}$ are each independently hydrogen or $C_{1-6}$alkyl.

3. A compound of claim 2, including pharmaceutically acceptable salts thereof, wherein:

$R^2$ is selected from the group consisting of hydrogen, halogen and $C_{1-6}$alkoxy;

$R_3$ and $R_4$ are hydrogen; and $R^5$ is selected from the group consisting of: —$C(O)R^8$, —$C(O)NR^9R^{10}$, —$C(=NR^{12})(R^{11})$, aryl, heteroaryl and heteroalicyclic.

4. A compound of claim 3, including pharmaceutically acceptable salts thereof, wherein:

$R^2$ is halogen or $C_{1-6}$alkoxy;

$R^5$ is phenyl, said phenyl optionally substituted with a $C_{1-4}$alkoxy, $C_{1-4}$thioalkoxy or halogen;

$R^{15}$ and $R^{19}$ are each hydrogen;

$R^{20}$ is hydrogen or methyl; and

A is phenyl.

5. A compound of claim 4, including pharmaceutically acceptable salts thereof, wherein:

$R^2$ is fluoro or methoxy;

$R^5$ is phenyl, said phenyl optionally substituted with a methoxy, thiomethoxy, or fluoro; and $R^{20}$ is hydrogen.

6. A compound of claim 3, including pharmaceutically acceptable salts thereof, wherein:

$R^2$ is halogen or $C_{1-6}$alkoxy;

$R^5$ is selected from the group consisting of —$C(O)NR^9R^{10}$, —$C(=NR^{12})(R^{11})$ and heteroaryl in which said heteroaryl is tetrazolyl or oxadiazolyl and said heteroaryl is optionally substituted with one to two $C_{1-6}$alkyl, dihalomethyl, trihalomethyl or halogen;

$R^{15}$ and $R^{19}$ are each hydrogen;

$R^{20}$ is hydrogen or $C_{1-6}$alkyl; and

A is heteroaryl, said heteroaryl selected from the group consisting of pyridinyl, furanyl and thienyl and said heteroaryl optionally substituted with a halogen.

7. A compound of claim 6, including pharmaceutically acceptable salts thereof, wherein:

$R^2$ is fluoro $R^5$ is selected from the group consisting of 2H-tetrazolyl, 2-dihalomethyl-2H-tetrazolyl, [1,2,4]-oxadiazolyl, 5-amino-[1,2,4]-oxadiazolyl, 5-trihalomethyl-[1,2,4]-oxadiazolyl, —$C(O)NH_2$ and —$C(=NOH)NH_2$;

$R^{20}$ is hydrogen or methyl; and

A is pyridinyl.

8. A compound of claim 6, including pharmaceutically acceptable salts thereof, wherein:

$R^2$ is fluoro;

$R^5$ is 2H-tetrazolyl or 2-methyl-2H-tetrazolyl;

$R^{20}$ is hydrogen; and

A is furanyl or thienyl, in which said furanyl is optionally substituted with a chloro or bromo.

9. A compound of claim 3, including pharmaceutically acceptable salts thereof, wherein:

$R^2$ is selected from the group consisting of hydrogen, fluoro or methoxy;

$R^5$ is —C(O)NR$^9$R$^{10}$;

$R^{15}$ and $R^{19}$ are each hydrogen;

$R^{20}$ is hydrogen or methyl; and

A is phenyl.

10. A compound of claim 9, including pharmaceutically acceptable salts thereof, wherein:

$R^2$ is hydrogen; and $R^9$ and $R^{10}$ are each independently selected from the group consisting of hydrogen, $C_{1-6}$ alkyl optionally substituted with a di($C_{1-4}$alkyl)amino, methylsulfonyl, phenylsulfonyl, and tetrazolyl, or $R^9$ and $R^{10}$ taken together with the nitrogen to which they are attached are 4-benzylpiperazin-1-yl.

11. A compound of claim 9, including pharmaceutically acceptable salts thereof, wherein:

$R^2$ is methoxy;

$R^{20}$ is hydrogen; and $R^9$ and $R^{10}$ are each independently hydrogen or methyl.

12. A compound of claim 9, including pharmaceutically acceptable salts thereof, wherein:

$R^2$ is fluoro;

$R^{20}$ is methyl; and $R^9$ and $R^{10}$ are each independently selected from the group consisting of hydrogen, $C_{1-6}$alkyl and morpholin-4-ylethyl.

13. A compound of claim 9, including pharmaceutically acceptable salts thereof, wherein:

$R^2$ is fluoro; and $R^{20}$ is hydrogen.

14. A compound of claim 3, including pharmaceutically acceptable salts thereof, wherein:

$R^2$ is hydrogen, methoxy or fluoro;

$R^5$ is —C(O)R$^8$;

$R^{15}$ and $R^{19}$ are each hydrogen;

$R^{20}$ is hydrogen or methyl; and

A is phenyl.

15. A compound of claim 14, including pharmaceutically acceptable salts thereof, wherein:

$R^2$ is methoxy or fluoro; and $R^8$ is $C_{1-6}$alkyl.

16. The compound of claim 15, including pharmaceutically acceptable salts thereof, wherein:

$R^2$ is methoxy;

$R^8$ is methyl; and $R^{20}$ is hydrogen.

17. A compound of claim 3, including pharmaceutically acceptable salts thereof, wherein:

$R^2$ is selected from the group consisting of hydrogen, methoxy and halogen;

$R^5$ is heteroaryl;

$R^{15}$ and $R^{19}$ are each hydrogen;

$R^{20}$ is hydrogen or methyl; and

A is phenyl, said phenyl optionally substituted with one to two of the same or different cyano, fluoro, trifluoromethyl, amino, nitro, and C(O)NH$_2$.

18. A compound of claim 17, including pharmaceutically acceptable salts thereof, wherein:

$R^5$ is heteroaryl, said heteroaryl selected from the group consisting of pyridinyl, pyrimidinyl, furanyl, thienyl, benzothienyl, thiazolyl, oxazolyl, benzooxazolyl, imidazolyl, benzoimidazolyl, oxadiazolyl, pyrazolyl, triazolyl, tetrazolyl, 1H-imidazo[4,5-b]pyridin-2-yl, and 1H-imidazo[4,5-c]pyridin-2-yl.

19. A compound of claim 3, including pharmaceutically acceptable salts thereof, wherein:

$R^2$ is selected from the group consisting of hydrogen, methoxy and fluoro;

$R^5$ is heteroalicyclic, said heteroalicyclic selected from the group consisting of 5-oxo-4,5-dihydro-[1,2,4]oxadiazol-3-yl, 4,5-dihydro-thiazol-2-yl, 5-oxo4,5-dihydro-[1,3,4]oxadiazol-2-yl and 4,5-dihydro-1H-imidazol-2-yl;

$R^{15}$ and $R^{19}$ are each hydrogen;

$R^{20}$ is hydrogen or methyl; and

A is phenyl.

20. A compound of claim 3, including pharmaceutically acceptable salts thereof, wherein:

$R^2$ is selected from the group consisting of hydrogen, methoxy and fluoro;

$R^5$ is —C(=NR$^{12}$)(R$^{11}$);

A is phenyl or $C_{1-6}$alkoxy;

$R^{11}$ is selected from the group consisting of hydrogen, hydroxy, NHCO$_2$C(CH$_3$)$_3$ and OCH$_2$CO$_2$H; and $R^{12}$ is selected from the group consisting of hydrogen, ethoxy and NR$^{21}$R$^{22}$;

$R^{15}$ and $R^{19}$ are each hydrogen;

$R^{20}$ is hydrogen or methyl;

$R^{21}$ and $R^{22}$ are each independently selected from the group consisting of hydrogen, amino, $C_{1-6}$alkyl, cyclopropyl and NHCO$_2$C(CH$_3$)$_3$.

21. A compound of claim 5, including pharmaceutically acceptable salts thereof, selected from the group consisting of:

1-(4-Benzoyl-piperazin-1-yl)-2-(4-fluoro-7-phenyl-1H-indol-3-yl)-ethane-1,2-dione;

1-(4-Benzoyl-piperazin-1-yl)-2-[4-fluoro-7-(2-methylsulfanyl-phenyl)-1H-indol-3-yl]-ethane-1,2-dione;

1-(4-Benzoyl-piperazin-1-yl)-2-[7-(4-fluoro-phenyl)-4-methoxy-1H-indol-3-yl]-ethane-1,2-dione; and 1-(4-Benzoyl-piperazin-1-yl)-2-[4-fluoro-7-(4-methoxy-phenyl)-1H-indol-3-yl]-ethane-1,2-dione.

22. A compound of claim 7, including pharmaceutically acceptable salts thereof, selected from the group consisting of:

1-[4-Fluoro-7-(2H-tetrazol-5-yl)-1H-indol-3-yl]-2-[4-(pyridine-2-carbonyl)-piperazin-1-yl]-ethane-1,2-dione;

1-[4-Fluoro-7-(2H-tetrazol-5-yl)-1H-indol-3-yl]-2-[2-(R)-methyl-4-(pyridine-2-carbonyl)-piperazin-1-yl]-ethane-1,2-dione;

1-[7-(2-Difluoromethyl-2H-tetrazol-5-yl)-4-fluoro-1H-indol-3-yl]-2-[4-(pyridine-2-carbonyl)-piperazin-1-yl]-ethane-1,2-dione;

4-Fluoro-N-hydroxy-3-{2-oxo-2-[4-(pyridine-2-carbonyl)-piperazin-1-yl]-acetyl}-1H-indole-7-carboxamidine;

4-Fluoro-3-{2-oxo-2-[4-(pyridine-2-carbonyl)-piperazin-1-yl]-acetyl}-1H-indole-7-carboxylic acid amide;

4-Fluoro-N-hydroxy-3-{2-[2-(R)-methyl-4-(pyridine-2-carbonyl)-piperazin-1-yl]-2-oxo-acetyl}-1H-indole-7-carboxamidine;

4-Fluoro-3-{2-[2-(R)-methyl-4-(pyridine-2-carbonyl)-piperazin-1-yl]-2-oxo-acetyl}-1H-indole-7-carboxylic acid amide;

1-[4-Fluoro-7-(5-trichloromethyl-[1,2,4]oxadiazol-3-yl)-1H-indol-3-yl]-2-[2-(R)-methyl4-(pyridine-2-carbonyl)-piperazin-1-yl]-ethane-1,2-dione;

1-[4-Fluoro-7-(5-trichloromethyl-[1,2,4]oxadiazol-3-yl)-1H-indol-3-yl]-2-[4-(pyridine-2-carbonyl)-piperazin-1-yl]-ethane-1,2-dione;

1-[7-(5-Amino-[1,2,4]oxadiazol-3-yl)-4-fluoro-1H-indol-3-yl]-2-[4-(pyridine-2-carbonyl)-piperazin-1-yl]-ethane-1,2-dione;

1-[7-(5-Amino-[1,2,4]oxadiazol-3-yl)-4-fluoro-1H-indol-3-yl]-2-[2-(R)-methyl4-(pyridine-2-carbonyl)-piperazin-1-yl]-ethane-1,2-dione;

1-(4-Fluoro-7-[1,2,4]oxadiazol-3-yl-1H-indol-3-yl)-2-[4-(pyridine-2-carbonyl)-piperazin-1-yl]-ethane-1,2-dione; and 1-(4-Fluoro-7-[1,2,4]oxadiazol-3-yl-1H-indol-3-yl)-2-[2-(R)-methyl-4-(pyridine-2-carbonyl)-piperazin-1-yl]-ethane-1,2-dione.

23. A compound of claim 8, including pharmaceutically acceptable salts thereof, selected from the group consisting of:

1-[4-Fluoro-7-(2H-tetrazol-5-yl)-1H-indol-3-yl]-2-[4-(furan-2-carbonyl)-piperazin-1-yl]-ethane-1,2-dione;

1-[4-(5-Chloro-furan-2-carbonyl)-piperazin-1-yl]-2-[4-fluoro-7-(2H-tetrazol-5-yl)-1H-indol-3-yl]-ethane-1,2-dione;

1-[4-(5-Bromo-furan-2-carbonyl)-piperazin-1-yl]-2-[4-fluoro-7-(2H-tetrazol-5-yl)-1H-indol-3-yl]-ethane-1,2-dione;

1-[4-Fluoro-7-(2H-tetrazol-5-yl)-1H-indol-3-yl]-2-[4-(thiophene-2-carbonyl)-piperazin-1-yl]-ethane-1,2-dione;

1-[4-Fluoro-7-(2-methyl-2H-tetrazol-5-yl)-1H-indol-3-yl]-2-[4-(furan-2-carbonyl)-piperazin-1-yl]-ethane-1,2-dione;

1-[4-(5-Chloro-furan-2-carbonyl)-piperazin-1-yl]-2-[4-fluoro-7-(2-methyl-2H-tetrazol-5-yl)-1H-indol-3-yl]-ethane-1,2-dione;

1-[4-(5-Bromo-furan-2-carbonyl)-piperazin-1-yl]-2-[4-fluoro-7-(2-methyl-2H-tetrazol-5-yl-1H-indol-3-yl]-ethane-1,2-dione; and 1-[4-Fluoro-7-(2-methyl-2H-tetrazol-5-yl)-1H-indol-3-yl]-2-[4-(thiophene-2-carbonyl)-piperazin-1-yl]-ethane-1,2-dione.

24. A compound of claim 10, including pharmaceutically acceptable salts thereof, selected from the group consisting of:

N-{3-[2-(4-Benzoyl-piperazin-1-yl)-2-oxo-acetyl]-1H-indole-7-carbonyl}-methanesulfonamide;

N-{3-[2-(4-Benzoyl-piperazin-1-yl)-2-oxo-acetyl]-1H-indole-7-carbonyl}-benzenesulfonamide;

3-[2-(4-Benzoyl-piperazin-1-yl)-2-oxo-acetyl]-1H-indole-7-carboxylic acid (1H-tetrazol-5-yl)-amide;

3-[2-(4-Benzoyl-2-(R)-methyl-piperazin-1-yl)-2-oxo-acetyl]-1H-indole-7-carboxylic acid methylamide;

3-[2-(4-Benzoyl-2-(R)-methyl-piperazin-1-yl)-2-oxo-acetyl]-1H-indole-7-carboxylic acid dimethylamide;

3-[2-(4-Benzoyl-2-(R)-methyl-piperazin-1-yl)-2-oxo-acetyl]-1H-indole-7-carboxylic acid (2-diethylamino-ethyl)-amide;

3-[2-(4-Benzoyl-2-(R)-methyl-piperazin-1-yl)-2-oxo-acetyl]-1H-indole-7-carboxylic acid ethylamide; and 1-(4-Benzoyl-2-(R)-methyl-piperazin-1-yl)-2-[7-(4-benzyl-piperazine-1-carbonyl)-1H-indol-3-yl]-ethane-1,2-dione.

25. A compound of claim 11, including pharmaceutically acceptable salts thereof selected from:

3-[2-(4-Benzoyl-piperazin-1-yl)-2-oxo-acetyl]-4-methoxy-1H-indole-7-carboxylic acid methylamide; or 3-[2-(4-Benzoyl-piperazin-1-yl)-2-oxo-acetyl]-4-methoxy-1H-indole-7-carboxylic acid amide.

26. A compound of claim 12, including pharmaceutically acceptable salts thereof, selected from the group consisting of:

3-[2-(4-Benzoyl-piperazin-1-yl)-2-oxo-acetyl]-4-fluoro-1H-indole-7-carboxylic acid (2-dimethylaminoethyl)-amide;

3-[2-(4-Benzoyl-2-(R)-methyl-piperazin-1-yl)-2-oxo-acetyl]-4-fluoro-1H-indole-7-carboxylic acid (2-morpholin-4-yl-ethyl)-amide; and 3-[2-(4-Benzoyl-2-(R)-methyl-piperazin-1-yl)-2-oxo-acetyl]-4-fluoro-1H-indole-7-carboxylic acid amide.

27. The compound of claim 13, including pharmaceutically acceptable salts thereof, selected from the group consisting of:

3-[2-(4-Benzoyl-piperazin-1-yl)-2-oxo-acetyl]-4-fluoro-1H-indole-7-carboxylic acid pyridin-3-ylamide;

3-[2-(4-Benzoyl-piperazin-1-yl)-2-oxo-acetyl]-4-fluoro-1H-indole-7-carboxylic acid (4,5-dihydro-thiazol-2-yl)-amide;

3-[2-(4-Benzoyl-piperazin-1-yl)-2-oxo-acetyl]-4-fluoro-1H-indole-7-carboxylic acid (3-methyl-isoxazol-5-yl)-amide;

3-[2-(4-Benzoyl-piperazin-1-yl)-2-oxo-acetyl]-4-fluoro-1H-indole-7-carboxylic acid pyridin-2-ylamide;

3-[2-(4-Benzoyl-piperazin-1-yl)-2-oxo-acetyl]-4-fluoro-1H-indole-7-carboxylic acid pyridin-4-ylamide;

N-{3-[2-(4-Benzoyl-piperazin-1-yl)-2-oxo-acetyl]-4-fluoro-1H-indole-7-carbonyl}-benzenesulfonamide;

3-[2-(4-Benzoyl-piperazin-1-yl)-2-oxo-acetyl]-4-fluoro-1H-indole-7-carboxylic acid (1H-benzoimidazol-2-yl)-amide;

3-[2-(4-Benzoyl-piperazin-1-yl)-2-oxo-acetyl]-4-fluoro-1H-indole-7-carboxylic acid amide;

3-[2-(4-Benzoyl-piperazin-1-yl)-2-oxo-acetyl]-4-fluoro-1H-indole-7-carboxylic acid (2-dimethylaminoethyl)-amide;

3-[2-(4-Benzoyl-piperazin-1-yl)-2-oxo-acetyl]-4-fluoro-1H-indole-7-carboxylic acid benzylamide;

3-[2-(4-Benzoyl-piperazin-1-yl-2-oxo-acetyl]-4-fluoro-1H-indole-7-carboxylic acid methoxy-amide;

3-[2-(4-Benzoyl-piperazin-1-yl)-2-oxo-acetyl]-4-fluoro-1H-indole-7-carboxylic acid methylamide;

3-[2-(4-Benzoyl-piperazin-1-yl)-2-oxo-acetyl]-4-fluoro-1H-indole-7-carboxylic acid [2-(1H-indol-3-yl)-ethyl]-amide;

3-[2-(4-Benzoyl-piperazin-1-yl-2-oxo-acetyl]-4-fluoro-1H-indole-7-carboxylic acid [2-(1H-imidazol-4-yl)-ethyl]-amide;

3-[2-(4-Benzoyl-piperazin-1-yl)-2-oxo-acetyl]-4-fluoro-1H-indole-7-carboxylic acid (furan-2-ylmethyl)-amide;

3-[2-(4-Benzoyl-piperazin-1-yl)-2-oxo-acetyl]-4-fluoro-1H-indole-7-carboxylic acid (thiophen-2-ylmethyl)-amide;

3-[2-(4-Benzoyl-piperazin-1-yl)-2-oxo-acetyl]-4-fluoro-1H-indole-7-carboxylic acid (2-morpholin-4-yl-ethyl)-amide;

3-[2-(4-Benzoyl-piperazin-1-yl)-2-oxo-acetyl]-4-fluoro-1H-indole-7-carboxylic acid (1H-benzoimidazol-2-ylmethyl)-amide;

3-[2-(4-Benzoyl-piperazin-1-yl)-2-oxo-acetyl]-4-fluoro-1H-indole-7-carboxylic acid (2H-tetrazol-5-yl)-amide;

3-[2-(4-Benzoyl-piperazin-1-yl)-2-oxo-acetyl]-4-fluoro-1H-indole-7-carboxylic acid (2H-pyrazol-3-yl)-amide;

3-[2-(4-Benzoyl-piperazin-1-yl)-2-oxo-acetyl]-4-fluoro-1H-indole-7-carboxylic acid isoxazol-3-ylamide;

3-[2-(4-Benzoyl-piperazin-1-yl-2-oxo-acetyl]-4-fluoro-1H-indole-7-carboxylic acid thiazol-2-ylamide;

3-[2-(4-Benzoyl-piperazin-1-yl-2-oxo-acetyl]-4-fluoro-1H-indole-7-carboxylic acid [1,3,4]thiadiazol-2-ylamide;

3-[2-(4-Benzoyl-piperazin-1-yl)-2-oxo-acetyl]-4-fluoro-1H-indole-7-carboxylic acid benzothiazol-2-ylamide;

N-{3-[2-(4-Benzoyl-piperazin-1-yl)-2-oxo-acetyl]-4-fluoro-1H-indole-7-carbonyl}-methanesulfonamide;

1-[7-(4-Benzoyl-piperazine-1-carbonyl)-4-fluoro-1H-indol-3-yl]-2-(4-benzoyl-piperazin-1-yl-ethane-1,2-dione;

3-[2-(4-Benzoyl-piperazin-1-yl)-2-oxo-acetyl]-4-fluoro-1H-indole-7-carboxylic acid (2,2-dimethoxyethyl)-amide;

N'-{3-[2-(4-Benzoyl-piperazin-1-yl)-2-oxo-acetyl]-4-fluoro-1H-indole-7-carbonyl}-hydrazinecarboxylic acid tert-butyl ester;

3-[2-(4-Benzoyl-piperazin-1-yl)-2-oxo-acetyl]-4-fluoro-1H-indole-7-carboxylic acid hydrazide;

3-[2-(4-Benzoyl-piperazin-1-yl)-2-oxo-acetyl]-4-fluoro-1H-indole-7-carboxylic acid (2-methoxy-ethyl)-amide;

[2-({3-[2-(4-Benzoyl-piperazin-1-yl)-2-oxo-acetyl]-4-fluoro-1H-indole-7-carbonyl}-amino)-ethyl]-carbamic acid tert-butyl ester;

3-[2-(4-Benzoyl-piperazin-1-yl)-2-oxo-acetyl]-4-fluoro-1H-indole-7-carboxylic acid (2-amino-ethyl)-amide;

3-[2-(4-Benzoyl-piperazin-1-yl)-2-oxo-acetyl]-4-fluoro-1H-indole-7-carboxylic acid (2,6-dimethyl-pyrimidin-4-yl)-amide;

3-[2-(4-Benzoyl-piperazin-1-yl)-2-oxo-acetyl]-4-fluoro-1H-indole-7-carboxylic acid (6-methoxy-benzothiazol-2-yl)-amide;

3-[2-(4-Benzoyl-piperazin-1-yl)-2-oxo-acetyl]-4-fluoro-1H-indole-7-carboxylic acid (5-methyl-thiazol-2-yl)-amide;

3-[2-(4-Benzoyl-piperazin-1-yl)-2-oxo-acetyl]-4-fluoro-1H-indole-7-carboxylic acid (5-tert-butyl-thiazol-2-yl)-amide; and 3-[2-(4-Benzoyl-piperazin-1-yl)-2-oxo-acetyl]-4-fluoro-1H-indole-7-carboxylic acid isoquinolin-1-ylamide.

28. The compound of claim 17, including pharmaceutically acceptable salts thereof, selected from the group consisting of:

1-(4-Benzoyl-piperazin-1-yl)-2-[7-(5-chloro-thiophen-2-yl)-4-fluoro-1H-indol-3-yl]-ethane-1,2-dione;

1-(4-Benzoyl-piperazin-1-yl)-2-[4-fluoro-7-(2-methyl-2H-tetrazol-5-yl)-1H-indol-3-yl]-ethane-1,2-dione;

5-{3-[2-(4-Benzoyl-piperazin-1-yl)-2-oxo-acetyl]-4-fluoro-1H-indol-7-yl}-tetrazol-2-yl)-acetic acid methyl ester;

1-(4-Benzoyl-piperazin-1-yl)-2-[7-(2-ethyl-2H-tetrazol-5-yl)-4-fluoro-1H-indol-3-yl]-ethane-1,2-dione;

1-(4-Benzoyl-piperazin-1-yl)-2-[7-(2-propyl-2H-tetrazol-5-yl)-4-fluoro-1H-indol-3-yl]-ethane-1,2-dione;

1-(4-Benzoyl-piperazin-1-yl)-2-[7-(2-benzyl-2H-tetrazol-5-yl)-4-fluoro-1H-indol-3-yl]-ethane-1,2-dione;

1-(4-Benzoyl-piperazin-1-yl)-2-[7-(2-allyl-2H-tetrazol-5-yl)-4-fluoro-1H-indol-3-yl]-ethane-1,2-dione;

1-(4-Benzoyl-piperazin-1-yl)-2-[4-fluoro-7-(5-methoxy-[1,2,4]oxadiazol-3-yl)-1H-indol-3-yl]-ethane-1,2-dione;

(5-{3-[2-(4-Benzoyl-piperazin-1-yl)-2-oxo-acetyl]-4-fluoro-1H-indol-7-yl}-tetrazol-2-yl)-acetic acid;

(5-{3-[2-(4-Benzoyl-piperazin-1-yl)-2-oxo-acetyl]-4-fluoro-1H-indol-7-yl}-tetrazol-2-yl)-N-methyl-acetamide;

1-(4-Benzoyl-piperazin-1-yl)-2-[4-fluoro-7-(5-methyl-2H-[1,2,4]triazol-3-yl)-1H-indol-3-yl]-ethane-1,2-dione;

1-(4-Benzoyl-piperazin-1-yl)-2-(4-fluoro-7-(5-methyl-[1,2,4]oxadiazol-3-yl)-1H-indol-3-yl)-ethane-1,2-dione;

1-(4-Benzoyl-piperazin-1-yl)-2-(4-fluoro-7-(5-trichloromethyl-[1,2,4]oxadiazol-3-yl)-1H-indol-3-yl)-ethane-1,2-dione;

1-(4-Benzoyl-piperazin-1-yl)-2-[7-(5-cyclopropylamino-[1,2,4]oxadiazol-3-yl)-4-fluoro-1H-indol-3-yl]-ethane-1,2-dione;

1-(4-Benzoyl-piperazin-1-yl)-2-[7-(5-amino-[1,2,4]oxadiazol-3-yl)-4-fluoro-1H-indol-3-yl]-ethane-1,2-dione;

1-[7-(3-Benzoyl-3H-imidazol4-yl)-4-fluoro-1H-indol-3-yl]-2-(4-benzoyl-piperazin-1-yl)-ethane-1,2-dione;

5-{3-[2-(4-Benzoyl-piperazin-1-yl)-2-oxo-acetyl]-4-fluoro-1H-indol-7-yl}-1H-pyrazole-3-carboxylic acid ethyl ester;

5-{3-[2-(4-Benzoyl-piperazin-1-yl)-2-oxo-acetyl]-4-fluoro-1H-indol-7-yl}-isoxazole-3-carboxylic acid ethyl ester;

5-{3-[2-(4-Benzoyl-piperazin-1-yl)-2-oxo-acetyl]-4-fluoro-1H-indol-7-yl}-1H-pyrazole-3-carboxylic acid;

5-{3-[2-(4-Benzoyl-piperazin-1-yl)-2-oxo-acetyl]-4-fluoro-1H-indol-7-yl}1H-pyrazole-3-carboxylic acid methylamide;

1-[7-(5-Amino-[1,3,4]oxadiazol-2-yl)-4-fluoro-1H-indol-3-yl]-2-(4-benzoyl-piperazin-1-yl)-ethane-1,2-dione;

N-(3-{3-[2-(4-Benzoyl-piperazin-1-yl)-2-oxo-acetyl]-4-fluoro-1H-indol-7-yl}-[1,2,4]oxadiazol-5-yl-acetamide;

1-(4-Benzoyl-piperazin-1-yl)-2-[7-(5-chloromethyl-[1,2,4]oxadiazol-3-yl)-4-fluoro-1H-indol-3-yl]-ethane-1,2-dione;

(3-{3-[2-(4-Benzoyl-piperazin-1-yl)-2-oxo-acetyl]-4-fluoro-1H-indol-7-yl}-[1,2,4]oxadiazol-5-yl)-acetic acid methyl ester;

2-(3-{3-[2-(4-Benzoyl-piperazin-1-yl)-2-oxo-acetyl]-4-fluoro-1H-indol-7-yl}-[1,2,4]oxadiazol-5-yl)-N-methyl-acetamide;

(3-{3-[2-(4-Benzoyl-piperazin-1-yl)-2-oxo-acetyl]-4-fluoro-1H-indol-7-yl}-[1,2,4]oxadiazol-5-yl)-acetic acid;

3-{3-[2-(4-Benzoyl-piperazin-1-yl)-2-oxo-acetyl]-4-fluoro-1H-indol-7-yl}-[1,2,4]oxadiazole-5-carboxylic acid methyl ester;

3-{3-[2-(4-Benzoyl-piperazin-1-yl)-2-oxo-acetyl]-4-fluoro-1H-indol-7-yl}-[1,2,4]oxadiazole-5-carboxylic acid methylamide;

3-{3-[2-(4-Benzoyl-piperazin-1-yl)-2-oxo-acetyl]-4-fluoro-1H-indol-7-yl}-[1,2,4]oxadiazole-5-carboxylic acid amide;

2-(5-{3-[2-(4-Benzoyl-piperazin-1-yl)-2-oxo-acetyl]-4-fluoro-1H-indol-7-yl}-tetrazol-2-yl)-acetamide;

3-(5-{3-[2-(4-Benzoyl-piperazin-1-yl)-2-oxo-acetyl]-4-fluoro-1H-indol-7-yl}-tetrazol-2-ylmethyl)-benzoic acid methyl ester;

3-(5-{3-[2-(4-Benzoyl-piperazin-1-yl)-2-oxo-acetyl]-4-fluoro-1H-indol-7-yl}-tetrazol-2-ylmethyl)-benzoic acid;

3-(5-{3-[2-(4-Benzoyl-piperazin-1-yl)-2-oxo-acetyl]-4-fluoro-1H-indol-7-yl}-tetrazol-2-ylmethyl)-benzamide;

2-(5-{3-[2-(4-Benzoyl-piperazin-1-yl)-2-oxo-acetyl]-4-fluoro-1H-indol-7-yl}-tetrazol-2-ylmethyl)-benzoic acid methyl ester;

2-(5-{3-(2-(4-Benzoyl-piperazin-1-yl)-2-oxo-acetyl]-4-fluoro-1H-indol-7-yl}-tetrazol-2-ylmethyl)-benzoic acid;

2-(5-{3-[2-(4-Benzoyl-piperazin-1-yl)-2-oxo-acetyl]-4-fluoro-1H-indol-7-yl}-tetrazol-2-ylmethyl)-benzamide;

4-(5-{3-[2-(4-Benzoyl-piperazin-1-yl)-2-oxo-acetyl]-4-fluoro-1H-indol-7-yl}-tetrazol-2-ylmethyl)-benzoic acid methyl ester;

4-(5-{3-[2-(4-Benzoyl-piperazin-1-yl)-2-oxo-acetyl]-4-fluoro-1H-indol-7-yl}-tetrazol-2-ylmethyl)-benzoic acid;

4-(5-{3-[2-(4-Benzoyl-piperazin-1-yl)-2-oxo-acetyl]-4-fluoro-1H-indol-7-yl}-tetrazol-2-ylmethyl)-benzamide;

Acetic acid 5-{3-[2-(4-benzoyl-piperazin-1-yl)-2-oxo-acetyl]-4-fluoro-1H-indol-7-yl}-tetrazol-2-yl methyl ester;

2,2-Dimethyl-propionic acid 5-{3-[2-(4-benzoyl-piperazin-1-yl)-2-oxo-acetyl]-4-fluoro-1H-indol-7-yl}-tetrazol-2-yl methyl ester;

1-(4-Benzoyl-piperazin-1-yl)-2-{4-fluoro-7-[2-(2-hydroxy-ethyl)-2H-tetrazol-5-yl]-1H-indol-3-yl}-ethane-1,2-dione;

2-[2-(5-{3-[2-(4-Benzoyl-piperazin-1-yl)-2-oxo-acetyl]-4-fluoro-1H-indol-7-yl}-tetrazol-2-yl-ethyl]-isoindole-1,3-dione;

1-(4-Benzoyl-piperazin-1-yl)-2-{7-[2-(2-diethylamino-ethyl)-2H-tetrazol-5-yl]-4-fluoro-1H-indol-3-yl}-ethane-1,2-dione;

4-(5-{3-[2-(4-Benzoyi-piperazin-1-yl)-2-oxo-acetyl]-4-fluoro-1H-indol-7-yl}-tetrazol-2-yl)-butyronitrile;

1-(4-Benzoyl-piperazin-1-yl)-2-[4-fluoro-7-(5-pyridin-4-yl-4H-[1,2,4]triazol-3-yl)-1H-indol-3-yl]-ethane-1,2-dione;

1-(4-Benzoyl-piperazin-1-yl)-2-[4-fluoro-7-(5-pyridin-3-yl-4H-[1,2,4]triazol-3-yl)-1H-indol-3-yl]-ethane-1,2-dione;

(5-{3-[2-(4-Benzoyl-piperazin-1-yl)-2-oxo-acetyl]-4-fluoro-1H-indol-7-yl}-4H-[1,2,4]triazol-3-yl)-acetonitrile;

5-{3-[2-(4-Benzoyl-piperazin-1-yl-2-oxo-acetyl]-4-fluoro-1H-indol-7-yl}-4H-[1,2,4]triazole-3-carboxylic acid amide;

1-(4-Benzoyl-piperazin-1-yl)-2-[4-fluoro-7-(5-pyrazin-2-yl-4H-[1,2,4]triazol-3-yl)-1H-indol-3-yl]-ethane-1,2-dione;

3-{3-[2-(4-Benzoyl-piperazin-1-yl-2-oxo-acetyl]-4-fluoro-1H-indol-7-yl}-4H-[1,2,4,5]tetrazine-1-carboxylic acid tert-butyl ester;

1-[7-(5-Aminomethyl-[1,2,4]oxadiazol-3-yl)-4-fluoro-1H-indol-3-yl]-2-(4-benzoyl-piperazin-1-yl-ethane-1,2-dione;

1-(4-Benzoyl-piperazin-1-yl)-2-[4-fluoro-7-(5-methylaminomethyl-[1,2,4]oxadiazol-3-yl)-1H-indol-3-yl]-ethane-1,2-dione;

1-(4-Benzoyl-piperazin-1-yl)-2-[4-fluoro-7-(5-dimethylaminomethyl-[1,2,4]oxadiazol-3-yl-1H-indol-3-yl]-ethane-1,2-dione;

1-(4-Benzoyl-piperazin-1-yl-2-[4-fluoro-7-(5-hydroxymethyl-[1,2,4]oxadiazol-3-yl)-1H-indol-3-yl]-ethane-1,2-dione;

(3-{3-[2-(4-Benzoyl-piperazin-1-yl-2-oxo-acetyl]-4-fluoro-1H-indol-7-yl}-[1,2,4]oxadiazol-5-ylamino)-acetic acid methyl ester;

(3-{3-[2-(4-Benzoyl-piperazin-1-yl)-2-oxo-acetyl]-4-fluoro-1H-indol-7-yl}-[1,2,4]oxadiazol-5-ylamino)-acetic acid;

2-(3-{3-[2-(4-Benzoyl-piperazin-1-yl)-2-oxo-acetyl]-4-fluoro-1H-indol-7-yl}-[1,2,4]oxadiazol-5-ylamino)-acetamide;

2-(3-{3-[2-(4-Benzoyl-piperazin-1-yl)-2-oxo-acetyl]-4-fluoro-1H-indol-7-yl}-[1,2,4]oxadiazol-5-ylamino)-N-methyl-acetamide;

(3-{3-[2-(4-Benzoyl-piperazin-1-yl)-2-oxo-acetyl]-4-fluoro-1H-indol-7-yl}-[1,2,4]triazol-1-yl)-acetic acid methyl ester;

2-(3-{3-[2-(4-Benzoyl-piperazin-1-yl)-2-oxo-acetyl]-4-fluoro-1H-indol-7-yl}-[1,2,4]triazol-1-yl)-N-methyl-acetamide;

2-{3-[2-(4-Benzoyl-piperazin-1-yl)-2-oxo-acetyl]-4-fluoro-1H-indol-7-yl}-1H-imidazole-4-carboxylic acid methyl ester;

2-{3-[2-(4-Benzoyl-piperazin-1-yl)-2-oxo-acetyl]-4-fluoro-1H-indol-7-yl}-1H-imidazole-4-carboxylic acid methylamide;

1-[7-(5-Amino-[1,2,4]oxadiazol-3-yl)-4-fluoro-1H-indol-3-yl]-2-(4-benzoyl-2-methyl-piperazin-1-yl)-ethane-1,2-dione;

1-(4-Benzoyl-piperazin-1-yl)-2-[7-(5-dimethylamino-[1,2,4]oxadiazol-3-yl)-4-fluoro-1H-indol-3-yl]-ethane-1,2-dione;

1-(4-Benzoyl-piperazin-1-yl)-2-[4-fluoro-7-(5-methylamino-[1,2,4]oxadiazol-3-yl)-1H-indol-3-yl]-ethane-1,2-dione;

1-(4-Benzoyl-piperazin-1-yl)-2-[4-fluoro-7-(5-isopropylamino-[1,2,4]oxadiazol-3-yl)-1H-indol-3-yl]-ethane-1,2-dione;

1-(4-Benzoyl-2-(R)-methyl-piperazin-1-yl)-2-{4-fluoro-7-[5-(2-morpholin-4-yl-ethylamino)-[1,2,4]oxadiazol-3-yl]-1H-indol-3-yl}-ethane-1,2-dione;

1-(4-Benzoyl-2-(R)-methyl-piperazin-1-yl)-2-[7-(5-sec-butylamino-[1,2,4]oxadiazol-3-yl)-4-fluoro-1H-indol-3-yl]-ethane-1,2-dione;

1-(4-Benzoyl-2-(R)-methyl-piperazin-1-yl)-2-[7-(5-cyclobutylamino-[1,2,4]oxadiazol-3-yl)-4-fluoro-1H-indol-3-yl]-ethane-1,2-dione;

1-(4-Benzoyl-2-(R)-methyl-piperazin-1-yl)-2-[7-(5-cyclopentylamino-[1,2,4]oxadiazol-3-yl)-4-fluoro-1H-indol-3-yl]-ethane-1,2-dione;

1-(4-Benzoyl-2-(R)-methyl-piperazin-1-yl)-2-[4-fluoro-7-(2-methyl-2H-tetrazol-5-yl)-1H-indol-3-yl]-ethane-1,2-dione;

1-(4-Benzoyl-2-(R)-methyl-piperazin-1-yl)-2-[4-fluoro-7-(5-methyl-[1,2,4]oxadiazol-3-yl)-1H-indol-3-yl]-ethane-1,2-dione;

1-(4-Benzoyl-2-(R)-methyl-piperazin-1-yl)-2-[7-(5-cyclopropyl-[1,2,4]oxadiazol-3-yl)-4-fluoro-1H-indol-3-yl]-ethane-1,2-dione;

1-(4-Benzoyl-2-(R)-methyl-piperazin-1-yl)-2-[4-fluoro-7-(5-trifluoromethyl-[1,2,4]oxadiazol-3-yl)-1H-indol-3-yl]-ethane-1,2-dione;

1-(4-Benzoyl-2-(R)-methyl-piperazin-1-yl)-2-(4-fluoro-7-[1,2,4]oxadiazol-3-yl-1H-indol-3-yl)-ethane-1,2-dione;

3-{3-[2-(4-Benzoyl-2-(R)-methyl-piperazin-1-yl)-2-oxo-acetyl]-4-fluoro-1H-indol-7-yl}-[1,2,4]oxadiazole-5-carboxylic acid methyl ester;

1-(4-Benzoyl-piperazin-1-yl)-2-[4-fluoro-7-(5-trichloromethyl-[1,3,4]oxadiazol-2-yl)-1H-indol-3-yl]-ethane-1,2-dione;

1-(4-Benzoyl-piperazin-1-yl)-2-[7-(5-chloromethyl-1H-[1,2,4]triazol-3-yl)-4-fluoro-1H-indol-3-yl]-ethane-1,2-dione; and 1-(4-Benzoyl-piperazin-1-yl)-2-{4-fluoro-7-[3-(furan-2-ylmethanesulfonylmethyl)-[1,2,4]oxadiazol-5-yl]-1H-indol-3-yl}-ethane-1,2-dione;

1-(4-Benzoyl-piperazin-1-yl)-2-{4-fluoro-7-[3-(thiophen-2-ylsulfanylmethyl)-[1,2,4]oxadiazol-5-yl]-1H-indol-3-yl}-ethane-1,2-dione;

1-(4-Benzoyl-piperazin-1-yl)-2-[4-fluoro-7-(3-phenyl-[1,2,4]oxadiazol-5-yl)-1H-indol-3-yl]-ethane-1,2-dione;

1-(4-Benzoyl-piperazin-1-yl)-2-{4-fluoro-7-[3-(pyridin-2-ylsulfanylmethyl)-[1,2,4]oxadiazol-5-yl]-1H-indol-3-yl}-ethane-1,2-dione;

1-(4-Benzoyl-piperazin-1-yl)-2-{4-fluoro-7-[3-(4-fluoro-phenyl)-[1,2,4]oxadiazol-5-yl]-1H-indol-3-yl}-ethane-1,2-dione;

1-(4-Benzoyl-piperazin-1-yl)-2-{4-fluoro-7-[3-(2-oxo-2-pyrrolidin-1-yl-ethyl)-[1,2,4]oxadiazol-5-yl]-1H-indol-3-yl}-ethane-1,2-dione;

1-(4-Benzoyl-piperazin-1-yl)-2-[7-(3-benzyl-[1,2,4]oxadiazol-5-yl)-4-fluoro-1H-indol-3-yl]-ethane-1,2-dione;

1-(4-Benzoyl-piperazin-1-yl)-2-{4-fluoro-7-[3-(5-methyl-isoxazol-3-yl)-[1,2,4]oxadiazol-5-yl]-1H-indol-3-yl}-ethane-1,2-dione; and 1-(4-Benzoyl-piperazin-1-yl)-2-(7-{3-[2-(3,5-dimethyl-pyrazol-1-yl)-ethyl]-[1,2,4]oxadiazol-5-yl}-4-fluoro-1H-indol-3-yl)-ethane-1,2-dione.

29. The compound of claim 18, including pharmaceutically acceptable salts thereof, selected from the group consisting of:

1-(4-Benzoyl-piperazin-1-yl)-2-(4-fluoro-7-pyridin-2-yl-1H-indol-3-yl)-ethane-1,2-dione;

1-(4-Benzoyl-piperazin-1-yl)-2-(4-fluoro-7-pyridin-2-yl-1H-indol-3-yl)-ethane-1,2-dione;

1-(4-Benzoyl-piperazin-1-yl)-2-(4-methoxy-7-pyridin-3-yl-1H-indol-3-yl)-ethane-1,2-dione;

1-(4-Benzoyl-piperazin-1-yl)-2-(4-methoxy-7-pyridin-3-yl-1H-indol-3-yl)-ethane-1,2-dione;

1-(4-Benzoyl-piperazin-1-yl)-2-(4-fluoro-7-pyrimidin-5-yl-1H-indol-3-yl)-ethane-1,2-dione;

1-(4-Benzoyl-piperazin-1-yl)-2-(4-methoxy-7-pyrimidin-5-yl-1H-indol-3-yl)-ethane-1,2-dione;

1-(4-Benzoyl-piperazin-1-yl)-2-(7-furan-2-yl-4-methoxy-1H-indol-3-yl)-ethane-1,2-dione;

1-(4-Benzoyl-piperazin-1-yl)-2-(4-fluoro-7-thiophen-2-yl-1H-indol-3-yl)-ethane-1,2-dione;

1-(4-Benzoyl-piperazin-1-yl)-2-(4-fluoro-7-thiophen-3-yl)-1H-indol-3-yl)-ethane-1,2-dione;

1-(4-Benzoyl-piperazin-1-yl)-2-(4-fluoro-7-thiazol-2-yl-1H-indol-3-yl)-ethane-1,2-dione;

1-(4-Benzoyl-piperazin-1-yl)-2-(4-methoxy-7-thiazol-2-yl-1H-indol-3-yl)-ethane-1,2-dione 1-(4-Benzoyl-piperazin-1-yl)-2-[7-(5-chloro-thiophen-2-yl)-4-fluoro-1H-indol-3-yl]-ethane-1,2-dione;

1-(4-Benzoyl-piperazin-1-yl)-2-(4-fluoro-7-oxazol-5-yl-1H-indol-3-yl)-ethane-1,2-dione;

1-(7-Benzooxazol-2-yl-4-fluoro-1H-indol-3-yl)-2-(4-benzoyl-piperazin-1-yl)-ethane-1,2-dione;

1-(7-Benzo[b]thiophen-2-yl-4-methoxy-1H-indol-3-yl)-2-(4-benzoyl-piperazin-1-yl)-ethane-1,2-dione;

1-(4-Benzoyl-piperazin-1-yl)-2-[4-fluoro-7-(2H-tetrazol-5-yl)-1H-indol-3-yl]-ethane-1,2-dione;

1-(4-Benzoyl-2-(R)-methyl-piperazin-1-yl-2-[4-fluoro-7-(2H-tetrazol-5-yl)-1H-indol-3-yl]-ethane-1,2-dione;

1-(4-Benzoyl-piperazin-1-yl)-2-(4-fluoro-7-oxazol-2-yl-1H-indol-3-yl)-ethane-1,2-dione;

1-[7-(1H-Benzoimidazol-2-yl-4-fluoro-1H-indol-3-yl)-2-(4-benzoyl-piperazin-1-yl)-ethane-1,2-dione;

1-(4-Benzoyl-piperazin-1-yl)-2-(4-fluoro-7-[1,2,4]oxadiazol-3-yl-1H-indol-3-yl)-ethane-1,2-dione;

1-(4-Benzoyl-piperazin-1-yl)-2-[4-fluoro-7-(3H-imidazol-4-yl)-1H-indol-3-yl]-ethane-1,2-dione;

1-(4-Benzoyl-piperazin-1-yl)-2-(4-fluoro-7-[1,3,4]oxadiazol-2-yl-1H-indol-3-yl)-ethane-1,2-dione;

1-(4-Benzoyl-piperazin-1-yl)-2-[4-fluoro-7-(1H-[1,2,4]triazol-3-yl)-1H-indol-3-yl]-ethane-1,2-dione;

1-(4-Benzoyl-piperazin-1-yl)-2-[4-methoxy-7-(1H-[1,2,4]triazol-3-yl)-1H-indol-3-yl]-ethane-1,2-dione;

1-(4-Benzoyl-piperazin-1-yl)-2-(4-fluoro-7-pyrazol-1-yl-1H-indol-3-yl)-ethane-1,2-dione;

1-(4-Benzoyl-piperazin-1-yl)-2-(4-fluoro-7-imidazol-1-yl-1H-indol-3-yl)-ethane-1,2-dione;

1-(4-Benzoyl-piperazin-1-yl)-2-(4-fluoro-7-[1,2,4]triazol-1-yl-1H-indol-3-yl)-ethane-1,2-dione;

1-(4-Benzoyl-piperazin-1-yl)-2-(4-methoxy-7-[1,2,4]oxadiazol-3-yl-1H-indol-3-yl)-ethane-1,2-dione;

1-(4-Benzoyl-piperazin-1-yl)-2-[4-fluoro-7-(1H-imidazo[4,5-c]pyridin-2-yl)-1H-indol-3-yl]-ethane-1,2-dione; and 1-(4-Benzoyl-piperazin-1-yl)-2-[4-fluoro-7-(1H-imidazo[4,5-b]pyridin-2-yl)-1H-indol-3-yl]-ethane-1,2-dione 1-(4-Benzoyl-piperazin-1-yl)-2-[4-methoxy-7-(5-methyl-2H-[1,2,4]triazol-3-yl)-1H-indol-3-yl]-ethane-1,2-dione.

30. A compound of claim 19, including pharmaceutically acceptable salts thereof, selected from the group consisting of:

1-(4-Benzoyl-piperazin-1-yl)-2-[4-fluoro-7-(5-oxo4,5-dihydro-[1,2,4]oxadiazol-3-yl)-1H-indol-3-yl]-ethane-1,2-dione;

3-[2-(4-Benzoyl-piperazin-1-yl)-2-oxo-acetyl]-4-fluoro-1H-indole-7-carboxylic acid (4,5-dihydro-thiazol-2-yl)-amide;

1-(4-Benzoyl-piperazin-1-yl)-2-[4-fluoro-7-(5-oxo-4,5-dihydro-[1,3,4]oxadiazol-2-yl)-1H-indol-3-yl]-ethane-1,2-dione;

1-(4-Benzoyl-piperazin-1-yl)-2-[7-(4,5-dihydro-1H-imidazol-2-yl)-4-fluoro-1H-indol-3-yl]-ethane-1,2-dione; and 1-(4-Benzoyl-2-(R)-methyl-piperazin-1-yl)-2-[4-fluoro-7-(5-oxo-4,5-dihydro-[1,2,4]oxadiazol-3-yl)-1H-indol-3-yl]-ethane-1,2-dione.

31. A compound of claim 20, including pharmaceutically acceptable salts thereof, selected from the group consisting of:

3-[2-(4-Benzoyl-piperazin-1-yl)-2-oxo-acetyl]-4-fluoro-N-hydroxy-1H-indole-7-carboxamidine;

3-[2-(4-Benzoyl-piperazin-1-yl-2-oxo-acetyl]-4-fluoro-1H-indole-7-carbaldehyde oxime;

{3-[2-(4-Benzoyl-piperazin-1-yl)-2-oxo-acetyl]-4-fluoro-1H-indol-7-ylmethyleneaminooxy}-acetic acid;

3-[2-(4-Benzoyl-piperazin-1-yl)-2-oxo-acetyl]-4-fluoro-1H-indole-7-carboximidic acid ethyl ester;

3-[2-(4-Benzoyl-piperazin-1-yl)-2-oxo-acetyl]-N-cyclopropyl-4-fluoro-1H-indole-7-carboxamidine;

3-[2-(4-Benzoyl-piperazin-1-yl)-2-oxo-acetyl]-N-amino4-fluoro-1H-indole-7-carboxamidine;

N'-(Amino-{3-[2-(4-benzoyl-piperazin-1-yl)-2-oxo-acetyl]-4-fluoro-1H-indol-7-yl}-methylene)-hydrazinecarboxylic acid tert-butyl ester;

N'-[{3-[2-(4-Benzoyl-piperazin-1-yl)-2-oxo-acetyl]-4-fluoro-1H-indol-7-yl}-(tert-butoxycarbonyl-hydrazono)-methyl]-hydrazinecarboxylic acid tert-butyl ester;

4-{2-[4-Fluoro-7-(N-hydroxycarbamimidoyl)-1H-indol-3-yl]-2-oxo-acetyl}-piperazine-1-carboxylic acid tert-butyl ester;

3-[2-(4-Benzoyl-piperazin-1-yl)-2-oxo-acetyl]-4-methoxy-1H-indole-7-carbaldehyde oxime; and 3-[2-(4-Benzoyl-2-(R)-methyl-piperazin-1-yl)-2-oxo-acetyl]-4-fluoro-N-hydroxy-1H-indole-7-carboxamidine.

32. A pharmaceutical formulation which comprises an antiviral effective amount of a compound of Formula I, including pharmaceutically acceptable salts thereof, as claimed in any of claims 1–31, and a pharmaceutically acceptable carrier, adjuvant or diluent.

33. A method for treating mammals infected with the HIV virus, comprising administering to said mammal an antiviral effective amount of a compound of Formula I, including pharmaceutically acceptable salts thereof, as claimed in any of claims 1–31.

* * * * *